United States Patent
Jones et al.

(10) Patent No.: US 9,673,030 B2
(45) Date of Patent: Jun. 6, 2017

(54) COMPUTER READABLE STORAGE MEDIUMS, METHODS AND SYSTEMS FOR NORMALIZING CHEMICAL PROFILES IN BIOLOGICAL OR MEDICAL SAMPLES DETECTED BY MASS SPECTROMETRY

(75) Inventors: Dean P. Jones, Decatur, GA (US); Quinlyn A. Soltow, Atlanta, GA (US)

(73) Assignee: Emory University, Atlanta, GA (US)

( * ) Notice: Subject to any disclaimer, the term of this patent is extended or adjusted under 35 U.S.C. 154(b) by 1356 days.

(21) Appl. No.: 13/109,642

(22) Filed: May 17, 2011

(65) Prior Publication Data

US 2011/0282587 A1    Nov. 17, 2011

Related U.S. Application Data

(60) Provisional application No. 61/345,294, filed on May 17, 2010.

(51) Int. Cl.

| | |
|---|---|
| G01N 33/48 | (2006.01) |
| G01N 33/50 | (2006.01) |
| H01J 49/00 | (2006.01) |
| G06F 19/12 | (2011.01) |
| G06F 17/10 | (2006.01) |
| G06F 19/24 | (2011.01) |

(52) U.S. Cl.
CPC ......... *H01J 49/0009* (2013.01); *G06F 17/10* (2013.01); *G06F 19/12* (2013.01); *G06F 19/24* (2013.01); *H01J 49/0036* (2013.01)

(58) Field of Classification Search
None
See application file for complete search history.

(56) References Cited

U.S. PATENT DOCUMENTS

| | | |
|---|---|---|
| 6,680,203 B2 | 1/2004 | Dasseux et al. |
| 6,974,702 B2 | 12/2005 | Dasseux et al. |
| 7,451,052 B2 | 11/2008 | Wang et al. |
| 7,632,686 B2 | 12/2009 | Anderson |

(Continued)

FOREIGN PATENT DOCUMENTS

| | | |
|---|---|---|
| WO | 2009134439 A2 | 11/2009 |

OTHER PUBLICATIONS

Anderson, et al., 2007, "Control of extracellular cysteine/cystine redox state by HT-29 cells is independent of cellular glutathione", Am J Physiol Regul Integr Comp Physiol, 3 (293): R1069-R1075.

(Continued)

*Primary Examiner* — Russell S Negin
(74) *Attorney, Agent, or Firm* — Emory Patent Group

(57) ABSTRACT

Described herein are computer-readable storage mediums, methods and systems useful for analyzing samples via mass spectrometry. Aspects described herein include methods for normalizing mass spectrometry data that include providing a reference set of mass spectrometry data obtained from a first external standard sample having one or more isotopic standards, wherein the reference set of mass spectrometry data comprises one or more m/z intensity ratios. Methods described herein are useful for reducing errors based on instrument response and ionization efficiencies and improve reproducibility of data from instrument to instrument and from day to day.

20 Claims, 18 Drawing Sheets

(56) References Cited

U.S. PATENT DOCUMENTS

2005/0059017 A1* 3/2005 Oldham et al. .................... 435/6
2006/0200316 A1 9/2006 Kanani et al.

OTHER PUBLICATIONS

Bohus et al., (2008), "Temporal Metabonomic Modeling of l-Arginine-Induced Exocrine Pancreatitis", Journal of Proteome Research, 7(10): 4435-4445.
Chen, et al., 2009, "Serum metabolomics reveals irreversible inhibition of fatty acid beta-oxidation through the suppression of PPARalpha activation as a contributing mechanism of acetaminophen-induced hepatotoxicity", Chem Res Toxicol, 4 (22): 699-707.
Coen, et al., 2007, "The Mechanism of Galactosamine Toxicity Revisited; A Metabonomic Study", J Proteome Res, 7 (6): 2711-2719.
Cui, et al., 2008, "Metabolite identification via the Madison Metabolomics Consortium Database", Nat Biotechnol, 26 (2): 162-164.
Deport, C., 2006, "Comprehensive combinatory standard correction: A calibration method for handling instrumental drifts of gas chromatography—mass spectrometry systems", J Chrom A, 1-2 (1116): 248-258.
Fiehn, O., 2002, "Metabolomics—the link between genotypes and phenotypes", Plant Mol Biol, 1-2 (48): 155-171.
Gibney, et al., 2005, "Metabolomics in human nutrition: opportunities and challenges", Am J Clin Nutr, 3 (82): 497-503.
Gika, et al., 2008, "Liquid chromatography and ultra-performance liquid chromatography—mass spectrometry fingerprinting of human urine sample stability under different handling and storage conditions for metabonomics studies", J Chromatogr A, 1-2 (1189): 314-322.
Go, et al., 2011, "Cysteine/cystine redox signaling in cardiovascular disease.", Free Radic Biol Med, 4 (50): 495-509.
Iyer, et al., 2009, "Cysteine redox potential determines pro-inflammatory IL-1beta levels.", PLoS One, 3 (4): e5017.
Iyer, et al., 2009, "Oxidation of plasma cysteine/cystine redox state in endotoxin-induced lung injury.", Am J Respir Cell Mol Biol, 1 (40): 90-98.
Johnson, et al., 2008, "A rapid LC-FTMS method for the analysis of cysteine, cystine and cysteine/cysteine steady-state redox potential in human plasma", Clin Chim Acta, 1-2 (396): 43-48.
Jones, et al., 2004, "Cysteine/cystine couple is a newly recognized node in the circuitry for biologic redox signaling and control.", FASEB J, 11 (18): 1246-1248.
Jones, et al., 2011, "Dietary sulfur amino acid effects on fasting plasma cysteine/cystine redox potential in humans.", Nutrition, 2 (27): 199-205.
Kanani, et al., 2007, "Data correction strategy for metabolomics analysis using gas chromatography-mass spectrometry," Metab Engr, 1 (9): 39-51.
Kemsley, et al., 2007, "Multivariate techniques and their application in nutrition: a metabolomics case study", Br J Nutr, 1 (98): 1-14.
Kuhara, T. 2007, "Noninvasive human metabolome analysis for differential diagnosis of inborn errors of metabolism", J Chromatogr B Analyt Technol Biomed Life Sci, 1 (855): 42-50.
Kuhara, T., 2005, "Gas Chromatographic-Mass spectrometric Urinary Metabolome Analysis to Study Mutations of Inborn Errors of Metabolism", Mass Spectrom Rev, 6 (24): 814-827.
Li, et al., 2007, "Pharmacometabonomic Phenotyping Reveals Different Responses to Xenobiotic Intervention in Rats", J Proteome Res, 4 (6): 1364-1370.
Lindon, et al., 2005, "The Consortium for Metabonomic Toxicology (COMET): Aims, Activities and Achievements", Pharmacogenomics, 7 (6): 691. Bohus, E. et al., 2008, "Temporal Metabonomic Modeling of L-Arginine-Induced Exocrine Pancreatitis", J Proteome Res, 10 (7): 4435-4445.
Mamas, et al., 2011, "The role of metabolites and metabolomics in clinically applicable biomarkers of disease.", Arch Toxicol, 1 (85): 5-17.
Mannery, et al., 2010, "Oxidation of plasma cysteine/cystine and GSH/GSSG redox potentials by acetaminophen and sulfur amino acid insufficiency sin humans.", J Pharmacol Exp Ther, 3 (333): 939-947.
Miller, M., 2007, "Environmental Metabolomics: A SWOT Analysis (Strengths, Weaknesses, Opportunities, and Threats)", J. Proteome Res, 2 (6): 540-545.
Nkabyo, et al., 2005, "Extracellular cysteine/cystine redox regulates the p44/p42 MAPK pathway by metalloproteinase-dependent epidermal growth factor receptor signaling.", Am J Physiol Gastrointest Liver Physiol, 1 (289): G70-G78.
Nordström, et al., 2006, "Nonlinear Data Alignment for UPLC-MS and HPLC-MS Based Metabolomics: Quantitative Analysis of Endogenous and Exogenous Metabolites in Human Serum", Anal Chem, 10 (78): 3289-3295.
Pavón, et al., 2003, "Calibration Transfer for Solving the Signal Instability in Quantitative Headspace-Mass Spectrometry", Anal Chem, 22 (75): 6361-6367.
Pavón, et al., 2006, "Strategies for qualitative and quantitative analyses with mass spectrometry-based electronic noses", Trends Anal Chem, 3 (25): 257-266.
Raikos, et al., 2009, "Analysis of anaesthetics and analgesics in human urine by headspace SPME and GC", J Sep Sci, 7 (32): 1018-1026.
Rezzi, et al., 2007, "Human Metabolic Phenotypes Link Directly to Specific Dietary Preferences in Healthy Individuals", J Proteome Res, 11 (6): 4469-4477.
Sysi-Aho, et al., 2007, "Normalization method for metabolomics data using optimal selection of multiple internal standards", BMC Bioinformatics, (8): 93-112.
Walsh, et al., 2006, "Effect of acute dietary standardization on the urinary, plasma, and salivary metabolomic profiles of healthy humans", Am J Clin Nutr, 3 (84): 531-539.
Walsh, et al., 2007, "Influence of acute phytochemical intake on human urinary metabolomic profiles", Am J Clin Nutr, 6 (86): 1687-1693.
Wang, et al., 2009, "Systems toxicology study of doxorubicin on rats using ultra performance liquid chromatography coupled with mass spectrometry based metabolomics.", Metabolomics, 4 (5): 407-418.
Want, et al., 2006, "Solvent-Dependent Metabolite Distribution, Clustering, and Protein Extraction for Serum Profiling with Mass Spectrometry", Anal Chem, 3 (78): 743-752.
Weckwerth, W., 2003, "Metabolomics in Systems Biology", Annu Rev Plant Biol, (54): 669-689.
Yu, et al., Aug. 2009, "apLCMS—adaptive processing of high-resolution LC/MS data", Bioinformatics, 15 (25): 1930-1936.

* cited by examiner

COMPUTER READABLE STORAGE MEDIUMS, METHODS AND SYSTEMS FOR NORMALIZING CHEMICAL PROFILES IN BIOLOGICAL OR MEDICAL SAMPLES DETECTED BY MASS SPECTROMETRY

PRIOR APPLICATION

This application claims priority to U.S. Provisional Application No. 61/345,294 filed May 17, 2010, which is hereby incorporated by reference.

STATEMENT REGARDING FEDERALLY SPONSORED RESEARCH OR DEVELOPMENT

This disclosure was made with United States governmental support under Award No. P01 ES 016731 awarded by the National Institutes of Health and the National Institute of Environmental Health Sciences. The U.S. government may have certain rights in the disclosure.

BACKGROUND

This disclosure is in the field of mass spectrometry. This disclosure relates generally to computer readable storage mediums, methods and systems for normalizing and standardizing mass spectrometry data. Normalization and standardization are necessary to compare data across instruments or time. Stable isotope dilution methods or external standard calibrations are not scalable to hundreds to thousands of chemicals in complex biological extracts. Surrogate standardization is limited by chemical properties and dynamic range.

Currently, no universal normalization protocol has been accepted for use with liquid chromatography-mass spectrometry (LC-MS) based metabolomics. A proposed method for normalization, called NOMIS (normalization using optimal selection of multiple internal standards), was published in 2007 by Sysi-Aho et al. (Sysi-Aho et al., Normalization method for metabolomics data using optimal selection of multiple internal standards, BMC Bioinformatics, 2007, 8:93). NOMIS provides a sound technique for normalization of LC/MS data by using a mathematical model that optimally assigns normalization factors for each metabolite measured based on internal standard profiles. However, these analyses use log transformation that are unable to deal with features that contain a zero value, use no external standard, and have only been shown to be suitable for lipid profiling with a mass to charge range (m/z) of 300-1600.

Another strategy developed for normalization of mass-spectrometry data utilizes a calibration transfer algorithm where the signal variation observed for a calibration model is used to correct experimental intensities to a date the calibration model was constructed. Pavon et al. describes this technique and utilizes the average intensities of a number of calibration transfer samples for the correction (Pavón et al., Calibration Transfer for Solving the Signal Instability in Quantitative Headspace-Mass spectrometry, Anal. Chem. 2003, 75, 6361-6367 and Pavón et al., Strategies for qualitative and quantitative analyses with mass spectrometry-based electronic noses, Trends Anal. Chem., 2006, 25, 257-266).

Deport et al. describes a method for normalization of gas chromatography-mass spectrometry (GC-MS) data where a number of internal standards are analyzed with a sample and each sample peak area is normalized against each of the possible internal standard combinations to determine which combination provides the best discrimination of a specific sample peak (Deport et al., Comprehensive combinatory standard correction: A calibration method for handling instrumental drifts of gas chromatography-mass spectrometry systems, J. Chrom A, 2006, 1116, 248-258).

SUMMARY

Provided herein are computer readable mediums, methods and systems for analyzing samples via mass spectrometry and for normalizing mass spectrometry data. Also provided are methods for normalizing metabolomics data and methods of diagnosing diseases.

In some embodiments, the disclosure may be related to a method of analyzing a test sample via mass spectrometry. The method may comprise the steps of: providing a reference set of mass spectrometry data obtained from a first external standard sample having one or more isotopic standards, wherein the reference set of mass spectrometry data comprises one or more m/z intensity ratios, receiving a first set of mass spectrometry data from the test sample having the one or more isotopic standards, wherein the first set of mass spectrometry data comprises one or more m/z intensity ratios; receiving at least a second set of mass spectrometry data from a second external standard sample having the one or more isotopic standards, wherein the second set of mass spectrometry data comprises one or more m/z intensity ratios; generating one or more m/z intensity ratio normalization factors based on the second mass spectrometry data set and the reference mass spectrometry data table; and generating normalized intensity ratios for the test sample based on the normalization factors and the first mass spectrometry data set.

In some embodiments, the first external standard sample and the second external standard samples may be the same, substantially the same or from the same biologically derived material. In other embodiments, the reference set of mass spectrometry data may comprise a mass spectrometry data table. In further embodiments, the reference set of mass spectrometry data may include a reference isotopic standard or a combination of reference isotopic standards for the one or more m/z features.

In some embodiments, the providing the reference set of mass spectrometry data may include: receiving at least one reference set of mass spectrometry data obtained from a first external standard sample having one or more isotopic standards, wherein the reference set of mass spectrometry data comprises one or more m/z intensity ratios; determining intensity ratios of one or more m/z features for each isotropic standard; comparing intensities for one or more m/z features from the reference set of mass spectrometry data with intensities for the one or more isotopic standards from the reference set of mass spectrometry data; selecting a reference isotopic standard or a combination of reference isotopic standards for each of the one or more m/z features from the reference set of mass spectrometry data; and generating a reference data table, the reference data table associating the one or more m/z features from the reference set of mass spectrometry data with at least each selected corresponding intensity ratio. In further embodiments, the step of receiving may include receiving a plurality of reference sets of mass spectrometry data. In some embodiments, the criteria for selecting the reference isotopic standard for each m/z feature from the reference set of mass spectrometry data includes a lowest intensity ratio coefficient of variation for that m/z feature.

In other embodiments, the first, second and reference sets of mass spectrometry data may comprise liquid chromatography-mass spectrometry data, gas chromatography-mass spectrometry data or Fourier transform mass spectrometry data, direct infusion mass spectrometry data, capillary electrophoresis mass spectrometry data, ion mobility shift mass spectrometry data, desorption electrospray ionization mass spectrometry data, nanostructure initiator mass spectrometry or matrix assisted mass spectrometry data. In other embodiments, the concentrations of the one or more isotopic standards in the test sample, the first external standard sample and the second standard sample may be the same. In some embodiments, the first external standard sample, the test sample and the second external standard sample may comprise a biological fluid. In some embodiments, the first set of mass spectrometry data, the second set of mass spectrometry data and the reference set of mass spectrometry data may comprise metabolomic data or metabonomic data. In further embodiments, the reference set of mass spectrometry data may be received before or after the second set of mass spectrometry data. In some embodiments, the second set of mass spectrometry data may be received before or after the first set of mass spectrometry data.

In other embodiments, the disclosure may be related to a method of generating a reference data table. The method may comprise the steps of: receiving a mass spectrometry data set on a standard sample having one or more isotopic standards, the mass spectrometry data set comprising intensities for one or more m/z features including the one or more isotopic standards; comparing intensities for one or more m/z features with intensities for the one or more isotopic standards; determining a reference isotopic standard or a combination of a isotopic standard for each of the one or more m/z features; and generating a data table, the data table including one or more m/z entries corresponding to the one or more m/z features, wherein each m/z entry of the data table comprises an intensity ratio of one or more m/z features divided by the intensity of the reference isotopic standard or combination of reference isotopic standards for those one or more m/z features. In some embodiments, the step of receiving the mass spectrometry data may be repeated one or more times. In other embodiments, the method may further comprise determining a coefficient of variation for the ratios of intensities of each of the one or more m/z features to each of the one or more isotopic standards. The determining the reference isotopic standard or combination of reference isotopic standards for each of the one or more m/z features may be based on the criteria. In some embodiments, the criteria may include a lowest intensity ratio coefficient of variation for that m/z feature.

In other embodiments, the disclosure may be related to a computer readable storage medium for storing instructions for analyzing a test sample via mass spectrometry. The instructions may comprise: providing a reference set of mass spectrometry data obtained from a first external standard sample having one or more isotopic standards, wherein the reference set of mass spectrometry data comprises one or more m/z intensity ratios, receiving a first set of mass spectrometry data from the test sample having the one or more isotopic standards, wherein the first set of mass spectrometry data comprises one or more m/z intensity ratios; receiving at least a second set of mass spectrometry data from a second external standard sample having the one or more isotopic standards, wherein the second set of mass spectrometry data comprises one or more m/z intensity ratios; generating one or more m/z intensity ratio normalization factors based on the second mass spectrometry data set and the reference mass spectrometry data table; and generating normalized intensity ratios for the test sample based on the normalization factors and the first mass spectrometry data set. In some embodiments, the reference set of mass spectrometry data may comprise a mass spectrometry data table. In further embodiments, the reference set of mass spectrometry data may include a reference isotopic standard or a combination of reference standards for the one or more m/z features. In some embodiments, the providing the reference set of mass spectrometry data may include: receiving at least one reference set of mass spectrometry data obtained from a first external standard sample having one or more isotopic standards, wherein the reference set of mass spectrometry data comprises one or more m/z intensity ratios; determining intensity ratios of one or more m/z features for each isotropic standard; comparing intensities for one or more m/z features from the reference set of mass spectrometry data with intensities for the one or more isotopic standards from the reference set of mass spectrometry data; selecting a reference isotopic standard or a combination of reference isotopic standards for each of the one or more m/z features from the reference set of mass spectrometry data; and generating a reference data table, the reference data table associating the one or more m/z features from the reference set of mass spectrometry data with at least each selected corresponding intensity ratio.

In other embodiments, a method of analyzing a test sample via mass spectrometry may comprise the steps of: i) providing a reference set of mass spectrometry data obtained from a first external standard sample having one or more isotopic standards, wherein the reference set of mass spectrometry data comprises one or more m/z intensity ratios, wherein each m/z intensity ratio is the intensity of one or more m/z features divided by the intensity of a reference isotopic standard or a combination of reference isotopic standards for those one or more m/z features; ii) providing the test sample; iii) adding the one or more isotopic standards to the test sample; iv) receiving a first set of mass spectrometry data from the test sample having the one or more isotopic standards, wherein the first set of mass spectrometry data comprises one or more m/z intensity ratios, wherein each m/z intensity ratio is the intensity of one or more m/z features divided by the intensity of the reference isotopic standard or combination of reference isotopic standards for those one or more m/z feature; v) providing a second external standard sample; vi) adding the one or more isotopic standards to the second external standard sample; vii) receiving a second set of mass spectrometry data from the second external standard sample having the one or more isotopic standards, wherein the second set of mass spectrometry data comprises one or more m/z intensity ratios, wherein each m/z intensity ratio is the intensity of one or more m/z features divided by the intensity of the reference isotopic standard or combination of reference isotopic standards for those one or more m/z features; viii) dividing one or more m/z intensity ratios of the reference mass spectrometry data set by a corresponding m/z intensity ratio from the second mass spectrometry data set, thereby receiving one or more m/z intensity ratio normalization factors; and ix) multiplying one or more m/z intensity ratios of the first mass spectrometry data set by a corresponding m/z intensity ratio normalization factor to generate one or more normalized m/z intensity ratios for the test sample.

Mass spectrometry data useful in aspects described herein include, but are not limited to: liquid chromatography-mass spectrometry data, gas chromatography-mass spectrometry data, Fourier transform mass spectrometry data, direct infusion mass spectrometry data, capillary electrophoresis mass spectrometry data, ion mobility shift mass spectrometry data, desorption electrospray ionization mass spectrometry data or matrix assisted mass spectrometry data such as matrix assisted laser desorption ionization mass spectrometry data.

In some embodiments, the first external standard sample and the second external standard samples may be the same, substantially the same or from the same biologically derived material. As used in this context, the term "substantially the same" indicates that two or more samples are of the same origin and may include minor changes (e.g. less than 5% difference) in composition, for example due to degradation, storage or sample treatment. In a specific embodiment, the majority of components of two or more samples, which are substantially the same, may be considered identical. As used in this context, the term "from the same biologically derived material" refers to two or more samples which are obtained, for example as aliquots, from a common biological sample, such as a pooled biological sample.

In some embodiments, the first external standard sample, the second external standard sample or both may be NIST reference standards. In further embodiments, the first external standard sample, the test sample and the second external standard sample may comprise a biological fluid. In further embodiments, the first external standard sample, the second external standard sample or both may be pooled biological fluid reference samples obtained from a plurality of subjects. Useful biological fluids include, but are not limited to: plasma, urine, bile, cerebrospinal fluid, bronchoalveolar lavage fluid, saliva, tears, exhaled breath condensate, serum, whole blood, tissue extracts, cell extracts, sub-cellular fractions, mitochondrial sub-cellular fractions and nucleic sub-cellular fractions.

In other embodiments, the first set of mass spectrometry data, the second set of mass spectrometry data and the reference set of mass spectrometry data may each comprise intensities for one or more m/z features including intensities for each of the one or more isotopic standards. In some embodiments, each m/z feature may correspond to a single analyte. For some embodiments, multiple m/z features may arise from a single analyte. Optionally, each m/z intensity may comprise an integrated area or integrated intensity. Optionally, the reference set of mass spectrometry data may comprise mass spectrometry data in a data table. In some embodiments, the reference set of mass spectrometry data may be provided as a data table. In further embodiments, the reference isotopic standards or combinations of reference isotopic standards for m/z features may be indicated in the reference set of mass spectrometry data.

In certain embodiments, a method of this aspect may further comprise the steps of: i) receiving the reference set of mass spectrometry data on the second external standard sample having one or more isotopic standards; ii) comparing intensities for one or more m/z features from the reference set of mass spectrometry data with intensities for the one or more isotopic standards from the reference set of mass spectrometry data, thereby determining a reference isotopic standard or a combinations of reference isotopic standards for each of the one or more m/z features from the reference set of mass spectrometry data; and iii) populating a data table with one or more m/z entries corresponding to the one or more m/z features from the reference set of mass spectrometry data, wherein each m/z entry of the data table comprises an intensity ratio equal to the intensity of one or more m/z features from the reference set of mass spectrometry data divided by the intensity of the reference isotopic standard or combination of reference isotopic standards for those one or more m/z features. Optionally, the step of receiving the reference set of mass spectrometry data may be repeated one or more times and the comparing step comprises determining a coefficient of variation for the ratios of intensities of each of the one or more m/z features from the reference set of mass spectrometry data to each of the one or more isotopic standards from the reference set of mass spectrometry data. In an exemplary embodiment, the reference isotopic standard for each m/z feature from the reference set of mass spectrometry data is selected as the isotopic standard having the lowest intensity ratio coefficient of variation for that m/z feature.

In some embodiments, the one or more isotopic standards may comprise stable isotopic standard compounds. Useful isotopic standards include, but are not limited to: [$^{13}C_6$]-D-glucose, [$^{15}N$]-indole, [2-$^{15}N$]-L-lysine dihydrochloride, [$^{13}C_5$]-L-glutamic acid, [$^{13}C_7$]-benzoic acid, [3,4-$^{13}C_2$]-cholesterol, [$^{15}N$]-L-tyrosine, [trimethyl-$^{13}C_3$]-caffeine, [$^{15}N2$]-uracil, [3,3-$^{13}C_2$]-cystine, [1,2-$^{13}C_2$]-palmitic acid, [$^{15}N$, $^{13}C_5$]-L-methionine, [$^{15}N$]-choline chloride, and any combination of these. Useful isotopic standards include, but are not limited to: (±)-Cotinine-methyl-D3, (1R,2S)-(−)-Ephedrine-D3 (N-methyl-D3) hydrochloride, (1S,2R)-(+)-Ephedrine-D3 (N-methyl-D3) hydrochloride, (1S,2S)-(+)-Pseudoephedrine-N-methyl-D3 hydrochloride, (2-Chloroethyl)trimethyl-D9-ammonium chloride, (Trimethylsilyl)acetylene-13C2, (Trimethylsilyl)acetylene-D, ±-Catechin-2,3,4-13C3, ±-Epicatechin-2,3,4-13C3, 1-(3-Aminophenyl)acetylene-1,2-13C2, 1-(3-Aminophenyl)acetylene-1-13C, 1-(3-Aminophenyl)acetylene-2-13C,1,1,1,3,3,3-Hexachloropropane-13C3, 1,1,1,3,3,3-Hexafluoro-2-(fluoromethoxy)propane-D3, 1,1,1,3,3,3-Hexafluoro-2-propan(ol-D), 1,1,1,3,3,3-Hexafluoro-2-propanol-D2, 1,1,1-Trichloroethane-2,2,2-D3, 1,1,2,2-Tetrachloroethane-D2, 1,1,4,4-Tetraphenyl-1,3-butadiene-D22, 1,10-Phenanthroline-D8, 1,2,3-Trichloropropane-13C3, 1,2,4,5-Benzenetetracarboxylic dianhydride-D2, 1,2,4,5-Tetrachlorobenzene-D2, 1,2,4,5-Tetramethylbenzene-D14, 1,2,4-Triazole-15N3, 1,2,4-Trichlorobenzene-D3, 1,2-Dibromoethane-13C2, 1,2-Dibromoethane-D3, 1,2-Dibromoethane-D4, 1,2-Dichlorobenzene-D4, 1,2-Dichloroethane-D4, 1,2-Dimyristoyl-rac-glycero-3-phosphocholine-D72 hydrate, 1,2-Propane (diol-D2), 1,2-Propane-D6-Diol, 1,2-Propanediol-1,2-13C2, 1,2-Propanediol-D8, 1,3,5-Triazine-D3, 1,3,5-Trichlorobenzene-D3, 1,3-Butadiene-D6, 1,3-Diamino(propane-D6), 1,3-Dibromopropane-1,3-13C2, 1,3-Dibromopropane-13C3, 1,3-Dibromopropane-2-13C, 1,3-Dibromopropane-D6, 1,3-Dichlorobenzene-D4, 1,3-Dichloroisopropyl-D5 alcohol, 1,3-Difluorobenzene-D4, 1,3-Dinitrobenzene-13C6, 1,3-Dinitrobenzene-15N2, 1,3-Dinitrobenzene-D4, 1,3-Dithiane-2-13C, 1,3-Dithiane-2-13C-2,2-D2, 1,3-Propane-D6-Diol, 1,3-Propanediol-1,3-13C2, 1,3-Propanediol-13C3, 1,3-Propanediol-2-13C, 1,3-Propanediol-D8, 1,4-Bis (trifluoromethyl)benzene-13C6, 1,4-Bis[(phenyl-3-propanesulfonate)phosphine]butane disodium salt, 1,4-Butanediol-1,1,2,2,3,3,4,4-D8, 1,4-Butanediol-13C4, 1,4-Butanediol-2,2,3,3-D4, 1,4-Diamino(butane-D8) dihydrochloride, 1,4-Diaminobutane-1,4-13C2, 1,4-Diaminobutane-13C4, 1,4-Diaminobutane-15N2 dihydrochloride, 1,4-Diaminobutane-2,2,3,3-D4 dihydrochloride, 1,4-Dibromobenzene-D4, 1,4-Dibromobutane-2,2,3,3-D4, 1,4-Dibromobutane-D8, 1,4-Dichlorobenzene-D4, 1,4-Difluorobenzene-D4, 1,4-Dioxane-13C4, 1,4-Phenylenediamine-15N2, 1,4-Phenylenediamine-2,3,5,6-D4, 1,4-Phenylenediamine-D8, 1,6-Diaminohexane-1,1,6,6-D4, 1,6-Diaminohexane-1,6-13C2, 1,6-Diaminohexane- 15N2, 1,6-Diaminohexane-2,2,5,5-D4, 1,6-Diaminohexane-3,3,4,4-D4, 1,7-Dibromoheptane-1,2,6,7-13C4, 1,7-Heptanediol-2,4,6-13C3, 1,8-Diaminonaphthalene-D10, 11-DEOXYCORTISOL(21,21-D2), 11-Deoxycortisol-2,2,4,6,6-D5, 17-ALPHA-ETHYNYLESTRADIOL(2,4,16,16-D4), 17-HYDROXYPROGESTERONE(2,2,4,6,6,21,21,21-D8), 17α-(Acetoxy-1-13C,2,2,2-D3)-6-methyl-4,6-pregnadiene-3,20-dione, 17β-Estradiol-16,16,17-D3, 17β-Estradiol-2,3,4-13C3, 17β-Estradiol-2,4,16,16,17-D5 97, 18-Hydroxycorticosterone, 18-Hydroxycorticosterone-9,11,12,12-D4, 19-NORTESTOSTERONE(16,16,17-D3), 1-Amino(octane-D17), 1-Aminonaphthalene-D7, 1-Bromo-3-chloropropane-13C3,1-Bromo-3-chloropropane-D6, 1-Bromo-3-fluorobenzene-13C6, 1-Bromo-4-fluorobenzene-D4, 1-Bromobutane-4,4,4-D3,1-Bromobutane-D9, 1-Bromodecane-10,10,10-D3, 1-Bromodecane-D21, 1-Bromododecane-1-13C, 1-Bromododecane-12,12,12-D3, 1-Bromododecane-D25, 1-Bromohexadecane-16,16,16-D3, 1-Bromohexadecane-D33, 1-Bromohexane-1-13C, 1-Bromohexane-13C6, 1-Bromohexane-D13, 1-Bromononane-1,1,2,2-D4, 1-Bromooctadecane-D37, 1-Bromooctane-D17, 1-Bromopentane-5,5,5-D3, 1-Bromopentane-D11, 1-Bromopropane-1,1,2,2-D4, 1-Bromopropane-1,1,3,3,3-D5, 1-Bromopropane-13C3, 1-Bromopropane-2,3-13C2, 1-Bromopropane-3,3,3-D3, 1-Bromopropane-D7, 1-Bromotridecane-1,1,2,2-D4, 1-Butan(ol-D), 1-Butan-D9-ol, 1-Butanol-13C4,1-Butanol-4,4,4-D3, 1-Butanol-D10, 1-Butene-1-13C, 1-Chlorobutane-D9, 1-Decyne-1,2-13C2, 1-Dodecan-D25-ol, 1-Dodecanol-1-13C, 1-Dodecene-1,2-13C2, 1-Ethyl-3-methylimidazolium chloride-D11, 1-Hexadecan-D33-ol, 1-Hexan-D13-ol, 1-Hexanol-13C6, 1-Hexylamine-15N, 1-Iodobutane-D9, 1-Iodopropane-D7, 1-Methylimidazole-D6, 1-Methylnaphthalene-D10, 1-Naphthol-2,3,4,5,6,7,8-D7 97, 1-Octan-D17-ol, 1-Octanethiol-1-13C, 1-Octanol-1-13C, 1-Octanol-D18, 1-Pentan(ol-D), 1-Pentan-D11-ol, 1-Pentanol-1-13C, 1-Phenyl-13C6-1-Dodecanone, 1-Phenyl-2-propanone-1-13C, 1-Phenyl-D5-ethanol, 1-Phenylethan-1,2,2,2-D4-ol, 1-Phenylethan-1-D1-ol, 1-Phenylethanol-1,2-13C2, 1-Phenylethanol-1-13C, 1-Phenylethanol-2,2,2-D3, 1-Phenylethanol-2-13C, 1-Phenylethanol-D10, 1-Propan(ol-D), 1-Propanol-1,1,2,2,3,3,3-D7, 1-Propanol-1,1-D2, 1-Propanol-1-13C, 1-Propanol-13C3, 1-Propanol-2,2-D2, 1-Propanol-3,3,3-D3, 1-Propanol-D8, 1-Tetradecan-D29-ol, 2-(1-Naphthyl)pentane-1,2-13C2, 2-(2-Ethoxyethoxy)ethan(ol-D) 97, 2-(2-Iodoethyl-13C2)-2-methyl-13C-Dioxolane-2-13C, 2-(4-Aminophenyl)acetic acid-1-13C, 2-(Methyl-13C,D3-thio)adenine, 2-(Propyl-2,3-13C2)pentanoic-4,5-13C2 acid, 2,2'-Thiodiethanol 13C4,2,2,2-Trifluoroethan(ol-D), 2,2,2-Trifluoroethanol-1,1-D2, 2,2,2-Trifluoroethanol-D3, 2,2,3,3,3-Pentafluoropropan-D2-ol, 2,2,4-Trimethylpentane-D18, 2,2'-Dipyridyl-D8, 2,2-Dimethylpropanol-17O 20,2,3-Butanediol-13C4, 2,3-Dimethyl-1,3-butadiene-D10, 2,4,5-Trichlorophenol-3,6-D2, 2,4,6-Tribromoaniline-13C6, 2,4,6-Trichloroanisole-D5, 2,4,6-Trichlorophenol-3,5-D2, 2,4-Diamino-15N2-1,3,5-triazine, 2,4-Diamino-15N2-6-nitrotoluene, 2,4-Dichlorophenol-13C6, 2,4-Dichlorophenol-3,5,6-D3, 2,4-Dimethylphenol-3,5,6-D3, 2,4-Dinitrotoluene-3,5,6-D3, 2,5-Dimethoxytetrahydrofuran-2,3,3,4,4,5-D6, 2,5-Dimethyl-13C2-furan, 2,6-Di(tert-butyl-D9)-4-methyl(phenol-3,5,O-D3), 2,6-Di(tert-butyl-D9)-4-methyl(phenol-3,5-D2), 2,6-Dichlorobenzylidene-3,4,5-D3-aminoguanidine acetate, 2,6-Diethylaniline-15N, 2,6-Diethylaniline-D15, 2,6-Difluorobenzamide-α-13C,15N, 2,6-Dimethyl-D6-nitrobenzene, 2,6-Dimethylphenol-3,4,5-D3,OD, 2,6-Dinitrotoluene-α,α,α-D3, 2,6-Lutidine-Dimethyl-D6, 2'-Chlorodiphenyl-2,3,4,5,6-D5, 2'-Deoxyadenosine-13C10,15N5 5'-triphosphate sodium salt, 2'-Deoxyadenosine-13C10,15N5-monophosphate sodium salt, 2'-Deoxycytidine-13C9,15N3 5'-monophosphate sodium salt, 2'-Deoxycytidine-13C9,15N3 5'-triphosphate sodium salt, 2'-Deoxyguanosine-13C10,15N5 5'-monophosphate sodium salt, 2'-Deoxyguanosine-13C10,15N5 5'-triphosphate sodium salt, 21-DEOXYCORTISOL(D8), 2-Amino-15N-4,6-Dimethoxypyrimidine-15N2, 2-Amino-1-butanol-1,1-D2, 2-Amino-2-methyl-D3-butane-D8, 2-Aminonaphthalene-D7, 2-Bromo-2-chloro-1,1,1-trifluoroethane-D, 2-Bromo-2-methylpropane-D9, 2-Bromobenzyl amine-phenyl-13C6 hydrochloride, 2-Bromoethanol-1,1,2,2-D4, 2-Bromoethanol-13C2, 2-Bromoethanol-13C2, 1,1,2,2-D4, 2-Bromoethanol-2-13C, 2-Bromoiodobenzene-13C6, 2-Bromopropane-2-D1, 2-Bromopropane-D7, 2-Bromopropionic acid-1-13C, 2-Butanone-1,1,1,3,3-D5, 2-Butanone-4,4,4-D3, 2-Butene-1,1,1-D3, 2-Butoxyethan(ol-D), 2-Butoxyethanol-13C6, 2-Chloro-1-(difluoromethoxy)-1,1,2-trifluoroethane-D2, 2-Chloro-2-methylpropane-D9, 2-Chloro-4-ethylamino-15N-6-isopropylamino-1,3,5-triazine, 2-Chloro-4-ethyl-D5-amino-6-isopropylamino-1,3,5-triazine, 2-Chloro-4-fluorotoluene-α-13C, 2-Chloroethanol-1,1,2,2-D4, 2-Chlorophenol-3,4,5,6-D4, 2-Chloropropane-D7, 2-HYDROXYESTRADIOL(13,14,15,16,17,18-13C6), 2-HYDROXYESTRONE(13,14,15,16,17,18-13C6), 2-HYDROXYESTRONE-3-METHYL ETHER(13,14,15,16,17,18-13C6), 2-Iodoethanol-1,1,2,2-D4, 2-Iodopropane-1-13C, 2-Iodopropane-D7, 2-Keto-3-(methyl-13C)-butyric acid-4-13C sodium salt, 2-Keto-3-(methyl-13C,d2)-butyric acid-4-13C,d2 sodium salt, 2-Keto-3-(methyl-D3)-butyric acid-1,2,3,4-13C4 sodium salt, 2-Keto-3-(methyl-D3)-butyric acid-1,2,3,4-13C4, 3-D1 sodium salt, 2-Keto-3-(methyl-D3)-butyric acid-4-13C sodium salt, 2-Keto-3-methyl-13C-butyric-4-13C, 3-D acid sodium salt, 2-Keto-3-methylbutyric acid-13C5, 3-D1 sodium salt, 2-Keto-3-methylbutyric acid-3-D1 sodium salt hydrate, 2-Keto-4-(methyl-D3)-pentanoic acid sodium salt, 2-Keto-4-methylpentanoic acid-1-13C sodium salt, 2-Ketobutyric acid-13C4, 3,3-D2 sodium salt hydrate, 2-Ketobutyric acid-3,3-D2 sodium salt hydrate, 2-Ketobutyric acid-4-13C sodium salt hydrate, 2-Ketobutyric acid-4-13C,3,3,4,4,4-D5 sodium salt hydrate, 2-Ketobutyric acid-4-13C,3,3-D2 sodium salt hydrate, 2-Ketobutyric acid-4-13C,4-D2 sodium salt hydrate, 2-Ketobutyric acid-4-13C,4-D1 sodium salt hydrate, 2-Ketopentanedioic acid-D6, 2-Mercaptoethanol-1,1,2,2-D4, 2-Mercaptoethanol-1-13C, 2-Mercaptoethanol-13C2, 2-Mercaptoethanol-D6, 2-METHOXYESTRADIOL(13,14,15,16,17,18-13C6), 2-METHOXYESTRONE (13,14,15,16,17,18-13C6), 2-Methoxyethanol-13C3, 2-Methoxypropene-D8, 2-Methyl-1,3-butadiene-1-13C, 2-Methyl-1,3-butadiene-3-13C, 2-Methyl-13C-furan, 2-Methyl-2,4-pentane-D12-Diol, 2-Methyl-2-butene-2-13C, 2-Methyl-2-nitropropane-15N, 2-Methyl-2-nitropropane-D9, 2-Methylimidazole-D6, 2-Methylnaphthalene-D10, 2-Methylpentane-D14, 2-Methylpropane-2-D, 2-Methylpropene-D8, 2-Naphthalene-D7-sulfonic acid hydrate, 2-Naphthol-1,3,4,5,6,7,8-D7 97, 2-Nitrobenzenesulfenyl chloride-13C6, 2-Nitrophenol-3,4,5,6-D4, 2-Nitropropane-D7, 2-Pentanone-1,1,1,3,3-D5, 2-Pentene-2-13C, 2-Phenoxyethanol-1,1-D2, 2-Phenyl-13C6-phenol, 2-Picoline-D7 97, 2-Picolinic-D4 acid, 2-Propan(ol-D), 2-Propanol-1,1,1,3,3,3-D6, 2-Propanol-1,1,1-D3, 2-Propanol-1,3-13C2, 2-Propanol-13C3, 2-Propanol-17O 20, 2-Propanol-2-13C, 2-Propanol-D1,2-Propanol-D8, 2-Pyrrolidinone-5-carboxylic acid-D7, 3-(Trimethoxysilyl)propyl-N,N,N-trimethylammonium-15N chloride, 3-(Trimethylsilyl)-1-propanesulfonic acid-D6 sodium salt, 3-(Trimethylsilyl)propionic acid- D4 sodium salt, 3,3'-Diiodo-L-thyronine-(phenoxy-13C6) (T2), 3,3'-(1,3-Phenylenedioxy)dianiline-15N2, 3,3',5'-Triiodothyronine-Diiodophenyl-13C6 (reverse T3), 3,3',5-Triiodothyronine-tyrosine ring-13C6 (T3), 3,3'-Diiodo-L-thyronine (T2), 3,4,5-Trimethylphenol-2,6-D2,3,4-Dihydroxy-3-cyclobutene-1,2-Dione-D2,3,4-Dihydroxybenzo(nitrile-13C,15N), 3,5-Dimethylphenol-2,4,6-D3,3-ALPHA,5-BETA-TETRAHYDRODEOXYCORTICOSTERONE(17,21,21-D3), 3-Bromo-1-propan-D6-ol, 3-Bromo-1-propanol-13C3, 3-Chloro-1,2-propanediol-1,1,2,3,3-D5, 3-Chloro-L-alanine-15N, 3-Ethyl-3-pentan(ol-D), 3-Heptanone solution NMR reference standard, 1% in chloroform-D, 3-Hydroxy-4-(hydroxymethyl)-5-(hydroxymethyl-D2)-2-methylpyridine, 3-Hydroxybenzo(nitrile-13C,15N), 3-Hydroxypropionitrile-2,2,3,3-D4, 3-Iodothyronamine-(ethylamino-1,1,2,2-D4) hydrochloride, 3-Methoxy-13C,D3-benzyl-α-13C,α,α-D2 bromide, 3-Methylhexane-D16, 3-Nitroaniline-2,4,5,6-D4, 3-Nitroaniline-N,N-D2, 3-Nitro-L-tyrosine-13C9, 4-(Chlorophenyl)phenyl-D5 ether, 4-(Dimethyl-13C2-amino)antipyrine, 4-(Ethyl-1-13C)benzoic acid, 4-(Ethyl-2-13C)benzoic acid, 4-(Trifluoromethyl)benzoic acid-α-13C, 4,4,5,5,5-Pentafluoro-1-pentan-D6-ol, 4,4'-Bipyridyl-D8, 4,4'-Methylene-13C-Dianiline, 4'-Bromoacetophenone-ring-13C6, 4'-Chloroacetophenone-2',3',5',6'-D4, 4-Amino-15N2-chloro-6-isopropylamino-1,3,5-triazine, 4-Amino-5-chloro-2-(methoxy-13C, D3)-benzoic acid, 4-Aminobutyric acid-15N, 4-Aminobutyric acid-2,2,3,3,4,4-D6 97, 4-Aminobutyric acid-2,2-D2, 4-Aminophenol-D7, 4-Aminopiperidine-2,2,3,3,4,5,5,6,6-D9, 4-Aminopyridine-D6, 4-Amino-TEMPO-piperidinyl-D17, 4-ANDROSTENE-3,17-DIONE new!(2,2,4,6,6-D5), 4-ANDROSTENE-3,17-DIONE new! (2,2,4,6,6-D5), 4-ANDROSTENE-3,17-DIONE(2,2,4,6,6,16,16-D7), 4-Bromo-1-butene-13C4, 4-Bromobenz-2,3,5,6-D4-aldehyde, 4-Bromonitrobenzene-13C6, 4-Bromophenyl phenyl-D5 ether, 4-Chloro-3-methylphenol-2,6-D2, 4-Chloroaniline-15N, 4-Chlorobenzaldehyde-2,3,5,6-D4, 4-Chlorobenzaldehyde-α-13C, 4-Chlorobenzoic acid-α-13C, 4-Chlorobenzoyl chloride-α-13C, 4-Chlorostyrene-D7, 4-Fluorobenzoic acid-α-13C-2,3,5,6-D4, 4-Fluorobenzoyl-carbonyl-13C chloride, 4-Hydroxy-4-methyl-2-pentanone-D12, 4-Hydroxybenzaldehyde-1-13C, 4-Hydroxybenzaldehyde-2,3,5,6-D4, 4-Hydroxybenzaldehyde-2,3,5,6-D4,OD, 4-Hydroxybenzaldehyde-2-D1 97, 4-Hydroxybenzaldehyde-D6, 4-Hydroxybenzaldehyde-α-D1, 4-Hydroxybenzoic acid-13C7, 4-Hydroxybenzoic acid-ring-13C6, 4-Hydroxybenzoic acid-α-13C, 4-HYDROXYESTRONE(13,14,15,16,17,18-13C6), 4-Hydroxyfentanyl-phenyl-D5, 4-Hydroxy-TEMPO-D17 97, 4-Iodonitrobenzene-13C6, 4-Methoxy-13C,D3-benzoic acid, 4-Methoxybenz-2-D1-aldehyde, 4-Methoxybenz-3-D1-aldehyde 97, 4-Methoxybenzaldehyde-α-13C,α-D1, 4-Methoxybenzaldehyde-α-D1, 4-Methoxybenzoic acid-α-13C, 4-METHOXYESTRADIOL(13,14,15,16,17,18-13C6), 4-METHOXYESTRONE (13,14,15,16,17,18-13C6), 4-Methyl-2-pentanone-1,1,3,3-D5, 4-Methylanisole-2,3,5,6-D4, 4-Methylvaleric acid-1-13C, 4-Nitroaniline-15N2, 4-Nitrobenzaldehyde-2,3,5,6-D4, 4-Nitrophenol-1,2,6-13C3, 4-Nitrophenol-2,3,5,6-D4, 4-Nonylphenol-2,3,5,6-D4, 4-Oxo-2,2,6,6-tetramethylpiperidine-D17-1-15N, 4-Oxo-TEMPO-D16, free radical, 4-Oxo-TEMPO-D16, 1-15N, free radical, 4-Picoline-methyl-D3,4-PREGNEN-21-OL-3,20-DIONE(2,2,4,6,6,17,21,21-D8), 5A-ANDROSTAN-17A-METHYL-17B-OL-3-ONE(1,2,4,5A-D4), 5-ALPHA-DIHYDROTESTOSTERONE(1,2,4,5-D4), 5-ALPHA-PREGNAN-3-ALPHA-OL-20-ONE(17,21,21,21-D4), 5-ALPHA-PREGNAN-3-BETA-OL-20-ONE(17A,21,21,21-D4+), 5-ALPHA-PREGNANE-3,20-DIONE(1,2,4,5,6,7-D6), 5-ALPHA-PREGNANE-3-ALPHA,21-DIOL-20-ONE(17,21,21-D3), 5-Aminolevulinic acid-1-13C hydrochloride, 5-Aminolevulinic acid-3-13C hydrochloride, 5-Aminolevulinic acid-5-13C hydrochloride, 5-BETA-PREGNAN-3-ALPHA-OL-20-ONE(17,21,21,21-D4), 5-BETA-PREGNANE-3,20-DIONE(1,2,4,5,6,7-D6), 5-Bromopentanoic acid-2,2,5,5-D4, 5-Ethyl-5-(4-hydroxyphenyl)-3-methyl-D3 hydantoin, 5-Fluoro-DL-tryptophan-2,4,6,7-D4 97, 5-Fluorouracil-15N2, 5-Methyl-D3-uridine-6-D1,7-DEHYDROCHOLESTEROL(25,26,26,26,27,27,27-D7), Acenaphthene-D10, Acenaphthylene-D8, Acetaldehyde-1-13C, Acetaldehyde-13C2, Acetaldehyde-2,2,2-D3, Acetaldehyde-D4, Acetamide-15N, Acetanilide-(ring-13C6, carbonyl-13C), Acetanilide-15N, Acetic acid-1-13C, Acetic acid-1-13C,d4, Acetic acid-12C2, Acetic acid-13C2, Acetic acid-13C2,D4, Acetic acid-18O2, Acetic acid-2,2,2-D3, Acetic acid-2-13C, Acetic acid-2-13C,2,2,2-D3, Acetic acid-2-13C,D4, Acetic acid-D1, Acetic acid-D4, Acetic anhydride-1,1'-13C2, Acetic anhydride-1,1'-13C2,D6, Acetic anhydride-13C4, Acetic anhydride-13C4,D6, Acetic anhydride-2,2'-13C2, Acetic anhydride-2,2'-13C2,D6, Acetic anhydride-D6, Acetone-1,3-13C2, Acetone-13C3, Acetone-18O, Acetone-2-13C, Acetone-2-13C,D6, Acetone-D6, Acetonitrile-1-13C, Acetonitrile-1-13C,15N, Acetonitrile-13C2, Acetonitrile-13C2,15N, Acetonitrile-15N, Acetonitrile-2-13C, Acetonitrile-D3, Acetophenone-13C8, Acetophenone-2',3',4',5',6'-D5, Acetophenone-D8, Acetophenone-ring-13C6, Acetophenone-α,β-13C2, Acetophenone-α-13C, Acetophenone-β,β,β-D3, Acetophenone-β-13C, Acetyl-2-13C chloride, Acetyl bromide-13C2, Acetyl chloride-1-13C, Acetyl chloride-1-13C,D3, Acetyl chloride-13C2, Acetyl chloride-D3, Acetyl-1,2-13C2 coenzyme A lithium salt, Acetyl-1-13C bromide, Acetyl-1-13C-L-carnitine hydrochloride, Acetyl-13C2-L-carnitine HCl, Acetylacetone-D8, Acetyl-D3-L-carnitine hydrochloride, Acetylene-13C2, Acetylsalicylic acid-α-13C, Acetylsalicyloyl chloride-α-13C, Acrolein-13C3, Acrolein-2-13C, Acrylamide-1-13C, Acrylamide-13C3, Acrylamide-2,3,3-D3, Acrylic acid-1-13C, Acrylic acid-13C3, Acrylic acid-D4, Acrylonitrile-1-13C, Acrylonitrile-13C3, Acrylonitrile-15N, Acrylonitrile-2-13C, Acrylonitrile-2-D, Acrylonitrile-3-13C, Acrylonitrile-D3, Adamantane-D16, Adenine-1,3-15N2, Adenosine-13C10 5'-triphosphate sodium salt, Adenosine-13C10, 15N5 5'-monophosphate sodium salt, Adenosine-13C10,15N5 5'-triphosphate sodium salt, Adenosine-15N5 5'-triphosphate sodium salt, Adipic acid-1,6-13C2, Adipic acid-2,2,5,5-D4, Adipic acid-D10, Adipic-D8 acid dihydrazide, Adiponitrile-D8, Adipoyl-D8 chloride, Allyl alcoh(ol-D), Allyl alcohol-1-13C, Allyl alcohol-2-13C, Allyl alcohol-D6, Allyl chloride-1-13C, Allyl-D5 alcohol, Aluminum oxide, activated, deuterated, Aluminum oxide-18O3, Ammonia-14N, Ammonia-15N, Ammonia-15N,D3, Ammonia-D3, AMMONIUM ACETATE(15N), Ammonium acetate-D3, Ammonium acetate-D7, Ammonium bromide-79Br, Ammonium bromide-81Br, AMMONIUM CHLORIDE(15N), AMMONIUM HYDROXIDE (15N), AMMONIUM NITRATE(15N2), AMMONIUM NITRATE(AMMONIUM-15N), AMMONIUM NITRATE (NITRATE-15N), Ammonium nitrate-15N, AMMONIUM SULFATE(15N2), AMMONIUM SULFATE(15N2; D8), Ammonium-14N chloride, Ammonium-14N2 sulfate, Ammonium-14N2 sulfate solution, Ammonium-14N2, sulfate-16O4, Ammonium-15N acetate, Ammonium-15N acetate-13C2, Ammonium-15N bromide, Ammonium-15N calcium nitrate-15N3, Ammonium-15N chloride, Ammonium-15N chloride, Ammonium-15N dihydrogen phosphate, Ammonium-15N hydroxide solution, Ammonium- 15N nitrate, Ammonium-15N,D4 deuteroxide solution, Ammonium-15N2 carbonate-13C, Ammonium-15N2 sulfate, Ammonium-15N2 sulfate 10, Ammonium-15N2,D8 sulfate, Ammonium-D4 acetate, Ammonium-D4 bromide, Ammonium-D4 chloride, Ammonium-D4 deuteroxide solution in D2O, Ammonium-D4 dideuteriumphosphate, Ammonium-D4 nitrate, Ammonium-D4 thiocyanate, Ammonium-D8 sulfate, Ampicillin-15N, ANDROSTERONE(16,16-D2), Aniline-1-13C, Aniline-13C6, Aniline-13C6 hydrochloride, Aniline-15N, Aniline-2,3,4,5,6-D5, Aniline-4-13C, Aniline-D7, Anisole-1-13C, Anisole-2,3,4,5,6-D5, Anisole-2,4,6-D3, Anisole-D8, Anisole-methyl-D3, Anisole-ring-13C6, Anthracene-D10, Anthraquinone-D8, Argon-36Ar, Argon-36Ar 50, Argon-38Ar 95, Argon-40Ar 99.95, Barium carbonate-13C, Behenic-D43 acid, Benz[a]anthracene-D12, Benz-13C6-aldehyde, Benz-13C6-oxazole, Benzaldehyde-2,3,4,5,6-D5, Benzaldehyde-D6, Benzaldehyde-α-13C, Benzaldehyde-α-13C,d6, Benzaldehyde-α-13C,α-D1, Benzaldehyde-α-D1, Benzamide-15N, Benzamide-α-13C, Benzene-1,2,3,5-D4, Benzene-1,2-13C2, Benzene-1,3,5-D3, Benzene-12C6, Benzene-13C1, Benzene-13C6, Benzene-13C6,D6, Benzene-D1, Benzene-D5, Benzene-D6, Benzenesulfonamide-13C6, Benzidine-rings-D8, Benzo[a]pyrene-7,8-D2, Benzo[a]pyrene-7-D, Benzo[a]pyrene-8-D, Benzo[a]pyrene-D12, Benzo[b]fluoranthene-D12, Benzo[e]pyrene-D12, Benzoic acid-12C7 99.9 12C, Benzoic acid-13C7, Benzoic acid-2,3,4,5,6-D5, Benzoic acid-4-13C, Benzoic acid-D, Benzoic acid-ring-13C6, Benzoic acid-α-13C, Benzoic-1-13C acid, Benzoin-rings-D10, Benzonitrile-D5, Benzophenone-2,3,4,5,6-D5, Benzophenone-carbonyl-13C, Benzophenone-D10, Benzophenone-α-13C-3,3',4,4'-tetracarboxylic dianhydride, Benzoyl chloride-D5, Benzoyl chloride-ring-13C6, Benzoyl chloride-α-13C, Benzyl (phenylthiomethyl-13C) ether, Benzyl alcohol-ring-13C6, Benzyl alcohol-α,α-D2, Benzyl alcohol-α-13C, Benzyl alcohol-α-13C-α,α-D2, Benzyl bromide-D7, Benzyl bromide-ring-13C6, Benzyl bromide-α,α-D2, Benzyl bromide-α-13C, Benzyl butyl phthalate-3,4,5,6-D4, Benzyl chloride-D7, Benzyl chloride-ring-13C6, Benzyl chloride-α-13C, Benzyl cyanide-13C2, Benzyl cyanide-2,2-D2, Benzyl cyanide-cyano-13C, Benzyl cyanide-D7, Benzyl cyanide-α-13C, Benzyl isocyanate-15N, Benzyl-1-13C bromide, Benzyl-2,3,4,5,6-D5 alcohol, Benzyl-2,3,4,5,6-D5 chloride, Benzyl-2,3,4,5,6-D5 cyanide, Benzylamine-15N, Benzyl-D7 alcohol, Benzyl-α,α-D2 chloride, Betaine-trimethyl-D9 hydrochloride, Bis(2-chloroethyl)-13C4-amine hydrochloride, Bis(2-ethylhexyl)phthalate-3,4,5,6-D4, Bis(4-aminophenyl)ether-15N2, Bis(4-aminophenyl)ether-D12 97, Bis(cyclopentadienyl)zirconium chloride deuteride, Bis(hexamethylene)triamine-8-15N, Bisphenol A (rings-13C12), Bisphenol A-(methyl-D6), Bisphenol A-(rings-D8), Bisphenol A-D16, Bis-tris-D19, Biuret-13C2, Biuret-15N3, Boc-Ala-OH-1-13C, Boc-Ala-OH-12C3 99.9 12C, Boc-Ala-OH-13C3, Boc-Ala-OH-13C3,15N, Boc-Ala-OH-15N, Boc-Ala-OH-2-13C, Boc-Ala-OH-2-13C,15N, Boc-Ala-OH-3,3,3-D3, Boc-Asn-OH-α-amine-15N, Boc-Asp-OH-15N, Boc-Asp-OH-3-13C, Boc-Asp-OH-4-13C, Boc-D-Ala-OH-3-13C, Boc-Gln-OH-15N2, Boc-Glu-OBzl-13C5,15N, Boc-Glu-OH-1-13C, Boc-Glu-OH-15N, Boc-Gly-OH-1-13C, Boc-Gly-OH-1-13C,15N, Boc-Gly-OH-13C2, Boc-Gly-OH-13C2,15N, Boc-Gly-OH-15N, Boc-Gly-OH-2,2-D2, Boc-Gly-OH-2-13C, Boc-Gly-OH-2-13C,15N, Boc-Leu-OH-1-13C monohydrate, Boc-Leu-OH-2-13C,15N monohydrate, Boc-Leu-OH-5,5,5-D3 monohydrate, Boc-Lys(Z)—OH-α-15N, Boc-Lys(Z)—OH-ϵ-15N, Boc-Met-OH-13C, Boc-Met-OH-methyl-13C, Boc-ON-(tert-butyl-D9), Boc-Phe-OH-1-13C, Boc-Phe-OH-15N, Boc-Phe-OH-2-13C, Boc-Phe-OH-3-13C, Boc-Phe-OH-phenyl-D5, Boc-Phe-OH-phenyl-D5-2,3,3-D3, Boc-Tyr-OH-15N, Boc-Val-OH-1-13C, Boc-Val-OH-D8, Borane-D3-THF complex solution, Boric acid-10B, Boric acid-11B, Boric acid-D3, Boric oxide-18O3, Boron oxide-10B, Boron-10B trifluoride diethyl etherate, Boron-11B oxide, Bromoacetic acid-1-13C, Bromoacetic acid-1-13C,18O2, Bromoacetic acid-13C2, Bromoacetic acid-13C2,D3, Bromoacetic acid-18O2 95, Bromoacetic acid-2-13C, Bromoacetic acid-D3, Bromobenzene-1-13C, Bromobenzene-13C6, Bromobenzene-4-13C, Bromobenzene-D5, Bromochloroacetic acid-1-13C, Bromochloromethane-D2, Bromocyclohexane-D11, Bromocyclopentane-D9, Bromodichloroacetic acid-1-13C, Bromoethane-1,1,2,2-D4, Bromoethane-1,1-D2, Bromoethane-1-13C, Bromoethane-13C2, Bromoethane-2,2,2-D3, Bromoethane-2-13C, Bromoethane-2-D1, Bromoethane-D5, Bromoform-13C, Bromoform-13C, Bromoform-D, Bromomethane-13C, Bromomethane-D1, Bromomethane-D2, Bromomethane-D3, Bromotrichloromethane-13C, Bupivacaine-butyl-1-13C, Butadiene sulfone-2,2,5,5-D4, Butane-1,1,1,4,4,4-D6, Butane-1,1,1-D3, Butane-1,4-13C2, Butane-1-13C, Butane-13C4, Butane-D10, Butyl acrylate-1-13C, Butyl acrylate-2-13C, Butyl phenyl-13C6 ether, Butyric acid-1,2-13C2, Butyric acid-1-13C, Butyric acid-2-13C, Butyric acid-4,4,4-D3, Butyric acid-D8, Butyric-D7 acid, Caffeine-(3-methyl-13C), Caffeine-trimethyl-13C3, Calcium carbonate-13C, CALCIUM NITRATE(15N2), Calcium nitrate-15N2, Calcium nitrate-15N2 10, Calcium nitrate-15N2 tetrahydrate, Carbamazepine-carboxamide-13C,15N, Carbon dioxide-17O2, Carbon dioxide-18O2, Carbon monoxide-17O, Carbon monoxide-18O, Carbon-13C, Carbon-13C dioxide, Carbon-13C dioxide-17O2, Carbon-13C dioxide-18O2, Carbon-13C disulfide, Carbon-13C monoxide, Carbon-13C monoxide-18O Gas, Carbon-13C tetrabromide, Carbonyl-13C sulfide, Carbonyl-13C,18O sulfide, Carbonyl-18O sulfide, Cetyl(pyridinium-D5) chloride monohydrate, CHENODEOXYCHOLIC ACID(11,12-D2), Chenodeoxycholic acid-2,2,4,4-D4, Chenodeoxycholic-2,2,3,4,4-D5 acid, Chloroacetic acid-1-13C, Chloroacetic acid-13C2, Chloroacetic acid-2-13C, Chloroacetic acid-D3, Chloroacetyl chloride-1-13C, Chloroacetyl chloride-13C2, Chloroacetyl chloride-2-13C, Chlorobenzene-1-13C, Chlorobenzene-13C6, Chlorobenzene-4-13C, Chlorobenzene-D5, Chlorocyclohexane-D11, Chlorodibromoacetic acid-1-13C, Chloroethane-1,1-D2, Chloroethane-1-13C, Chloroethane-13C2, Chloroethane-2,2,2-D3, Chloroethane-2-13C, Chloroethane-D5, Chloroform-13C, Chloroform-13C,D, Chloroform-D, Chloromethane-13C, Chloromethane-D3, Chlorpyrifos-Diethyl-D10, Chlorzoxazone-2-13C-3-15N-hydroxyl-18O, CHOLESTANE(3,3-D2), Cholestenone(D5), CHOLESTEROL(25,26,26,26,27,27,27-D7), CHOLESTEROL(3-D1), CHOLESTEROL(4-13C), Cholesterol-2,2,3,4,4,6-D6, Cholesterol-25,26,27-13C3, Cholesterol-3,4-13C2, CHOLESTEROL-3-OCTANOATE(OCTANOATE-1-13C), Cholesterol-4-13C, Cholesteryl octanoate-1-13C, CHOLIC ACID(2,2,4,4-D4), CHOLIC ACID(24-13C), CHOLIC ACID(CARBOXYL-13C), Cholic acid-2,2,4,4-D4, Cholic-2,2,3,4,4-D5 acid, Cholic-24-13C acid, Choline bromide-methyl-13C1, Choline bromide-trimethyl-D9, Choline chloride-1,1,2,2-D4, Choline chloride-1-13C, Choline chloride-15N, Choline chloride-trimethyl-D9, Choline-1,1,2,2-D4 bromide, Choline-D13 bromide-(N,N,N-trimethyl-D9, 1,1,2,2-D4), Chrysene-D12, cis-Decahydronaphthalene-D18, cis-Styrene-(β)-D 96, cis-Urocanic acid-1,2,3-13C3, cis-Vaccenic acid-1-13C, Citrazinic acid-13C6, Citric acid-1,5-13C2, Citric acid-13C6, Citric acid-2,2,4,4-D4, Citric acid-2, 4-13C2, Clemastine-phenyl-D5 hydrochloride, Copper(I) cyanide-13C, Copper(I) cyanide-13C,15N, Copper(I) cyanide-15N, CORTICOSTERONE(2,2,4,6,6,17A,21,2'-D8), CORTISOL(1,2-D2), CORTISOL(9,11,12,12-D4), CORTISOL(9,12,12-D3), Creatine-(guanidino-13C) monohydrate, Creatine-(methyl-13C) monohydrate, Creatine-(methyl-D3) monohydrate, Creatinine-(methyl-13C), Creatinine-(methyl-D3), Cyanamide-13C solution, Cyanamide-13C,15N2 solution, Cyanamide-15N2 solution, Cyanogen bromide-13C, Cyanogen bromide-13C,15N, Cyanogen-15N bromide, Cyanuric chloride-13C3, Cyclohexan(ol-D), Cyclohexan-D11-ol, Cyclohexane-D11, Cyclohexane-D12, Cyclohexanol-1-13C, Cyclohexanol-D12, Cyclohexanone-1-13C, Cyclohexanone-2,2,6,6-D4, Cyclohexanone-D10, Cyclohexene-D10, Cyclohexyl-13C6-amine, Cyclooctane-D16, Cyclopentane-13C1, Cyclopentane-D10, Cyclopentane-D9, Cyclopentanol-1-13C, Cyclopentanone-1-13C, Cyclopentanone-2,2,5,5-D4, Cyclopropylmethan-D2-ol, Cytidine-13C$_9$ 5'-triphosphate sodium salt, Cytidine-13C9, 15N3 5'-monophosphate sodium salt, Cytidine-13C9,15N3 5'-triphosphate sodium salt, Cytidine-15N3 5'-triphosphate sodium salt, Cytosine-1,3-15N2, Cytosine-2, 4-13C2,15N3, D-Alanine-1-13C, D-Alanine-13C3, D-Alanine-15N, D-Alanine-2-13C, D-Alanine-3,3,3-D3, D-Alanine-3-13C, Decahydronaphthalene-D18, Decane-D22, Decanoic acid-1, 2-13C2, Decanoic acid-10-13C, Decanoic acid-1-13C, Decanoic-10,10,10-D3 acid, Decanoic-D19 acid, DEHYDROEPIANDROSTERONE (DHEA)(2,2,3,4,4,6-D6), Dehydroepiandrosterone-2,2,3,4,4,6-D6 85, DEOXYCHOLIC ACID(24-13C), DEOXYCHOLIC ACID(24-13C), DEOXYCHOLIC ACID(24-13C), DEOXYCHOLIC ACID(24-13C), Deoxycholic acid-2,2,4,4-D4, Desethyloxybutynin chloride-ethyl-D5, Desmethylraclopride, Deuterium, Deuterium bromide, Deuterium chloride, Deuterium hydride, Deuterium iodide, Deuterium oxide, Deuterium oxide-18O, Deuterium sulfide, D-Fructose-1,6-13C2, D-Fructose-1-13C, D-Fructose-13C6, D-Fructose-2-13C, D-Fructose-6,6-D2, D-Fructose-6-13C, D-Galactose-1-13C, D-Galactose-13C6, D-Galactose-1-D, D-Glucosamine-1-13C hydrochloride, D-Glucosamine-1-13C,15N hydrochloride, D-Glucosamine-15N hydrochloride, D-Glucose-1,2,3, 4,5,6,6-D7 97, D-Glucose-1,2,3-13C3, D-Glucose-1,2-13C2, D-Glucose-1,6-13C2, D-Glucose-1-13C, D-Glucose-12C6 99.9, D-Glucose-13C6, D-Glucose-13C6, D-Glucose-13C6, 1,2,3,4,5,6,6-D7, D-Glucose-1-D, D-Glucose-2,5-13C2, D-Glucose-2-13C, D-Glucose-2-D1, D-Glucose-3-13C, D-Glucose-3-D1, D-Glucose-4,5-13C2, D-Glucose-5-13C, D-Glucose-6,6-D2, D-Glucose-6-13C, D-Glucose-D12 97, D-Glutamic acid-5-13C, Di(ethylene glycol-D2), Di(propyl-3,3,3-D3)amine, Diammonium-15N2 hydrogen phosphate, Diazinon-Diethyl-D10, Dibenzothiophene-D8, Dibromoacetic acid-1-13C, Dibromomethane-D2, Dibutyl phthalate-3,4,5,6-D4, Dichloroacetic acid-1-13C, Dichloroacetic acid-D2, Dichloroacetyl chloride-13C2, Dichloroacetyl chloride-2-13C, Dichlorofluoromethane-D, Dichloromethane-12C,D2, Dichloromethane-13C, Dichloromethane-D2, Dicyanodiamide-13C2, Dicyanodiamide-15N4, Diethyl (phenylsulfinylmethyl-13C)phosphonate, Diethyl (phenylthiomethyl-13C)phosphonate, Diethyl 2-phthalimidomalonate-2-13C, Diethyl acetamidomalonate-1,2,3-13C3, Diethyl acetamidomalonate-15N, Diethyl acetamidomalonate-2-13C, 15N, Diethyl carbonate-13C5, Diethyl glutarate-13C5, Diethyl malonate-1,2,3-13C3, Diethyl malonate-1,3-13C2, Diethyl malonate-2-13C, Diethyl malonate-D2, Diethyl oxalate-13C2, Diethyl phthalate-3,4,5,6-D4, Diethyl succinate-2,2,3,3-D4, Diethyl-1,1,1',1'-D4-stilbestrol-3,3',5,5'-D4, Diethylamine-15N hydrochloride, Diethylamine-D11, Diethylamine-N-D1, Diethyl-D10-amine, Diethyl-D10-amine hydrochloride, DIETHYLSTILBESTROL (CIS/TRANS MIX)(RING-3,3',5,5'-DIETHYL-1,1,1',1'-D8), DIHYDROTESTOSTERONE(16,16,17-D3), Diiodomethane-13C, Diiodomethane-13C,d2, Diiodomethane-D2, Diisobutyl phthalate-3,4,5,6-D4, Diisopropyl-13C6 ether, Diisopropylamine-15N, Dimethenamid-D3, Dimethyl[2-oxo-2-(cyclohexyl-D11)ethyl]phosphonate, Dimethyl acetylenedicarboxylate-13C4, Dimethyl carbonate-13C3, Dimethyl ether-D6, Dimethyl phthalate-3,4,5,6-D4, Dimethyl succinate-2,2,3,3-D4, Dimethyl sulfate-13C2, Dimethyl sulfate-13C2,d6, Dimethyl sulfate-D6, Dimethyl sulfide-D6, Dimethyl sulfone-D6, Dimethyl sulfoxide-12C2, Dimethyl sulfoxide-13C2, Dimethyl sulfoxide-D6, Dimethyl terephthalate-2,3,5,6-D4, Dimethyl terephthalate-α,α'-13C2, Dimethyl-1,1,1-D3-amine hydrochloride, Dimethyl-13C2 sulfide, Dimethylamine-13C2 hydrochloride, Dimethylamine-13C2,15N hydrochloride, Dimethylamine-15N, Dimethylamine-15N hydrochloride, Dimethylamine-D7, Dimethylamine-D7 deuteriochloride, Dimethyl-D6 disulfide, Dimethyl-D6 phthalate, Dimethyl-D6-amine, Dimethyl-D6-amine hydrochloride, Dimethyl-D6-cyanamide, Di-n-nonyl phthalate-3,4,5,6-D4, Dioctyl phthalate-3,4,5,6-D4, Dipentyl phthalate-3,4,5,6-D4, Diphenyl carbonate-13C, Diphenyl sulfide-D10, Diphenyl sulfoxide-D10, Diphenyl(silane-D2) 97, Diphenyl-13C12, Diphenyl-D10, Dipotassium deuterium phosphate, DL-3-Benzyloxy-1,2-propane-1,1,2,3,3-D5-diol, DL-3-Hydroxytetradecanoic acid-2,2,3,4,4-D5, D-Lactose-1-13C, DL-Alanine-1-13C, DL-Alanine-1-13C,2-D, DL-Alanine-13C3, DL-Alanine-15N, DL-Alanine-2,3,3,3-D4, DL-Alanine-2,3-13C2, DL-Alanine-2-13C, DL-Alanine-2-13C,2-D, DL-Alanine-2-13C,3,3,3-D3, DL-Alanine-2-D, DL-Alanine-3,3,3-D3, DL-Alanine-3-13C, DL-Alanine-3-13C,2-D, DL-Allantoin-5-13C,1-15N, DL-Aspartic acid-1,4-13C2, DL-Aspartic acid-1-13C, DL-Aspartic acid-2,3,3-D3, DL-Aspartic acid-2-13C, DL-Aspartic acid-2-13C,15N, DL-Aspartic acid-3-13C, DL-Aspartic acid-4-13C, DL-Dithiothreitol-D10, DL-ESTRADIOL(13,14,15,16,17,18-13C6), D-Leucine-1-13C, D-Leucine-15N, D-Leucine-2-D1, DL-Glutamic acid-1-13C, DL-Glutamic acid-13C5, DL-Glutamic acid-2,3,3,4,4-D5, DL-Glutamic acid-2-13C, DL-Glutamic acid-3,3-D2, DL-Glutamic acid-3-13C, DL-Glutamic acid-5-13C, DL-Glyceraldehyde-1-13C, DL-Glyceric-2,2,2-D3 acid calcium salt dihydrate, DL-Histidine-1-13C, DL-Histidine-ring-15N2, DL-Histidine-α-15N, DL-Homocystine-1,1'-13C2, DL-Homocystine-3,3,3',3',4,4,4',4'-D8, DL-Isoleucine-2-13C/DL-Alloisoleucine-2-13C (approx. 1:1), DL-Isopropylideneglycerol-1,1,2,3,3-D5, DL-Leucine-1,2-13C2, DL-Leucine-1-13C, DL-Leucine-15N, DL-Leucine-2,3,3-D3, DL-Leucine-2-13C, DL-Leucine-D10, DL-Leucine-isopropyl-D7, DL-Lysine-1,2-13C2 dihydrochloride, DL-Lysine-1-13C dihydrochloride, DL-Lysine-2-13C dihydrochloride, DL-Lysine-2-15N dihydrochloride, DL-Lysine-3,3,4,4,5,5,6,6-D8 dihydrochloride, DL-Lysine-4,4,5,5-D4 dihydrochloride, DL-Lysine-6-13C dihydrochloride, DL-Lysine-6-13C-ε-15N dihydrochloride, DL-Lysine-ε-15N dihydrochloride, DL-Malic acid-2,3,3-D3, DL-Malic acid-2-13C, DL-Methionine-1-13C, DL-Methionine-15N, DL-Methionine-2-D1, DL-Nicotine-methyl-D3, DL-Phenyl alanine-2-13C, DL-Phenyl-13C6-alanine, DL-Phenylalanine-1-13C, DL-Phenylalanine-15N, DL-Phenylalanine-3,3-D2, DL-Phenyl-D5-alanine, DL-Phenyl-D5-alanine-2,3,3-D3, DL-Pipecolinic acid-carboxy-13C, DL-Proline-1-13C, DL-Proline-2-D1, DL-Proline-4-13C, DL-Selenomethionine-methyl-13C1, DL-Serine-1-13C, DL-Serine-15N, DL-Serine-3-13C, DL-Tryptophan-2-13C, DL-Tyrosine-1-13C, DL-Tyrosine-15N, DL-Tyrosine-2-13C, DL-Tyrosine-3-13C, DL-Valine-1-13C, DL-Valine-15N, DL-Valine-2-13C, DL-Valine-2-D1, DL-Valine-D8, D-Mannitol-1-13C, D-Mannitol-1-13C,1,1-D2, D-Mannitol-13C6, D-Mannitol-2-13C, D-Mannose-1-13C, D-Mannose-13C6, D-Mannose-2-13C, D-Mannose-6-13C, D-Methionine-D3 (methyl-D3), D-Methionine-methyl-13C, Dodecane-13C12, Dodecane-D26, Dodecanedioic acid-1, 12-13C2, Dodecyl(benzene-13C6), Dodecylamine-15N, Dodecylphosphorylcholine-D38, Dopamine-1,1,2,2-D4 hydrochloride, Dotriacontane-D66, Doxylamine-D5, D-Phenylalanine-13C9,15N, D-Phenylglycine-15N, D-Proline-1-13C, D-Ribose-1,2-13C2, D-Ribose-1-13C, D-Ribose-2,3,4,5-13C4, D-Ribose-2-13C, D-Sorbitol-1,1,6,6-D4, D-Sorbitol-1-13C, D-Sorbitol-13C6, D-Sorbitol-2-13C, D-Valine-D8, D-Xylose-1-13C, Eicosane-D42, Epichlorohydrin-2-13C, Epichlorohydrin-2-D1 97, Epichlorohydrin-D5, EPICHOLESTEROL(3,4-13C2), Equilin-2,4,16,16-D4, Equilin-2,4,16,16-D4 3-sulfate sodium salt 97, Erythromycin-N,N-Dimethyl-13C2, Erythromycin-N-methyl-13C1 lactobionate salt, ESTRADIOL(2,4,16,16-D4), ESTRADIOL(3, 4-13C2), ESTRIOL (2,4-D2), ESTRONE 3-METHYL ETHER(13,14,15,16,17,18-13C6), ESTRONE(2,4,16,16,-D4), ESTRONE(3, 4-13C2), Estrone-2,3,4-13C3, Estrone-2,4,16,16-D4 3-sulfate sodium salt, Estrone-2,4,16,16-D4 95, Ethan(ol-D), Ethane-1,1,2,2-D4, Ethane-13C1, Ethane-13C2, Ethane-D1, Ethane-D5, Ethane-D5-thiol, Ethane-D6 gas, Ethanol-1,1,2,2,2-D5, Ethanol-1,1,2,2-D4-amine, Ethanol-1,1-D2, Ethanol-1-13C, Ethanol-13C2, Ethanol-18O 95 18O, Ethanol-2,2,2-D3, Ethanol-2-13C, Ethanolamine-13C2, Ethanolamine-13C2 hydrochloride, Ethanolamine-15N, Ethanolamine-2-13C, Ethanol-D6, Ether-D10, ETHISTERONE(ACETYLENE-13C2), Ethyl (phenylthiomethyl-13C) ether, Ethyl 3-(trimethylsilyl)propionate-2,2,3,3-D4, Ethyl 3-ketopentanoate-3,4,5-13C, Ethyl acetate-1, 2-13C2, Ethyl acetate-1-13C, Ethyl acetate-2-13C, Ethyl acetate-D8, Ethyl acetoacetate-1,2,3,4-13C4, Ethyl acetoacetate-1,3-13C2, Ethyl acetoacetate-2, 4-13C2, Ethyl acetoacetate-3,4-13C2, Ethyl acetoacetate-3-13C, Ethyl acetoacetate-4-13C, Ethyl bromoacetate-1-13C, Ethyl bromoacetate-13C2, Ethyl bromoacetate-2-13C, Ethyl cyano-13C, 15N-acetate-1,2-13C2, Ethyl formate-13C, Ethyl formate-D, Ethyl N,N-Dimethyloxamate-1,2-13C2, Ethyl N,N-Dimethyloxamate-2-13C, Ethyl nicotinate-13C6, Ethyl phenylacetate-1-13C, Ethyl propionate-1-13C, Ethyl pyruvate-2-13C, Ethyl(benzene-D5), Ethyl(benzene-D5) 97, Ethyl(phenylsulfinylmethyl-13C) ether, Ethyl(phenylsulfonylmethyl-13C) ether, Ethyl-1,1-D2 benzene-D5, Ethyl-1,1-D2-benzene, Ethyl-1-13C-benzene, Ethyl-13C2 chlorooxoacetate, Ethyl-13C2-benzene, Ethyl-2-13C-benzene, Ethylamine-15N, Ethylamine-15N hydrochloride, Ethylamine-N,N-D2, Ethylbenzene-D10, Ethyl-D5-amine, Ethyl-D5-amine hydrochloride, Ethyl-D5-benzene, Ethylene carbonate-13C, Ethylene carbonate-13C3, Ethylene carbonate-D4, Ethylene glycol-(OD)$_2$, Ethylene glycol-13C2, Ethylene glycol-D6, Ethylene oxide-13C2, Ethylene-13C1, Ethylene-13C2, Ethylene-D1, Ethylene-D3, Ethylene-D4, Ethylene-D4 glycol, Ethylene-D4 oxide, Ethylene-D4-Diamine, Ethylene-D4-Diamine dihydrochloride, Ethylenediamine-13C2 dihydrochloride, Ethylenediamine-15N2 dihydrochloride, Ethylenediaminetetraacetic acid-D4, Ethylenediaminetetraacetic-D12 acid, ETHYNYLESTRADIOL(20,21-13C2), Fluoranthene-D10, Fluorene-D10, Fluorobenzene-D5, Fluoromethane-13C, Fluoromethane-D3, Fmoc-3-Fluoroalanine-2-D1, Fmoc-Ala-OH-1-13C, Fmoc-Ala-OH-13C3, Fmoc-Ala-OH-15N, Fmoc-Ala-OH-2,3,3,3-D4, Fmoc-Ala-OH-2-13C, Fmoc-Ala-OH-3,3,3-D3, Fmoc-Ala-OH-3-13C, Fmoc-Arg(Pbf)-OH-13C6,15N4, Fmoc-Asn-OH-15N2, Fmoc-Asn-OH-amine-15N, Fmoc-Asp(OtBu)-OH-15N, Fmoc-Asp-OH-1-13C, Fmoc-Asp-OH-4-13C, Fmoc-Gln-(Trt)-OH-15N2, Fmoc-Glu(OtBu)-OH-15N, Fmoc-Gly-OH-1-13C, Fmoc-Gly-OH-13C2, Fmoc-Gly-OH-13C2,15N, Fmoc-Gly-OH-15N, Fmoc-Gly-OH-2,2-D2, Fmoc-Gly-OH-2-13C, Fmoc-Gly-OH-2-13C,15N, Fmoc-His(Trt)-OH-13C6, 15N3, Fmoc-Ile-OH-13C6,15N, Fmoc-Ile-OH-15N, Fmoc-Leu-OH-1-13C, Fmoc-Leu-OH-13C6,15N, Fmoc-Leu-OH-15N, Fmoc-Leu-OH-5,5,5-D3, Fmoc-Leu-OH-D10, Fmoc-Lys(Boc)-OH-13C6,15N2, Fmoc-Met-OH-1-13C, Fmoc-Met-OH-13C5,15N, Fmoc-Met-OH-15N, Fmoc-Phe-OH-13C9,15N, Fmoc-Phe-OH-15N, Fmoc-Phe-OH-phenyl-D5-2,3,3-D3, Fmoc-Pro-OH-13C5,15N, Fmoc-Pro-OH-15N, Fmoc-Ser(tBu)-OH-13C3,15N, Fmoc-Ser(tBu)-OH-15N, Fmoc-Thr(tBu)-OH-15N, Fmoc-Trp-OH-15N2, Fmoc-Trp-OH-α-15N, Fmoc-Tyr (t-Bu)-OH-13C9, 15N, Fmoc-Tyr(tBu)-OH-15N, Fmoc-Tyr-OH-15N, Fmoc-Val-OH-1-13C, Fmoc-Val-OH-13C5,15N, Fmoc-Val-OH-15N, Fmoc-Val-OH-D8, Formaldehyde-12C, Formaldehyde-13C, Formaldehyde-13C,D2, Formaldehyde-D2, Formamide-13C,15N, Formamide-15N, Formamide-15N,D2, Formamide-18O, Formamide-1-D, Formamide-D3, Formic acid-13C, Formic acid-D, Formic acid-D2, Formic-D acid, Fosphenyloin-2,4,5-13C3,15N2 disodium salt heptahydrate, Fumaric acid-13C4, Fumaric acid-13C4,d4, Fumaric acid-2,3-13C2, Fumaric acid-2,3-D2, Fumaric acid-D4, Furan-D4, Glycer(ol-D3), Glycerol formal-D2, Glycerol-1,1,2,3,3-D5, Glycerol-1,3-13C2, Glycerol-13C3, Glycerol-13C3,D8, Glycerol-2-13C, Glycerol-D8, Glyceryl 1,2-Distearate-3-octanoate-1-13C, Glyceryl 1,3-Dioctadecanoate-2-octanoate-1-13C, Glyceryl tri(octanoate-1-13C), Glyceryl tri(octanoate-D15), Glyceryl tri(oleate-1,2,3,7,8,9,10-13C7), Glyceryl tri(oleate-1-13C), Glyceryl tri(oleate-9,10-13C2), Glyceryl tri(palmitate-1,2-13C2), Glyceryl tri(palmitate-1-13C), Glyceryl tri(palmitate-16,16,16-D3), Glyceryl tri(palmitate-D31), Glyceryl tri (stearate-1-13C), Glyceryl tri(stearate-18,18,18-D3), Glyceryl-13C3 trioleate, Glyceryl-2-13C tripalmitate, Glycine-1-13C, Glycine-1-13C,15N, Glycine-1-13C,2,2-D2, Glycine-12C2,14N, Glycine-13C2, Glycine-13C2,15N, Glycine-13C2,15N ethyl ester hydrochloride, Glycine-15N, Glycine-15N,D5, Glycine-2,2-D2, Glycine-2-13C, Glycine-2-13C,15N, Glycine-D5, Glycine-N,N,O-D3, Glycocholic acid-glycyl-1-13C, Glycolic acid-1-13C, Glycolic acid-13C2, Glyphosate-2-13C, Glyphosate-2-13C,15N, Glyphosate-3-13C, Guaifenesin-glyceryl-13C3, Guanidine-13C hydrochloride, Guanidine-13C,15N3 hydrochloride, Guanidine-15N3 hydrochloride, Guanidineacetic acid-2,2-D2, Guanidine-D5 deuteriochloride, Guanosine-13C10 5' triphosphate sodium salt, Guanosine-13C10,15N5 5'-monophosphate sodium salt, Guanosine-13C10,15N5 5'-triphosphate sodium salt, Guanosine-15N5 5'-triphosphate sodium salt, Helium-3He, Heptane-1-13C, Heptane-D16, Heptanoic-5,6,7-13C3 acid, Heptanoic-D13 acid, Hexachlorobenzene-13C6, Hexachloroethane-13C, Hexadecane-1,2-13C2, Hexadecane-1-D1, Hexadecane-D34, Hexafluoroacetone deuterate, Hexamethylbenzene-D18, Hexane-1-13C, Hexane-D14, Hexanoic acid-1,2-13C2, Hexanoic acid-1-13C, Hexanoic acid-2,2-D2, Hexanoic acid-6,6,6-D3, Hexanoic-D11 acid, Hexatriacontane-D74, Hydrazine sulfate-15N2, Hydrazine-15N2 dihydrochloride, Hydrazine-15N2 monohydrate, Hydrazine-D4 dideuteriochloride, Hydrazine-D4 monodeuterate, Hydrocinnamic acid-1,2,3-13C3, Hydrocinnamic acid-2,3-13C2, Hydrocinnamic acid-D9,OH, Hydrogen peroxide-18O2 solution, Hydroquinone-D4 (ring-D4), Hydroquinone-D6, Hydroxylamine-15N hydrochloride, Hydroxylamine-D3 deuteriochloride, Hypophosphorous acid-D3 solution, Imidazole-15N2, Imidazole-2-13C,15N2, Imidazole-D4, Imidazole-D4 95, Imino(diacetic-D4) acid, Indole-2,4,5,6,7-D5-3-acetic acid, Indole-2,4,5,6,7-D5-3-acetic-2,2-D2 acid, Indole-3-acetic-2,2-D2 acid 97, Iodoacetamide-15N, Iodoacetic acid-1-13C, Iodoacetic acid-13C2, Iodoacetic acid-2-13C, Iodobenzene-13C6, Iodobenzene-D5, Iodoethane-1,1-D2, Iodoethane-1-13C, Iodoethane-13C2, Iodoethane-2,2,2-D3, Iodoethane-2-13C, Iodoethane-D5, Iodoform-13C, Iodoform-D, Iodomethane-12C 99.9 12C, Iodomethane-12C,D3 99.9 12C, Iodomethane-13C, Iodomethane-13C solution, Iodomethane-13C,D1, Iodomethane-13C,D2, Iodomethane-13C,D3, Iodomethane-D1, Iodomethane-D2, Iodomethane-D3, Iron(III) oxide-17O3, Isoamyl nitrite-15N, Isobutyric acid-1-13C, Isobutyric-D7 acid, Isophthalic acid-carboxy-13C2, Isophthaloyl-2,2'-13C2 chloride, Isopropyl-D7-amine, Isopropyl-D7-benzene, Isovaleraldehyde-1-13C, Isovaleric acid-1-13C, Isovanillin-2,5,6-D3, Krypton-78Kr, Krypton-80Kr, Krypton-82Kr, Krypton-83Kr, Krypton-84Kr, Krypton-86Kr, L-Alanine-1-13C, L-Alanine-1-13C,15N, L-Alanine-1-13C,3,3,3-D3, L-Alanine-12C3, L-Alanine-13C3, L-Alanine-13C3,15N, L-Alanine-15N, L-Alanine-2,3,3,3-D4, L-Alanine-2,3-13C2, L-Alanine-2-13C, L-Alanine-2-13C,15N, L-Alanine-2-D, L-Alanine-3,3-D3, L-Alanine-3-13C, L-Alanine-3-13C,3,3,3-D3, L-Arginine-13C6 hydrochloride, L-Arginine-13C6,15N4 hydrochloride, L-Arginine-15N4, L-Arginine-15N4 hydrochloride, L-Arginine-guanidineimino-15N2 hydrochloride, L-Ascorbic acid-1-13C, L-Asparagine (amide-15N) monohydrate, L-Asparagine (amine-15N) monohydrate, L-Asparagine-13C4 monohydrate, L-Asparagine-13C4,15N2, L-Asparagine-13C4,15N2 monohydrate, L-Asparagine-13C4,15N2,D8, L-Asparagine-15N2, L-Asparagine-15N2 monohydrate, L-Asparagine-15N2,D8, L-Asparagine-15N2, D8 monodeuterate, L-Asparagine-4-13C monohydrate, L-Aspartic acid-1,2-13C2, L-Aspartic acid-1-13C, L-Aspartic acid-1-13C,15N, L-Aspartic acid-13C4, L-Aspartic acid-13C4,15N, L-Aspartic acid-15N, L-Aspartic acid-15N,2,3,3-D3, L-Aspartic acid-2,3,3-D3, L-Aspartic acid-2-13C, L-Aspartic acid-2-13C,15N, L-Aspartic acid-3,4-13C2, L-Aspartic acid-3-13C, L-Aspartic acid-4-13C, L-Aspartic-15N acid β-benzylester derivative, Lauric acid-1,12-13C2, Lauric acid-1,2,3,4-13C4, Lauric acid-1,2-13C2, Lauric acid-1-13C, Lauric acid-12,12,12-D3, Lauric acid-12-13C, Lauric acid-2-13C, Lauric-2,2-D2 acid, Lauric-D23 acid, L-Cysteine-15N, L-Cystine-15N2, L-Fucose-1-13C, L-Glutamic acid-1-13C, L-Glutamic acid-13C5, L-Glutamic acid-13C5,15N, L-Glutamic acid-13C5,15N,d9, L-Glutamic acid-15N, L-Glutamic acid-15N,d9, L-Glutamic acid-2,3,3,4,4-D5, L-Glutamic acid-2-13C, L-Glutamic acid-3-13C, L-Glutamic acid-4-13C, L-Glutamic acid-5-13C, L-Glutamine-1,2-13C2, L-Glutamine-1-13C, L-Glutamine-13C5, L-Glutamine-13C5,15N2, L-Glutamine-13C5,15N2,d10, L-Glutamine-15N2, L-Glutamine-15N2,D10, L-Glutamine-2,3,3,4,4-D5, L-Glutamine-2-13C, L-Glutamine-2-13C-amine-15N, L-Glutamine-3-13C, L-Glutamine-5-13C, L-Glutamine-amide-15N, L-Glutamine-amine-15N, L-Histidine-13C6 hydrochloride monohydrate, L-Histidine-13C6, 15N3, L-Histidine-13C6,15N3 hydrochloride monohydrate, L-Histidine-13C6,α-amine-15N, L-Histidine-15N3 95, L-Histidine-amine-15N, Linoleic acid-13C18, Linolenic acid-13C18, L-Isoleucine-1-13C, L-Isoleucine-13C6,15N, L-Isoleucine-15N, Lithium acetate-13C2, Lithium aluminum deuteride, Lithium carbonate-7Li, Lithium deuteride, Lithium tri-tert-butoxyaluminodeuteride, Lithium-6 deuteride, Lithium-6Li chloride, Lithium-6Li chloride, Lithium-6Li chunks, Lithium-6Li deuteroxide, Lithium-6Li fluoride, Lithium-6Li hydroxide monohydrate, Lithium-6Li iodide, Lithium-6Li nitrate, Lithium-6Li2 carbonate, Lithium-6Li2 sulfate, Lithium-7Li, Lithium-7Li chloride, Lithium-7Li fluoride, Lithium-7Li hydroxide monohydrate, Lithium-7Li2 sulfate, Lithocholic acid-11,12-D2, Lithocholic acid-2,2,3,4,4-D5, Lithocholic acid-2,2,4,4-D4, L-Lactic acid-1-13C, L-Lactic acid-3,3,3-D3, L-Leucine-1,2-13C2, L-Leucine-1-13C, L-Leucine-1-13C,15N, L-Leucine-13C6, L-Leucine-13C6,15N, L-Leucine-13C6,D10, L-Leucine-15N, L-Leucine-2-13C, L-Leucine-2-13C,15N, L-Leucine-2-D1, L-Leucine-3-13C, L-Leucine-3-13C,15N, L-Leucine-3-D1, L-Leucine-4-D1, L-Leucine-5,5,5-D3, L-Leucine-D10, L-Leucine-isopropyl-D7, L-Lysine-1-13C hydrochloride, L-Lysine-13C6 hydrochloride, L-Lysine-13C6,15N2 hydrochloride, L-Lysine-15N2 hydrochloride, L-Lysine-2-13C hydrochloride, L-Lysine-2-15N dihydrochloride, L-Lysine-2-15N hydrochloride, L-Lysine-3,3,4,4,5,5,6,6-D8 hydrochloride, L-Lysine-4,4,5,5-D4 hydrochloride, L-Lysine-6-13C dihydrochloride, L-Lysine-6-13C hydrochloride, L-Lysine-6-13C,ε-15N hydrochloride, L-Lysine-ε-15N hydrochloride, L-Malic acid-1-13C, L-Methionine-1-13C, L-Methionine-13C5,15N, L-Methionine-15N, L-Methionine-2-13C, L-Methionine-2-13C,15N, L-Methionine-2-D1, L-Methionine-carboxy-13C,methyl-D3, L-Methionine-methyl-13C,D1, L-Methionine-methyl-13C,D2, L-Methionine-methyl-13C,D3, L-Methionine-methyl-D3, L-Norvaline-1-13C, L-Phenyl-1-13C-alanine, L-Phenyl-13C6-alanine, L-Phenylalanine-1-13C, L-Phenylalanine-13C9,15N, L-Phenylalanine-15N, L-Phenylalanine-2-13C, L-Phenylalanine-2-D1, L-Phenylalanine-3,3-D2, L-Phenylalanine-3-13C, L-Phenyl-D5-alanine, L-Phenyl-D5-alanine-2,3,3-D3, L-Proline-1-13C, L-Proline-13C5,15N, L-Proline-15N, L-Selenomethionine-methyl-13C1, L-Serine-1,2-13C2, L-Serine-1-13C, L-Serine-13C3, L-Serine-13C3,15N, L-Serine-15N, L-Serine-2,3-13C2, L-Serine-2-13C, L-Serine-3-13C, L-Threonine-1-13C, L-Threonine-13C4, 15N, L-Threonine-15N, L-Tryptophan-1-13C, L-Tryptophan-13C11,15N2, L-Tryptophan-15N2, L-Tryptophan-amino-15N, L-Tryptophan-D5(indole-D5), L-Tryptophan-indole ring-2-13C, L-Tyrosine-(4-hydroxy-17O), L-Tyrosine-(4-hydroxy-18O), L-Tyrosine-1,2,3-13C3, L-Tyrosine-1-13C, L-Tyrosine-13C9, L-Tyrosine-13C9, 15N, L-Tyrosine-15N, L-Tyrosine-2-13C, L-Tyrosine-2-13C,15N, L-Tyrosine-3,3-D2, L-Tyrosine-3-13C, L-Tyrosine-D2 (phenyl-2,6-D2), L-Tyrosine-phenyl-13C6, L-Tyrosine-phenyl-3,5-D2, L-Tyrosine-phenyl-4-13C, L-Tyrosine-phenyl-D4, L-Valine-1-13C, L-Valine-13C5, 15N, L-Valine-13C5,15N, L-Valine-15N, L-Valine-2-13C, L-Valine-D8, Maleic acid-2,3-13C2, Maleic acid-2,3-D2, Maleic anhydride-1,4-13C2, Maleic anhydride-1-13C, Maleic anhydride-2,3-13C2, Maleic anhydride-D2, Malonic acid-1,3-13C2, Malonic acid-13C3, Malonic acid-2-13C, Malonic acid-D4, Malonyl-13C3 coenzyme A lithium salt, m-Cresol-D8, Melamine-D6, Melamine-triamine-15N3, Mesityl-D10 oxide, Mesitylene-D12, Methacetin-methoxy-13C, Methan(ol-D), Methan(ol-D),13C, Methan-D1-ol, Methan-D2-ol, Methane-12C, Methane-D1, Methane-D2, Methane-D3, Methane-D3-sulfonyl chloride, Methane-D3-thiol, Methane-D4, Methanethiol-13C, Methanethiol-D4, Methanethiol-S-D, Methanol-12C, Methanol-12C,D4, Methanol-13C, Methanol-13C,D2, Methanol-13C,D3, Methanol-13C,D4, Methanol-17O, Methanol-18O, Methanol-D3, Methanol-D4, Methyl 3-(Boc)-amino-15N-2,2-Dimethylpropionate-3-13C, Methyl 3-(Boc)amino-2,2-Dimethylpropionate-1-13C, Methyl 4-iodobenzoate-ring-13C6, Methyl benzoate-D8, Methyl benzoate-α-13C, Methyl bromoacetate-1-13C, Methyl bromoacetate-2,2-D2, Methyl dichloroacetate-1-13C, Methyl formate-12C, Methyl formate-13C, Methyl formate-D, Methyl isonicotinate-D4 (ring-D4), Methyl methacrylate-D5, Methyl methacrylate-D8, Methyl meth-D3-acrylate, Methyl oleate-1-13C, Methyl palmitate-13C16, Methyl stearate-13C18, Methyl(cyclohexane-D11), Methyl-13C phenyl sulfide, Methyl-13C phenyl sulfone, Methyl-13C phenyl sulfoxide, Methyl-13C trifluoromethane sulfonate, Methyl-13C,D3 p-toluenesulfonate, Methyl-13C,D3-amine hydrochloride, Methyl-13C-triphenylphosphonium iodide, Methylacetylene-D4, Methylamine-13C, Methylamine-13C hydrochloride, Methylamine-13C,15N, Methylamine-15N, Methylamine-15N hydrochloride, Methylamine-D2 deuteriochloride, Methylamine-D5, Methylamine-D5 deuteriochloride, Methylamine-N,N-D2, Methylcyclohexane-D14, Methyl-D1-amine-15N, Methyl-D3 isocyanate, Methyl-D3 salicylate-OD, Methyl-D3 tribromoacetate, Methyl-D3 trifluoromethane sulfonate, Methyl-D3-amine, Methyl-D3-amine hydrochloride, Methyl-D3-amine-15N hydrochloride, Methyl-D3-malonic acid, Methyl-D3-triphenylphosphonium bromide, Methyl-D3-triphenylphosphonium iodide, Methylphosphonic-13C dichloride, Mevalonolactone-1,2-13C2, Mevalonolactone-1-13C, Mevalonolactone-2-13C, Mevalonolactone-5-13C, Mevalonolactone-methyl-13C1, Mevalonolactone-methyl-D3, m-Xylene-D10, m-Xylene-Dimethyl-13C2, m-Xylene-Dimethyl-D6, Myristic acid-1,2-13C2, Myristic acid-1-13C, Myristic acid-13,13,14,14,14-D5, Myristic acid-13C14, Myristic acid-14-13C, Myristic-D27 acid, Myristoyl-1-13C chloride, N-(Chloromethyl-13C)phthalimide, N-(Chloromethyl-13C)phthalimide-15N,N-(Chloromethyl-13C)succinimide, N-(Chloromethyl-13C)succinimide-15N,N,N-Dimethyl(form-13C,D)amide, N,N-Dimethyl-13C2-formamide, N,N-Dimethylacetamide-1,2-13C2, N,N-Dimethylacetamide-D9, N,N-Dimethyl-D6-formamide, N,N-Dimethyl-D6-glycine hydrochloride, N,N-Dimethylformamide-15N, N,N-Dimethylformamide-carbonyl-13C, N,N-Dimethylformamide-D1, N,N-Dimethylformamide-D7, N,O-Bis(trimethyl-D9-silyl)acetamide, N-Acetoxy-D3-succinimide, N-Acetyl-DL-alanine-2-D, N-Acetyl-DL-alanine-3,3,3-D3, N-Acetyl-D-neuraminic acid-1,2,3-13C3, N-Acetyl-L-aspartic acid-2,3,3-D3, N-Acetyl-L-methionine-15N, Naphthalene-1,2,3,4,9,10-13C6, Naphthalene-1,2,3,4-13C4, Naphthalene-1-13C, Naphthalene-13C10, Naphthalene-D8, N-Butylpyridinium chloride-D14, Neon-20Ne, Neon-21Ne, Neon-22Ne, N-Ethylpiperazine-2,3-13C2, Nicotinamide-amide-15N, Nicotinic acid-ring-D4, Nifedipine-13C8, Nitric acid-D solution in D2O, Nitric-15N acid solution, Nitric-15N oxide, Nitrilotriacetic acid-D9, Nitrobenzene-13C6, Nitrobenzene-15N, Nitrobenzene-D5, Nitrobenzene-D5, Nitrobenzene-D5, Nitroethane-1,1-D2, Nitroethane-1-13C, Nitrogen-14N2, Nitrogen-15N dioxide, Nitrogen-15N2, Nitromethane-13C, Nitromethane-13C,D3, Nitromethane-15N, Nitromethane-D3, Nitrous oxide-15N2, Nitrous oxide-15N2,18O, N-Methyl-4-piperidyl acetate-1-13C, N-Methylacetamide-15N,N-Methylacetamide-D7, N-Methyl-D3-2-pyrrolidinone-D6, N-Methyl-D3-4-phenylpyridinium iodide, N-Methyl-D3-formamide, N-Methyl-D3-pyrrolidine, N-Methyldiethanolamine-15N,N-Methylformamide-1-13C, N-Methylformamide-18O, N-Methylformanilide-1-13C, N-Methylpiperazine-2,2,3,3,5,5,6,6-D8, N-Methylpyrrolidine-2,2,3,3,4,4,5,5-D8, N-Nitrosodiethan-D8-olamine, N-Nitrosodimethylamine-D6, N-Nitrosodiphenylamine-2,2',4,4',6,6'-D6, Nonadecane-D40, Nonane-D20, NORETHINDRONE(ETHYNYL-13C2), N-Propionyl-13C3-oxysuccinimide, N-Propionyloxy-D5-succinimide, o-Cresol-D8, Octacosane-D58, Octane-D18, Octanoic acid-1,2,3,4-13C4, Octanoic acid-1,2-13C2, Octanoic acid-1-13C, Octanoic acid-13C8, Octanoic acid-2-13C, Octanoic acid-5,6,7,8-13C4, Octanoic acid-7, 8-13C2, Octanoic acid-7-13C, Octanoic acid-8,8,8-D3, Octanoic acid-8-13C, Octanoic-D15 acid, Octanoyl-2,4,6,8-13C4 Coenzyme A, lithium salt, Octyl-β-D-glucopyranoside-D24, Oleic acid-1,2,3,7,8,9,10-13C7, Oleic acid-1-13C, Oleic acid-13C18, Oleic acid-9,10-13C2, Oleic acid-9,10-D2 96, Oleoyl-1-13C-L-carnitine hydrochloride, Oleoyl-13C18 coenzyme A lithium salt, O-Methylisourea-13C hydrochloride, O-Methylisourea-13C,15N2 hydrochloride, O-Methylisourea-D6 deuteriochloride, o-Toluic-ring-D4-methyl-D3 acid, o-Toluidine-15N, Oxalic acid-13C2 dihydrate, Oxybutynin chloride-phenyl-D5, Oxygen-16O2, Oxygen-17O2, Oxygen-18O2, o-Xylene-3,4,5,6-D4 (phenyl-3,4,5,6-D4), o-Xylene-D10, o-Xylene-Dimethyl-13C2, o-Xylene-Dimethyl-D6, Palmitic acid-1,2,3,4-13C4, Palmitic acid-1,2-13C2, Palmitic acid-1-13C, Palmitic acid-13C16, Palmitic acid-15,15,16,16,16-D5, Palmitic acid-15,16-13C2, Palmitic acid-16,16,16-D3, Palmitic acid-16-13C, Palmitic acid-2,2-D2, Palmitic acid-2,4,6,8,10,12,14,16-13C8, Palmitic acid-2-13C, Palmitic acid-5,6,7,8-13C4, Palmitic acid-D31, Palmitoleic acid-13C16, Palmitoyl-1-13C coenzyme A lithium salt, Palmitoyl-1-13C-L-carnitine hydrochloride, Palmitoyl-13C16 coenzyme A, Palmitoyl-13C16-L-carnitine hydrochloride, Paraformaldehyde-13C, Paraformaldehyde-D2, p-Benzoquinone-D4, p-Cresol-2,3,5,6-D4, p-Cresol-D8, p-Cresol-methyl-13C, Pentachlorophenol-13C6, Pentadecane-D32, Pentafluorophen(ol-D), Pentane-D12, Perchloric acid-D solution in D2O, Perylene-D12, Phenacetin-ethoxy-1-13C, Phenacetin-ethoxy-2-13C, Phenacetin-ethoxy-D5, Phenanthrene-9,10-13C2, Phenanthrene-D10, Phenethyl-1,1,2,2-D4-amine, Phenethyl-1,2-13C2-amine, Phenethyl-1-13C-amine, Phenethyl-2-13C-amine, Phenol-1-13C, Phenol-13C6, Phenol-18O, Phenol-2,3,4,5,6-D5, Phenol-2,4,6-D3, Phenol-2,4,6-D3, Phenol-3,5-D2, Phenol-4-13C, Phenol-4-D1, Phenol-D6, Phenyl acetylene-1-13C, Phenyl isocyanate-15N, Phenyl vinyl-1,2-13C2 sulfoxide, Phenyl vinyl-1-13C sulfone, Phenyl vinyl-1,2-13C sulfone, Phenyl vinyl-1,2-13C2 sulfide, Phenyl vinyl-113C sulfide, Phenyl vinyl-1-13C sulfoxide, Phenyl vinyl-2-13C sulfide, Phenyl vinyl-2-13C sulfone, Phenyl vinyl-2-13C sulfoxide, Phenyl-13C6 isocyanate, Phenyl-13C6-acetic acid, Phenylacetic acid-1,2-13C2, Phenylacetic acid-1-13C, Phenylacetic acid-2-13C, Phenylacetic acid-α,α-D2, Phenylacetic-D7 acid, Phenylacetylene-1,2-13C2, Phenylacetylene-2-13C, Phenylacetylene-D, Phenylacetylene-D6, Phenyl-D5 isocyanate, Phenyl-D5-acetic acid, Phenyltrichlorosilane-D5, Phosgene-12C, Phosgene-13C, Phospho(enol)pyruvic acid-1-13C potassium salt, Phospho(enol)pyruvic acid-3-13C potassium salt, Phosphoenolpyruvic-2-13C acid potassium salt, Phosphoric acid-16O4, Phosphoric acid-17O4, Phosphoric acid-18O4, Phosphoric acid-D3, Phthalic acid-2,2'-13C2, Phthalic anhydride-D4, Phthalic-13C6 anhydride, Phthalic-3,4,5,6-D4 acid, Phthalimide-15N, Phthalimide-15N potassium salt, Phthaloyl chloride-2,2'-13C2, Pimelic-D10 acid, piperazine-2,2,3,3,5,5,6,6-D8 dihydrochloride, Piperidine-D11, Poly(ethylene-1,2-D2), Poly(ethylene-13C2), Poly(ethylene-D4), Poly(propylene-1-13C), Poly(propylene-2-13C), Poly(styrene-D8), Poly(styrene-α-13C), Poly(styrene-β-13C), Potassium bicarbonate-13C, Potassium carbonate-13C, Potassium cyanate-15N, Potassium cyanide-13C, Potassium cyanide-13C,15N, Potassium cyanide-15N, Potassium cyanoborodeuteride, Potassium deuteroxide, Potassium dideuterium phosphate, Potassium formate-D, Potassium linoleate-13C18, Potassium nitrate-14N, Potassium nitrate-15N, Potassium nitrate-15N,18O3, Potassium oleate-1-13C, Potassium palmitate-1,2,3,4-13C4, Potassium palmitate-1,3,5,7,9-13C5, Potassium palmitate-1-13C, Potassium palmitate-13C16, Potassium palmitate-16,16,16-D3, Potassium palmitate-16-D, Potassium palmitate-2,2-D2, Potassium palmitate-D31, Potassium selenocyanate-13C,15N, Potassium thiocyanate-13C, Potassium thiocyanate-13C,15N, Potassium thiocyanate-15N, PREGNENOLONE(17,21,21,21-D4), PROGESTERONE(2,2,6,6,17,21,21,21-D8), PROGESTERONE(3, 4-13C2), Promethazine-D4 hydrochloride, Propadiene-D4, Propane-1,1,1,2,3,3,3-D7, Propane-1,1,1,3,3,3-D6, Propane-1-13C, Propane-13C3, Propane-2,2-D2, Propane-D8, Propene-13C3, Propene-2-13C, Propene-D6, Propionaldehyde-1-13C, Propionaldehyde-2,2-D2, Propionic acid-1-13C, Propionic acid-13C3, Propionic acid-2,2-D2, Propionic acid-2,3-13C2, Propionic acid-3,3,3-D3, Propionic acid-D6, Propionic anhydride-D10, Propionic-2,2-D2 acid-D, Propionic-D5 acid, Propionitrile-D5, Propionyl chloride-1-13C, Propionyl chloride-13C3, Propylamine-15N, Propylamine-15N hydrochloride, Propyl-D7 chloroformate, Propyl-D7-amine, Propylene oxide-D6, Propyne-3,3,3-D3, Propyne-3-13C, p-Terphenyl-D14, p-Toluenesulfonamide-15N, p-Toluic acid-α-13C, p-Xylene-D10, p-Xylene-D4 (phenyl-D4), p-Xylene-Dimethyl-13C2, p-Xylene-Dimethyl-D6, Pyrazine-D4, Pyrene-4,5,9,10-13C4, Pyrene-D10, Pyridine-15N, Pyridine-D5, Pyridine-D5 N-oxide, Pyrrole-D5, Pyrrolidine-2,2,3,3,4,4,5,5-D8, Pyruvic acid-1,2-13C2 (free acid), Pyruvic-1-13C acid (free acid), Pyruvic-2-13C acid (free acid), Quinoline-D7, R-(-)-2-Amino-1-propanol-13C3, Resorcinol-D6, Resorufin-D6, Resveratrol-phenyl-13C6, Ritalinic acid-(phenyl-13C6), Salbutamol-tert-butyl-D9, Salicylic acid-D6, Salicylic acid-α-13C, S-Allyl-D5-L-cysteine, Sarcosine-D3 (methyl-D3), Sarcosine-methyl-13C, Sebacic acid-C-D16, Selenourea-13C,15N1, Silicon dioxide-18O2, Silver carbonate-13C, Silver cyanide-13C,15N, SODIUM 17B-ESTRADIOL 3-SULFATE(2,4,16,16-D4), Sodium 2-chloropropionate-13C3, Sodium 2-hydroxyethoxy-D4 acetate-D2, Sodium 4-methylvalerate-1-13C, Sodium acetate-1-13C, Sodium acetate-1-13C,D3, Sodium acetate-13C2, Sodium acetate-13C2,D3, Sodium acetate-18O2, Sodium acetate-2-13C, Sodium acetate-2-13C,D3, Sodium acetate-D3, Sodium azide-1-15N (terminal N), Sodium benzoate-3,4,5-D3, Sodium benzoate-D5, Sodium bicarbonate-12C, Sodium bicarbonate-13C, Sodium borodeuteride, Sodium butyrate-1,2-13C2, Sodium butyrate-1-13C, Sodium butyrate-13C4, Sodium butyrate-2,4-13C2, Sodium butyrate-2-13C, Sodium butyrate-3-13C, Sodium butyrate-4-13C, Sodium carbonate-12C, Sodium carbonate-13C, Sodium cyanoborodeuteride, Sodium D-3-hydroxybutyrate-1,3-13C2, Sodium deuteroxide in D2O, Sodium DL-3-hydroxybutyrate-1,3-13C2, Sodium DL-3-hydroxybutyrate-13C4, Sodium DL-3-hydroxybutyrate-2,4-13C2, Sodium DL-3-hydroxybutyrate-4-13C, Sodium dodecyl sulfate-1-D1, Sodium dodecyl sulfate-D25, SODIUM ESTRONE 3-SULFATE(13,14,15,16,17,18-13C6), SODIUM ESTRONE 3-SULFATE(2,4,16,16-D4), Sodium formate-12C, Sodium formate-13C, Sodium formate-13C,18O2, Sodium formate-13C,D, Sodium formate-D, Sodium fumarate-2,3-13C2, Sodium hydroxide-16O solution, Sodium isovalerate-1-13C, Sodium L-lactate-1-13C solution, Sodium L-lactate-2,3-13C solution, Sodium L-lactate-2-13C solution, Sodium L-lactate-2-D1 solution, Sodium L-lactate-3,3,3-D3 solution, Sodium L-lactate-3-13C solution, Sodium nitrate-14N, Sodium nitrate-15N, Sodium nitrite-15N, Sodium octanoate-1-13C, Sodium oxalate-13C2, Sodium palmitate-2,4,6,8,10,12,14,16-13C8, Sodium perchlorate-18O4, Sodium phosphate monobasic-16O4, Sodium propionate-1,2-13C2, Sodium propionate-1-13C, Sodium propionate-13C3, Sodium propionate-2,3-13C2, Sodium propionate-2-13C, Sodium propionate-3-13C, Sodium propionate-D5, Sodium pyruvate-1,2-13C2, Sodium pyruvate-1-13C, Sodium pyruvate-13C3, Sodium pyruvate-2,3-13C2, Sodium pyruvate-2-13C, Sodium pyruvate-3-13C, Sodium pyruvate-3-13C, 3,3,3-D3, Sodium trifluoroacetate-1-13C, Spermidine-butane-D8 trihydrochloride, Stearic acid-1,2-13C2, Stearic acid-1-13C, Stearic acid-13C18, Stearic acid-18,18,18-D3, Stearic acid-18-13C, Stearic acid-2,2-D2, Stearic acid-2-13C, Stearic-17,17,18,18,18-D5 acid, Stearic-D35 acid, Stearoyl-13C18 coenzyme A lithium salt, Styrene dibromide-ethyl-2-13C, Styrene-13C8, Styrene-2,3,4,5,6-D5, Styrene-D8, Styrene-ring-13C6, Styrene-α,β,β-D3, Styrene-α,β-13C2, Styrene-α,2,3,4,5,6-D6, Styrene-α-13C, Styrene-α-D1, Styrene-β,β-D2, Styrene-β-13C, Suberic acid-2,2,7,7-D4 bis(3-sulfo-N-hydroxysuccinimide ester) disodium salt, Succinic acid-1,2-13C2, Succinic acid-1,4-13C2, Succinic acid-13C4, Succinic acid-2,2,3,3-D4, Succinic acid-2,3-13C2, Succinic acid-D6, Succinic anhydride-1,4-13C2, Succinic anhydride-13C4, Succinic anhydride-2,2,3,3-D4, Succinimide-15N, Succinonitrile-D4, Sulfur-32S, Sulfur-34S, Sulfuric acid-18O4 solution, Sulfuric acid-D2 solution in D2O, Taurine-13C2, Taurine-15N, Terephthalic acid-2,2'-13C2, Terephthalic-2,3,5,6-D4 acid, Terephthaloyl chloride-2,2'-13C2, Terephthaloyl-D4 chloride, Terfenadine-(butanol-1,2,2-D3), tert-Amyl methyl-D3 ether, tert-Amyl-13C3 methyl ether, tert-Butan(ol-D), tert-Butan-D9-ol, tert-Butanol-13C4, tert-Butanol-D10, tert-Butyl bromoacetate-2-13C, tert-Butyl ethyl ether-trimethyl-13C3, tert-Butyl methyl ether-13C5, tert-Butyl methyl ether-D12, tert-Butyl methyl-D3 ether, tert-Butyl-1,2-13C2 methyl ether, tert-Butyl-D9-amine, TESTOSTERONE(1,2-D2), TESTOSTERONE(2,2,4,6,6,-D5), TESTOSTERONE(3, 4-13C2), Tetrabutyl-D36-tin, Tetrachloroethylene-13C1, Tetrachloroethylene-13C2, Tetracosane-D50, Tetracosanoic acid-1-13C, Tetradecanoic-14,14,14-D3 acid, Tetradecyl-D29-amine, Tetrahydrofuran-D8, Tetrahydrofuran-D8 99.95, Tetramethylammonium-15N chloride, Tetramethyl-D12 orthosilicate, Tetramethyl-D12-ammonium bromide, Tetramethyl-D12-ammonium chloride, Tetrapropylammonium-15N bromide, Tetrapropyl-D28 ammonium bromide, Thiourea-13C, Thiourea-13C,15N2, Thiourea-15N2, Thiourea-D4, Thymidine-13C10, 15N2 5'-monophosphate sodium salt, Thymidine-13C10,15N2 5'-triphosphate sodium salt, Thymine-D4 (methyl-D3,6-D1), Tolan-D10 97, Toluene-1-13C, Toluene-12C7, Toluene-13C7, Toluene-2,3,4,5,6-D5, Toluene-4-13C, Toluene-D8, Toluene-phenyl-13C6, Toluene-α,α,α-D3, Toluene-α-13C, trans/trans-1-Phenyl-D5-4-phenyl-1,3-butadiene, trans-4-Phenyl-3-buten-2-one-1,1,1,3-D4, trans-4-Phenyl-3-buten-2-one-D10, trans-Chalcone-D12, trans-Cinnamic acid-β,2,3,4,5,6-D6, trans-Cinnamic-D7 acid, trans-Styrene-(β)-D, trans-Styrene-α,β-D2, trans-Vaccenic acid-1-13C, Triacontane-D62, Tribromoacetic acid-1-13C, Tributyltin chloride-D27, Tributyltin deuteride, Trichloroacetic acid-1-13C, Trichloroacetic-2-13C acid, Trichloroethylene-13C2, Trichloroethylene-D, Tridecane-D28, Tridecanoic-2,2-D2 acid, Triethyl phosphonoacetate-2-13C, Triethyl(silane-D), Triethyl-13C6 phosphate, Triethyl-D15-amine, Triethylorthoformate-formyl-13C1, Trifluoroacetic acid-D, Trimethyl-13C3-amine hydrochloride, Trimethylamine-15N, Trimethylamine-15N hydrochloride, Trimethyl-D9-amine, Trimethyl-D9-amine deuteriochloride, Trimethyl-D9-amine hydrochloride, Trimethyl-D9-amine-15N hydrochloride, Trimethyl-D9-chlorosilane, Trimethyl-D9-phosphine, Trimethylsilyl cyanide-13C,15N, Triphenyl phosphate-D15, Triphenyl(methanol-13C), Triphenyl-D15-phosphine oxide, Triphenyl-D15-tin chloride, Triphenylene-D12, Triphenyl-phosphine-D15, Triphosgene-13C3, Tris(hydroxymethyl-D3)amino-D2-methane, Tris-D11 solution in D2O, Undecanoic acid-1-13C, Uracil-15N2, Uracil-2-13C, Uracil-2-13C,15N2, UREA(13C; 15N2), Urea-12C, Urea-13C, Urea-13C,15N2, Urea-14N2, Urea-15N2, Urea-15N2,18O, Urea-18O, Urea-D4, Urethane-D5 (ethyl-D5), Uric acid-1,3-15N2, Uridine-13C9 5'-triphosphate sodium salt, Uridine-13C9,15N2 5'-monophosphate sodium salt, Uridine-13C9, 15N2 5'-triphosphate sodium salt, Uridine-15N2 5'-triphosphate sodium salt, Valeric acid-2-13C, Valeric acid-3,4,5-13C3, Valeric acid-5-13C, Valeric-D9 acid, Vanillin-S-D1, Vanillin-D3, Vanillin-methoxy-13C, Vanillin-ring-13C6, Vanillin-α-13C, Veratraldehyde-2-13C, Veratraldehyde-3,4-13C1, Vinyl chloride-D3, Vinyl-13C2 acetate, Vinyl-13C2 Bromide gas, Vinyl-D3 bromide, Vitamin E acetate (trimethyl-D9), Water-16O, Water-17O, Water-18O, Xenon-124Xe, Xenon-126Xe, Xenon-128Xe, Xenon-$^{129}$Xe, Xenon-131Xe, Xenon-132Xe, Xenon-134Xe, Xenon-136Xe, Zinc cyanide-13C2, 15N2, Zinc propionate-2-13C, 3,3,3-D3, α-Cyano-4-hydroxycinnamic acid-D7, α-Methyl-styrene-2-13C, β-Alanine-13C3,15N, β-Alanine-15N, β-D-Glucose-1-C-D pentaacetate, γ-Butyrolactone-D6 and any combination of these.

In some embodiments, the one or more isotopic standards in the test sample, the first external standard sample and second external standard sample may be the same and optionally the one or more isotopic standards may be provided at the same concentrations in the test sample, the first external standard sample and the second standard sample. In some embodiments, further external standard samples may be utilized and optionally the isotopic standards in the further external standard samples may be the same and/or in the same concentrations as in the test sample, the first external standard sample and the second standard sample.

In some embodiments, the first set of mass spectrometry data, the second set of mass spectrometry data and the reference set of mass spectrometry data may comprise metabolomic data or metabonomic data. In certain embodiments, the first set of mass spectrometry data, the second set of mass spectrometry data and the reference set of mass spectrometry data sets may comprise metabolomic data or metabonomic data for 100 or more analytes, 200 or more analytes, 1000 to 2000 analytes or 7000 or more analytes. In other embodiments, the first set of mass spectrometry data, the second set of mass spectrometry data and the reference set of mass spectrometry data sets may comprise targeted metabolomic data or targeted metabonomic data for 5 to 20 analytes or 5 to 200 analytes. As used herein, the terms "targeted metabolomic data" and "targeted metabonomic data" refer to a subset of a larger group of metabolomic or metabonomic data. In one embodiment, a set of metabonomic or metabolomic data may comprise intensities or concentrations of 200 or more metabolites in a biological solution and a set of targeted metabolomic or metabonomic data comprise intensities or concentrations for a selected 5 to 20 of the 200 or more metabolites.

Optionally, the reference set of mass spectrometry data may be received before or after the second set of mass spectrometry data. Optionally, the second set of mass spectrometry data may be received before or after the first set of mass spectrometry data. In some embodiments, the step of receiving the first set of mass spectrometry data may be repeated one or more times and the step of receiving the second set of mass spectrometry data may be repeated one or more times. In an exemplary embodiment, the first set of mass spectrometry data and the second set of mass spectrometry data may be received within 12 or 24 hours of one another. In another embodiment, the first set of mass spectrometry data and the second set of mass spectrometry data may be received within 15 to 20 minutes of one another. For applications utilizing high-throughput mass spectrometry, the second set of mass spectrometry data may be received a short time before or after the first set of mass spectrometry data, for example on the order of minutes or hours.

In some embodiments, methods of this aspect are useful for analyzing samples via mass spectrometry on different mass spectrometers and optionally via different chromatographic separation techniques. In a specific embodiment, the first set of mass spectrometry data and the second set of mass spectrometry data may be received from a first mass spectrometer and the reference set of mass spectrometry data may be received from a second mass spectrometer different from the first mass spectrometer. Useful types of mass spectrometers include, but are not limited to: a gas chromatography mass spectrometer, a liquid chromatography mass spectrometer, a Fourier transform mass spectrometer, a direct infusion mass spectrometer, a capillary electrophoresis mass spectrometer, an ion mobility shift mass spectrometer, a desorption electrospray ionization mass spectrometer, a nanostructure initiator mass spectrometer or a matrix assisted mass spectrometer such as matrix assisted laser desorption ionization mass spectrometry.

In another aspect, the disclosure relates to methods for making a normalization or standardization data table. A method of this aspect may comprise the steps of: i) receiving a mass spectrometry data set on a standard sample having one or more isotopic standards, the mass spectrometry data set comprising intensities for one or more m/z features including the one or more isotopic standards; ii) comparing intensities for one or more m/z features with intensities for the one or more isotopic standards, thereby determining a reference isotopic standard or a combination of reference isotopic standards for each of the one or more m/z features; and iii) populating a data table with one or more m/z entries corresponding to the one or more m/z features, wherein each m/z entry of the data table comprises an intensity ratio of one or more m/z features divided by the intensity of the reference isotopic standard or reference isotopic standards for the one or more m/z features. Optionally, the step of receiving the mass spectrometry data may be repeated one or more times and the comparing step may comprise determining a coefficient of variation for the ratios of intensities of each of the one or more m/z features to each of the one or more isotopic standards. In a specific embodiment, the reference isotopic standard for each m/z feature may be selected as the isotopic standard having the lowest coefficient of variation for that m/z feature.

In another aspect, the disclosure is related to systems for analyzing a sample via mass spectrometry and/or for normalizing mass spectrometry data. In a specific embodiment, aspect system may be configured for performing a method described herein. A system of this aspect may comprise: i) a an analytical instrument system configured to obtain and transmit the first set of mass spectrometry data and the second set of mass spectrometry data; and ii) a computer system configured to receive the first set of mass spectrometry data and the second set of mass spectrometry data, the computer including a memory storage device for storing the reference set of mass spectrometry data; and a processor.

In another aspect, of the disclosure relates to a method for normalizing or standardizing metabolomics and/or metabonomics data. A method of this aspect may comprise the steps of: i) providing a reference set of metabolomics or metabonomics data obtained by mass spectrometry on a first external standard sample having one or more isotopic standards, wherein the reference set of metabolomics or metabonomics data comprises one or more m/z intensity ratios for a plurality of target metabolites, wherein each m/z intensity ratio is the intensity of a single m/z feature divided by the intensity of a reference isotopic standard for that single m/z feature; ii) providing a first set of metabolomics or metabonomics data obtained by mass spectrometry on a test sample having the one or more isotopic standards, wherein the first set of metabolomics or metabonomics data comprises one or more m/z intensity ratios for the plurality of target metabolites, wherein each m/z intensity ratio is the intensity of a single m/z feature divided by the intensity of the reference isotopic standard for that single m/z feature; iii) providing a second set of metabolomics or metabonomics data obtained by mass spectrometry on a second external standard sample having the one or more isotopic standards, wherein the second set of metabolomics or metabonomics data comprises one or more m/z intensity ratios for the plurality of target metabolites, wherein each m/z intensity ratio is the intensity of a single m/z feature divided by the intensity of the reference isotopic standard for that single m/z feature; iv) dividing one or more m/z intensity ratios of the reference metabolomics data set by a corresponding m/z intensity ratio from the second metabolomics data set, thereby receiving one or more m/z intensity ratio normalization factors; and v) multiplying one or more m/z intensity ratios of the first metabolomics or metabonomics data set by a corresponding m/z intensity ratio normalization factor.

In another aspect, the disclosure relates to methods of diagnosing diseases. A method of this aspect may comprise the steps of: i) analyzing a biological fluid sample of a test subject by a method described herein, wherein the test sample comprises biological fluid from the test subject and the first and second external standard samples comprise a reference biological fluid sample; ii) analyzing a biological fluid sample of a reference subject by a method described herein, wherein the test sample comprises biological fluid from the reference subject and the first and second external standard samples comprise a reference biological fluid sample; and iii) comparing at least a portion of the normalized mass spectrometry data sets from the test and reference subjects, thereby diagnosing the disease. Optionally, the reference subject may comprise a known diseased individual. Optionally the reference subject may comprise a known disease-free individual. In an embodiment, the reference subject may be the test subject, for example at an earlier moment in time. In another embodiment, the mass spectrometry data may set useful for methods of this aspect comprise normalized metabolomic profiles or metabolomic fingerprints for the test and reference subjects. In certain embodiments, normalized m/z intensity ratios may be received and/or compared for 100 or more metabolites, 200 or more metabolites, 1000 to 2000 metabolites or 7000 or more metabolites. In another embodiment, only a portion of the normalized m/z intensity ratios which are received may be actually compared. For example, in embodiments normalized m/z intensity ratios may be compared for 5 to 20 metabolites or 5 to 200 metabolites.

Without wishing to be bound by any particular theory, there can be discussion herein of beliefs or understandings of underlying principles relating to the disclosure. It is recognized that regardless of the ultimate correctness of any mechanistic explanation or hypothesis, an embodiment of the disclosure can nonetheless be operative and useful.

DETAILED DESCRIPTION

Figure 1:
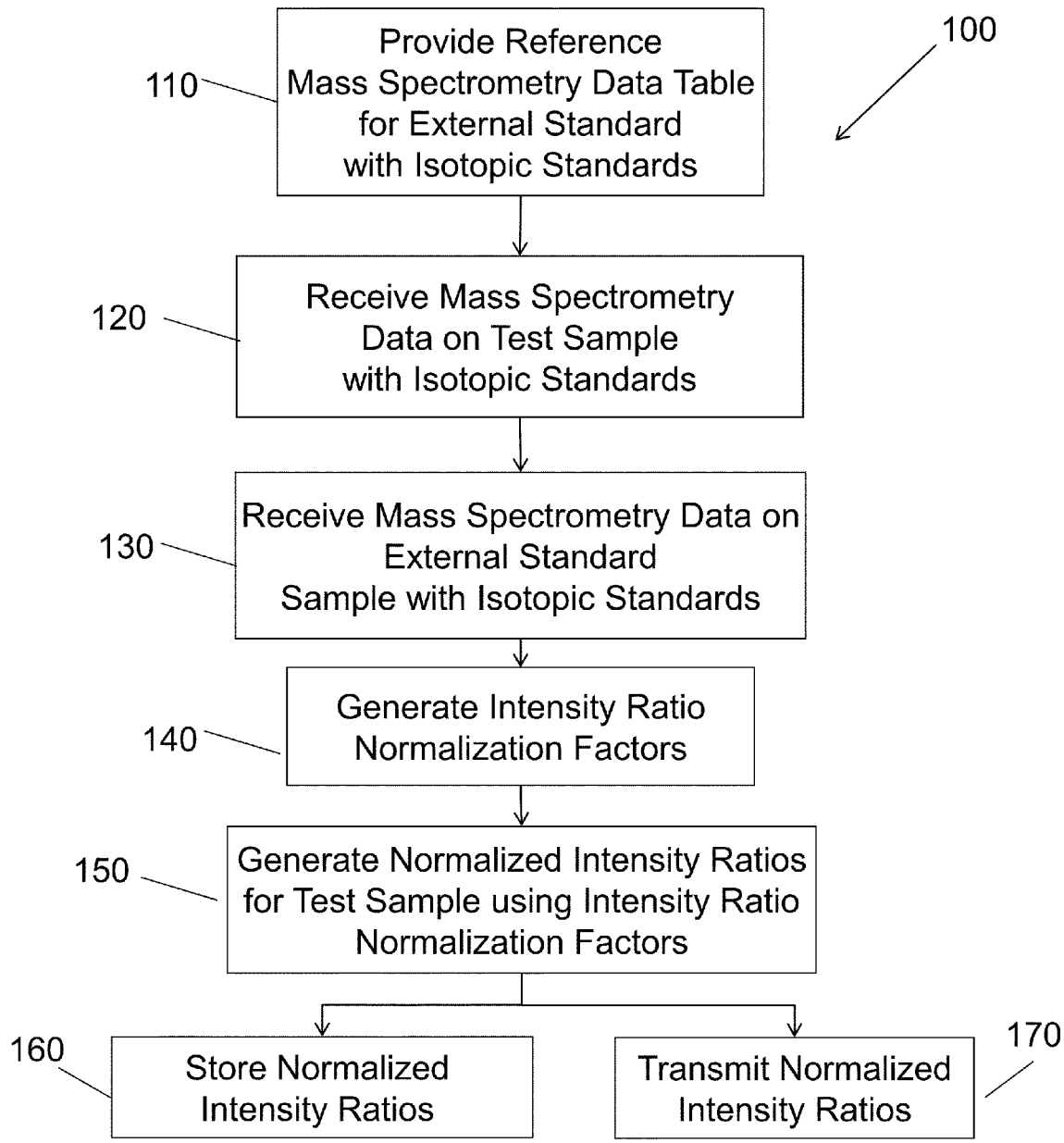
FIG. 1 provides an overview of for a method for analyzing a sample via mass spectrometry to generate normalized intensity ratios according to an embodiment.

In general the terms and phrases used herein have their art-recognized meaning, which can be found by reference to standard texts, journal references and contexts known to those skilled in the art. The following definitions are provided to clarify their specific use in the context of the disclosure.

"Set of mass spectrometry data" refers to the raw, normalized or reduced data output of a mass spectrometer for a single sample. In some embodiments, a set of mass spectrometry data may comprise ion intensity as a function of mass to charge ratio (m/z) and/or chromatographic elution time. In some embodiments, a set of mass spectrometry data may comprise intensities for one or more m/z features or peaks. In some embodiments, a set of mass spectrometry data may comprise ratios of intensities. In some embodiments, a set of mass spectrometry data may be stored as a database or a data table.

"External standard sample" refers to a sample useful as a reference, for normalization, for comparison and/or for otherwise interpreting or standardizing mass spectrometry data. In some embodiments, an external standard sample may comprise a NIST reference standard. In some embodiments, an external standard sample may comprise a sample having known concentrations of components.

"Isotopic standard" refers to a compound comprising one or more elements having a mass number different from the element's most abundant mass number. Isotopic standards are useful for some embodiments as they are distinguishable from chemically identical compounds but composed of elements of only the most abundant mass numbers. An isotopic standard is "stable" if it is composed of elements which are not radioactive or only decay over exceedingly long timescales. In one embodiment, an isotopic standard may be added to a sample analyzed by mass spectrometry to provide a reference data point in a mass spectrometry data set. In certain embodiments, isotopic standards may be added in known concentrations to a sample analyzed by mass spectrometry.

The term "m/z feature" refers to a portion of a set of mass spectrometry data corresponding to a single mass to charge species. "Intensity of an m/z feature" generally refers to a measure of the ion current detected as originating from a single mass to charge species; in some embodiments, the intensity of an m/z feature corresponds to integrated ion intensities corresponding to ion current originating from a single mass to charge species. In some embodiments, intensities of m/z features may be provided as relative intensities. "Intensity of the reference isotopic standard for an m/z feature" refers to a measure of the ion current detected for a single mass to charge species originating from a single isotopic standard corresponding to the reference isotopic standard for the m/z feature. "M/z intensity ratio" refers to a ratio of intensities of two m/z features. For some embodiments, the term "intensity" may be equivalent to the terms "integral", "area", "integrated area," and "peak height".

"Reference isotopic standard for an m/z feature" refers to the isotopic standard added to a sample analyzed by mass spectrometry that is observed in a set of mass spectrometry data obtained from an external standard sample and that meet certain criteria. In some embodiments, "reference isotopic standard" may be the isotopic standard having the lowest coefficient of variation between the ratios of intensities of the m/z feature and the m/z feature corresponding to the isotopic standard. In other embodiments, the criteria for "reference isotopic standard" may be based on different parameters. In some embodiments, "a combination of reference isotopic standards" refers to multiple isotopic standards, added to a sample, which are observed to meet certain criteria. In some embodiments, "a combination of reference isotopic standards" may be the lowest intensity ratio coefficient of variation, for example, when the individual intensities from the multiple isotopic standards are summed, averaged or otherwise combined. Like "reference isotopic standard," in other embodiments, the criteria for "a combination of reference isotopic standards" may be based on different parameters.

"Coefficient of variation" refers to a statistical measure of the spread of a plurality of values. In some embodiments, a coefficient of variation may be a standard deviation of a plurality of values. In other embodiments, other statistical approaches to evaluate the best or most consistent internal standard may be, additionally or alternatively, used.

"Normalization factor" refers to a number used to normalize, standardize, or otherwise correct a measurement. In some embodiments, normalization factors may be used to remove or reduce errors from measured concentrations, intensities and/or intensity ratios. In some embodiments, normalization factors may be used to scale concentrations, intensities and/or intensity ratios to allow two or more measured concentrations, intensities and/or intensity ratios to be compared with one another.

As used herein, the term "normalize" refers to a process of scaling one or more values to allow values to be relatively compared with one another. As used herein, the term "standardize" refers to a process of scaling one or more values to allow values to be absolutely compared with one another or with other known values.

"Metabolomic data", "metabonomic data", "metabolomic profile" and "metabolomic fingerprint" refer to a measure of one or more metabolites in a biological fluid sample. In some embodiments, metabolomic or metabonomic data may comprise concentration measurements or relative concentration measurements for one or more metabolites in a biological fluid sample from a test subject.

"Analyte" as used herein refers to a compound dissolved or otherwise present in a solution. "Metabolite" refers to a metabolism product, intermediate or environmental chemical, for example present in a body fluid such as plasma. In some embodiments, the term "metabolite" may refer to small molecules, for example having a molecular weight less than 1700 Dalton.

"Biological sample" refers to a sample, such as a fluid, extracted from, produced by or otherwise obtained from a living animal, organism or tissue. In some embodiments, biological sample may be obtained from a human. In other embodiments, biological sample may be obtained from a non-human animal, for example a vertebrate such as a bird, a reptile, a mammal, an amphibian, or a fish. Accordingly, aspects of the present disclosure are useful for veterinary applications. In yet other embodiments, biological sample may be obtained from a plant. In yet other embodiments, biological sample may be obtained from an invertebrate. Useful biological samples may include, but are not limited to: plasma, urine, bile, cerebrospinal fluid, bronchoalveolar lavage fluid, saliva, tears, exhaled breath condensate, serum, whole blood, tissue extracts, cell extracts, sub-cellular fractions, mitochondrial sub-cellular fractions, and nucleic sub-cellular fractions.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure.

While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The methods of the disclosure are not limited to the steps described herein. The steps may be individually modified or omitted, as well as additional steps may be added.

Unless stated otherwise as apparent from the following discussion, it will be appreciated that terms such as "evaluating," "providing," "causing," "computing," "combining," "comparing," "generating," "determining," "obtaining," "processing," "computing," "selecting," "estimating," "storing," "displaying," "transmitting," "retrieving," "receiving" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure.

The computer-readable storage mediums, methods, and systems, described herein are useful for analyzing samples via mass spectrometry. Aspects described herein include computer-readable storage mediums, methods, and systems for normalizing mass spectrometry data, computer-readable storage mediums, methods, and systems for standardization of metabolic profiles, and computer-readable storage mediums, methods, and systems, for comparing mass spectrometry data obtained from different mass spectrometers and/or at different times or on dates. Computer-readable storage mediums, methods, and systems described herein may be useful for reducing errors based on instrument response and ionization efficiencies and improving reproducibility of data from instrument to instrument and from day to day. These may also be useful in providing information regarding the operability of the instrument, such as accuracy of the instrument.

Normalization Method

FIG. 1 illustrates an overview of a method 100 for analyzing a sample via mass spectrometry according to some embodiments. In step 110, a primary reference set of mass spectrometry data for an external standard sample having one or more added isotopic standards may be provided. In some embodiments, providing a primary reference set of mass spectrometry data may include generating, selecting, and/or retrieving a primary reference set of mass spectrometry data. The primary reference set may be specific to a test sample and external standard sample. In some embodiments, the primary reference set may be selected from a plurality of primary reference sets. In some embodiments, the primary reference sets may be selected from sets stored locally. In other embodiments, the primary reference sets may be additionally or alternatively stored on a remote computer for use on that remote computer or another computer.

Figure 2:
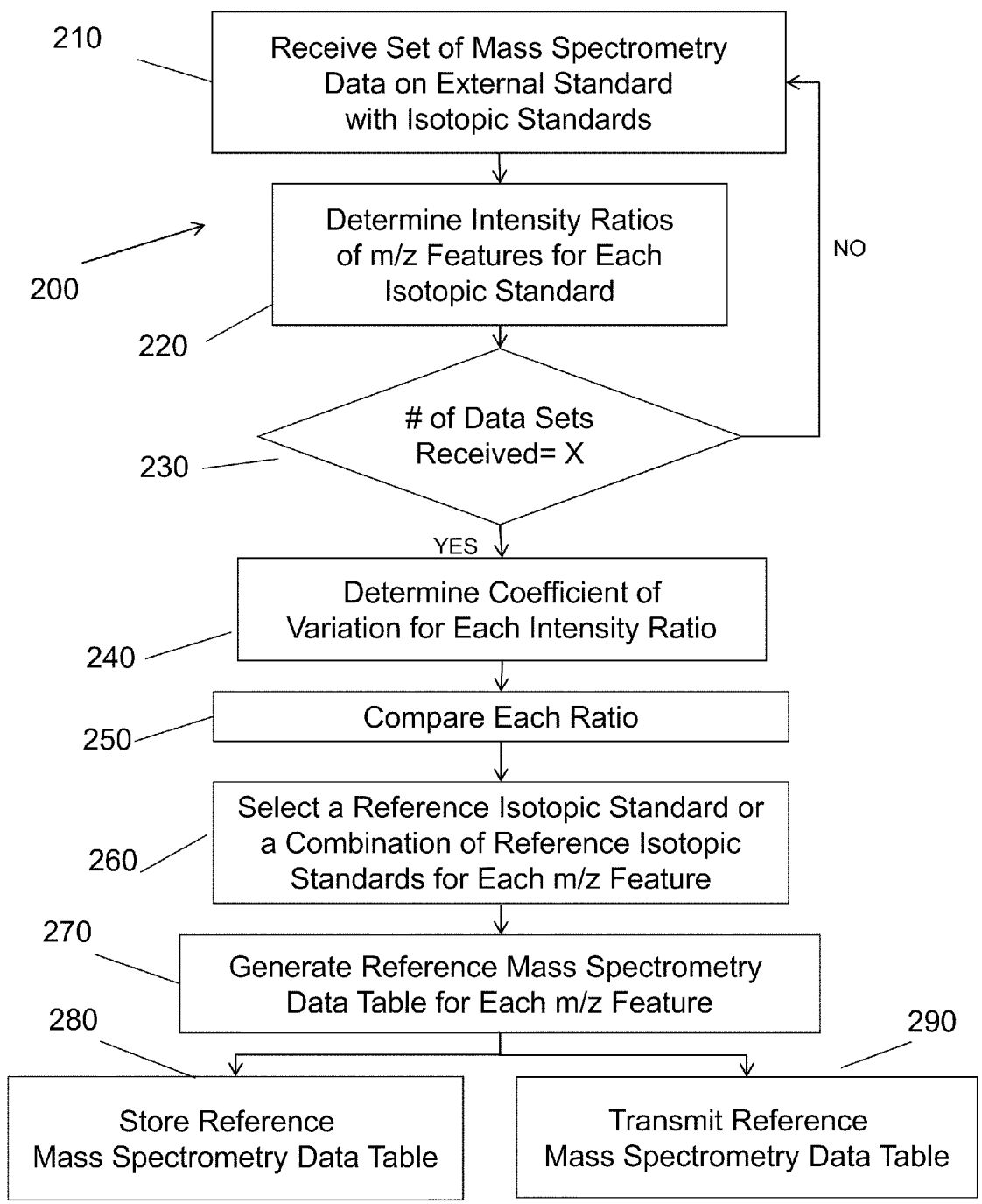
FIG. 2 provides an overview of embodiment method for generating a normalization data table according to an embodiment.

In some embodiments, the reference mass spectrometry data set may be generated as a data table or database. FIG. 2 illustrates an overview of a method 200 for generating such a data table according to some embodiments. First, in step 210, a mass spectrometry data set for an external standard sample having one or more added isotopic standards may be received from an analytical system (such as a mass spectrometer). Next, in step 220, intensities of m/z features in the mass spectrum may be ratioed with intensities of features corresponding to each of the isotopic standards to determine intensity ratios. As shown in step 230, these steps may be optionally repeated at certain times to allow for sufficient repeat measurements to determine coefficients of variation for each intensity ratio. In some embodiments, these steps may be repeated until data for five, ten, or any number of runs have been received. In other embodiments, steps 210 and 220 may be performed once before determining the coefficient of variation for each intensity ratio. After a predetermined number of the intensities of m/z features in the mass spectrum are ratioed, the coefficient of variation for each intensity ratio for each feature may be determined in step 240. The method is not limited to determining the coefficient of variation for each intensity ratio for each feature. In other embodiments, other parameters for each intensity ratio for each feature may be determined in step 240. In further embodiments, step 240 may be omitted.

Some embodiments may include steps 250 and 260 if a plurality of sets of mass spectrometry data were received. If more than one set of mass spectrometry data was received, each ratio may be compare d in step 240. In some embodiments, the coefficient of variation for each feature provided in each set may be compared in step 250. In other embodiments, other parameters of the ratio may be compared. Then, in step 260, one or more coefficient of variations or parameters may be selected as the reference isotopic standard or combination of reference of isotopic standards for each m/z feature to generate the reference mass spectrometry data table. The reference isotopic standard or combination of reference isotopic standards may be selected based on criteria. In some embodiments, the "criteria for selecting reference isotopic standard or combination of reference isotopic standards may be based on the coefficient of variation for each feature. In some embodiments, the criteria may include the lowest coefficient of variation for the feature. In other embodiments, other criteria may be used to select the reference isotopic standard or combination of reference isotopic standards for each feature. If other criteria are used to select a reference isotopic standard or a combination of reference isotopic standards for each m/z feature, steps 240 through 260 may also be adjusted accordingly.

Then, a reference mass spectrometry data table may be generated in step 270. After the table is generated, in some embodiments, the data table may be stored as shown in step 280. In some embodiments, the data table may be stored on the computer generating the data table. In other embodiments, additionally or alternatively, in step 290, the data table may be transmitted to another computer for further processing, storing, and/or displaying (or causing to display or store). Additionally, the generated data table may be displayed on the computer generating the data table.

Figure 3:
FIG. 3 provides an excerpt of an exemplary normalization data table.

In some embodiments, the data table may be populated with entries for m/z features in the mass spectrum, for example entries showing mass to charge ratio of the feature (m/z), retention time for the feature, reference isotopic standard or a combination of reference isotopic standards, and the ratio of the intensity of the feature to the intensity of the reference isotopic standard or a combination of reference isotopic standards. In some embodiments, the data table may include all of these entries. In other embodiments, the data table may include some or additional entries. FIG. 3 shows an excerpt from an example data table. As shown in table 300, column 310 lists the m/z features in the mass spectrum, column 320 lists the retention time for the feature, column 330 lists the reference isotopic standard, and column 340 lists the ratio of the intensity of the feature to the intensity of the reference isotopic standard. In the table 300, the reference isotopic standard is the lowest coefficient of variation for the feature.

Next after the reference mass spectrometry data table for an external standard with isotopic standards is selected, in step 120, a set of mass spectrometry data for a test sample having the one or more added isotopic standards may be received from an analytical system (e.g., a mass spectrometer). After which, the method may further include an optional step 130 of receiving mass spectrometry data on an external standard sample with isotopic standards.

Mass spectrometry data on an external sample may be received any time. For example, the mass spectrometry data on test sample may be received concurrently with the mass spectrometry data on external standard sample. In other embodiments, the mass spectrometry data on test sample may be received before or after the mass spectrometry data on the external standard sample is received. In further embodiments, the mass spectrometry data on the external standard sample may be received more than once. For example, the mass spectrometry data on the external standard sample may be received before and after the mass spectrometry data on test sample is received; alternatively, the mass spectrometry data on the external standard sample may be received concurrently and before and/or after the mass spectrometry data on test sample is received.

In some embodiments, mass spectrometry data on an external standard may be received every time mass spectrometry data on a test sample is received. In other embodiments, mass spectrometry data on an external standard may be received at specific times during the analysis of a batch of an external standard. In further embodiments, the External Reference Sample may be run a plurality of times for each instance mass spectrometry data on an external standard should received, and thus a plurality of sets of data on an external standard may be received at a specific interval or time. For example, the External Reference Sample may be run in duplicate at certain times and thus two sets of data on an external standard may be received every time mass spectrometry data on a test sample is received or at specific times.

Figure 4:
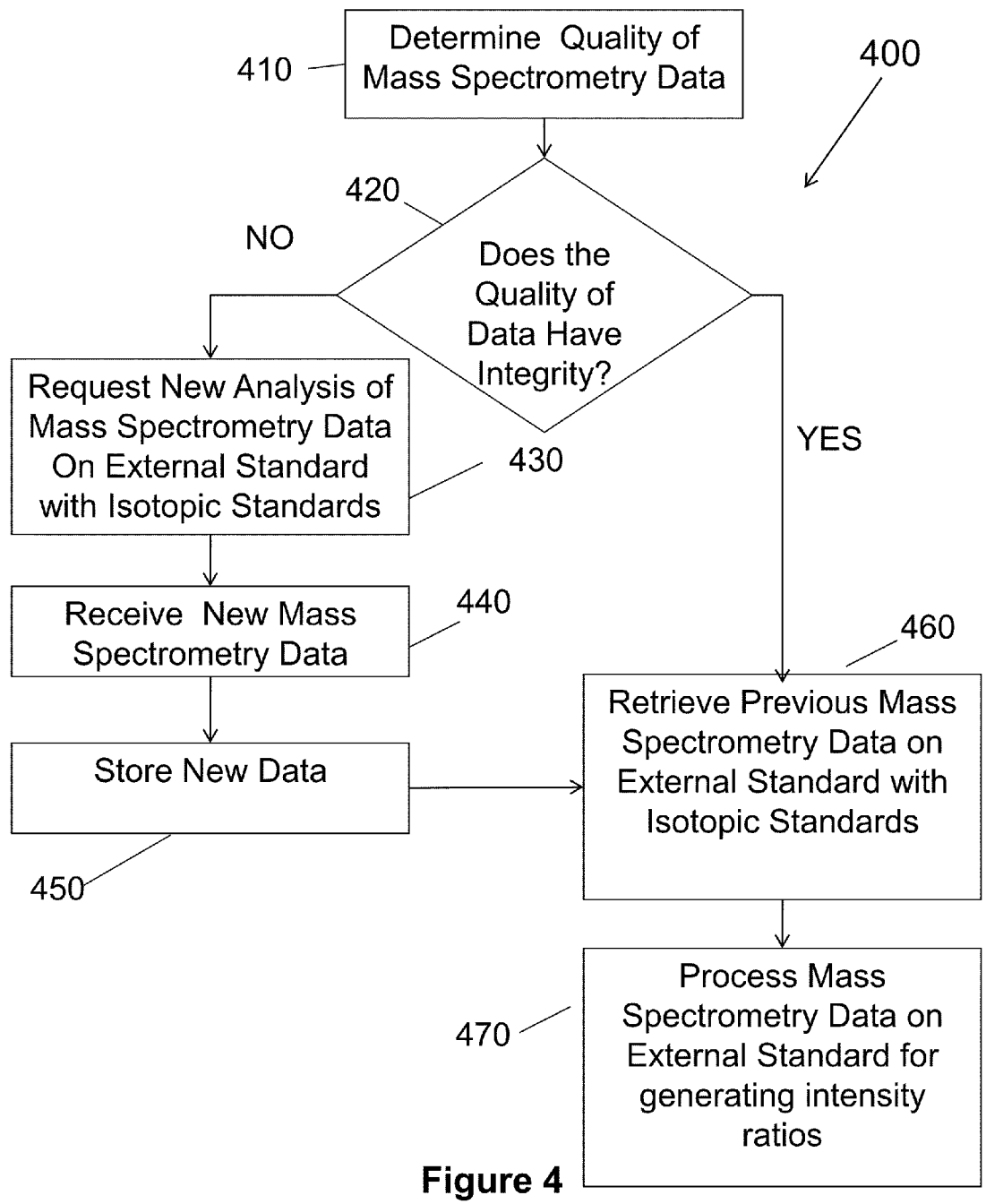
FIG. 4 provides an overview of a method for receiving mass spectrometry data on an external standard with isotopic standards according to an embodiment.

FIG. 4 illustrates an overview of a method 400 for receiving mass spectrometry data on an external standard with isotopic standards according to some embodiments. As shown in FIG. 4 in step 410, the quality of the mass spectrometry data may determine. In some embodiments, the quality of data with respect to the test sample may be determined. In other embodiments, the quality of data with respect to the external standard may be evaluated. The quality of the data may be evaluated to determine whether new or more current mass spectrometry data on an external standard should be received. In some embodiments, the quality of data may determine that a new external standard should be used. Next, in step 420, the quality of data is evaluated to determine whether the data has integrity. In some embodiments, the quality of data may be based on the number of test sample sets received. For example, if the number of test sample sets is greater or equal to a certain number, the data may not be considered to have "integrity." The number of test samples may be associated to the operating condition of the analytical instrument. For example, after the $19^{th}$ test sample, the data may not be considered to have integrity, so that at every $20^{th}$ sample, mass spectrometry data on an external standard should be received. Additionally, in some embodiments, mass spectrometry data on an external standard may be received before or right after mass spectrometry data on a first test sample. In other embodiments, the quality of the data may be determined based on other criteria. For example, the data may indicate that the external standard used is no longer viable.

In some embodiments, if the data is determined to have "integrity," then the previous mass spectrometry data on external standards that was received may be retrieved in step 460. In some embodiments, the previous mass spectrometry data may be the most recent data received. In other embodiments, the previous mass spectrometry data may be all or some of the data received for any length of time. For example, the previous mass spectrometry data received that day may be retrieved. The data on external standard may then be processed for generating intensity ratios in step 470. In some embodiments, only the most recent data received is processed. In other embodiments, all or some of the previous data received for any length of time may be processed. For example, all or some of the previous mass spectrometry data may be averaged.

In some embodiments, if the data is determined not to have "integrity," then a request for a new analysis or run of the External Standard may be transmitted in step 430. In some embodiments, a request for a new External Standard may also be transmitted. After the new mass spectrometry data is received in step 440, the data may optionally be stored locally or remotely in step 450 before processing (step 470). In some embodiments, before the processing for the generation of intensity ratios (step 470), the data for previous External Reference Sample, may also be optionally obtained. The new and previous mass spectrometry data on external standard with isotopic standards may be processed before generating intensity ratios. For example, the new and previous mass spectrometry data may be averaged. In other embodiments, only the most recent or new mass spectrometry data may be processed to generate intensity ratios.

It will be understood that steps 430 and 450 are optional. In other embodiments, step 470, the processing of mass spectrometry data on an external standard may await to receive new mass spectrometry data if the data is not considered to have "integrity," before generating the intensity ratios.

In some embodiments, the data for the External Reference Samples may be stored. In further embodiments, the data for the External Reference Samples may be stored in data table. In further embodiments, the generated normalization factor for each m/z may be stored in a data table. In some embodiments, the data may be stored locally or remotely. Further, the data may provide be used to detail the operation of the instrument. For example, the data table may provide a way to correct variations in instrument response for every individual chemical feature. Further, in some embodiments, when a significant variation in the normalization factors is detected (by the system (embodiments described below), the system may display or transmit the operation status of the analytical instrument. In some embodiments, the operation status may be a request to change the operation of the analytical instrument.

In step 140, intensity ratio normalization factors for m/z features in the mass spectrum may be generated. In some embodiments, the intensity ratio normalization factors may be generated using the reference mass spectrometry data set and the received mass spectrometry data set. In other embodiments, the intensity ratio normalization factors may be generated using other normalization data in addition to or in alternative of the obtained mass spectrometry data set.

Next, in step 150, the normalized intensity ratios for features in the test sample mass spectrometry data set may be generated. In some embodiments, the normalized intensity ratios may be generated using the generated intensity ratio normalization factors. In other embodiments, the normalized intensity ratios may be generated based on the reference mass spectrometry data table alone.

Although steps 120 through 150 are shown in a specific order, it will be understood that steps 120 through 150 may occur in any sequence or at any time. In other embodiments, the method may not include steps 130 through 140; if the method does not include steps 130 through 140, then the normalized intensity ratios may be generated based solely on the reference mass spectrometry data table.

After the normalized intensity ratios are generated, in some embodiments, the ratios may be stored as shown in step 160. In some embodiments, the ratios may be stored on the computer generating the ratios. In other embodiments, additionally or alternatively, in step 170, the ratios may be transmitted to another computer for further processing, storing, and/or displaying. Additionally, the generated ratios may also be displayed on the computer generating the ratios.

Figure 5:
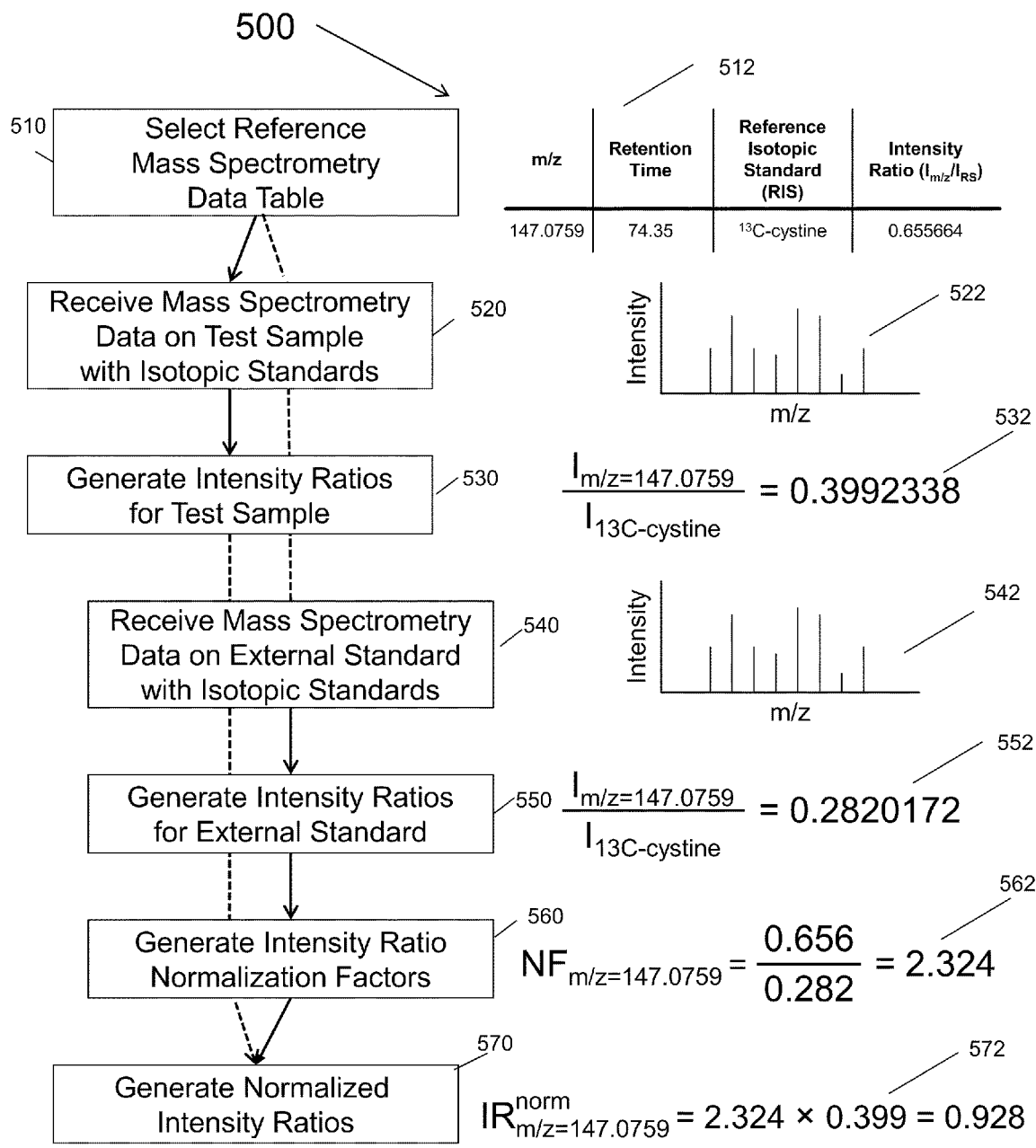
FIG. 5 provides an overview of a method for analyzing a test sample via mass spectrometry according to an embodiment.

FIG. 5 illustrates an overview of a method 500 for normalizing mass spectrometry data according to some embodiments, including a sample calculation next to the corresponding step. Initially, in step 510, a reference mass spectrometry data table for the test sample to be normalized listing reference isotopic standards for m/z features and ratios for the intensity of the features to the intensity of the reference isotopic standards may be selected. As shown in the excerpt 512 (from a data table for that test sample), the reference isotopic standard for m/z 147.0759 is 13C-cystine. The reference mass spectrometry data table may be selected from a plurality of reference mass spectrometry data tables, each data table for a specific feature or sample. Next, in step 520, a mass spectrometry data set for a test sample having one or more added isotopic standards may be received from an analytical system (such as a mass spectrometer). The intensity for that feature is shown as a graphical representation in 522. Next, in step 530, the intensity ratios for the test sample may be generated. Intensity ratios may be computed for the features in the mass spectrum, such as ratios of the intensity of the features to the intensity of the reference isotopic standard. An example of an intensity ratio calculation for a test sample is shown in 532.

The intensity ratios may be then normalized. As shown in step 540, to another (a second) mass spectrometry data set on an external standard sample having one or more added isotopic standards may be received. In some embodiments, the mass spectrometry data set on an external standard sample may be received according to method 400 shown in FIG. 4. In this embodiment, the external standard sample is the same as used for generation of the reference data table. Intensity ratios may be generated, as shown in step 550, for the features in the mass spectrum, such as ratios of the intensity of the features to the intensity of the reference isotopic standard. An example of an intensity ratio calculation for an external standard is shown in 552.

Next, these intensity ratios may then be ratioed to the intensity ratios from the reference data table to generate normalization factors in step 550. An example of an intensity ratio normalization factor calculation is shown in 552.

Although steps 520 through 550 are shown in a specific order, it will be understood that these steps are not limited to that sequence. Like steps 130 through 150, steps 520 through 550 may occur in any sequence or at any time.

Finally, the normalization factors may then be used to normalize the intensity ratios for the test sample, as shown in 560, thereby generating normalized intensity ratios. An example of a normalization intensity ratio calculation is shown in 562.

Figure 6:
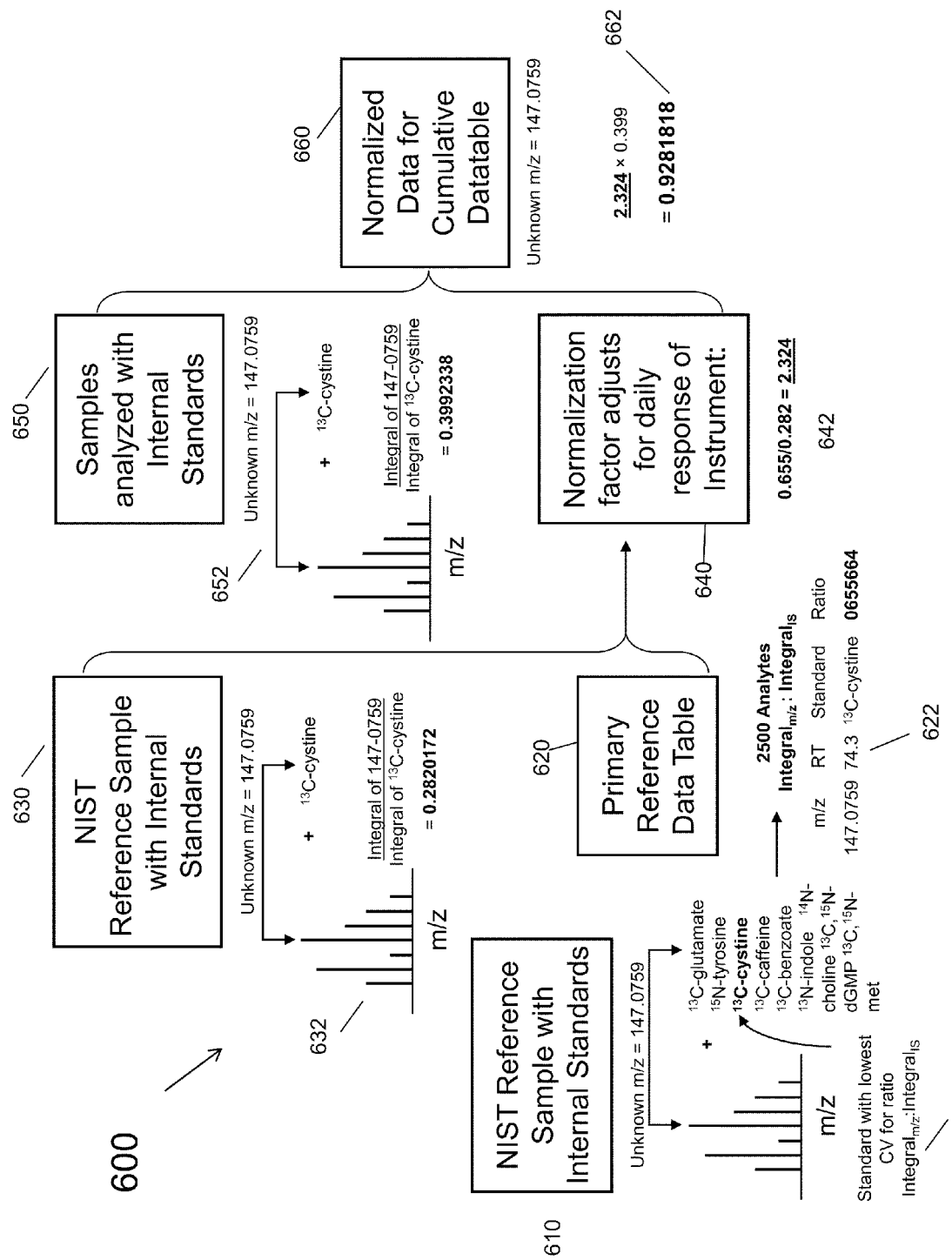
FIG. 6 provides an overview of an embodiment for analyzing a sample via mass spectrometry using NIST standards as reference samples.

After the normalized intensity ratios are generated, like method 100, in some embodiments, the ratios may be stored. In some embodiments, the ratios may be stored on the computer generating the ratios. In other embodiments, additionally or alternatively, the ratios may be transmitted to another computer for further processing, storing, and/or displaying. Additionally, the ratios may also be displayed on the computer generating the ratios. FIG. 6 illustrates an overview of a method 600 for analyzing a sample via mass spectrometry using NIST standards as reference samples, according to some embodiments. First, as shown in step 610, duplicate mass spectra data for a NIST reference sample having one or more added internal standards may be received. An example of mass spectra data is shown in 612. Next, in step 620, a primary reference data table may be generated. To generate the data table, intensity ratios of features in each mass spectrum may be generated, where intensities of features are ratioed to each of the intensities of the added internal standards. The internal standard with the lowest intensity ratio coefficient of variation (CV) may be selected as the reference internal standard and the primary reference data table may be generated. An example of an intensity ratio normalization calculation is shown in 622.

Next, in step 630, the NIST reference sample having the one or more added internal standards may be run again on the mass spectrometer and normalization factors are computed, for example to adjust the daily response of the instrument. An example of an intensity ratio normalization calculation is shown in 632. The NIST reference sample may be run any time after the primary reference table is generated. In some embodiments, the NIST reference sample may be run concurrently with the analysis of a test sample. In other embodiments, the NIST reference sample may be run before or after the analysis of a test sample. In further embodiments, the running of the NIST reference sample may be repeated at different times.

As above, in step 640, the normalization factors may be calculated as ratios of intensity ratios. An example of an intensity ratio normalization factor calculation is shown in 643. In step 650, the test sample may be run on the mass spectrometer. An example of mass spectra data for the test sample is shown in 650. Then, in step 660, the intensity ratios for features in the spectrum may be normalized using the generated normalization factors. An example of an intensity ratio normalization calculation is shown in 662. Optionally, these normalized intensity ratios may then be added to a cumulative data table, for example to allow cumulative tracking of the changes of the intensity ratios as a function of time.

System Implementation

Figure 7:
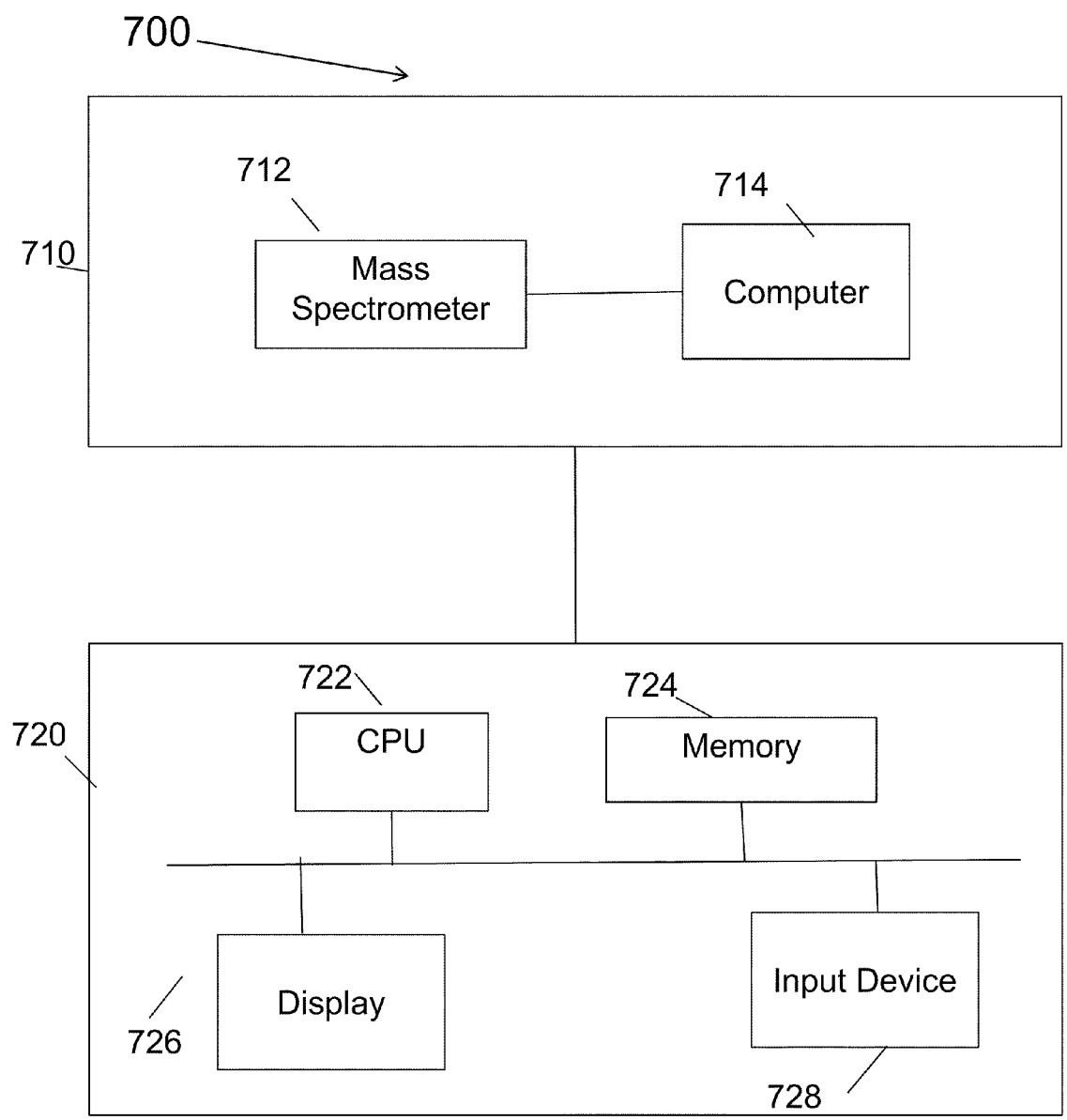
FIG. 7 shows an example of a system for generating normalized ratios according to an embodiment.

Although not limited to any particular hardware configuration, the present method may be implemented as software by a system. FIG. 7 shows an example of a system 700 that is capable of analyzing and obtaining mass spectroscopy data. The system 700 may include an analytical system 710 that is communication with a computer system 720. In some embodiments, the analytical system 710 may include an analytical instrument 712 capable of analyzing mass spectroscopy data. In some embodiments, the analytical instrument 712 may be any known mass spectrometer having any known configuration. In some embodiments, the analytical instrument 710 may be an LC-MS instrument having any known configuration. The analytical system 710 may further, optionally, include a computer 714 for controlling the analytical instrument 712. The computer may have a similar configuration as computer system 720.

The computer system 720 may be configured to receive mass spectroscopy data from the analytical instrument 710. In some embodiments, the computer system 720 may be a local computer system that is locally connected to the analytical instrument 710 (i.e., a local computer system) by local area network connections. In other embodiments, the computer system 720 may be a remote computer system that is configured to communicate with the analytical instrument 710 by the internet or other network connections. In some embodiments, the local computer system may be configured to process and generate the normalized intensity ratios. In other embodiments, the local computer system may transmit the mass spectroscopy data to a second, remote, computer system for some or all of the processing and generating of the normalized intensity ratios. In some embodiments, the remote computer system may communicate with a plurality of local computer systems and/or analytical instruments.

The computer system 720 may include a number of modules that communicate with each other through electrical and/or data connections (not shown). Data connections may be direct wired links or may be fiber optic connections or wireless communications links or the like. The computer system 720 may also be connected to permanent or back-up memory storage, a network, or may communicate with a separate system control through a link (not shown). The modules may include a CPU 722, a memory 724, an input device 726, and a display 728. The computer system 720 may also be connected to another computer system as well as a network.

The CPU 722 may be one or more of any known central processing unit, including but not limited to a processor, or a microprocessor. The CPU 722 may be coupled directly or indirectly to memory elements. The memory 724 may include random access memory (RAM), read only memory (ROM), disk drive, tape drive, etc., or a combinations thereof). The memory may also include a frame buffer for storing image data arrays.

The described processes (e.g., FIGS. 1 and 2 through 6) may be implemented as a routine that is stored in memory 724 and executed by the CPU 722. As such, the computer system 720 may be a general purpose computer system that becomes a specific purpose computer system when executing the routine of the disclosure. The computer system 720 may also include an operating system and micro instruction code. The various processes and functions described herein may either be part of the micro instruction code or part of the application program or routine (or combination thereof) that is executed via the operating system. In addition, various other peripheral devices may be connected to the computer platform such as an additional data storage device, a printing device, and I/O devices.

The input device 728 may include a mouse, joystick, keyboard, track ball, touch activated screen, light wand, voice control, or any similar or equivalent input device, and may be used for interactive geometry prescription. The input device 728 may control the production, display of images on the display 726, and printing of the images by a printer interface. The display 726 may be any known display screen. The computer system may also include a printer interface, which may be any known printer, either locally or network connected.

EXAMPLES

The disclosure may be further understood by the following non-limiting examples.

Example 1: Internal Standard-External Reference Sampling Procedure for Normalization of Samples Detected by Mass Spectrometry Liquid chromatography-mass spectrometry (LC/MS) can yield over 2000 reproducible features representing hundreds to more than a thousand chemicals from a single drop of blood in 10 min. Because of the short run time, routine use allows for analysis of a large number of samples per day by a single investigator on a single mass spectrometer. However, the power of this technique cannot be fully utilized unless data from different laboratories is quantitatively comparable. The disclosed normalization procedure allows comparisons of chemical features from a large number of samples collected at different times or by different mass spectrometers. Implementation of this normalization procedure to metabolic data collected on any LC/MS allows for cumulative datasets where comparisons can be made. This is useful for research and clinical medicine.

The Internal Standard-External Reference Sample normalization procedure for human plasma requires a reference human plasma sample and a stable isotopic standard mixture. For instance, the reference plasma sample can be created by mixing plasma from multiple healthy individuals. This reference sample is then combined with the stable isotopic standard mixture to create an External Reference Sample.

A stable isotopic standard mix is selected to cover a broad range of properties represented in low molecular weight chemicals. For instance, stable isotopic standard mix A includes [$^{13}C_6$]-D-glucose, [$^{15}N$]-indole, [2-$^{15}N$]-lysine dihydrochloride, [$^{13}C_5$]-L-glutamic acid, [$^{13}C_7$]-benzoic acid, [3,4-$^{13}C_2$]-cholesterol, [$^{15}N$]-L-tyrosine, [trimethyl-$^{13}C_3$]-caffeine, [$^{15}N_2$]-uracil, [3,3-$^{13}C_2$]-cystine, [1,2-$^{13}C_2$]-palmitic acid, [15N,$^{13}$C5]-L-methionine, and [$^{15}N$]-choline chloride. Concentrations of the stable isotopic standards in this isotope mix are set to useful values within the dynamic range of the instrument. For example, this can be similar to the fasting plasma concentration for common metabolites or set to give a final concentration of, for example, 10 μM. The same isotopic standard mix is added as an Internal Standard to each plasma test sample at the same concentrations as added to the External Reference Sample. This allows direct comparison of instrument response by detection of each m/z feature relative to the low molecular weight chemical found in the stable isotopic standard mix.

Creation of the Original Normalization Data Table for the Procedure:

A normalization table provides a method to normalize data for a sample set to a common standard to correct for instrument response. This allows all data regardless of instrument or analysis time to be normalized to a common response pattern. An example normalization table was created from 8 replicate analyses (shown in FIG. 3) of the External Reference Sample. An m/z data table was generated with associated integrals for each of the 8 analyses. The integrals for each m/z were referenced against the integrals of each of the stable isotopic standards, and the ratio providing the lowest coefficient of variation is selected to represent the reference isotopic reference for normalization of that particular m/z. The normalization data table was then created in which each m/z feature has a corresponding value representing the ratio of the area of the m/z to the area of the appropriate isotopic reference. When a new External Reference Sample or Isotopic Standard Mix is prepared, a corresponding normalization data table is created to allow data based on the new standards to be compatible with the original data table. Once the concentration of a specific chemical has been determined in the External Reference Sample, these values are used to estimate concentrations in the test samples.

Use of the Normalization Procedure in Test Sample Sets:

a. An External Reference Sample is run in duplicate at the beginning and after every 20th sample. A standard table is created in which each m/z feature has a corresponding value representing the ratio of the area of the m/z to the area of the appropriate stable isotopic reference. These areas are then used to create a normalization factor (relative to the Original Normalization Data Table) for the instrument response for each m/z feature. The table of these normalization factors for each m/z provides a way to correct for variations in instrument response for every individual chemical feature.

b. The isotopic standard mix is included in each sample, and each sample is run in duplicate. A data table is created in which the integral for each m/z feature is ratioed to the respective isotopic reference, and then normalized for instrument response (using the normalization factor determined in part a) to provide a quantitative measure of that m/z feature. Each m/z is now in a form that has been normalized for instrument response for that particular feature. The data table containing these normalized values is now comparable to other normalized sample sets independent of instrument or analysis time. This provides a platform in which concentrations of unknowns can be determined retrospectively when chemical structure is established and the Original Normalization Data Table is calibrated with appropriate authentic standards.

The advantages of the current normalization procedure are that it has been tested with smaller biomolecules with a mass range of m/z 85-850 that are more chemically diverse (nucleotides, amino acids, lipids, pyrroles, alcohols, amines, etc.). Further, this method of normalization utilizes an external reference sample and internal standard to account for intra- or inter-instrument variability.

Normalization using this procedure minimizes the difficult problem of reproducibility in chromatographic elution because the mass resolution and mass accuracy are sufficient to resolve >90% of the m/z features without consideration of the elution time for some applications. The procedure also corrects for different ionization efficiency by normalizing the peaks using multiple internal and external standards to establish an instrument response factor for each mass spectrum.

Example 2: A Top-Down LC-FTMS Method for Clinical Metabolomics Using Reproducible Mass-to-Charge Features of Plasma Fourier-transform Ion Cyclotron Resonance mass spectrometry (FTMS) has sufficient mass resolution and mass accuracy to provide a predicted elemental composition for ions in the m/z range of many small biomolecules. This example describes a method using LC-FTMS to quantify features in plasma based upon m/z. The method uses a $C_{18}$ pre-column for desalting, a short anion exchange liquid chromatography column for separation and FTMS for detection. A self-adjusting peak detection routine quantifies m/z features based upon ion intensity. The method detected 2,124 reproducible features in 10-min analyses of 10 µL it extracts of human plasma. Predicted elemental compositions for 22% of these features matched metabolites in the Madison Metabolomics Consortium Database (MMCD). Most features were common to different individuals and had coefficients of variation of <10%. Statistical analysis showed 770 features contributed to inter-individual variation. Intra-sample, inter-sample and inter-column variability testing established validity for statistical comparisons within sample sets up to 80 samples run in duplicate. Thus, the results establish an approach for an integrated view of human metabolism, or "top-down" metabolic profiling which can be used for discovery of metabolic associations of disease regardless of whether the chemical identities of the metabolites are known.

The profile of metabolites in human plasma reflects the product of all influences, such as genetics, epigenetics, diet, behavior and environmental exposures, that affect health outcome and disease state. Development of a method that provides rapid, reproducible metabolic profiles could therefore be useful to evaluate and predict health and monitor disease risk, leading to personalized medicine.

Researchers have developed GC-MS and LC-MS methods designed to monitor the changes in the metabolic profile brought about by experimental, environmental and dietary changes. One of the most important findings of these studies is 70-90% of the metabolic features detected do not correspond to known metabolites. MS/MS studies on selected unknowns show product ion spectra common to organic biomolecules suggesting these unknowns are uncharacterized metabolites. Because of the high percentage of unknown metabolites found in biological samples, there is need for methods to obtain accurate, reproducible metabolic profiles independent of the chemical identity.

The present example describes a rapid LC-FTMS method that relies on the high mass accuracy and mass resolution of the FTMS to generate a metabolic profile of human plasma. The method was tested for reliability and reproducibility using a self-adjusting peak identification and quantification method along with bioinformatics and biostatistical analyses. The results establish the utility of the method for sample sets up to 80 samples run in duplicate. With appropriate normalization procedures, the method can be applied to large scale epidemiologic studies for discovery of new metabolic determinants of disease.

Experimental:

Materials. Sodium bicarbonate, heparin, acetonitrile (HPLC grade) and water (HPLC grade) were from Sigma-Aldrich (St. Louis). Formic acid (puriss. p.a. 98%) was from Fluka.

Human Subjects.

This study was approved by the Emory University Institutional Review Board (Protocol #581-2006). Subjects were recruited from Emory University and were self-described as healthy. This is a methods development protocol; there were no inclusion or exclusion criteria for participation other than voluntary participation and informed consent. Demographic information and personal health information were not collected. Each participant gave his/her informed consent prior to inclusion in the study.

Sample Collection and Preparation.

Blood was collected with a 21-gauge butterfly needle from the antecubital vein, and 1.35 mL was added to 0.15 mL of solution containing 90 mM ammonium bicarbonate and 2.5 mg/mL heparin. The tubes were inverted twice to mix and then centrifuged at 13,000 g for 2 minutes. Plasma aliquots were stored at −80° C. Acetonitrile was added to plasma (2:1) to precipitate protein. Samples were centrifuged at 13,000 g for 5 min and supernatant was stored at 4° C. until injected onto the LC-FTMS.

High Pressure Liquid Chromatography.

Analyte separation was done with a Hamilton PRPX-110S (2.1×10 cm) anion exchange column using a formic acid gradient. Preliminary studies showed that inclusion of a short, end-capped $C_{18}$ pre-column (Higgins Analytical Targa guard) was necessary for desalting and optimal separation. Initial chromatographic conditions were the same as described in J. M. Johnson, F. H. Strobel, M. Reed et al., Clin Chim Acta 396 (1-2), 43 (2008); however, a number of lyso-phosphatidylcholine species accumulated on the column, causing ion suppression and loss of sensitivity. Consequently, a column wash, using 2% formic acid in acetonitrile, was introduced between analyses. The minimum wash time to prevent accumulation of the phospholipids was 10 minutes. To avoid loss of analysis time during the wash, a Switchos (LC Packings) column switch was used to allow collection of data from a second column while the first column was undergoing an off-line wash.

The final chromatography consisted of a 2-min period of 0.1% formic acid in 1:1 water, acetonitrile mix (solution A), followed by a 6-min gradient from 0.1% to 1% formic acid (constant 50% acetonitrile) and 2 min at 1% formic acid to elute strongly anionic chemicals. The flow rate was 0.35 ml/min. At 10 min, the columns were switched and initial conditions of 0.1% formic acid were run for 2 min at 0.5 ml/min to equilibrate the new column prior to the next injection.

Mass Spectrometry.

Analyte detection was done with a Thermo LTQ-FT (Thermo Fisher, San Diego, Calif.). The maximum scan range for optimum ion transfer efficiency to the ion cyclotron resonance (ICR) cell is one decade; because a solvent peak was observed at m/z=82, the decade was selected to cover m/z from 85 to 850. This range includes 91% of a compiled list of 1,464 human metabolites (see Table 1, below). Ionization parameters were optimized using a standard mixture containing methionine, carboxymethyl-cysteine, cystine, cysteine-glutathione disulfide, carboxymethyl-glutathione and glutathione disulfide. A single microscan was unable to effectively detect both lower and higher molecular weight chemicals within this mixture, so a wide range scan was used. Optimum conditions were a spray voltage of 5.5 kV, sheath gas of 40 (arbitrary units), capillary temperature of 275° C., capillary voltage of 44 V and tube lens of 120 V. Ion transfer optics was tuned automatically.

FT-ICR parameters were tested to produce the shortest scan time which retained the sensitivity to detect a maximum number of reproducible features while still maintaining high mass accuracy and mass resolution. For this purpose, plasma samples were used along with a peak selection routine which excluded random signals and eliminated features present in the background. Mass resolution of 50,000 was chosen because it increased the scan speed to 500 msec while still maintaining resolution within the chosen m/z decade. The maximum number of ions collected in the ICR cell for each scan was varied to test sensitivity vs. loss of mass accuracy due to ion-ion distortion. The optimum number of ions collected for each scan was $3 \times 10^6$.

Data Collection and Processing.

Data were collected continuously over the 10 min chromatographic separation and stored on the local computer hard drive as .raw files. These files were converted using Xcalibur file converter software (Thermo Fisher, San Diego, Calif.) to .cdf files for further data processing. A software package operating within the R framework was used for feature detection and development of metabolic feature tables containing m/z, retention time and ion intensity for each feature. The software performs 5 major processing steps: 1) A filter is used to reduce noise and detect regions of the spectrum that contain peaks. 2) Peaks are identified in the spectrum and summarized in terms of peak location (m/z and retention time), peak width and intensity. 3) Retention time is corrected across the spectrum in terms of a relative retention time. 4) Peaks are aligned across multiple spectra. 5) Spectra are reanalyzed to capture peaks originally missed because of weak signal to noise filter. Once a feature table was obtained, the apLCMS package was used for 3D visualization. Further downstream analyses were performed in R, including determination of coefficients of variation (CV), the analysis of underlying structure using Principal Component Analysis (PCA), and the identification of metabolites that are present in different amounts using the Statistical Analysis of Microarrays (SAM). The false discovery rate (FDR) was used to define statistical significance.

Results and Discussion.

Figure 8:
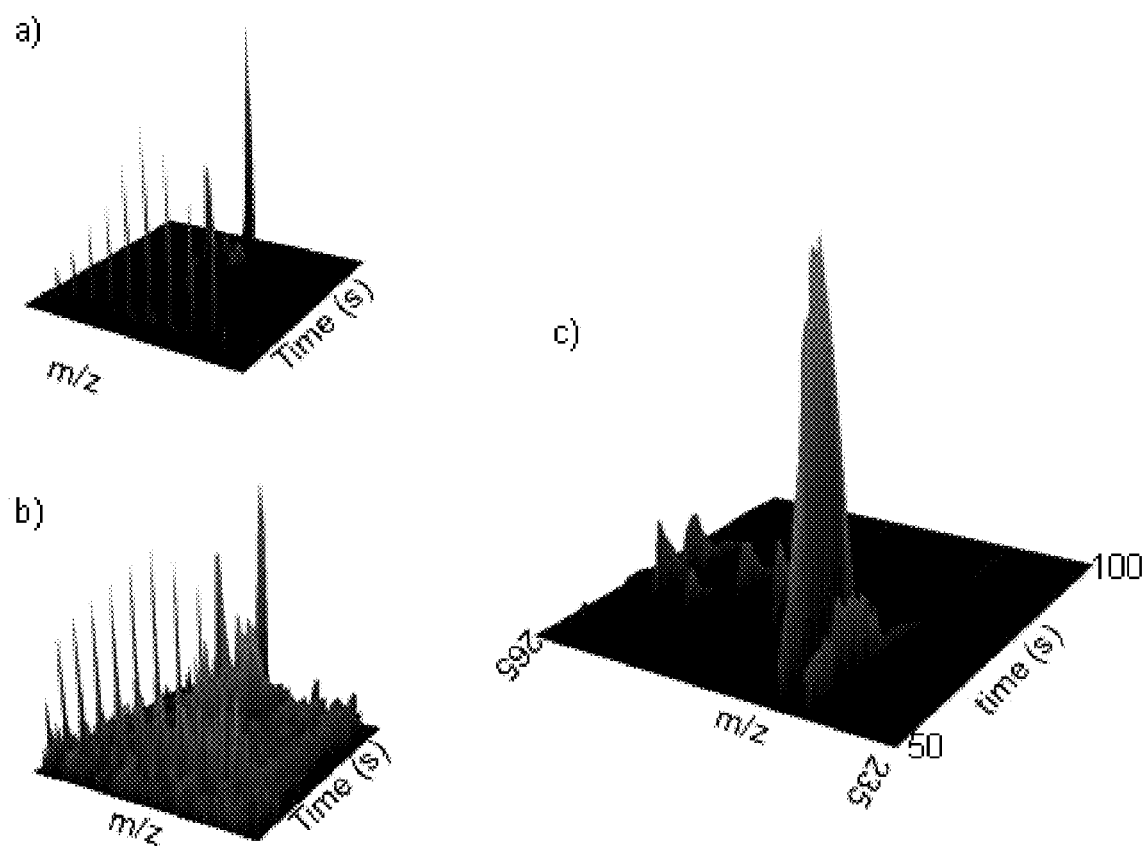
FIG. 8 provides data illustrating a feature profile of human plasma obtained by 10 minute LC-FTMS analysis.

To develop the method, six replicates of plasma extracts from 4 individuals were analyzed to determine the number of reproducible features detected and to test the signal reproducibility. The data were processed using the apLCMS program and 1,995 peaks were detected. A series of 3D plots were constructed from a representative spectrum to visualize the distribution of the data over the m/z and run time ranges (FIG. 8). The original spectrum shows large peaks corresponding to a series of sodium formate clusters at the beginning of the run (desalting of the plasma) and lyso-phosphatidylcholine species eluting toward the end of the run (FIG. 8a). Because of the high abundance of these features, we used a cube root transformation to view the distribution of lower intensity peaks (FIG. 8b). This landscape projection of m/z and RT clearly shows the complexity of the data in terms of the number of features detected. An expanded plot shows that individual m/z features elute with time as expected for discrete analytes (FIG. 8c). In the foreground [$^{13}C_2$]-cystine is seen, spiked into the plasma before processing, and endogenously produced cystine eluting at the same time. The smaller peaks in the background are unknown chemicals.

Figure 13:
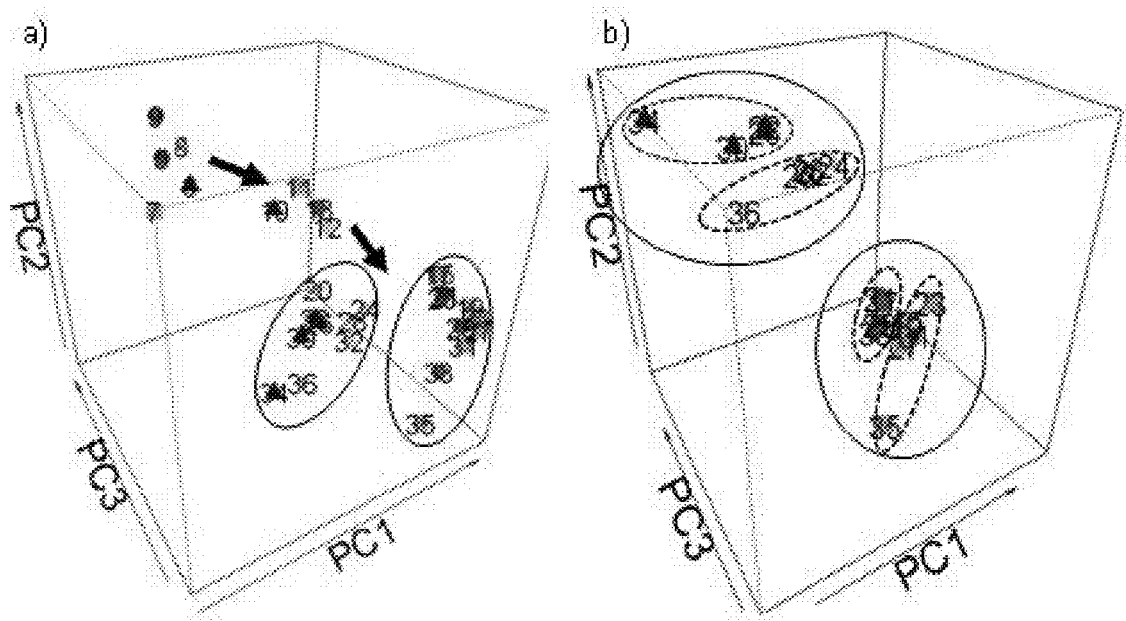
FIG. 13 provides an initial PCA analysis showing separation by run-time and column.

To determine the stability of detection with time, or average elution difference, multiple injections with the same sample were performed. Because it is difficult to visualize systemic change in all 1,995 features, a data reduction technique, Principal Component Analysis (PCA), was used to determine if systemic changes occurred in elution from run to run or if drift occurred over time. PCA showed a clear effect of injection number for the first 8-10 runs (4-5 on each column) before becoming reproducible (FIG. 13A). This showed that a wash-in time of 4-5 runs per column was needed for column stability before beginning to collect the data. Consequently, a 5-run wash-in for each column was added as a routine component of the method for initiation of analysis of new sample sets.

To determine whether metabolic profiles (obtained after an appropriate wash-in period) differed from series to series, PCA was performed for data collected concurrently from two columns with identical lot number but with a different history in terms of number of analytical runs. PCA showed clear separation for spectra obtained concurrently using different columns (FIG. 13B). Hence, either the columns with different histories do not capture the same metabolic information or the separations require a normalization procedure for combination into a common data set.

Figure 14:
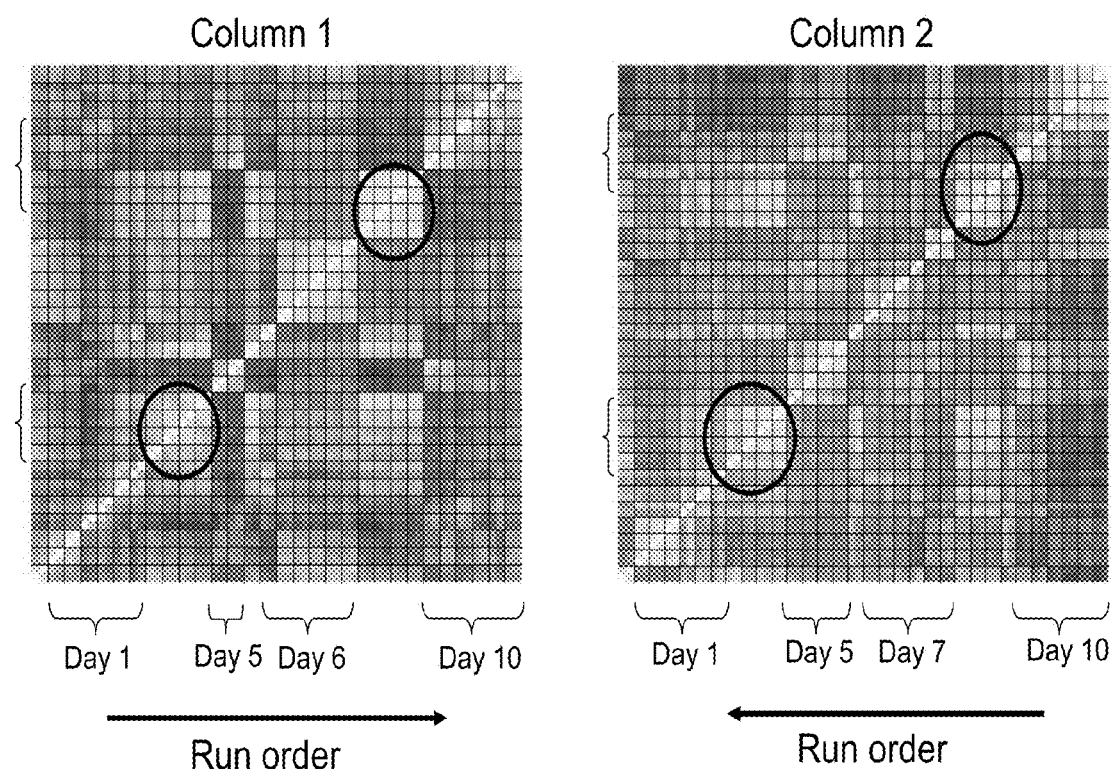
FIG. 14 provides a correlation analysis showing experimental results obtained from each column giving the same experimental answer.

It was hypothesized that the difference by column was largely an indication of the need for normalization between columns, i.e., that an experimental series would yield the same answer when analyzed separately on each of two columns even though the data from the two columns could not be combined for analysis. To test this hypothesis, plasma samples from an individual covering 34 time points over a 10 day period were used and the plasma analyzed concurrently, in duplicate, on two different columns. For each column, samples were alternately run in reverse order to test for patterns that drifted from run to run. Correlation analysis was run separately for each column; the two columns showed the same correlation patterns, and these patterns did not change over the length of the run or according to sample order (FIG. 14). In a parallel experiment, it was validated that results did not change for a series of up to 80 (data not shown). Consequently, these results demonstrate that after an initial wash-in, the data from the two columns provide the same metabolic patterns even though the individual spectra from the different columns cannot be directly combined for analysis.

Because of the high mass accuracy and high resolution of the FTMS, it is possible to predict elemental composition of small molecules so that tentative identities of common metabolites can be obtained. Because most human metabolic databases contain metabolites derived from xenobiotics and prescription drugs as well as endogenous metabolites derived from required nutrients, a database with 1,464 endogenously produced metabolites and 1,769 di- and tri-peptides with their calculated exact mass and m/z was created (Table 1). With the 1,995 features found in human plasma, the endogenous metabolism database was searched against the experimental m/z and found 209 (10%) matches. These matches include amino acids, carbohydrates, phospholipids and energy intermediates. In comparison, a search against the web-based Madison Metabolomics Consortium Database (MMCD) which includes plant metabolites, drugs and common environmental metabolites, restricting mass accuracy to 10 ppm, revealed 445 (22%) matches. Of these matches, 213 (12%) were represented by only one chemical in the database. Thus, the data show that most of the m/z features represent unknown chemicals in human plasma, highlighting a need to develop common feature tables to guide research in metabolic profiling for personalized medicine.

To investigate how many of these features represented isotopes and adducts of other chemicals, a sub-set ranging in size from 150-250 m/z was examined. Restricting inclusion to those present in at least 50% of analyses and resulted in a list of 150 features. Of these, 39% matched to the MMCD with a mass tolerance of 10 ppm. 7% matched our database of di-peptides. 2% were likely Na+ and K+ adducts of common metabolites and 2% corresponded to acetonitrile adducts of known metabolites with a [M+H]+ peak at the same retention time. 6% of the m/z values showed a significant (+2) isotopic pattern indicating the presence of the halogens Cl and Br. 1% showed a (+1) isotopic pattern indicating 13C and [M]+ and [M+H]+ isotopes, but most of the features were not at a significant intensity to visualize $^{13}C$ peaks. 1% was multiply charged species. These results show of the common m/z features detected, only 11% represent adducts, isotopes and multiple charged species.

To test the within series signal variation for detection of individual features in human plasma, samples from 4 individuals were run at least 6 times on the same column. A total of 2,124 features were detected in at least 1 spectrum with 1,847 being present in at least 25% of the spectra and 1166 present in 75% of the spectra. The number of features present in replicate samples was calculated to be: 88.8% in subject 1, 88.6% in subject 2, 87.4% in subject 3 and 86.2% in subject 4. These results show that duplicate analyses are sufficient to capture about 2,000 metabolic features.

Figure 9:
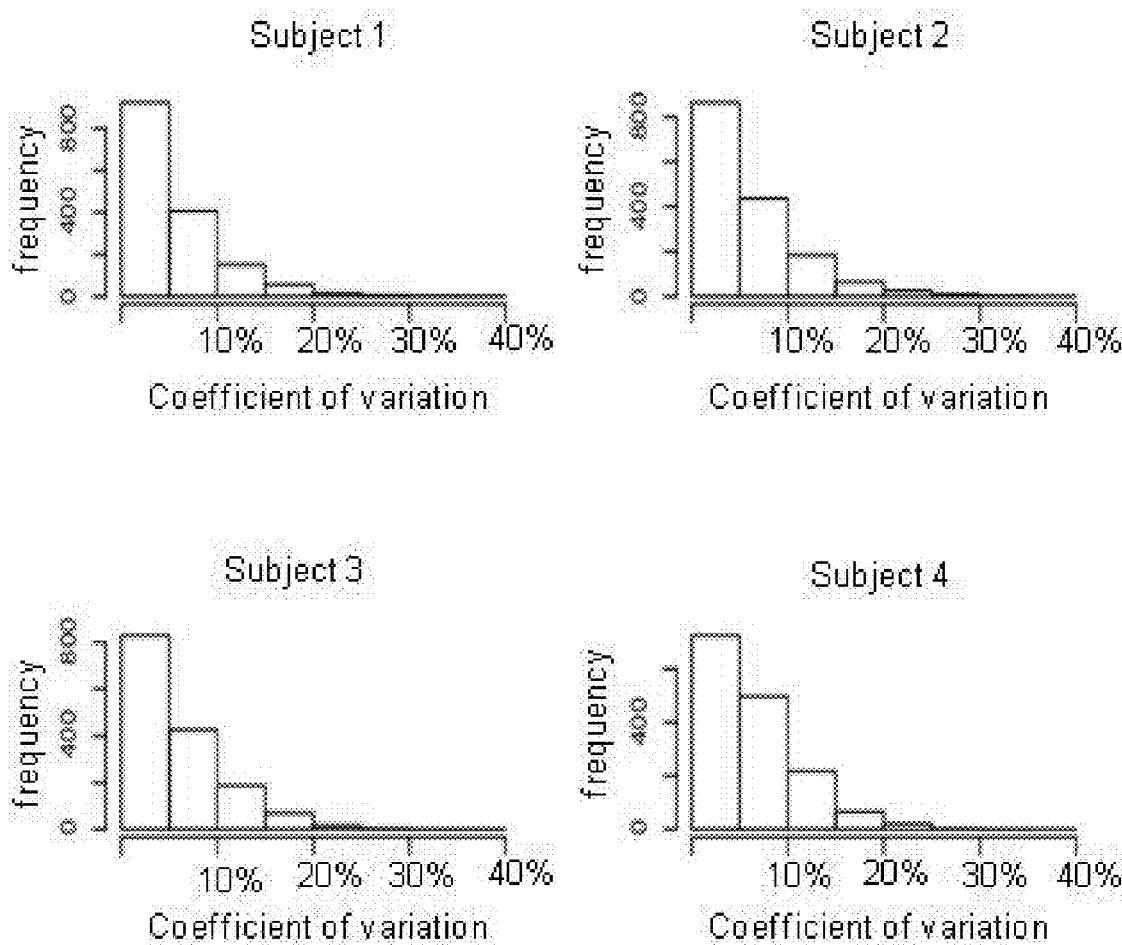
FIG. 9 provides data illustrating a histogram showing the number of peaks with ranges of signal variation from LC-FTMS analysis of human plasma from 4 subjects.

Coefficients of variation (CV) were calculated for the features that were detected in each individual (FIG. 9). For all 4 individuals, at least 80% of the features had a CV of less than 10%, and more than 90% of features had a CV less than 20%. Thus, the results show the method is highly reproducible for at least 1,700 of the features detected within a single sample set.

Figure 10:
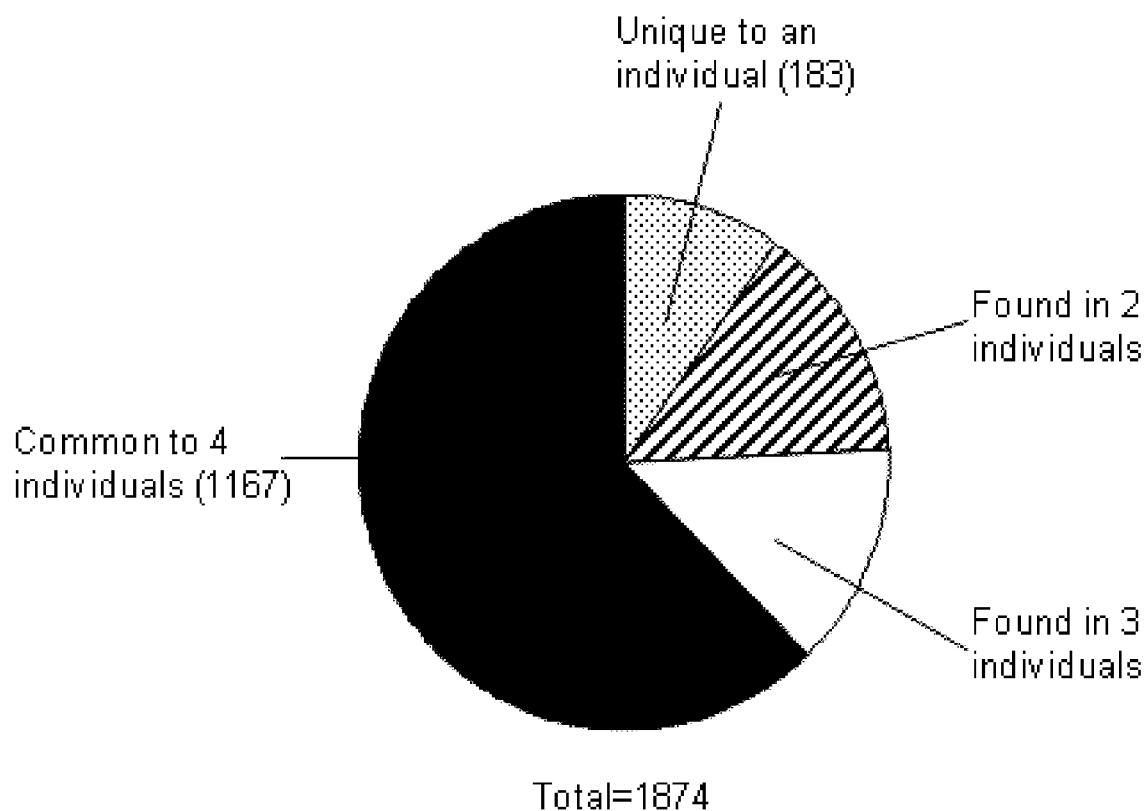
FIG. 10 provides data comparing inter-individual LC-FTMS metabolic profiles of human plasma.

The capability of the metabolic profiling method was focused to determine differences in metabolite levels found in the individuals as well as to detect novel metabolites that could be used as biomarkers of disease. Using the 1,874 features that were found in at least 50% of an individual's spectra, it was determined how many were unique to an individual and how many were common to multiple individuals (FIG. 10). Results showed only 10% of the features were unique to an individual, while 62% were common to all 4 individuals. The remaining 28% were common to some, but not all individuals. These results indicate that creation of a database of common human metabolites based on accurate mass is feasible, and further suggests that 'normal' ranges could be defined in terms of the ion intensities even without knowing chemical identity. This commonality also suggests that the chemical identities of unknown metabolites can be obtained by using pooled samples from different individuals without having to go back to the original subject.

Figure 11:
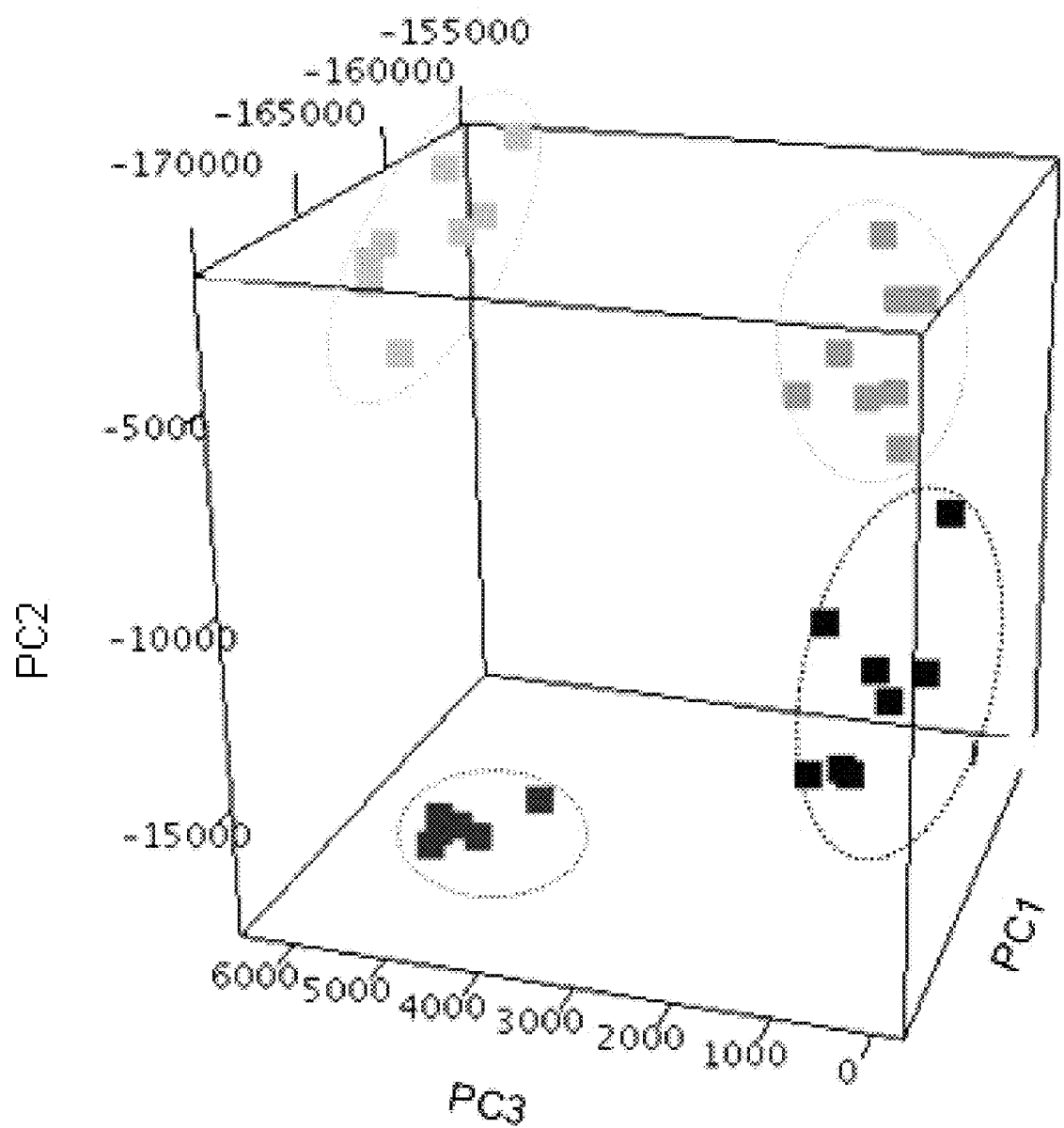
FIG. 11 provides data showing a three-dimensional plot of unsupervised principal component analysis of LC-FTMS data for replicate plasma samples from 4 healthy individuals.
Figure 12:
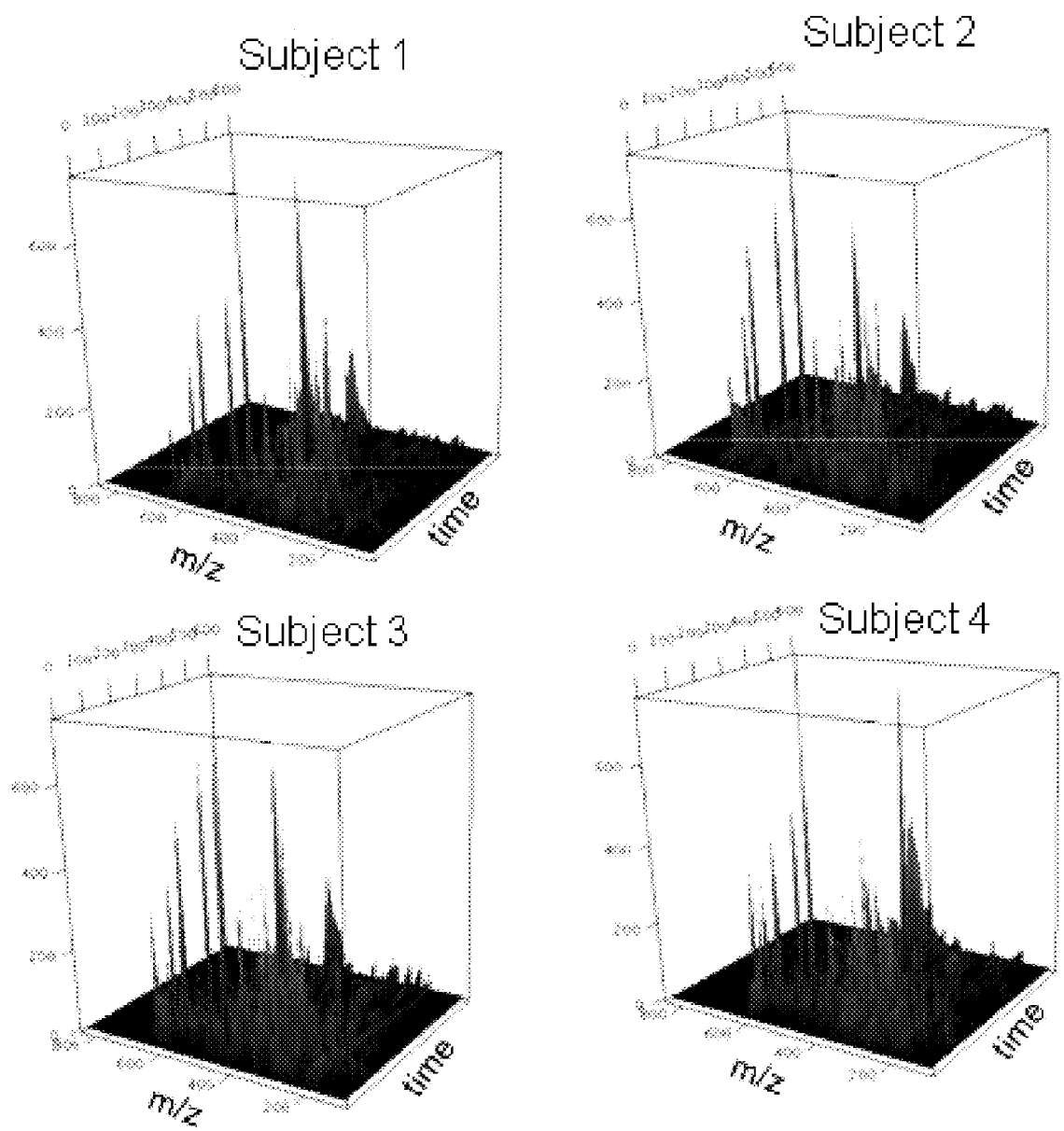
FIG. 12 provides data illustrating a three-dimensional landscape projection of features which distinguish 4 individuals' metabolic profiles.
Figure 15:
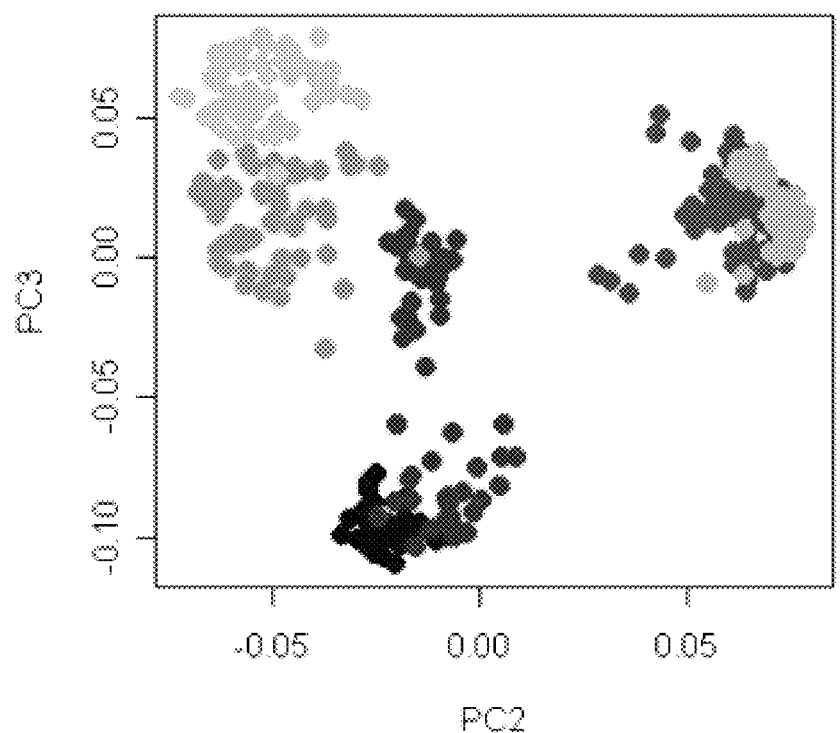
FIG. 15 provides data showing intra-individual variation is smaller than inter-individual variation even with variable dietary intake.

An underlying assumption for development of metabolomics for personalized medicine is that a personalized metabolic "fingerprint" can be determined with sufficient sensitivity and precision to distinguish a healthy individual from an unhealthy individual. Although this more global health-related question was beyond the scope of the study, PCA was used to test whether the LC-FTMS method could distinguish between 4 individuals. Repeat analyses showed clear separation by individual (FIG. 11). In a further study, repeat data were examined from 6 individuals fed a chemically defined diet over a 10 day period. Results showed intra-individual variation was smaller than inter-individual variation even when controlling for diet (FIG. 15). To further look into the basis for the separation, Statistical Analysis of Microarrays (SAM) was used with a false discovery rate (FDR) set at 0.1%. Results showed that 770 features differed significantly between individuals. Landscape plots of these 770 features for each individual show that while many of these features are common to all 4, the ion intensity can vary widely (FIG. 12). Thus, the data show that the LC-FTMS method is sensitive enough to provide individual metabolic fingerprints which can distinguish individuals in terms of differences of common plasma metabolites.

In another study, with a targeted metabolomics approach it was found that cystine was significantly higher in individuals over the age of 60 compared to individuals under the age of 30. These samples were reexamined to see if the 'top-down' method could detect this difference. The results showed a significant difference (p=0.002) in the levels of cystine between the 2 groups as was found in the targeted study. The top-down approach was also able to find 32 other m/z features that differed between groups with a p-value less than 0.01 suggesting that with appropriate development the approach could be suitable for personalized medicine.

Targeted analysis of known chemicals is a critical component of diagnostic medicine and, in plant research, is often the only way of studying the phenotypic changes brought on by genetic mutations. The fields of pharmacology and toxicology have also made extensive use of studying the metabolic fates of exogenously produced small molecule organic compounds. As computing power grows, the ability to collect, process and store huge amounts of data advances, and clinical and epidemiological researchers have become interested in global metabolic profiling. Thus, the simple, rapid, reproducible method described herein is capable of being used in a clinical setting to provide a global metabolic profile. Importantly, the present method provides a means to detect and report metabolites in terms of high mass accuracy m/z regardless of chemical identity. This characteristic can facilitate use of LC-FTMS for discovery of unrecognized associations between metabolites and disease and for characterization of novel metabolites.

In summary, this example describes a rapid, reproducible and sensitive LC-FTMS metabolic profiling method for human plasma that relies on the high mass accuracy and resolution of the FTMS. The method allows quantitative comparisons of about 2000 metabolic features in experimental designs containing up to 80 samples. The method is suitable to evaluate specific metabolic changes in association with genetics, diet, behavior and environmental exposure as risk factors for disease.

Figure Captions.

FIG. 8. Feature profile of human plasma obtained by 10 min LC-FTMS analysis. Eluate was ionized by ESI in the positive ion mode. Data were visualized using R software as 3-dimensional projections in which the surface plane represents the m/z and elution time, while the projection (z-axis) represents the ion signal intensity. A. Raw data. B. Cubed root-transformation of data to enhance visualization of lower abundance peaks. C. Magnification of m/z 235-265 and RT 50-100 to enhance visualization of individual peaks. The largest peak corresponded to the [13C2]-cystine which was spiked into the plasma prior to deproteination and the peak at 241.0311 corresponds to endogenous cystine. Additional analytes detected represent unknown chemicals in human plasma.

FIG. 9. Histogram showing number of peaks with ranges of signal variation from LC-FTMS analysis. Variation is expressed as coefficient of variation (CV) obtained from analysis using automated noise level selection and separation, and smoothing-based feature alignment for peak selection. Ten microliter samples from 4 individuals were analyzed by LC-FTMS with either 6 replicates (Subject 1) or 8 replicates (Subjects 2-4). Results show that most features have CV below 10%.

FIG. 10. Inter-individual comparison of LC-FTMS metabolic profiles of human plasma. To obtain a sample reflective of real variability in humans, plasma samples were collected from 4 healthy individuals (1 male, 3 females) without control of diet or other lifestyle factors. Following analysis by LC-FTMS, feature profiles were compared among individuals. Results showed that among the features detected, most were common to all individuals and only 10% were found in only one subject. Thus, even without control for diet or other factors, the predominance of m/z features detected by the LC-FTMS method were common among individuals.

FIG. 11. Three-dimensional plot of unsupervised Principal Component Analysis (PCA) of LC-FTMS data for replicate plasma samples from 4 healthy individuals. PCA was performed to determine whether variation in the metabolic profiles of individuals was greater than the metabolic variation due to the variability of detection by LC-FTMS. Results show that replicate spectra separate according to individual despite the cumulative variability of thousands of m/z features.

FIG. 12. Three-dimensional landscape projection of features which distinguish individuals. Statistical Analysis of Microarrys (SAM) using False Discovery Rate (FDR) of 0.1% was applied to the spectra of 4 individuals to determine feature that differ significantly between individuals. This method removes all features that do not differ between individuals. Results showed that 770 features with unique m/z were significantly different between individuals. Projections of these 770 features reveal unique individual metabolic landscapes of the individuals.

FIG. 13A. Initial PCA analysis shows separation by run-time and column. Plasma was collected from 4 individuals, identified by colors, and run in 6 replicates on 2 columns. Results show a need for an 8 to 10 run wash-in period and a strong separation by column. FIG. 13B. After wash-in analyses were removed from the analysis, PCA shows a strong separation by column, indicated by solid circles, with a secondary separation by individual, indicated by broken circles.

FIG. 14. Correlation analysis shows experimental results obtained from each column gives the same experimental answer. Plasma from another experiment was run using LF-FTMS method. Samples were run in duplicate on each of 2 columns in reverse order. Correlation analysis using R software shows that neither column nor run time changed the pattern of results although the individual columns did show unique characteristics.

FIG. 15. Intra-individual variation is smaller than inter-individual variation even with variable dietary intake. Plasma was collected from 6 individuals. Briefly, 34 samples were collected from each individual over a 10 day time course and included fasting and postprandial samples with a nutritionally complete and a nutritionally deficient diet. The metabolic profile was analyzed for each sample and PCA analysis done to visualize the results. Projections including PC1 (not shown) also separated grey and green and red and blue, but individuals represented by purple and gold were still close.

TABLE 1

Endogenous Metabolism Database

| Metabolite | Elemental formula | Precise Mass | M + 1H | 10 ppm− | 10 ppm+ |
|---|---|---|---|---|---|
| acetaldehyde | C2H4O | 44.0262 | 45.0335 | 45.0330 | 45.0339 |
| formate | CH2O2 | 46.0055 | 47.0127 | 47.0123 | 47.0132 |
| ethanol | C2H6O | 46.0419 | 47.0491 | 47.0487 | 47.0496 |
| 2-propyn-1-al | C3H2O | 54.0106 | 55.0178 | 55.0173 | 55.0184 |

TABLE 1-continued

Endogenous Metabolism Database

| Metabolite | Elemental formula | Precise Mass | M + 1H | 10 ppm− | 10 ppm+ |
|---|---|---|---|---|---|
| acrolein | C3H4O | 56.0262 | 57.0335 | 57.0329 | 57.0341 |
| 2-propyn-1-ol | C3H4O | 56.0262 | 57.0335 | 57.0329 | 57.0341 |
| acetone | C3H6O | 58.0419 | 59.0491 | 59.0485 | 59.0497 |
| propanal | C3H6O | 58.0419 | 59.0491 | 59.0485 | 59.0497 |
| acetamide | C2H5NO | 59.0371 | 60.0444 | 60.0438 | 60.0450 |
| guanidine | CH5N3 | 59.0483 | 60.0556 | 60.0550 | 60.0562 |
| trimethylamine | C3H9N | 59.0735 | 60.0808 | 60.0802 | 60.0814 |
| acetic acid | C2H4O2 | 60.0211 | 61.0284 | 61.0278 | 61.0290 |
| glycolaldehyde | C2H4O2 | 60.0211 | 61.0284 | 61.0278 | 61.0290 |
| urea | CH4N2O | 60.0324 | 61.0396 | 61.0390 | 61.0402 |
| 1-propanol | C3H8O | 60.0575 | 61.0648 | 61.0642 | 61.0654 |
| 2-propanol | C3H8O | 60.0575 | 61.0648 | 61.0642 | 61.0654 |
| carbamate | CH3NO2 | 61.0164 | 62.0236 | 62.0230 | 62.0243 |
| ethanolamine | C2H7NO | 61.0528 | 62.0600 | 62.0594 | 62.0607 |
| carbonic acid | CH2O3 | 62.0004 | 63.0077 | 63.0070 | 63.0083 |
| ethylene glycol | C2H6O2 | 62.0368 | 63.0440 | 63.0434 | 63.0447 |
| aminoimidazole | C3H5N2 | 69.0453 | 70.0525 | 70.0518 | 70.0532 |
| propynoate | C3H2O2 | 70.0055 | 71.0127 | 71.0120 | 71.0135 |
| 3-butynol | C4H6O | 70.0419 | 71.0491 | 71.0484 | 71.0498 |
| methylglyoxal | C3H4O2 | 72.0211 | 73.0284 | 73.0277 | 73.0291 |
| butyraldehyde | C4H8O | 72.0575 | 73.0648 | 73.0641 | 73.0655 |
| aminoacetone | C3H7NO | 73.0528 | 74.0600 | 74.0593 | 74.0608 |
| methylguanidine | C2H7N3 | 73.0640 | 74.0713 | 74.0705 | 74.0720 |
| glyoxylic acid | C2H2O3 | 74.0004 | 75.0077 | 75.0069 | 75.0084 |
| hydroxyacetone | C3H6O2 | 74.0368 | 75.0440 | 75.0433 | 75.0448 |
| lactaldehyde | C3H6O2 | 74.0368 | 75.0440 | 75.0433 | 75.0448 |
| propanoate | C3H6O2 | 74.0368 | 75.0440 | 75.0433 | 75.0448 |
| 1-butanol | C4H10O | 74.0732 | 75.0804 | 75.0797 | 75.0812 |
| 1,3-diaminopropane | C3H10N2 | 74.0844 | 75.0917 | 75.0909 | 75.0924 |
| glycine | C2H5NO2 | 75.0320 | 76.0393 | 76.0385 | 76.0401 |
| 1-amino-propan-2-ol | C3H9NO | 75.0684 | 76.0757 | 76.0749 | 76.0764 |
| trimethylamine N-oxide | C3H9NO | 75.0684 | 76.0757 | 76.0749 | 76.0764 |
| glycolate | C2H4O3 | 76.0160 | 77.0233 | 77.0225 | 77.0241 |
| 1,2-propandiol | C3H8O2 | 76.0524 | 77.0597 | 77.0589 | 77.0605 |
| cysteamine | C2H7NS | 77.0299 | 78.0372 | 78.0364 | 78.0380 |
| piperideine | C5H9N | 83.0735 | 84.0808 | 84.0799 | 84.0816 |
| imidazolone | C3H4N2O | 84.0324 | 85.0396 | 85.0388 | 85.0405 |
| 3-butynoate | C4H6O2 | 86.0368 | 87.0440 | 87.0432 | 87.0449 |
| 2-aminoacrylate | C3H5NO2 | 87.0320 | 88.0393 | 88.0384 | 88.0402 |
| 4-aminobutyraldehyde | C4H9NO | 87.0684 | 88.0757 | 88.0748 | 88.0766 |
| pyruvic acid | C3H4O3 | 88.0160 | 89.0233 | 89.0224 | 89.0242 |
| malonate semialdehyde | C3H4O3 | 88.0160 | 89.0233 | 89.0224 | 89.0242 |
| acetoin | C4H8O2 | 88.0524 | 89.0597 | 89.0588 | 89.0606 |
| butyric acid | C4H8O2 | 88.0524 | 89.0597 | 89.0588 | 89.0606 |
| α-alanine | C3H7NO2 | 89.0477 | 90.0549 | 90.0540 | 90.0558 |
| β-alanine | C3H7NO2 | 89.0477 | 90.0549 | 90.0540 | 90.0558 |
| sarcosine | C3H7NO2 | 89.0477 | 90.0549 | 90.0540 | 90.0558 |
| oxalic acid | C2H2O4 | 89.9953 | 91.0026 | 91.0017 | 91.0035 |
| lactic acid | C3H6O3 | 90.0317 | 91.0390 | 91.0380 | 91.0399 |
| 3-hydroxypropionate | C3H6O3 | 90.0317 | 91.0390 | 91.0380 | 91.0399 |
| glyceraldehyde | C3H6O3 | 90.0317 | 91.0390 | 91.0380 | 91.0399 |
| glycerone | C3H6O3 | 90.0317 | 91.0390 | 91.0380 | 91.0399 |
| 2,3 butanediol | C4H10O2 | 90.0681 | 91.0753 | 91.0744 | 91.0763 |
| 3-amino-isobutyrate | C4H9NO2 | 91.0633 | 92.0706 | 92.0697 | 92.0715 |
| glycerol | C3H8O3 | 92.0473 | 93.0546 | 93.0537 | 93.0555 |
| isocaproic aldehyde | C6H12O | 100.0888 | 101.0961 | 101.0951 | 101.0971 |
| putrescine | C4H12N2 | 100.1000 | 101.1073 | 101.1063 | 101.1083 |
| 1-aminocyclopropane-1-carboxylate | C4H7NO2 | 101.0477 | 102.0549 | 102.0539 | 102.0560 |
| acetoacetic acid | C4H6O3 | 102.0317 | 103.0390 | 103.0379 | 103.0400 |
| 2-oxo-butyrate | C4H6O3 | 102.0317 | 103.0390 | 103.0379 | 103.0400 |
| methylmalonate semialdehyde | C4H6O3 | 102.0317 | 103.0390 | 103.0379 | 103.0400 |
| succinate semialdehyde | C4H6O3 | 102.0317 | 103.0390 | 103.0379 | 103.0400 |
| formiminoglycine | C3H6N2O2 | 102.0429 | 103.0502 | 103.0492 | 103.0512 |
| betaine aldehyde | C5H12NO | 102.0919 | 103.0992 | 103.0981 | 103.1002 |
| cadaverine | C5H14N2 | 102.1157 | 103.1230 | 103.1219 | 103.1240 |
| β-amino-isobutyric acid | C4H9NO2 | 103.0633 | 104.0706 | 104.0696 | 104.0716 |
| 4-amino-butyrate | C4H9NO2 | 103.0633 | 104.0706 | 104.0696 | 104.0716 |
| dimethylglycine | C4H9NO2 | 103.0633 | 104.0706 | 104.0696 | 104.0716 |
| γ-αμινο-ισοβυτψριχ αχιδ | C4H9NO2 | 103.0633 | 104.0706 | 104.0696 | 104.0716 |
| hydroxypyruvate | C3H4O4 | 104.0109 | 105.0182 | 105.0172 | 105.0193 |
| malonate | C3H4O4 | 104.0109 | 105.0182 | 105.0172 | 105.0193 |
| tartronate semialdehyde | C3H4O4 | 104.0109 | 105.0182 | 105.0172 | 105.0193 |
| 2-hydroxybutyrate | C4H8O3 | 104.0473 | 105.0546 | 105.0536 | 105.0557 |
| 3-hydroxybutyric acid | C4H8O3 | 104.0473 | 105.0546 | 105.0536 | 105.0557 |

TABLE 1-continued

Endogenous Metabolism Database

| Metabolite | Elemental formula | Precise Mass | M + 1H | 10 ppm− | 10 ppm+ |
|---|---|---|---|---|---|
| 3-hydroxyisobutyrate | C4H8O3 | 104.0473 | 105.0546 | 105.0536 | 105.0557 |
| 4-hydroxybutyrate | C4H8O3 | 104.0473 | 105.0546 | 105.0536 | 105.0557 |
| choline | C5H14NO | 104.1075 | 105.1148 | 105.1138 | 105.1159 |
| serine | C3H7NO3 | 105.0426 | 106.0499 | 106.0488 | 106.0509 |
| diethanolamine | C4H11NO2 | 105.0790 | 106.0862 | 106.0852 | 106.0873 |
| glycerate | C3H6O4 | 106.0266 | 107.0339 | 107.0328 | 107.0349 |
| nicotinamide | C6H6N2O | 106.0531 | 107.0604 | 107.0593 | 107.0614 |
| hypotaurine | C2H7NO2S | 109.0197 | 110.0270 | 110.0259 | 110.0281 |
| catechol | C6H6O2 | 109.0289 | 110.0362 | 110.0351 | 110.0373 |
| 2-aminophenol | C6H7NO | 109.0528 | 110.0600 | 110.0589 | 110.0611 |
| pyrrole-2-carboxylate | C5H4NO2 | 110.0242 | 111.0315 | 111.0304 | 111.0326 |
| 1,4-benzenediol | C6H6O2 | 110.0368 | 111.0440 | 111.0429 | 111.0452 |
| pyrocatechol | C6H6O2 | 110.0368 | 111.0440 | 111.0429 | 111.0452 |
| imidazole-4-acetaldehyde | C5H6N2O | 110.0480 | 111.0553 | 111.0542 | 111.0564 |
| 2,5-dihydroxy-pyridine | C5H5NO2 | 111.0320 | 112.0393 | 112.0382 | 112.0404 |
| cytosine | C4H5N3O | 111.0432 | 112.0505 | 112.0494 | 112.0516 |
| histamine | C5H9N3 | 111.0796 | 112.0869 | 112.0858 | 112.0880 |
| uracil | C4H4N2O2 | 112.0273 | 113.0345 | 113.0334 | 113.0357 |
| 5-amino-4-imidazole carboxylate | C4H5N2O2 | 113.0351 | 114.0424 | 114.0412 | 114.0435 |
| 1-pyrroline 2-carboxylate | C5H7NO2 | 113.0477 | 114.0549 | 114.0538 | 114.0561 |
| 1-pyrroline-5-carboxylate | C5H7NO2 | 113.0477 | 114.0549 | 114.0538 | 114.0561 |
| creatinine | C4H7N3O | 113.0589 | 114.0662 | 114.0650 | 114.0673 |
| acetylenedicarboxylate | C4H2O4 | 113.9953 | 115.0026 | 115.0014 | 115.0037 |
| 2-oxo-pent-4-enoate | C5H6O3 | 114.0317 | 115.0390 | 115.0378 | 115.0401 |
| 5,6-dihydrouracil | C4H6N2O2 | 114.0429 | 115.0502 | 115.0490 | 115.0513 |
| allyl sulfide | C6H10S | 114.0503 | 115.0576 | 115.0564 | 115.0587 |
| maleamate | C4H5NO3 | 115.0269 | 116.0342 | 116.0330 | 116.0354 |
| proline | C5H9NO2 | 115.0633 | 116.0706 | 116.0694 | 116.0718 |
| fumaric acid | C4H4O4 | 116.0109 | 117.0182 | 117.0170 | 117.0194 |
| maleate | C4H4O4 | 116.0109 | 117.0182 | 117.0170 | 117.0194 |
| 2-oxoisovalerate | C5H8O3 | 116.0473 | 117.0546 | 117.0534 | 117.0558 |
| glutarate semialdehyde | C5H8O3 | 116.0473 | 117.0546 | 117.0534 | 117.0558 |
| 5-aminopentanamide | C5H12N2O | 116.0950 | 117.1022 | 117.1011 | 117.1034 |
| 2-aminoacetoacetate | C4H7NO3 | 117.0426 | 118.0499 | 118.0487 | 118.0510 |
| aspartate-4-semialdehyde | C4H7NO3 | 117.0426 | 118.0499 | 118.0487 | 118.0510 |
| guanidinoaceatate | C3H7N3O2 | 117.0538 | 118.0611 | 118.0599 | 118.0623 |
| indole | C8H7N | 117.0578 | 118.0651 | 118.0639 | 118.0663 |
| 5-aminovalerate | C5H11NO2 | 117.0790 | 118.0862 | 118.0851 | 118.0874 |
| succinic acid | C4H6O4 | 118.0266 | 119.0339 | 119.0327 | 119.0351 |
| methylmalonate | C4H6O4 | 118.0266 | 119.0339 | 119.0327 | 119.0351 |
| N-methylhydantoin | C3H6N2O2 | 118.0378 | 119.0451 | 119.0439 | 119.0463 |
| 2,4-diaminobutanoate | C4H10N2O2 | 118.0742 | 119.0815 | 119.0803 | 119.0827 |
| betaine | C5H12NO2 | 118.0868 | 119.0941 | 119.0929 | 119.0953 |
| homoserine | C4H9NO3 | 119.0582 | 120.0655 | 120.0643 | 120.0667 |
| threonine | C4H9NO3 | 119.0582 | 120.0655 | 120.0643 | 120.0667 |
| 3-mercaptopyruvate | C3H4O3S | 119.9881 | 120.9954 | 120.9942 | 120.9966 |
| 3-(methylthio) propionic acid | C4H8O2S | 120.0245 | 121.0318 | 121.0306 | 121.0330 |
| N-carbanoylsarcosine | C3H8N2O3 | 120.0535 | 121.0607 | 121.0595 | 121.0620 |
| pehnylacetaldehyde | C8H8O | 120.0575 | 121.0648 | 121.0636 | 121.0660 |
| 3-mercaptolactate | C3H5O3S | 120.9959 | 122.0032 | 122.0020 | 122.0044 |
| cysteine | C3H7NO2S | 121.0197 | 122.0270 | 122.0258 | 122.0282 |
| phenylethylamine | C8H11N | 121.0891 | 122.0964 | 122.0952 | 122.0976 |
| phenylethylalcohol | C8H10O | 122.0732 | 123.0804 | 123.0792 | 123.0817 |
| niacin | C6H5NO2 | 123.0320 | 124.0393 | 124.0381 | 124.0405 |
| methylimidazole acetaldehyde | C6H8N2O | 124.0637 | 125.0709 | 125.0697 | 125.0722 |
| glutaric acid | C5H8O4 | 124.0749 | 125.0822 | 125.0809 | 125.0834 |
| taurine | C2H7NO3S | 125.0146 | 126.0219 | 126.0207 | 126.0232 |
| 5-methylcytosine | C5H7N3O | 125.0589 | 126.0662 | 126.0649 | 126.0674 |
| N-methylhistamine | C6H11N3 | 125.0953 | 126.1026 | 126.1013 | 126.1038 |
| formyl phosphate | CH3O5P | 125.9712 | 126.9785 | 126.9772 | 126.9798 |
| imidazole acetic acid | C5H6N2O2 | 126.0429 | 127.0502 | 127.0489 | 127.0515 |
| thymine | C5H6N2O2 | 126.0429 | 127.0502 | 127.0489 | 127.0515 |
| 4-amino-4-imidazolecarboxyamide | C4H6N4O | 126.0541 | 127.0614 | 127.0601 | 127.0627 |
| cholesten-3-on | C8H14O | 126.1045 | 127.1117 | 127.1105 | 127.1130 |
| ethanolamine phosphate | C2H8NO4P | 127.0155 | 128.0227 | 128.0214 | 128.0240 |
| 2,3,4,5-tetrahydropyridine-3-carboxylate | C6H9NO2 | 127.0633 | 128.0706 | 128.0693 | 128.0719 |
| piperideine-2-carboxylate | C6H9NO2 | 127.0633 | 128.0706 | 128.0693 | 128.0719 |
| barbiturate | C4H4N2O3 | 128.0222 | 129.0294 | 129.0282 | 129.0307 |
| 5,6-dihydrothymine | C5H8N2O2 | 128.0586 | 129.0658 | 129.0645 | 129.0671 |
| 1-pyrroline-3-hydroxy-5-carboxylate | C5H7NO3 | 129.0426 | 130.0499 | 130.0486 | 130.0512 |
| 1-pyrroline-4-hydroxy-2-carboxylate | C5H7NO3 | 129.0426 | 130.0499 | 130.0486 | 130.0512 |
| 4-oxoproline | C5H7NO3 | 129.0426 | 130.0499 | 130.0486 | 130.0512 |

TABLE 1-continued

Endogenous Metabolism Database

| Metabolite | Elemental formula | Precise Mass | M + 1H | 10 ppm− | 10 ppm+ |
|---|---|---|---|---|---|
| α-ketoisocaproic acid | C6H9O3 | 129.0552 | 130.0624 | 130.0611 | 130.0637 |
| N4-acetylaminobutanal | C6H11NO2 | 129.0790 | 130.0862 | 130.0849 | 130.0875 |
| pipecolate | C6H11NO2 | 129.0790 | 130.0862 | 130.0849 | 130.0875 |
| 4-guanidinobutanal | C5H11N3O | 129.0902 | 130.0975 | 130.0962 | 130.0988 |
| itaconate | C5H6O4 | 130.0266 | 131.0339 | 131.0326 | 131.0352 |
| 2-oxoglutarate semialdehyde | C5H6O4 | 130.0266 | 131.0339 | 131.0326 | 131.0352 |
| citraconate | C5H6O4 | 130.0266 | 131.0339 | 131.0326 | 131.0352 |
| mesaconate | C5H6O4 | 130.0266 | 131.0339 | 131.0326 | 131.0352 |
| 2-oxo-3-methylvalerate | C6H10O3 | 130.0630 | 131.0703 | 131.0689 | 131.0716 |
| 2-oxo-isocaproate | C6H10O3 | 130.0630 | 131.0703 | 131.0689 | 131.0716 |
| 3-oxo-4-methylpentanoic acid | C6H10O3 | 130.0630 | 131.0703 | 131.0689 | 131.0716 |
| N-acetylputrescine | C6H14N2O | 130.1106 | 131.1179 | 131.1166 | 131.1192 |
| agmatine | C5H14N4 | 130.1218 | 131.1291 | 131.1278 | 131.1304 |
| 4-trimethylammoniobutanal | C7H16NO+ | 130.1232 | 131.1305 | 131.1291 | 131.1318 |
| coprostanol | C8H18O | 130.1358 | 131.1430 | 131.1417 | 131.1443 |
| 2-oxosuccinamate | C4H5NO4 | 131.0218 | 132.0291 | 132.0278 | 132.0304 |
| hydroxyproline | C5H9NO3 | 131.0582 | 132.0655 | 132.0642 | 132.0668 |
| 2-oxo-5-aminovalerate | C5H9NO3 | 131.0582 | 132.0655 | 132.0642 | 132.0668 |
| 4-hydroxyglutamate semialdehyde | C5H9NO3 | 131.0582 | 132.0655 | 132.0642 | 132.0668 |
| 5-aminolevulinate | C5H9NO3 | 131.0582 | 132.0655 | 132.0642 | 132.0668 |
| glutamate-1-semialdehyde | C5H9NO3 | 131.0582 | 132.0655 | 132.0642 | 132.0668 |
| glutamate-5-semialdehyde | C5H9NO3 | 131.0582 | 132.0655 | 132.0642 | 132.0668 |
| creatine | C4H9N3O2 | 131.0695 | 132.0767 | 132.0754 | 132.0781 |
| isoleucine | C6H13NO2 | 131.0946 | 132.1019 | 132.1006 | 132.1032 |
| leucine | C6H13NO2 | 131.0946 | 132.1019 | 132.1006 | 132.1032 |
| norleucine | C6H13NO2 | 131.0946 | 132.1019 | 132.1006 | 132.1032 |
| β-leucine | C6H13NO2 | 131.0946 | 132.1019 | 132.1006 | 132.1032 |
| N-carbamoylputrescine | C5H13N3O | 131.1058 | 132.1131 | 132.1118 | 132.1144 |
| oxalacetic acid | C4H4O5 | 132.0059 | 133.0131 | 133.0118 | 133.0145 |
| 2-hydroxyethylenedicarboxylate | C4H4O5 | 132.0059 | 133.0131 | 133.0118 | 133.0145 |
| trans-2,3-epoxysuccinate | C4H4O5 | 132.0059 | 133.0131 | 133.0118 | 133.0145 |
| oxalureate | C3H4N2O4 | 132.0171 | 133.0244 | 133.0230 | 133.0257 |
| 2-acetolactate | C5H8O4 | 132.0422 | 133.0495 | 133.0482 | 133.0508 |
| 4-hydroxy-2-oxovalerate | C5H8O4 | 132.0422 | 133.0495 | 133.0482 | 133.0508 |
| glutarate | C5H8O4 | 132.0422 | 133.0495 | 133.0482 | 133.0508 |
| asparagine | C4H8N2O3 | 132.0535 | 133.0607 | 133.0594 | 133.0621 |
| 3-ureidopropionate | C4H8N2O3 | 132.0535 | 133.0607 | 133.0594 | 133.0621 |
| gly-gly | | 132.0535 | 133.0607 | 133.0594 | 133.0621 |
| ornithine | C5H12N2O2 | 132.0899 | 133.0971 | 133.0958 | 133.0985 |
| aspartic acid | C4H7NO4 | 133.0375 | 134.0448 | 134.0434 | 134.0461 |
| ureidoglycine | C3H7N3O3 | 133.0487 | 134.0560 | 134.0547 | 134.0573 |
| indoxyl | C8H7NO | 133.0528 | 134.0600 | 134.0587 | 134.0614 |
| malic acid | C4H6O5 | 134.0215 | 135.0288 | 135.0274 | 135.0301 |
| 3-dehydro threonate | C4H6O5 | 134.0215 | 135.0288 | 135.0274 | 135.0301 |
| ureidoglycolate | C3H6N2O4 | 134.0327 | 135.0400 | 135.0387 | 135.0414 |
| 2,3-dihydroxyisovalerate | C5H10O4 | 134.0579 | 135.0652 | 135.0638 | 135.0665 |
| deoxyribose | C5H10O4 | 134.0579 | 135.0652 | 135.0638 | 135.0665 |
| acetanilide | C8H8NO | 134.0606 | 135.0679 | 135.0665 | 135.0692 |
| picolinate | C7H5NO2 | 135.0320 | 136.0393 | 136.0379 | 136.0407 |
| homocysteine | C4H9NO2S | 135.0354 | 136.0427 | 136.0413 | 136.0440 |
| 4-chlorophenylacetate | C8H7O2Cl | 135.0446 | 136.0519 | 136.0505 | 136.0532 |
| adenine | C5H5N5 | 135.0545 | 136.0618 | 136.0604 | 136.0631 |
| phenylacetamide | C8H9NO | 135.0684 | 136.0757 | 136.0743 | 136.0770 |
| threonate | C4H8O5 | 136.0372 | 137.0444 | 137.0431 | 137.0458 |
| hypoxanthine | C5H4N4O | 136.0385 | 137.0458 | 137.0444 | 137.0471 |
| phenylacetic acid | C8H8O2 | 136.0524 | 137.0597 | 137.0583 | 137.0611 |
| 4-hydroxyphenylacetaldehyde | C8H8O2 | 136.0524 | 137.0597 | 137.0583 | 137.0611 |
| 4-aminobenzoate | C7H7NO2 | 137.0477 | 138.0549 | 138.0536 | 138.0563 |
| anthranilate | C7H7NO2 | 137.0477 | 138.0549 | 138.0536 | 138.0563 |
| tyramine | C8H11NO | 137.0841 | 138.0913 | 138.0900 | 138.0927 |
| acetyl-P | C2H3O5P | 137.9712 | 138.9785 | 138.9771 | 138.9799 |
| 4-hydroxybenzoate | C7H6O3 | 138.0317 | 139.0390 | 139.0376 | 139.0403 |
| gentisate aldehyde | C7H6O3 | 138.0317 | 139.0390 | 139.0376 | 139.0403 |
| urocanate | C6H6N2O2 | 138.0429 | 139.0502 | 139.0488 | 139.0516 |
| 4-hydroxyphenylethanol | C8H10O2 | 138.0681 | 139.0753 | 139.0740 | 139.0767 |
| O-phosphoethanolamine | C2H6NO4P | 139.0029 | 140.0101 | 140.0087 | 140.0115 |
| 6-hydroxy-nicotinate | C6H5NO3 | 139.0269 | 140.0342 | 140.0328 | 140.0356 |
| histidinal | C6H9N3O | 139.0745 | 140.0818 | 140.0804 | 140.0832 |
| methylimidazoleacetic acid | C6H8N2O2 | 140.0586 | 141.0658 | 141.0644 | 141.0672 |
| carbamoyl phosphate | CH4NO5P | 140.9821 | 141.9894 | 141.9880 | 141.9908 |
| histidinol | C6H11N3O | 141.0902 | 142.0975 | 142.0961 | 142.0989 |
| coenzyme M | C2H6O3S2 | 141.9758 | 142.9831 | 142.9817 | 142.9845 |
| 3-oxoadipate-enol-lactone | C6H6O4 | 142.0266 | 143.0339 | 143.0324 | 143.0353 |
| muconate | C6H6O4 | 142.0266 | 143.0339 | 143.0324 | 143.0353 |
| 5-methyl-barbiturate | C5H6N2O3 | 142.0378 | 143.0451 | 143.0437 | 143.0465 |

TABLE 1-continued

Endogenous Metabolism Database

| Metabolite | Elemental formula | Precise Mass | M + 1H | 10 ppm− | 10 ppm+ |
|---|---|---|---|---|---|
| imidazolone acetate | C5H6N2O3 | 142.0378 | 143.0451 | 143.0437 | 143.0465 |
| 2-methyleneglutarate | C6H8O4 | 144.0422 | 145.0495 | 145.0481 | 145.0510 |
| dimethylmaleate | C6H8O4 | 144.0422 | 145.0495 | 145.0481 | 145.0510 |
| methylitaconate | C6H8O4 | 144.0422 | 145.0495 | 145.0481 | 145.0510 |
| ectoine | C6H12N2O2 | 144.0899 | 145.0971 | 145.0957 | 145.0986 |
| 4-guanidinobutanamide | C5H12N4O | 144.1011 | 145.1084 | 145.1069 | 145.1098 |
| 2-oxo-glutaramate | C5H7NO4 | 145.0375 | 146.0448 | 146.0433 | 146.0462 |
| 4-oxoglutaramate | C5H7NO4 | 145.0375 | 146.0448 | 146.0433 | 146.0462 |
| 2-amino-5-oxohexanoate | C6H11NO3 | 145.0739 | 146.0812 | 146.0797 | 146.0826 |
| 2-aminoadipate 6-semialdehyde | C6H11NO3 | 145.0739 | 146.0812 | 146.0797 | 146.0826 |
| 2-oxo-6-aminocaproate | C6H11NO3 | 145.0739 | 146.0812 | 146.0797 | 146.0826 |
| 4-acetamidobutanoate | C6H11NO3 | 145.0739 | 146.0812 | 146.0797 | 146.0826 |
| 5-amino-3-oxohexanoic acid | C6H11NO3 | 145.0739 | 146.0812 | 146.0797 | 146.0826 |
| 4-guanidinobutyrate | C5H11N3O2 | 145.0851 | 146.0924 | 146.0909 | 146.0938 |
| 3,6-diaminohexonate | C6H13N2O2 | 145.0977 | 146.1050 | 146.1035 | 146.1064 |
| spermidine | C7H19N3 | 145.1579 | 146.1652 | 146.1637 | 146.1666 |
| 2-oxoglutaric acid | C5H6O5 | 146.0215 | 147.0288 | 147.0273 | 147.0302 |
| erythroascorbate | C5H6O5 | 146.0215 | 147.0288 | 147.0273 | 147.0302 |
| methyloxaloacetate | C5H6O5 | 146.0215 | 147.0288 | 147.0273 | 147.0302 |
| oxoglutaric acid | C5H6O5 | 146.0215 | 147.0288 | 147.0273 | 147.0302 |
| 4,5-dihydro-orotate | C4H6N2O4 | 146.0327 | 147.0400 | 147.0385 | 147.0415 |
| adipic acid | C6H10O4 | 146.0579 | 147.0652 | 147.0637 | 147.0666 |
| 2-aceto-2-hydroxybutyrate | C6H10O4 | 146.0579 | 147.0652 | 147.0637 | 147.0666 |
| 2-dehydropantoate | C6H10O4 | 146.0579 | 147.0652 | 147.0637 | 147.0666 |
| glutamine | C5H10N2O3 | 146.0691 | 147.0764 | 147.0749 | 147.0779 |
| 3-ureido-isobutyrate | C5H10N2O3 | 146.0691 | 147.0764 | 147.0749 | 147.0779 |
| gly-ala | | 146.0691 | 147.0764 | 147.0749 | 147.0779 |
| lysine | C6H14N2O2 | 146.1055 | 147.1128 | 147.1113 | 147.1143 |
| 3,5-diaminohexonate | C6H14N2O2 | 146.1055 | 147.1128 | 147.1113 | 147.1143 |
| δ1-piperideine-2-carboxylate | C6H14N2O2 | 146.1055 | 147.1128 | 147.1113 | 147.1143 |
| 4-trimethylammoniobutanoate | C7H16NO2+ | 146.1181 | 147.1254 | 147.1239 | 147.1268 |
| acetylcholine | C7H16NO2+ | 146.1181 | 147.1254 | 147.1239 | 147.1268 |
| indole-5,6-quinone | C8H5NO2 | 147.0320 | 148.0393 | 148.0378 | 148.0408 |
| glutamic acid | C5H9NO4 | 147.0531 | 148.0604 | 148.0589 | 148.0619 |
| 2-oxo-4-hydroxy-5-amino-valerate | C5H9NO4 | 147.0531 | 148.0604 | 148.0589 | 148.0619 |
| 3-methylaspartate | C5H9NO4 | 147.0531 | 148.0604 | 148.0589 | 148.0619 |
| isoglutamate | C5H9NO4 | 147.0531 | 148.0604 | 148.0589 | 148.0619 |
| O-acetylserine | C5H9NO4 | 147.0531 | 148.0604 | 148.0589 | 148.0619 |
| 2-hydroxy-3-oxosuccinate | C4H4O6 | 148.0008 | 149.0080 | 149.0065 | 149.0095 |
| dihydrofumarate | C4H4O6 | 148.0008 | 149.0080 | 149.0065 | 149.0095 |
| 4-methylthio-2-oxobutanoic acid | C5H8O3S | 148.0194 | 149.0267 | 149.0252 | 149.0282 |
| 2-dehydro-3-deoxy arabionate | C5H8O5 | 148.0372 | 149.0444 | 149.0429 | 149.0459 |
| 2-dehydro-3-deoxy xylonate | C5H8O5 | 148.0372 | 149.0444 | 149.0429 | 149.0459 |
| 2-hydroxyglutarate | C5H8O5 | 148.0372 | 149.0444 | 149.0429 | 149.0459 |
| 2-methylmalate | C5H8O5 | 148.0372 | 149.0444 | 149.0429 | 149.0459 |
| arabin-1,5-lactone | C5H8O5 | 148.0372 | 149.0444 | 149.0429 | 149.0459 |
| arabinono-1,4-lactone | C5H8O5 | 148.0372 | 149.0444 | 149.0429 | 149.0459 |
| citramalate | C5H8O5 | 148.0372 | 149.0444 | 149.0429 | 149.0459 |
| erythro-3-methylmalate | C5H8O5 | 148.0372 | 149.0444 | 149.0429 | 149.0459 |
| threo-3-methylmalate | C5H8O5 | 148.0372 | 149.0444 | 149.0429 | 149.0459 |
| xylonolactone | C5H8O5 | 148.0372 | 149.0444 | 149.0429 | 149.0459 |
| trans-cinnamate | C9H8O2 | 148.0524 | 149.0597 | 149.0582 | 149.0612 |
| 2,3-dihydroxy-3-methylvalerate | C6H12O4 | 148.0735 | 149.0808 | 149.0793 | 149.0823 |
| mevalonate | C6H12O4 | 148.0735 | 149.0808 | 149.0793 | 149.0823 |
| pantoate | C6H12O4 | 148.0735 | 149.0808 | 149.0793 | 149.0823 |
| 2-formylaminobenzaldehyde | C8H7NO2 | 149.0477 | 150.0549 | 150.0534 | 150.0564 |
| 5,6-dihydroxyindole | C8H7NO2 | 149.0477 | 150.0549 | 150.0534 | 150.0564 |
| dihydroxyindole | C8H7NO2 | 149.0477 | 150.0549 | 150.0534 | 150.0564 |
| methionine | C5H11NO2S | 149.0510 | 150.0583 | 150.0568 | 150.0598 |
| triethanolamine | C6H15NO3 | 149.1052 | 150.1125 | 150.1110 | 150.1140 |
| tartrate | C4H6O6 | 150.0164 | 151.0237 | 151.0222 | 151.0252 |
| guanine | C5H4N5O | 150.0416 | 151.0488 | 151.0473 | 151.0503 |
| arabinose | C5H10O5 | 150.0528 | 151.0601 | 151.0586 | 151.0616 |
| lyxose | C5H10O5 | 150.0528 | 151.0601 | 151.0586 | 151.0616 |
| ribose | C5H10O5 | 150.0528 | 151.0601 | 151.0586 | 151.0616 |
| ribulose | C5H10O5 | 150.0528 | 151.0601 | 151.0586 | 151.0616 |
| xylose | C5H10O5 | 150.0528 | 151.0601 | 151.0586 | 151.0616 |
| xylulose | C5H10O5 | 150.0528 | 151.0601 | 151.0586 | 151.0616 |
| phenylpropanoate | C9H10O2 | 150.0681 | 151.0753 | 151.0738 | 151.0769 |
| acetaminophen | C8H9NO2 | 151.0633 | 152.0706 | 152.0691 | 152.0721 |
| 4-hydroxyphenylacetaldehyde-oxime | C8H9NO2 | 151.0633 | 152.0706 | 152.0691 | 152.0721 |
| N-methyltyramine | C9H13NO | 151.0997 | 152.1070 | 152.1055 | 152.1085 |
| 3-sulfinylpyruvate | C3H4O5S | 151.9779 | 152.9852 | 152.9837 | 152.9867 |
| xanthine | C5H4N4O2 | 152.0334 | 153.0407 | 153.0391 | 153.0422 |

TABLE 1-continued

Endogenous Metabolism Database

| Metabolite | Elemental formula | Precise Mass | M + 1H | 10 ppm− | 10 ppm+ |
|---|---|---|---|---|---|
| cystamine | C4H12N2S2 | 152.0442 | 153.0515 | 153.0499 | 153.0530 |
| 2-hydroxyphenylacetate | C8H8O3 | 152.0473 | 153.0546 | 153.0531 | 153.0561 |
| 3,4-dihydroxyphenylacetaldehyde | C8H8O3 | 152.0473 | 153.0546 | 153.0531 | 153.0561 |
| 3-hydroxyphenylacetate | C8H8O3 | 152.0473 | 153.0546 | 153.0531 | 153.0561 |
| 4-hydroxyphenylacetate | C8H8O3 | 152.0473 | 153.0546 | 153.0531 | 153.0561 |
| arabitol | C5H12O5 | 152.0685 | 153.0757 | 153.0742 | 153.0773 |
| ribitol | C5H12O5 | 152.0685 | 153.0757 | 153.0742 | 153.0773 |
| xylitol | C5H12O5 | 152.0685 | 153.0757 | 153.0742 | 153.0773 |
| thiocysteine | C3H7NO2S2 | 152.9918 | 153.9991 | 153.9975 | 154.0006 |
| 3-sulfinoalanine | C3H7NO4S | 153.0096 | 154.0168 | 154.0153 | 154.0184 |
| 3-hydroxyanthranilate | C7H7NO3 | 153.0426 | 154.0499 | 154.0483 | 154.0514 |
| dopamine | C8H11NO2 | 153.0790 | 154.0862 | 154.0847 | 154.0878 |
| 4-(β-acetylaminoethyl) imidazole | C7H11N3O | 153.0902 | 154.0975 | 154.0959 | 154.0990 |
| propionyl phosphate | C3H7O5P | 154.0025 | 155.0098 | 155.0083 | 155.0114 |
| 3,4-dihydroxybenzoate | C7H6O4 | 154.0266 | 155.0339 | 155.0323 | 155.0354 |
| imidazol-5-yl-pyruvate | C6H6N2O3 | 154.0378 | 155.0451 | 155.0435 | 155.0466 |
| N-methylethanolamine phosphate | C3H10NO4P | 155.0342 | 156.0414 | 156.0399 | 156.0430 |
| 2,5-dihydroxybenzoate | C7H7O4 | 155.0344 | 156.0417 | 156.0401 | 156.0433 |
| histidine | C6H9N3O2 | 155.0695 | 156.0767 | 156.0752 | 156.0783 |
| 2-phosphoglycolate | C2H5O6P | 155.9818 | 156.9891 | 156.9875 | 156.9906 |
| methyl-CoM | C3H8O3S2 | 155.9915 | 156.9987 | 156.9972 | 157.0003 |
| orotic acid | C5H4N2O4 | 156.0171 | 157.0244 | 157.0228 | 157.0259 |
| 5-ureido-4-imidazole carboxylate | C5H6N3O3 | 156.0409 | 157.0482 | 157.0466 | 157.0497 |
| 4-imidazolone-5-propionate | C6H8N2O3 | 156.0535 | 157.0607 | 157.0592 | 157.0623 |
| imidazole lactate | C6H8N2O3 | 156.0535 | 157.0607 | 157.0592 | 157.0623 |
| 3-indoleacetonitrile | C10H8N2 | 156.0687 | 157.0760 | 157.0744 | 157.0776 |
| 2-amino-muconate | C6H7NO4 | 157.0375 | 158.0448 | 158.0432 | 158.0463 |
| 2-hydroxymuconate | C6H6O5 | 158.0215 | 159.0288 | 159.0272 | 159.0304 |
| 4-methylene-2-oxoglutarate | C6H6O5 | 158.0215 | 159.0288 | 159.0272 | 159.0304 |
| 5-oxohex-2-enedioate | C6H6O5 | 158.0215 | 159.0288 | 159.0272 | 159.0304 |
| allantoin | C4H6N4O3 | 158.0440 | 159.0512 | 159.0496 | 159.0528 |
| dimethylcitraconate | C7H10O4 | 158.0579 | 159.0652 | 159.0636 | 159.0668 |
| 4-methylene glutamine | C6H10N2O3 | 158.0691 | 159.0764 | 159.0748 | 159.0780 |
| 4-methylene glutamate | C6H9NO4 | 159.0531 | 160.0604 | 160.0588 | 160.0620 |
| valine | C5H11NO2 | 159.0882 | 160.0955 | 160.0939 | 160.0971 |
| 5-acetamidopentanoate | C7H13NO3 | 159.0895 | 160.0968 | 160.0952 | 160.0984 |
| 2,3-diketo 4-dexoy-epi-inositol | C6H8O5 | 160.0372 | 161.0444 | 161.0428 | 161.0460 |
| 2-oxoadipate | C6H8O5 | 160.0372 | 161.0444 | 161.0428 | 161.0460 |
| 3,5/4-trihydroxycyclohexa-1,2-dione | C6H8O5 | 160.0372 | 161.0444 | 161.0428 | 161.0460 |
| 3-oxo-adipate | C6H8O5 | 160.0372 | 161.0444 | 161.0428 | 161.0460 |
| 5-dehydro-4-deoxy-D-glucuronate | C6H8O6 | 160.0372 | 161.0444 | 161.0428 | 161.0460 |
| N-formiminoaspartate | C5H8N2O4 | 160.0484 | 161.0557 | 161.0540 | 161.0573 |
| allantoate | C4H8N4O3 | 160.0596 | 161.0669 | 161.0653 | 161.0685 |
| glycerol 3-P | C3H9O6P | 160.0621 | 161.0693 | 161.0677 | 161.0709 |
| 3-methyladipic acid | C7H12O4 | 160.0735 | 161.0808 | 161.0792 | 161.0824 |
| indole acetaldehyde | C10H10NO | 160.0762 | 161.0835 | 161.0819 | 161.0851 |
| N-γ-acetyldiaminobutyrate | C6H12N2O3 | 160.0848 | 161.0920 | 161.0904 | 161.0937 |
| ala-ala | | 160.0848 | 161.0920 | 161.0904 | 161.0937 |
| tryptamine | C10H12N2 | 160.1000 | 161.1073 | 161.1057 | 161.1089 |
| N-formyl aspartate | C5H7NO5 | 161.0324 | 162.0397 | 162.0381 | 162.0413 |
| 4,6-dihydroxyquinoline | C9H7NO2 | 161.0477 | 162.0549 | 162.0533 | 162.0566 |
| 4,8-dihydroxyquinoline | C9H7NO2 | 161.0477 | 162.0549 | 162.0533 | 162.0566 |
| α-aminoadipic acid | C6H11NO4 | 161.0688 | 162.0761 | 162.0744 | 162.0777 |
| 4-methyl glutamate | C6H11NO4 | 161.0688 | 162.0761 | 162.0744 | 162.0777 |
| N-methyl glutamate | C6H11NO4 | 161.0688 | 162.0761 | 162.0744 | 162.0777 |
| O-acetyl homoserine | C6H11NO4 | 161.0688 | 162.0761 | 162.0744 | 162.0777 |
| indole-3-ethanol | C10H11NO | 161.0841 | 162.0913 | 162.0897 | 162.0930 |
| 4-hydroxy-2-oxoglutarate | C5H6O6 | 162.0164 | 163.0237 | 163.0221 | 163.0253 |
| 1,2-dihydroxy-5-(methylthio) pent-1-en-3-one | C6H10O3S | 162.0351 | 163.0423 | 163.0407 | 163.0440 |
| 2,3-dimethylmalate | C6H10O5 | 162.0528 | 163.0601 | 163.0584 | 163.0617 |
| 2-ethylmalate | C6H10O5 | 162.0528 | 163.0601 | 163.0584 | 163.0617 |
| 3-ethylmalate | C6H10O5 | 162.0528 | 163.0601 | 163.0584 | 163.0617 |
| rhamno-1,4-lactone | C6H10O5 | 162.0528 | 163.0601 | 163.0584 | 163.0617 |
| gly-ser | | 162.0640 | 163.0713 | 163.0697 | 163.0729 |
| safrole | C10H10O2 | 162.0681 | 163.0753 | 163.0737 | 163.0770 |
| δ-ηψδροξψλψσινε | C6H14N2O3 | 162.1004 | 163.1077 | 163.1061 | 163.1093 |
| N6-hydroxylysine | C6H14N2O3 | 162.1004 | 163.1077 | 163.1061 | 163.1093 |
| carnitine | C7H16NO3 | 162.1130 | 163.1203 | 163.1186 | 163.1219 |
| nicotine | C10H14N2 | 162.1157 | 163.1230 | 163.1213 | 163.1246 |
| N-acetylcysteine | C5H9NO3S | 163.0303 | 164.0376 | 164.0359 | 164.0392 |
| erythro-4-hydroxyglutamate | C5H9NO5 | 163.0480 | 164.0553 | 164.0537 | 164.0570 |
| 3-methyldioxyindole | C9H9NO2 | 163.0633 | 164.0706 | 164.0690 | 164.0722 |
| parapyruvate | C6H8O6 | 164.0321 | 165.0393 | 165.0377 | 165.0410 |

TABLE 1-continued

Endogenous Metabolism Database

| Metabolite | Elemental formula | Precise Mass | M + 1H | 10 ppm− | 10 ppm+ |
|---|---|---|---|---|---|
| 2-hydroxy-3-phenylpropenoate | C9H8O3 | 164.0473 | 165.0546 | 165.0530 | 165.0563 |
| cinnamatedihydrodiol | C9H8O3 | 164.0473 | 165.0546 | 165.0530 | 165.0563 |
| p-coumaric acid | C9H8O3 | 164.0473 | 165.0546 | 165.0530 | 165.0563 |
| o-coumaric acid | C9H8O3 | 164.0473 | 165.0546 | 165.0530 | 165.0563 |
| phenylpyruvate | C9H8O3 | 164.0473 | 165.0546 | 165.0530 | 165.0563 |
| trans-3-hydroxycinnamate | C9H8O3 | 164.0473 | 165.0546 | 165.0530 | 165.0563 |
| fuculose | C6H12O5 | 164.0685 | 165.0757 | 165.0741 | 165.0774 |
| rhamnofuranose | C6H12O5 | 164.0685 | 165.0757 | 165.0741 | 165.0774 |
| rhamnose | C6H12O5 | 164.0685 | 165.0757 | 165.0741 | 165.0774 |
| rhamnulose | C6H12O5 | 164.0685 | 165.0757 | 165.0741 | 165.0774 |
| formylanthranilate | C8H7NO3 | 165.0426 | 166.0499 | 166.0482 | 166.0515 |
| methionine sulfoxide | C5H11NO3S | 165.0459 | 166.0532 | 166.0516 | 166.0549 |
| phenylalanine | C9H11NO2 | 165.0790 | 166.0862 | 166.0846 | 166.0879 |
| hordenine | C10H15NO | 165.1154 | 166.1226 | 166.1210 | 166.1243 |
| terephthalic acid | C8H6O4 | 166.0266 | 167.0339 | 167.0322 | 167.0355 |
| arabinonate | C5H10O6 | 166.0477 | 167.0550 | 167.0533 | 167.0567 |
| lyxonate | C5H10O6 | 166.0477 | 167.0550 | 167.0533 | 167.0567 |
| xylonate | C5H10O6 | 166.0477 | 167.0550 | 167.0533 | 167.0567 |
| 2-hydroxyphenylpropanoate | C9H10O3 | 166.0630 | 167.0703 | 167.0686 | 167.0719 |
| 3-hydroxyphenylpropanoate | C9H10O3 | 166.0630 | 167.0703 | 167.0686 | 167.0719 |
| 3-methoxy-4-hydroxyphenylacetaldehyde | C9H10O3 | 166.0630 | 167.0703 | 167.0686 | 167.0719 |
| phenylpropanoate-dihydrodiol | C9H10O3 | 166.0630 | 167.0703 | 167.0686 | 167.0719 |
| pyridoxal | C8H9NO3 | 167.0582 | 168.0655 | 168.0638 | 168.0672 |
| 3-methoxyanthranilate | C8H9NO3 | 167.0582 | 168.0655 | 168.0638 | 168.0672 |
| 3-methoxytyramine | C9H13NO2 | 167.0946 | 168.1019 | 168.1002 | 168.1036 |
| 3-sulfopyruvate | C3H4O6S | 167.9728 | 168.9801 | 168.9784 | 168.9818 |
| 2-phosphoglycerate | C3H5O6P | 167.9818 | 168.9891 | 168.9874 | 168.9908 |
| 3-phosphoglycerate | C3H5O6P | 167.9818 | 168.9891 | 168.9874 | 168.9908 |
| glyceraldehyde 3-P | C3H5O6P | 167.9818 | 168.9891 | 168.9874 | 168.9908 |
| phosphoenolpyruvate | C3H5O6P | 167.9818 | 168.9891 | 168.9874 | 168.9908 |
| butyryl-P | C4H9O5P | 168.0182 | 169.0255 | 169.0238 | 169.0272 |
| uric acid | C5H4N4O3 | 168.0283 | 169.0356 | 169.0339 | 169.0373 |
| 3,4-dihydroxymandelaldehyde | C8H8O4 | 168.0422 | 169.0495 | 169.0478 | 169.0512 |
| 3,4-dihydroxyphenylacetate | C8H8O4 | 168.0422 | 169.0495 | 169.0478 | 169.0512 |
| homogentisate | C8H8O4 | 168.0422 | 169.0495 | 169.0478 | 169.0512 |
| pyridoxamine | C8H12N2O2 | 168.0899 | 169.0971 | 169.0954 | 169.0988 |
| cysteic acid | C3H7NO5S | 169.0045 | 170.0117 | 170.0100 | 170.0134 |
| 2,3-dihydrodipicolinate | C7H7NO4 | 169.0375 | 170.0448 | 170.0431 | 170.0465 |
| phosphodimethylethanolamine | C4H12NO4P | 169.0498 | 170.0571 | 170.0554 | 170.0588 |
| pyridoxine | C8H11NO3 | 169.0739 | 170.0812 | 170.0795 | 170.0829 |
| norepinephrine | C8H11NO3 | 169.0739 | 170.0812 | 170.0795 | 170.0829 |
| 3-methylhistidine | C7H11N3O2 | 169.0851 | 170.0924 | 170.0907 | 170.0941 |
| N-methylhistidine | C7H11N3O2 | 169.0851 | 170.0924 | 170.0907 | 170.0941 |
| glycerone phosphate | C3H7O6P | 169.9974 | 171.0047 | 171.0030 | 171.0064 |
| thiourocanic acidq | C6H6N2O2S | 170.0150 | 171.0223 | 171.0205 | 171.0240 |
| 3,4-dihydroxyphenylethyleneglycol | C8H10O4 | 170.0579 | 171.0652 | 171.0635 | 171.0669 |
| 2,3,4,5-tetrahydrodipicolinate | C7H9NO4 | 171.0531 | 172.0604 | 172.0587 | 172.0621 |
| 2-oxohept-3-enedioate | C7H8O5 | 172.0372 | 173.0444 | 173.0427 | 173.0462 |
| hydantoin propionate | C6H8N2O4 | 172.0484 | 173.0557 | 173.0539 | 173.0574 |
| gly-pro | | 172.0848 | 173.0920 | 173.0903 | 173.0938 |
| N-acetylglutamate semialdehyde | C7H11NO4 | 173.0688 | 174.0761 | 174.0743 | 174.0778 |
| 2-oxoarginine | C6H11N3O3 | 173.0800 | 174.0873 | 174.0856 | 174.0890 |
| aconitic acid | C6H6O6 | 174.0164 | 175.0237 | 175.0219 | 175.0254 |
| dehydroascorbate | C6H6O6 | 174.0164 | 175.0237 | 175.0219 | 175.0254 |
| shikimate | C7H10O5 | 174.0528 | 175.0601 | 175.0583 | 175.0618 |
| N-forminoglutamate | C6H10N2O4 | 174.0640 | 175.0713 | 175.0696 | 175.0731 |
| indole-3-acetaldoxime | C10H10N2O | 174.0793 | 175.0866 | 175.0848 | 175.0883 |
| indole-3-acetamide | C10H10N2O | 174.0793 | 175.0866 | 175.0848 | 175.0883 |
| N-acetylornithine | C7H14N2O3 | 174.1004 | 175.1077 | 175.1059 | 175.1094 |
| arginine | C6H14N4O2 | 174.1117 | 175.1189 | 175.1172 | 175.1207 |
| N-methyltryptamine | C11H14N2 | 174.1157 | 175.1230 | 175.1212 | 175.1247 |
| monodehydroascorbate | C6H7O6 | 175.0242 | 176.0315 | 176.0298 | 176.0333 |
| 2-amino-3-oxoadipate | C6H9NO5 | 175.0480 | 176.0553 | 176.0536 | 176.0571 |
| N-acetylaspartate | C6H9NO5 | 175.0480 | 176.0553 | 176.0536 | 176.0571 |
| N-formyl glutamate | C6H9NO5 | 175.0480 | 176.0553 | 176.0536 | 176.0571 |
| indolyl-3-acetic acid | C10H9NO2 | 175.0633 | 176.0706 | 176.0688 | 176.0724 |
| 3-indoleglycolaldehyde | C10H9NO2 | 175.0633 | 176.0706 | 176.0688 | 176.0724 |
| 5-hydroxyindole acetaldehyde | C10H9NO2 | 175.0633 | 176.0706 | 176.0688 | 176.0724 |
| N-acetylindoxyl | C10H9NO2 | 175.0633 | 176.0706 | 176.0688 | 176.0724 |
| citrulline | C6H13N3O3 | 175.0957 | 176.1029 | 176.1012 | 176.1047 |
| ascorbic acid | C6H8O6 | 176.0321 | 177.0393 | 177.0376 | 177.0411 |
| 2-dehydro-glucono-1,5-lactone | C6H8O6 | 176.0321 | 177.0393 | 177.0376 | 177.0411 |
| 2-hydroxy-3-oxoadipate | C6H8O6 | 176.0321 | 177.0393 | 177.0376 | 177.0411 |

TABLE 1-continued

Endogenous Metabolism Database

| Metabolite | Elemental formula | Precise Mass | M + 1H | 10 ppm− | 10 ppm+ |
|---|---|---|---|---|---|
| 4,6-dihydroxy-2,5-dioxohexanoate | C6H8O6 | 176.0321 | 177.0393 | 177.0376 | 177.0411 |
| galacturonolactone | C6H8O6 | 176.0321 | 177.0393 | 177.0376 | 177.0411 |
| glucuronolactone | C6H8O6 | 176.0321 | 177.0393 | 177.0376 | 177.0411 |
| xylo-hexulonolactone | C6H8O6 | 176.0321 | 177.0393 | 177.0376 | 177.0411 |
| carbamylaspartic acid | C5H8N2O5 | 176.0433 | 177.0506 | 177.0488 | 177.0523 |
| 2-isopropylmalate | C7H12O5 | 176.0685 | 177.0757 | 177.0740 | 177.0775 |
| 2-propylmalate | C7H12O5 | 176.0685 | 177.0757 | 177.0740 | 177.0775 |
| 3-carboxy-3-hydroxyisocaproate | C7H12O5 | 176.0685 | 177.0757 | 177.0740 | 177.0775 |
| 3-isopropylmalate | C7H12O5 | 176.0685 | 177.0757 | 177.0740 | 177.0775 |
| 3-propylmalate | C7H12O5 | 176.0685 | 177.0757 | 177.0740 | 177.0775 |
| gly-thr | | 176.0797 | 177.0870 | 177.0852 | 177.0887 |
| ala-ser | | 176.0797 | 177.0870 | 177.0852 | 177.0887 |
| serotonin | C10H12N2O | 176.0950 | 177.1022 | 177.1005 | 177.1040 |
| N-formyl methionine | C6H11NO3S | 177.0459 | 178.0532 | 178.0514 | 178.0550 |
| 4-hydroxy-4-methylglutamate | C6H11NO5 | 177.0637 | 178.0710 | 178.0692 | 178.0728 |
| cysteinylglycine | C5H10N2O3S | 178.0412 | 179.0485 | 179.0467 | 179.0503 |
| gly-cys | | 178.0412 | 179.0485 | 179.0467 | 179.0503 |
| 2-dehydro-3-deoxy-galactonate | C6H10O6 | 178.0477 | 179.0550 | 179.0532 | 179.0568 |
| 2-dehydro-3-deoxygluconate | C6H10O6 | 178.0477 | 179.0550 | 179.0532 | 179.0568 |
| 2-dehydro-3-deoxy-rhamnonate | C6H10O6 | 178.0477 | 179.0550 | 179.0532 | 179.0568 |
| 2-dehydro-glucose | C6H10O6 | 178.0477 | 179.0550 | 179.0532 | 179.0568 |
| 2-dexoy-5-keto gluconic acid | C6H10O6 | 178.0477 | 179.0550 | 179.0532 | 179.0568 |
| 2-inosose | C6H10O6 | 178.0477 | 179.0550 | 179.0532 | 179.0568 |
| 3-keto-β-galactose | C6H10O6 | 178.0477 | 179.0550 | 179.0532 | 179.0568 |
| galactono-1,4-lactone | C6H10O6 | 178.0477 | 179.0550 | 179.0532 | 179.0568 |
| glucono-1,5-lactone | C6H10O6 | 178.0477 | 179.0550 | 179.0532 | 179.0568 |
| gulono-1,4-lactone | C6H10O6 | 178.0477 | 179.0550 | 179.0532 | 179.0568 |
| quinolinate | C8H5NO4 | 179.0218 | 180.0291 | 180.0273 | 180.0309 |
| cysteine (S-carboxymethyl) | C5H9NO4S | 179.0252 | 180.0325 | 180.0307 | 180.0343 |
| hippuric acid | C9H9NO3 | 179.0582 | 180.0655 | 180.0637 | 180.0673 |
| glucosamine | C6H13NO5 | 179.0793 | 180.0866 | 180.0848 | 180.0884 |
| 2-hydroxy-3-(4-hydoxyphenyl) propenoate | C9H8O4 | 180.0422 | 181.0495 | 181.0477 | 181.0513 |
| 4-hydroxyphenylpyruvate | C9H8O4 | 180.0422 | 181.0495 | 181.0477 | 181.0513 |
| trans-2,3-dihydroxycinnamate | C9H8O4 | 180.0422 | 181.0495 | 181.0477 | 181.0513 |
| 5-methylthio ribose | C6H12O4S | 180.0456 | 181.0529 | 181.0511 | 181.0547 |
| galactose | C6H12O6 | 180.0634 | 181.0706 | 181.0688 | 181.0724 |
| glucose | C6H12O6 | 180.0634 | 181.0706 | 181.0688 | 181.0724 |
| inositol | C6H12O6 | 180.0634 | 181.0706 | 181.0688 | 181.0724 |
| fructose | C6H12O6 | 180.0634 | 181.0706 | 181.0688 | 181.0724 |
| fuconate | C6H12O6 | 180.0634 | 181.0706 | 181.0688 | 181.0724 |
| mannose | C6H12O6 | 180.0634 | 181.0706 | 181.0688 | 181.0724 |
| mesoinositol | C6H12O6 | 180.0634 | 181.0706 | 181.0688 | 181.0724 |
| rhamnonate | C6H12O6 | 180.0634 | 181.0706 | 181.0688 | 181.0724 |
| sorbose | C6H12O6 | 180.0634 | 181.0706 | 181.0688 | 181.0724 |
| tagatose | C6H12O6 | 180.0634 | 181.0706 | 181.0688 | 181.0724 |
| theophylline | C7H8N4O2 | 180.0647 | 181.0720 | 181.0702 | 181.0738 |
| 3-hydroxykynurenamine | C9H12N2O2 | 180.0899 | 181.0971 | 181.0953 | 181.0989 |
| 5-hydroxykynurenamine | C9H12N2O2 | 180.0899 | 181.0971 | 181.0953 | 181.0989 |
| 4-hydroxymandelonitrile | C8H7NO4 | 181.0375 | 182.0448 | 182.0429 | 182.0466 |
| tyrosine | C9H11NO3 | 181.0739 | 182.0812 | 182.0793 | 182.0830 |
| β-tyrosine | C9H11NO3 | 181.0739 | 182.0812 | 182.0793 | 182.0830 |
| O-phosphocholine | C5H13NO4P | 182.0576 | 183.0649 | 183.0631 | 183.0668 |
| 2,3-dihydroxyphenylpropanoate | C9H10O4 | 182.0579 | 183.0652 | 183.0633 | 183.0670 |
| 3-methoxy-4-hydroxyphenylacetate | C9H10O4 | 182.0579 | 183.0652 | 183.0633 | 183.0670 |
| 3-methoxy-4-hydroxyphenylglycolaldehyde | C9H10O4 | 182.0579 | 183.0652 | 183.0633 | 183.0670 |
| 4-hydroxyphenyllactate | C9H10O4 | 182.0579 | 183.0652 | 183.0633 | 183.0670 |
| homovanillate | C9H10O4 | 182.0579 | 183.0652 | 183.0633 | 183.0670 |
| galactitol | C6H14O6 | 182.0790 | 183.0863 | 183.0845 | 183.0881 |
| mannitol | C6H14O6 | 182.0790 | 183.0863 | 183.0845 | 183.0881 |
| sorbitol | C6H14O6 | 182.0790 | 183.0863 | 183.0845 | 183.0881 |
| saccharin | C7H5NO3S | 182.9990 | 184.0063 | 184.0044 | 184.0081 |
| piperideine-2,6-dicarboxylate | C8H9NO4 | 183.0531 | 184.0604 | 184.0586 | 184.0623 |
| colinephosphoric acid | C5H14NO4P | 183.0655 | 184.0727 | 184.0709 | 184.0746 |
| epinephrine | C9H13NO3 | 183.0895 | 184.0968 | 184.0950 | 184.0986 |
| normetanephrine | C9H13NO3 | 183.0895 | 184.0968 | 184.0950 | 184.0986 |
| 3-P-hydroxypyruvate | C3H5O7P | 183.9767 | 184.9840 | 184.9821 | 184.9858 |
| 5-hydroxyisourate | C5H4N4O4 | 184.0232 | 185.0305 | 185.0286 | 185.0323 |
| 3,4-dihydroxymandelate | C8H8O5 | 184.0372 | 185.0444 | 185.0426 | 185.0463 |
| phosphorylcholine | C5H15NO4P | 184.0733 | 185.0806 | 185.0787 | 185.0824 |
| 3-methoxy-4-hydroxyphenylethyleneglycol | C9H12O4 | 184.0735 | 185.0808 | 185.0790 | 185.0827 |
| 3-P-serine | C3H8NO6P | 185.0083 | 186.0156 | 186.0138 | 186.0175 |

TABLE 1-continued

Endogenous Metabolism Database

| Metabolite | Elemental formula | Precise Mass | M + 1H | 10 ppm− | 10 ppm+ |
|---|---|---|---|---|---|
| 2-amino-3-carboxy-muconate semialdehyde | C7H7NO5 | 185.0324 | 186.0397 | 186.0378 | 186.0415 |
| 3-fumarylpyruvate | C7H6O6 | 186.0164 | 187.0237 | 187.0218 | 187.0256 |
| ala-pro | | 186.1004 | 187.1077 | 187.1058 | 187.1096 |
| thiohistidine | C6H9N3O2S | 187.0415 | 188.0488 | 188.0469 | 188.0507 |
| 2-oxo-6-acetoamidocaproate | C8H13NO4 | 187.0844 | 188.0917 | 188.0898 | 188.0936 |
| N2-acetylaminoadipate semialdehyde | C8H13NO4 | 187.0844 | 188.0917 | 188.0898 | 188.0936 |
| 3-dehydroshikimate | C7H8O6 | 188.0321 | 189.0393 | 189.0374 | 189.0412 |
| But-2-ene-1,2,3-tricarboxylate | C7H8O6 | 188.0321 | 189.0393 | 189.0374 | 189.0412 |
| homo-cis-aconitate | C7H8O6 | 188.0321 | 189.0393 | 189.0374 | 189.0412 |
| hyp-gly | | 188.0797 | 189.0870 | 189.0851 | 189.0888 |
| N-acetyl-lysine | C8H16N2O3 | 188.1161 | 189.1233 | 189.1215 | 189.1252 |
| gly-leu | | 188.1161 | 189.1233 | 189.1215 | 189.1252 |
| gly-ile | | 188.1161 | 189.1233 | 189.1215 | 189.1252 |
| n,n-dimethytryptamine | C12H16N2 | 188.1313 | 189.1386 | 189.1367 | 189.1405 |
| N6,N6,N6-trimethyllysine | C9H20N2O2+ | 188.1525 | 189.1597 | 189.1578 | 189.1616 |
| isocitric acid | C6H5O7 | 189.0035 | 190.0108 | 190.0089 | 190.0127 |
| kynurenate | C10H7NO3 | 189.0426 | 190.0499 | 190.0480 | 190.0518 |
| N-acetylisatin | C10H7NO3 | 189.0426 | 190.0499 | 190.0480 | 190.0518 |
| 2-amino-6-oxoheptanedioate | C7H11NO5 | 189.0637 | 190.0710 | 190.0691 | 190.0729 |
| N-acetyl-glutamate | C7H11NO5 | 189.0637 | 190.0710 | 190.0691 | 190.0729 |
| gly-gly-gly | | 189.0749 | 190.0822 | 190.0803 | 190.0841 |
| gly-asn | | 189.0749 | 190.0822 | 190.0803 | 190.0841 |
| oxalosuccinate | C6H6O7 | 190.0113 | 191.0186 | 191.0167 | 191.0205 |
| 2,4-dihydroxyhept-2-enedioate | C7H10O6 | 190.0477 | 191.0550 | 191.0531 | 191.0569 |
| 2-hydroxyhepta-2,4-dienedioate | C7H10O6 | 190.0477 | 191.0550 | 191.0531 | 191.0569 |
| 3-dehydroquinate | C7H10O6 | 190.0477 | 191.0550 | 191.0531 | 191.0569 |
| N-carbamylglutamate | C6H10N2O5 | 190.0589 | 191.0662 | 191.0643 | 191.0681 |
| gly-asp | | 190.0589 | 191.0662 | 191.0643 | 191.0681 |
| 2,6-diaminoheptanedioate | C7H14N2O4 | 190.0953 | 191.1026 | 191.1007 | 191.1045 |
| ala-thr | | 190.0953 | 191.1026 | 191.1007 | 191.1045 |
| N-(ω)-hydroxyarginine | C6H14N4O3 | 190.1066 | 191.1138 | 191.1119 | 191.1157 |
| 5-methoxytryptamine | C11H14N2O | 190.1106 | 191.1179 | 191.1160 | 191.1198 |
| N-methylserotonin | C11H14N2O | 190.1106 | 191.1179 | 191.1160 | 191.1198 |
| 5-hydroxy-indole acetate | C10H9NO3 | 191.0582 | 192.0655 | 192.0636 | 192.0674 |
| citric acid | C6H8O7 | 192.0270 | 193.0342 | 193.0323 | 193.0362 |
| 2,3-dioxogulonate | C6H8O7 | 192.0270 | 193.0342 | 193.0323 | 193.0362 |
| 2-dehydro-3-deoxy-D-glucarate | C6H8O7 | 192.0270 | 193.0342 | 193.0323 | 193.0362 |
| 4,5,6-trihydroxy-2,3-dioxohexanoate | C6H8O7 | 192.0270 | 193.0342 | 193.0323 | 193.0362 |
| 5-dehydro-4-deoxy-D-glucarate | C6H8O7 | 192.0270 | 193.0342 | 193.0323 | 193.0362 |
| ala-cys | | 192.0568 | 193.0641 | 193.0622 | 193.0660 |
| quinate | C7H12O6 | 192.0634 | 193.0706 | 193.0687 | 193.0726 |
| ser-ser | | 192.0746 | 193.0819 | 193.0799 | 193.0838 |
| O-acetylcarnitine | C8H18NO4 | 192.1236 | 193.1308 | 193.1289 | 193.1328 |
| 5,6-dihydroxyindole-2-carboxylate | C9H7NO4 | 193.0375 | 194.0448 | 194.0428 | 194.0467 |
| L-dopachrome | C9H7NO4 | 193.0375 | 194.0448 | 194.0428 | 194.0467 |
| homocysteine (S-carboxymethyl) | C6H11NO4S | 193.0409 | 194.0481 | 194.0462 | 194.0501 |
| phenylacetylglycine | C10H11NO3 | 193.0739 | 194.0812 | 194.0792 | 194.0831 |
| 2-dehydro-gluconate | C6H10O7 | 194.0426 | 195.0499 | 195.0479 | 195.0518 |
| 3-dehydro-L-gulonate | C6H10O7 | 194.0426 | 195.0499 | 195.0479 | 195.0518 |
| fructuronate | C6H10O7 | 194.0426 | 195.0499 | 195.0479 | 195.0518 |
| galacturonate | C6H10O7 | 194.0426 | 195.0499 | 195.0479 | 195.0518 |
| glucuronate | C6H10O7 | 194.0426 | 195.0499 | 195.0479 | 195.0518 |
| 1-O-methyl-myo-inositol | C7H14O6 | 194.0790 | 195.0863 | 195.0843 | 195.0882 |
| 3-O-methyl-myo-inositol | C7H14O6 | 194.0790 | 195.0863 | 195.0843 | 195.0882 |
| caffeine | C8H10N4O2 | 194.0804 | 195.0876 | 195.0857 | 195.0896 |
| 2-carboxy-2,3-dihydro-5,6-dihydroxyindole | C9H9NO4 | 195.0531 | 196.0604 | 196.0585 | 196.0624 |
| dopaquinone | C9H9NO4 | 195.0531 | 196.0604 | 196.0585 | 196.0624 |
| glucosaminate | C6H13NO6 | 195.0743 | 196.0815 | 196.0796 | 196.0835 |
| 3-(3,4-dihydroxyphenyl) pyruvate | C9H8O5 | 196.0372 | 197.0444 | 197.0425 | 197.0464 |
| altronate | C6H12O7 | 196.0583 | 197.0655 | 197.0636 | 197.0675 |
| galactonate | C6H12O7 | 196.0583 | 197.0655 | 197.0636 | 197.0675 |
| gluconate | C6H12O7 | 196.0583 | 197.0655 | 197.0636 | 197.0675 |
| gulonate | C6H12O7 | 196.0583 | 197.0655 | 197.0636 | 197.0675 |
| mannonate | C6H12O7 | 196.0583 | 197.0655 | 197.0636 | 197.0675 |
| tagaturonate | C6H10O7 | 196.0583 | 197.0655 | 197.0636 | 197.0675 |
| guanidino-acetate-P | C3H8N3O5P | 197.0196 | 198.0268 | 198.0249 | 198.0288 |
| dihydroxy-phenylalanine | C9H11NO4 | 197.0688 | 198.0761 | 198.0741 | 198.0780 |
| L-Dopa | C9H11NO4 | 197.0688 | 198.0761 | 198.0741 | 198.0780 |
| N-hydroxytyrosine | C9H11NO4 | 197.0688 | 198.0761 | 198.0741 | 198.0780 |
| metanephrine | C10H15NO3 | 197.1052 | 198.1125 | 198.1105 | 198.1144 |
| erythrose 4--P | C4H7O7P | 197.9924 | 198.9996 | 198.9976 | 199.0016 |

TABLE 1-continued

Endogenous Metabolism Database

| Metabolite | Elemental formula | Precise Mass | M + 1H | 10 ppm− | 10 ppm+ |
|---|---|---|---|---|---|
| O-phosphohomoserine | C4H9NO6P | 198.0162 | 199.0234 | 199.0215 | 199.0254 |
| 3-(3,4-dihydroxyphenyl) lactate | C9H10O5 | 198.0528 | 199.0601 | 199.0581 | 199.0621 |
| 3-methoxy-4-hydroxymandelate | C9H10O5 | 198.0528 | 199.0601 | 199.0581 | 199.0621 |
| hercynine | C9H16N3O2 | 198.1242 | 199.1315 | 199.1295 | 199.1335 |
| 2-hydroxy-5-carboxymethylmuconate | C8H8O6 | 200.0321 | 201.0393 | 201.0373 | 201.0413 |
| 4-maleylacetoacetate | C8H8O6 | 200.0321 | 201.0393 | 201.0373 | 201.0413 |
| S-sulfocysteine | C3H7NO5S2 | 200.9765 | 201.9838 | 201.9818 | 201.9858 |
| 5-hydroxy-2-oxo-4-ureido-2,5-dihydro-1H-imidazole-5-carboxylate | C5H6N4O5 | 202.0338 | 203.0411 | 203.0390 | 203.0431 |
| ser-pro | | 202.0953 | 203.1026 | 203.1006 | 203.1046 |
| hyp-ala | | 202.0953 | 203.1026 | 203.1006 | 203.1046 |
| ala-leu | | 202.1317 | 203.1390 | 203.1370 | 203.1410 |
| ala-ile | | 202.1317 | 203.1390 | 203.1370 | 203.1410 |
| spermine | C10H26N4 | 202.2157 | 203.2230 | 203.2210 | 203.2250 |
| 8-methoxykynurenate | C11H9NO3 | 203.0582 | 204.0655 | 204.0635 | 204.0675 |
| N2-acetylaminoadipate | C8H13NO5 | 203.0793 | 204.0866 | 204.0846 | 204.0887 |
| gly-gly-ala | | 203.0906 | 204.0979 | 204.0958 | 204.0999 |
| gly-gln | | 203.0906 | 204.0979 | 204.0958 | 204.0999 |
| ala-asn | | 203.0906 | 204.0979 | 204.0958 | 204.0999 |
| gly-lys | | 203.1270 | 204.1342 | 204.1322 | 204.1363 |
| oxaloglutarate | C7H8O7 | 204.0270 | 205.0342 | 205.0322 | 205.0363 |
| 1,4-dihydroxy-2-naphtoate | C11H8O4 | 204.0422 | 205.0495 | 205.0475 | 205.0516 |
| indole pyruvate | C11H10NO3 | 204.0661 | 205.0733 | 205.0713 | 205.0754 |
| gly-glu | | 204.0746 | 205.0819 | 205.0798 | 205.0839 |
| ala-asp | | 204.0746 | 205.0819 | 205.0798 | 205.0839 |
| tryptophan | C11H12N2O2 | 204.0899 | 205.0971 | 205.0951 | 205.0992 |
| N6-acetyl-N6-hydroxylysine | C8H16N2O4 | 204.1110 | 205.1183 | 205.1162 | 205.1203 |
| bufotenine | C12H16N2O | 204.1263 | 205.1335 | 205.1315 | 205.1356 |
| 6-methoxykynurenate | C10H7NO4 | 205.0375 | 206.0448 | 206.0427 | 206.0468 |
| thioctic acid amide | C8H15NOS2 | 205.0595 | 206.0668 | 206.0647 | 206.0688 |
| 5-methoxyindoleacetate | C11H11NO3 | 205.0739 | 206.0812 | 206.0791 | 206.0832 |
| pantothenol | C9H19NO4 | 205.1314 | 206.1387 | 206.1366 | 206.1407 |
| 3-hydroxy-N6,N6,N6-trimethyllysine | C9H21N2O3+ | 205.1552 | 206.1625 | 206.1604 | 206.1645 |
| 3-oxolomalate | C6H6O8 | 206.0062 | 207.0135 | 207.0114 | 207.0156 |
| 2-methylcitrate | C7H10O7 | 206.0426 | 207.0499 | 207.0478 | 207.0520 |
| homocitrate | C7H10O7 | 206.0426 | 207.0499 | 207.0478 | 207.0520 |
| homoisocitrate | C7H10O7 | 206.0426 | 207.0499 | 207.0478 | 207.0520 |
| lipoic acid | C8H14O2S2 | 206.0435 | 207.0508 | 207.0487 | 207.0529 |
| xanthurenate | C10H8NO4 | 206.0453 | 207.0526 | 207.0505 | 207.0547 |
| gly-met | | 206.0725 | 207.0798 | 207.0777 | 207.0818 |
| ser-thr | | 206.0902 | 207.0975 | 207.0954 | 207.0996 |
| ibuprofen | C13H18O2 | 206.1307 | 207.1379 | 207.1359 | 207.1400 |
| 2-formaminobenzoylacetate | C10H9NO4 | 207.0531 | 208.0604 | 208.0583 | 208.0625 |
| 4-(2-aminophenyl)-2,4-dioxobutanoate | C10H9NO4 | 207.0531 | 208.0604 | 208.0583 | 208.0625 |
| indole acetate | C10H9NO2 | 207.0531 | 208.0604 | 208.0583 | 208.0625 |
| dihydrolipoamide | C8H17NOS2 | 207.0751 | 208.0824 | 208.0803 | 208.0845 |
| N-acetylphenylalanine | C11H13NO3 | 207.0895 | 208.0968 | 208.0947 | 208.0989 |
| ser-cys | | 208.0518 | 209.0590 | 209.0569 | 209.0611 |
| dihydrolipoic acid | C8H16O2S2 | 208.0592 | 209.0664 | 209.0643 | 209.0685 |
| formyl-5-hydroxykynurenamine | C10H12N2O3 | 208.0848 | 209.0920 | 209.0900 | 209.0941 |
| kynurenine | C10H12N2O3 | 208.0848 | 209.0920 | 209.0900 | 209.0941 |
| 4-hydroxyphenylacetylglycine | C10H11NO4 | 209.0688 | 210.0761 | 210.0740 | 210.0782 |
| galactarate | C6H10O8 | 210.0375 | 211.0448 | 211.0427 | 211.0469 |
| glucarate | C6H10O8 | 210.0375 | 211.0448 | 211.0427 | 211.0469 |
| creatine-P | C4H10N3O5P | 211.0352 | 212.0425 | 212.0404 | 212.0446 |
| 5-(2'-formylethyl)-4,6-dihydroxypicolinate | C9H9NO5 | 211.0480 | 212.0553 | 212.0532 | 212.0574 |
| 4-aspartyl-P | C4H7NO7P | 211.9954 | 213.0027 | 213.0006 | 213.0048 |
| isophenoxazine | C12H8N2O2 | 212.0586 | 213.0658 | 213.0637 | 213.0680 |
| gly-his | | 212.0909 | 213.0982 | 213.0961 | 213.1003 |
| pro-pro | | 212.1161 | 213.1233 | 213.1212 | 213.1255 |
| indoxylsulfuric acid | C8H7NO4S | 213.0096 | 214.0168 | 214.0147 | 214.0190 |
| 1-deoxy xylulose 5-phosphate | C5H11O7P | 214.0237 | 215.0309 | 215.0288 | 215.0331 |
| 2-deoxyribose 1-phosphate | C5H11O7P | 214.0237 | 215.0309 | 215.0288 | 215.0331 |
| 2-deoxy-ribose-5-phosphate | C5H11O7P | 214.0237 | 215.0309 | 215.0288 | 215.0331 |
| glutamyl-P | C4H10NO7P | 215.0189 | 216.0262 | 216.0240 | 216.0283 |
| glycero-3-phosphoethanolamine | C5H14NO6P | 215.0553 | 216.0626 | 216.0604 | 216.0647 |
| 5-carboxy-2-oxohept-3-enedioate | C8H8O7 | 216.0270 | 217.0342 | 217.0321 | 217.0364 |
| 5-carboxymethyl-2-hydroxymuconate | C8H8O7 | 216.0270 | 217.0342 | 217.0321 | 217.0364 |
| gly-val | | 216.1096 | 217.1169 | 217.1147 | 217.1191 |

TABLE 1-continued

Endogenous Metabolism Database

| Metabolite | Elemental formula | Precise Mass | M + 1H | 10 ppm− | 10 ppm+ |
|---|---|---|---|---|---|
| pro-thr | | 216.1110 | 217.1183 | 217.1161 | 217.1204 |
| 3-methylindolepyruvate | C12H11NO3 | 217.0739 | 218.0812 | 218.0790 | 218.0833 |
| gly-ala-ala | | 217.1062 | 218.1135 | 218.1113 | 218.1157 |
| ala-gln | | 217.1062 | 218.1135 | 218.1113 | 218.1157 |
| ala-lys | | 217.1426 | 218.1499 | 218.1477 | 218.1521 |
| pro-cys | | 218.0725 | 219.0798 | 219.0776 | 219.0820 |
| ala-glu | | 218.0902 | 219.0975 | 219.0953 | 219.0997 |
| hyp-ser | | 218.0902 | 219.0975 | 219.0953 | 219.0997 |
| N-acetylserotonin | C12H14N2O2 | 218.1055 | 219.1128 | 219.1106 | 219.1150 |
| lysopine | C9H18N2O4 | 218.1266 | 219.1339 | 219.1317 | 219.1361 |
| ser-leu | | 218.1266 | 219.1339 | 219.1317 | 219.1361 |
| ser-ile | | 218.1266 | 219.1339 | 219.1317 | 219.1361 |
| histidinol-P | C6H10N3O4P | 219.0403 | 220.0476 | 220.0454 | 220.0498 |
| 5-hydroxyindolepyruvate | C11H9NO4 | 219.0531 | 220.0604 | 220.0582 | 220.0626 |
| O-succinylhomoserine | C8H13NO6 | 219.0743 | 220.0815 | 220.0793 | 220.0837 |
| gly-gly-ser | | 219.0855 | 220.0928 | 220.0906 | 220.0950 |
| ser-asn | | 219.0855 | 220.0928 | 220.0906 | 220.0950 |
| pantothenic acid | C9H17NO5 | 219.1106 | 220.1179 | 220.1157 | 220.1201 |
| imidazole acetol-P | C6H9N2O5P | 220.0243 | 221.0316 | 221.0294 | 221.0338 |
| ser-asp | | 220.0695 | 221.0768 | 221.0746 | 221.0790 |
| N-acetylmannosamine | C8H15NO6 | 220.0821 | 221.0894 | 221.0871 | 221.0916 |
| 5-hydroxytryptophan | C11H12N2O3 | 220.0848 | 221.0920 | 221.0898 | 221.0943 |
| N-formulkynurenine | C11H12N2O4 | 220.0848 | 221.0920 | 221.0898 | 221.0943 |
| ala-met | | 220.0881 | 221.0954 | 221.0932 | 221.0976 |
| thr-thr | | 220.1059 | 221.1132 | 221.1110 | 221.1154 |
| 7,8-dihydroxykynurenate | C10H7NO5 | 221.0324 | 222.0397 | 222.0375 | 222.0419 |
| 6-hydroxyindolelactate | C11H11NO4 | 221.0688 | 222.0761 | 222.0738 | 222.0783 |
| indolyl-3-lactic acid | C11H11NO4 | 221.0688 | 222.0761 | 222.0738 | 222.0783 |
| N-acetyl glucosamine | C8H15NO6 | 221.0899 | 222.0972 | 222.0950 | 222.0994 |
| 2-succinylbenzoate | C11H10O5 | 222.0528 | 223.0601 | 223.0578 | 223.0623 |
| cystathionine | C7H14N2O4S | 222.0674 | 223.0747 | 223.0724 | 223.0769 |
| thr-cys | | 222.0674 | 223.0747 | 223.0724 | 223.0769 |
| gly-phe | | 222.1004 | 223.1077 | 223.1055 | 223.1099 |
| 4-(2-amino-3-hydorxyphenyl)-2,4-dioxobutanoate | C10H9NO5 | 223.0480 | 224.0553 | 224.0531 | 224.0576 |
| 4(2-amino-5-hydroxyphenyl)-2,4-dixoxbutanoate | C10H9NO5 | 223.0480 | 224.0553 | 224.0531 | 224.0576 |
| 7,8-dihydro-7,8-dihydroxykynurenate | C10H9NO5 | 223.0480 | 224.0553 | 224.0531 | 224.0576 |
| cys-cys | | 224.0289 | 225.0362 | 225.0339 | 225.0384 |
| 3-hydroxy-kynurenine | C10H12N2O4 | 224.0797 | 225.0870 | 225.0847 | 225.0892 |
| 5-hydroxykynurenine | C10H12N2O4 | 224.0797 | 225.0870 | 225.0847 | 225.0892 |
| chorismate | C10H10O6 | 226.0477 | 227.0550 | 227.0527 | 227.0573 |
| isochorismate | C10H10O6 | 226.0477 | 227.0550 | 227.0527 | 227.0573 |
| prephenate | C10H10O6 | 226.0477 | 227.0550 | 227.0527 | 227.0573 |
| porphobilinogen | C10H14N2O4 | 226.0953 | 227.1026 | 227.1003 | 227.1049 |
| carnosine | C9H14N4O3 | 226.1066 | 227.1138 | 227.1116 | 227.1161 |
| ala-his | | 226.1066 | 227.1138 | 227.1116 | 227.1161 |
| serine phosphoethanolamine | C5H13N2O6P | 227.0427 | 228.0500 | 228.0477 | 228.0523 |
| 5-(2'-carboxyethyl)-4,6-dihydroxypicolinate | C9H9NO6 | 227.0430 | 228.0502 | 228.0480 | 228.0525 |
| stizolobinate | C9H9NO6 | 227.0430 | 228.0502 | 228.0480 | 228.0525 |
| 2'-deoxy-cytidine | C9H13N3O4 | 227.0906 | 228.0979 | 228.0956 | 228.1001 |
| (4-aminophenyl)-1,2,3,4-tetrahydroxypentane | C11H17NO4 | 227.1157 | 228.1230 | 228.1207 | 228.1253 |
| ribose 5-P | C5H9O8P | 228.0029 | 229.0102 | 229.0079 | 229.0125 |
| ribulose 5-P | C5H9O8P | 228.0029 | 229.0102 | 229.0079 | 229.0125 |
| xylulose 5-P | C5H9O8P | 228.0029 | 229.0102 | 229.0079 | 229.0125 |
| deoxyuridine | C9H12N2O5 | 228.0746 | 229.0819 | 229.0796 | 229.0842 |
| hyp-pro | | 228.1110 | 229.1183 | 229.1160 | 229.1205 |
| pro-leu | | 228.1474 | 229.1546 | 229.1524 | 229.1569 |
| pro-ile | | 228.1474 | 229.1546 | 229.1524 | 229.1569 |
| 4-(alanin-3-yl)-2-hydroxy-cis,cis-muconate 6-semialdehyde | C9H11NO6 | 229.0586 | 230.0659 | 230.0636 | 230.0682 |
| 5-(alanin-3-yl)-2-hydroxy-cis,cis-muconate 6-semialdehyde | C9H11NO6 | 229.0586 | 230.0659 | 230.0636 | 230.0682 |
| ergothioneine | C9H15N3O2S | 229.0885 | 230.0958 | 230.0935 | 230.0981 |
| gly-gly-pro | | 229.1062 | 230.1135 | 230.1112 | 230.1158 |
| pro-asn | | 229.1062 | 230.1135 | 230.1112 | 230.1158 |
| ribose 1-phosphate | C5H11O8P | 230.0186 | 231.0258 | 231.0235 | 231.0282 |
| xylulose 1-P | C5H11O8P | 230.0186 | 231.0258 | 231.0235 | 231.0282 |
| α-xylose 1-phosphate | C5H11O8P | 230.0186 | 231.0258 | 231.0235 | 231.0282 |
| pro-asp | | 230.0902 | 231.0975 | 231.0952 | 231.0998 |
| ala-val | | 230.1253 | 231.1326 | 231.1302 | 231.1349 |

TABLE 1-continued

Endogenous Metabolism Database

| Metabolite | Elemental formula | Precise Mass | M + 1H | 10 ppm− | 10 ppm+ |
|---|---|---|---|---|---|
| N-succinylglutamate 5-semialdehyde | C9H13NO6 | 231.0743 | 232.0815 | 232.0792 | 232.0839 |
| ala-ala-ala | | 231.1219 | 232.1292 | 232.1268 | 232.1315 |
| gly-arg | | 231.1331 | 232.1404 | 232.1381 | 232.1427 |
| ribitol-5-phosphate | C5H13O8P | 232.0342 | 233.0415 | 233.0392 | 233.0438 |
| N2-succinylornithine | C9H16N2O5 | 232.1059 | 233.1132 | 233.1108 | 233.1155 |
| N6-acetyl-2,6-diaminoheptanedioate | C9H16N2O5 | 232.1059 | 233.1132 | 233.1108 | 233.1155 |
| hyp-thr | | 232.1059 | 233.1132 | 233.1108 | 233.1155 |
| melatonin | C13H16N2O2 | 232.1212 | 233.1284 | 233.1261 | 233.1308 |
| thr-leu | | 232.1423 | 233.1496 | 233.1472 | 233.1519 |
| thr-ile | | 232.1423 | 233.1496 | 233.1472 | 233.1519 |
| gly-gly-thr | | 233.1011 | 234.1084 | 234.1061 | 234.1108 |
| gly-ala-ser | | 233.1011 | 234.1084 | 234.1061 | 234.1108 |
| ser-gln | | 233.1011 | 234.1084 | 234.1061 | 234.1108 |
| thr-asn | | 233.1011 | 234.1084 | 234.1061 | 234.1108 |
| ser-lys | | 233.1375 | 234.1448 | 234.1425 | 234.1471 |
| hyp-cys | | 234.0674 | 235.0747 | 235.0723 | 235.0770 |
| ser-glu | | 234.0852 | 235.0924 | 235.0901 | 235.0948 |
| thr-asp | | 234.0852 | 235.0924 | 235.0901 | 235.0948 |
| cys-leu | | 234.1038 | 235.1111 | 235.1087 | 235.1134 |
| cys-ile | | 234.1038 | 235.1111 | 235.1087 | 235.1134 |
| gly-gly-cys | | 235.0626 | 236.0699 | 236.0676 | 236.0723 |
| cys-asn | | 235.0626 | 236.0699 | 236.0676 | 236.0723 |
| D-erythro-imidazole-glycerol-P | C6H9N2O6P | 236.0192 | 237.0265 | 237.0241 | 237.0289 |
| cys-asp | | 236.0467 | 237.0539 | 237.0516 | 237.0563 |
| formylkynurenine | C11H12N2O4 | 236.0797 | 237.0870 | 237.0846 | 237.0893 |
| ser-met | | 236.0831 | 237.0903 | 237.0880 | 237.0927 |
| ala-phe | | 236.1161 | 237.1233 | 237.1210 | 237.1257 |
| 6-pyruvoyltetrahydropterin | C9H11N5O3 | 237.0862 | 238.0934 | 238.0911 | 238.0958 |
| erythro-1-(imidazol-4-yl) glycerol 3-phosphate | C6H11N2O6P | 238.0349 | 239.0422 | 239.0398 | 239.0446 |
| gly-tyr | | 238.0953 | 239.1026 | 239.1002 | 239.1050 |
| 5-P-β-ribosylamine | C6H10NO7P | 239.0189 | 240.0262 | 240.0238 | 240.0286 |
| cystine | C6H12N2O4S2 | 240.0238 | 241.0311 | 241.0287 | 241.0335 |
| homocarnosine | C10H16N4O3 | 240.1222 | 241.1295 | 241.1271 | 241.1319 |
| anserine | C10H16N4O3 | 240.1222 | 241.1295 | 241.1271 | 241.1319 |
| 16-hexadecanal | C16H32O | 240.2453 | 241.2526 | 241.2502 | 241.2550 |
| diphosphoglyceric acid | C3H3O10P2 | 241.0006 | 242.0079 | 242.0055 | 242.0103 |
| 5,6,7,8-tetrahydrobiopterin | C9H15N5O3 | 241.1175 | 242.1247 | 242.1223 | 242.1272 |
| 2,3-diketo-5-methylthiopentyl-1-phosphate | C6H11O6SP | 242.0008 | 243.0081 | 243.0057 | 243.0105 |
| 2-hydroxy-3-keto-5-methylthiopentyl-1-phosphate | C6H11O6SP | 242.0008 | 243.0081 | 243.0057 | 243.0105 |
| 5-phosphono-oxy-lysine | C6H15N2O6P | 242.0662 | 243.0735 | 243.0710 | 243.0759 |
| thymidine | C10H14N2O5 | 242.0902 | 243.0975 | 243.0951 | 243.0999 |
| ser-his | | 242.1015 | 243.1087 | 243.1063 | 243.1112 |
| 16-hexadecanol | C16H34O | 242.2610 | 243.2682 | 243.2658 | 243.2707 |
| cytidine | C9H13N3O5 | 243.0855 | 244.0928 | 244.0903 | 244.0952 |
| gly-ala-pro | | 243.1219 | 244.1292 | 244.1267 | 244.1316 |
| pro-gln | | 243.1219 | 244.1292 | 244.1267 | 244.1316 |
| pro-lys | | 243.1583 | 244.1655 | 244.1631 | 244.1680 |
| fucose-1P | C6H13O8P | 244.0342 | 245.0415 | 245.0390 | 245.0439 |
| fuculose-1P | C6H13O8P | 244.0342 | 245.0415 | 245.0390 | 245.0439 |
| mevalonate-5-P | C6H13O8P | 244.0342 | 245.0415 | 245.0390 | 245.0439 |
| rhamnulose-1P | C6H13O8P | 244.0342 | 245.0415 | 245.0390 | 245.0439 |
| pseudouridine | C9H12N2O6 | 244.0695 | 245.0768 | 245.0743 | 245.0792 |
| uridine | C9H12N2O6 | 244.0695 | 245.0768 | 245.0743 | 245.0792 |
| biotin | C10H16N2O3S | 244.0881 | 245.0954 | 245.0930 | 245.0979 |
| pro-glu | | 244.1059 | 245.1132 | 245.1107 | 245.1156 |
| hyp-hyp | | 244.1059 | 245.1132 | 245.1107 | 245.1156 |
| hyp-leu | | 244.1423 | 245.1496 | 245.1471 | 245.1520 |
| hyp-ile | | 244.1423 | 245.1496 | 245.1471 | 245.1520 |
| leu-leu | | 244.1787 | 245.1859 | 245.1835 | 245.1884 |
| leu-ile | | 244.1787 | 245.1859 | 245.1835 | 245.1884 |
| ile-ile | | 244.1787 | 245.1859 | 245.1835 | 245.1884 |
| hyp-asn | | 245.1011 | 246.1084 | 246.1060 | 246.1109 |
| gly-gly-leu | | 245.1375 | 246.1448 | 246.1423 | 246.1473 |
| gly-gly-ile | | 245.1375 | 246.1448 | 246.1423 | 246.1473 |
| leu-asn | | 245.1375 | 246.1448 | 246.1423 | 246.1473 |
| ile-asn | | 245.1375 | 246.1448 | 246.1423 | 246.1473 |
| ala-arg | | 245.1488 | 246.1560 | 246.1536 | 246.1585 |
| dimethylallyl-PP | C5H12O7P2 | 246.0047 | 247.0120 | 247.0095 | 247.0144 |
| isopentenyl-PP | C5H12O7P2 | 246.0047 | 247.0120 | 247.0095 | 247.0144 |
| phosphatidyl glycerol | C6H15O8P | 246.0499 | 247.0571 | 247.0547 | 247.0596 |

TABLE 1-continued

Endogenous Metabolism Database

| Metabolite | Elemental formula | Precise Mass | M + 1H | 10 ppm− | 10 ppm+ |
|---|---|---|---|---|---|
| hyp-asp | | 246.0852 | 247.0924 | 247.0900 | 247.0949 |
| gly-gly-asn | | 246.0964 | 247.1037 | 247.1012 | 247.1061 |
| asn-asn | | 246.0964 | 247.1037 | 247.1012 | 247.1061 |
| pro-met | | 246.1038 | 247.1111 | 247.1086 | 247.1135 |
| ser-val | | 246.1202 | 247.1275 | 247.1250 | 247.1299 |
| leu-asp | | 246.1215 | 247.1288 | 247.1263 | 247.1313 |
| ile-asp | | 246.1215 | 247.1288 | 247.1263 | 247.1313 |
| octopine | C9H18N4O4 | 246.1328 | 247.1400 | 247.1376 | 247.1425 |
| 2-C-methyl erythritol 4-phosphate | C5H13O9P | 247.0213 | 248.0286 | 248.0261 | 248.0311 |
| N-succinylglutamate | C9H13NO7 | 247.0692 | 248.0764 | 248.0740 | 248.0789 |
| gly-gly-asp | | 247.0804 | 248.0877 | 248.0852 | 248.0902 |
| asn-asp | | 247.0804 | 248.0877 | 248.0852 | 248.0902 |
| gly-ala-thr | | 247.1168 | 248.1241 | 248.1216 | 248.1265 |
| ala-ala-ser | | 247.1168 | 248.1241 | 248.1216 | 248.1265 |
| thr-gln | | 247.1168 | 248.1241 | 248.1216 | 248.1265 |
| thr-lys | | 247.1532 | 248.1605 | 248.1580 | 248.1629 |
| asp-asp | | 248.0644 | 249.0717 | 249.0692 | 249.0742 |
| 5-hydroxyindoleacetylglycine | C12H12N2O4 | 248.0797 | 249.0870 | 249.0845 | 249.0894 |
| thr-glu | | 248.1008 | 249.1081 | 249.1056 | 249.1106 |
| 6-hydroxymelatonin | C13H16N2O3 | 248.1161 | 249.1233 | 249.1209 | 249.1258 |
| abscisic aldehyde | C15H20O3 | 248.1412 | 249.1485 | 249.1460 | 249.1510 |
| linatine | C10H7N3O5 | 249.0385 | 250.0458 | 250.0433 | 250.0483 |
| gly-ala-cys | | 249.0783 | 250.0856 | 250.0831 | 250.0881 |
| cys-gln | | 249.0783 | 250.0856 | 250.0831 | 250.0881 |
| 6-S-Acetyldihydrolipoamide | C10H19NO2S2 | 249.0857 | 250.0930 | 250.0905 | 250.0955 |
| gly-ser-ser | | 249.0960 | 250.1033 | 250.1008 | 250.1058 |
| cys-lys | | 249.1147 | 250.1220 | 250.1195 | 250.1245 |
| cys-glu | | 250.0623 | 251.0696 | 251.0671 | 251.0721 |
| γ-glutamylcysteine | C8H14N2O5S | 250.0623 | 251.0696 | 251.0671 | 251.0721 |
| thr-met | | 250.0987 | 251.1060 | 251.1035 | 251.1085 |
| abscisic alcohol | C15H22O3 | 250.1569 | 251.1642 | 251.1616 | 251.1667 |
| xanthoxin | C15H22O3 | 250.1569 | 251.1642 | 251.1616 | 251.1667 |
| deoxyadenosine | C10H13N5O3 | 251.1018 | 252.1091 | 252.1066 | 252.1116 |
| shikimate-5-P | C7H9O8P | 252.0029 | 253.0102 | 253.0077 | 253.0127 |
| cys-met | | 252.0602 | 253.0675 | 253.0650 | 253.0700 |
| 5-hydroxy-N-formylkynurenine | C11H12N2O5 | 252.0746 | 253.0819 | 253.0793 | 253.0844 |
| deoxyinosine | C10H12N4O4 | 252.0858 | 253.0931 | 253.0906 | 253.0956 |
| ala-tyr | | 252.1110 | 253.1183 | 253.1157 | 253.1208 |
| ser-phe | | 252.1110 | 253.1183 | 253.1157 | 253.1208 |
| pro-his | | 252.1222 | 253.1295 | 253.1270 | 253.1320 |
| 5-(3'-carboxy-3'-oxopropenyl)-4,6-dihdroxypicolinate | C10H7NO7 | 253.0222 | 254.0295 | 254.0270 | 254.0320 |
| N-acetyl-glutamyl-P | C7H12NO7P | 253.0346 | 254.0418 | 254.0393 | 254.0444 |
| cysteine-homocystein disulfide | C7H14N2O4S2 | 254.0395 | 255.0467 | 255.0442 | 255.0493 |
| arginine-P | C6H15N4O5P | 254.0774 | 255.0847 | 255.0821 | 255.0872 |
| galactosylglycerol | C9H18O8 | 254.1001 | 255.1074 | 255.1049 | 255.1100 |
| 5-(3'-carboxy-3'-oxopropyl)-4,6-dihydroxypicolinate | C10H9NO7 | 255.0379 | 256.0451 | 256.0426 | 256.0477 |
| 2-amino-4-hydroxy-6-(erythro)-trihydroxypropyl-dihydropteridine | C9H13N5O4 | 255.0967 | 256.1040 | 256.1014 | 256.1066 |
| 2-dehydro-3-deoxy-6-P-gluconate | C6H9O9P | 255.9978 | 257.0051 | 257.0025 | 257.0077 |
| 6-P glucono-1,5-lactone | C6H9O9P | 255.9978 | 257.0051 | 257.0025 | 257.0077 |
| thr-his | | 256.1171 | 257.1244 | 257.1218 | 257.1270 |
| pro-val | | 256.1409 | 257.1482 | 257.1456 | 257.1508 |
| palmitic acid | C16H32O2 | 256.2402 | 257.2475 | 257.2449 | 257.2501 |
| glucosamine 6-P | C6H12NO8P | 257.0295 | 258.0367 | 258.0342 | 258.0393 |
| ala-ala-pro | | 257.1375 | 258.1448 | 258.1422 | 258.1474 |
| 2-dehydro-3-dexoy galactonate 6-P | C6H11O9P | 258.0135 | 259.0208 | 259.0182 | 259.0233 |
| 2-deoxy-5-keto glucosic acid 6-phosphate | C6H11O9P | 258.0135 | 259.0208 | 259.0182 | 259.0233 |
| 3-oxo-6-P-hexulose | C6H11O9P | 258.0135 | 259.0208 | 259.0182 | 259.0233 |
| fructose 6-P | C6H11O9P | 258.0135 | 259.0208 | 259.0182 | 259.0233 |
| galactose 1-P | C6H11O9P | 258.0135 | 259.0208 | 259.0182 | 259.0233 |
| glucose 1-P | C6H11O9P | 258.0135 | 259.0208 | 259.0182 | 259.0233 |
| glucose 6-P | C6H11O9P | 258.0135 | 259.0208 | 259.0182 | 259.0233 |
| inositol 1-P | C6H11O9P | 258.0135 | 259.0208 | 259.0182 | 259.0233 |
| Mannose 6-P | C6H11O9P | 258.0135 | 259.0208 | 259.0182 | 259.0233 |
| β-fructose 1-P | C6H11O9P | 258.0135 | 259.0208 | 259.0182 | 259.0233 |
| cys-his | | 258.0786 | 259.0859 | 259.0833 | 259.0885 |
| (1-ribosylimidazole)-4-acetate | C10H14N2O6 | 258.0852 | 259.0924 | 259.0898 | 259.0950 |
| 1-glycero-3-phosphocholine | C8H21NO6P | 258.1101 | 259.1173 | 259.1148 | 259.1199 |
| S-methyl-5-thioribulose 1-phosphate | C6H13O7SP | 259.0036 | 260.0108 | 260.0082 | 260.0134 |
| glucosamine 1-phosphate | C6H14NO8P | 259.0451 | 260.0524 | 260.0498 | 260.0550 |
| gly-ser-pro | | 259.1168 | 260.1241 | 260.1215 | 260.1267 |

TABLE 1-continued

Endogenous Metabolism Database

| Metabolite | Elemental formula | Precise Mass | M + 1H | 10 ppm− | 10 ppm+ |
|---|---|---|---|---|---|
| hyp-gln | | 259.1168 | 260.1241 | 260.1215 | 260.1267 |
| gly-ala-leu | | 259.1532 | 260.1605 | 260.1579 | 260.1631 |
| gly-ala-ile | | 259.1532 | 260.1605 | 260.1579 | 260.1631 |
| leu-gln | | 259.1532 | 260.1605 | 260.1579 | 260.1631 |
| ile-gln | | 259.1532 | 260.1605 | 260.1579 | 260.1631 |
| hyp-lys | | 259.1532 | 260.1605 | 260.1579 | 260.1631 |
| leu-lys | | 259.1896 | 260.1968 | 260.1942 | 260.1994 |
| ile-lys | | 259.1896 | 260.1968 | 260.1942 | 260.1994 |
| S-methyl-5-thioribose 1-phosphate | C6H13O7SP | 260.0114 | 261.0187 | 261.0160 | 261.0213 |
| arabin-3-hexulose 6-phosphate | C6H13O9P | 260.0291 | 261.0364 | 261.0338 | 261.0390 |
| inositol 3-phosphate | C6H13O9P | 260.0291 | 261.0364 | 261.0338 | 261.0390 |
| inositol 4-phosphate | C6H13O9P | 260.0291 | 261.0364 | 261.0338 | 261.0390 |
| tagatose 6-phosphate | C6H13O9P | 260.0291 | 261.0364 | 261.0338 | 261.0390 |
| hyp-glu | | 260.1008 | 261.1081 | 261.1055 | 261.1107 |
| gly-gly-gln | | 260.1120 | 261.1193 | 261.1167 | 261.1219 |
| gly-ala-asn | | 260.1120 | 261.1193 | 261.1167 | 261.1219 |
| asn-gln | | 260.1120 | 261.1193 | 261.1167 | 261.1219 |
| thr-val | | 260.1358 | 261.1431 | 261.1405 | 261.1457 |
| leu-glu | | 260.1372 | 261.1445 | 261.1419 | 261.1471 |
| ile-glu | | 260.1372 | 261.1445 | 261.1419 | 261.1471 |
| gly-gly-lys | | 260.1484 | 261.1557 | 261.1531 | 261.1583 |
| asn-lys | | 260.1484 | 261.1557 | 261.1531 | 261.1583 |
| gly-gly-glu | | 261.0960 | 262.1033 | 262.1007 | 262.1059 |
| gly-ala-asp | | 261.0960 | 262.1033 | 262.1007 | 262.1059 |
| asn-glu | | 261.0960 | 262.1033 | 262.1007 | 262.1059 |
| asp-gln | | 261.0960 | 262.1033 | 262.1007 | 262.1059 |
| gly-try | | 261.1186 | 262.1259 | 262.1232 | 262.1285 |
| ala-ala-thr | | 261.1324 | 262.1397 | 262.1371 | 262.1423 |
| asp-lys | | 261.1324 | 262.1397 | 262.1371 | 262.1423 |
| ser-arg | | 261.1437 | 262.1509 | 262.1483 | 262.1536 |
| 1,3-diphosphoglycerate | C3H4O10P2 | 261.9268 | 262.9341 | 262.9315 | 262.9367 |
| 2,3-diphosphoglycerate | C3H4O10P2 | 261.9268 | 262.9341 | 262.9315 | 262.9367 |
| 1-hydroxy-2-methyl-2butenyl 4-diphosphate | C5H12O8P2 | 261.9996 | 263.0069 | 263.0042 | 263.0095 |
| galactitol 1-phosphate | C6H15O9P | 262.0448 | 263.0521 | 263.0494 | 263.0547 |
| asp-glu | | 262.0801 | 263.0873 | 263.0847 | 263.0900 |
| cys-val | | 262.0974 | 263.1046 | 263.1020 | 263.1073 |
| hyp-met | | 262.0987 | 263.1060 | 263.1033 | 263.1086 |
| pro-phe | | 262.1317 | 263.1390 | 263.1364 | 263.1416 |
| leu-met | | 262.1351 | 263.1424 | 263.1397 | 263.1450 |
| ile-met | | 262.1351 | 263.1424 | 263.1397 | 263.1450 |
| gly-gly-met | | 263.0939 | 264.1012 | 264.0986 | 264.1039 |
| ala-ala-cys | | 263.0939 | 264.1012 | 264.0986 | 264.1039 |
| asn-met | | 263.0939 | 264.1012 | 264.0986 | 264.1039 |
| gly-ser-thr | | 263.1117 | 264.1190 | 264.1163 | 264.1216 |
| ala-ser-ser | | 263.1117 | 264.1190 | 264.1163 | 264.1216 |
| asp-met | | 264.0780 | 265.0852 | 265.0826 | 265.0879 |
| thiamine | C12H16N4OS | 264.1045 | 265.1117 | 265.1091 | 265.1144 |
| formyl-N-acetyl-5-methoxykynurenamine | C13H16N2O4 | 264.1110 | 265.1183 | 265.1156 | 265.1209 |
| phenylacetylglutamine | C13H16N2O4 | 264.1110 | 265.1183 | 265.1156 | 265.1209 |
| gly-ser-cys | | 265.0732 | 266.0805 | 266.0778 | 266.0831 |
| thr-phe | | 266.1266 | 267.1339 | 267.1312 | 267.1366 |
| xanthoxic acid | C15H22O4 | 266.1518 | 267.1591 | 267.1564 | 267.1617 |
| S-ribosyl homocysteine | C9H17NO6S | 267.0776 | 268.0849 | 268.0822 | 268.0876 |
| neuraminic acid | C9H17NO8 | 267.0954 | 268.1027 | 268.1000 | 268.1053 |
| deoxyguanosine | C10H13N5O4 | 267.0967 | 268.1040 | 268.1013 | 268.1067 |
| homocystine | C8H16N2O4S2 | 268.0551 | 269.0624 | 269.0597 | 269.0651 |
| inosine | C10H12N4O5 | 268.0807 | 269.0880 | 269.0853 | 269.0907 |
| xanthosine | C10H12N4O5 | 268.0807 | 269.0880 | 269.0853 | 269.0907 |
| cys-phe | | 268.0881 | 269.0954 | 269.0927 | 269.0981 |
| ser-tyr | | 268.1059 | 269.1132 | 269.1105 | 269.1159 |
| hyp-his | | 268.1171 | 269.1244 | 269.1217 | 269.1271 |
| leu-his | | 268.1535 | 269.1608 | 269.1581 | 269.1635 |
| ile-his | | 268.1535 | 269.1608 | 269.1581 | 269.1635 |
| N-acetylglutamate 5-phosphate | C7H12NO8P | 269.0295 | 270.0367 | 270.0340 | 270.0394 |
| gly-gly-his | | 269.1124 | 270.1196 | 270.1169 | 270.1223 |
| asn-his | | 269.1124 | 270.1196 | 270.1169 | 270.1223 |
| pro-gly-pro | | 269.1375 | 270.1448 | 270.1421 | 270.1475 |
| genistein | C15H10O5 | 270.0528 | 271.0601 | 271.0574 | 271.0628 |
| lombricine | C6H15N4O6P | 270.0723 | 271.0796 | 271.0769 | 271.0823 |
| asp-his | | 270.0964 | 271.1037 | 271.1009 | 271.1064 |
| estrone | C18H22O2 | 270.1620 | 271.1692 | 271.1665 | 271.1720 |
| retinol | C20H30O | 270.2348 | 271.2420 | 271.2393 | 271.2447 |
| pro-arg | | 271.1644 | 272.1717 | 272.1690 | 272.1744 |

TABLE 1-continued

Endogenous Metabolism Database

| Metabolite | Elemental formula | Precise Mass | M + 1H | 10 ppm− | 10 ppm+ |
|---|---|---|---|---|---|
| Galacturonate 1-P | C6H9O10P | 271.9927 | 273.0000 | 272.9973 | 273.0027 |
| glucuronate 1-P | C6H9O10P | 271.9927 | 273.0000 | 272.9973 | 273.0027 |
| arbutin | C12H16O7 | 272.0896 | 273.0968 | 273.0941 | 273.0996 |
| hyp-val | | 272.1358 | 273.1431 | 273.1404 | 273.1458 |
| leu-val | | 272.1722 | 273.1795 | 273.1768 | 273.1822 |
| ile-val | | 272.1722 | 273.1795 | 273.1768 | 273.1822 |
| estradiol-17β | C18H24O2 | 272.1776 | 273.1849 | 273.1822 | 273.1876 |
| gly-gly-val | | 273.1311 | 274.1384 | 274.1356 | 274.1411 |
| asn-val | | 273.1311 | 274.1384 | 274.1356 | 274.1411 |
| gly-pro-thr | | 273.1324 | 274.1397 | 274.1370 | 274.1425 |
| ala-ser-pro | | 273.1324 | 274.1397 | 274.1370 | 274.1425 |
| ala-ala-leu | | 273.1688 | 274.1761 | 274.1734 | 274.1788 |
| ala-ala-ile | | 273.1688 | 274.1761 | 274.1734 | 274.1788 |
| 6-phospho-2-dehydrogluconate | C6H11O10P | 274.0084 | 275.0157 | 275.0129 | 275.0184 |
| β-arabinose 1-phosphate | C6H11O10P | 274.0084 | 275.0157 | 275.0129 | 275.0184 |
| asp-val | | 274.1151 | 275.1224 | 275.1196 | 275.1251 |
| N2-succinylarginine | C10H18N4O5 | 274.1277 | 275.1350 | 275.1322 | 275.1377 |
| gly-ala-gln | | 274.1277 | 275.1350 | 275.1322 | 275.1377 |
| ala-ala-asn | | 274.1277 | 275.1350 | 275.1322 | 275.1377 |
| gln-gln | | 274.1277 | 275.1350 | 275.1322 | 275.1377 |
| gly-ala-lys | | 274.1641 | 275.1713 | 275.1686 | 275.1741 |
| gln-lys | | 274.1641 | 275.1713 | 275.1686 | 275.1741 |
| lys-lys | | 274.2005 | 275.2077 | 275.2050 | 275.2105 |
| 3-dehydro gulonate 6-phosphate | C6H12O10P | 275.0162 | 276.0235 | 276.0207 | 276.0262 |
| 6-P-gluconate | C6H12O10P | 275.0162 | 276.0235 | 276.0207 | 276.0262 |
| gly-pro-cys | | 275.0939 | 276.1012 | 276.0985 | 276.1040 |
| gly-ala-glu | | 275.1117 | 276.1190 | 276.1162 | 276.1217 |
| ala-ala-asp | | 275.1117 | 276.1190 | 276.1162 | 276.1217 |
| gln-glu | | 275.1117 | 276.1190 | 276.1162 | 276.1217 |
| ala-try | | 275.1342 | 276.1415 | 276.1388 | 276.1443 |
| gly-ser-leu | | 275.1481 | 276.1554 | 276.1526 | 276.1581 |
| gly-ser-ile | | 275.1481 | 276.1554 | 276.1526 | 276.1581 |
| lys-glu | | 275.1481 | 276.1554 | 276.1526 | 276.1581 |
| thr-arg | | 275.1593 | 276.1666 | 276.1638 | 276.1694 |
| glu-glu | | 276.0957 | 277.1030 | 277.1002 | 277.1058 |
| gly-ser-asn | | 276.1069 | 277.1142 | 277.1114 | 277.1170 |
| saccharopine | C11H20N2O6 | 276.1321 | 277.1394 | 277.1366 | 277.1421 |
| gly-ser-asp | | 277.0910 | 278.0982 | 278.0955 | 278.1010 |
| gly-ala-met | | 277.1096 | 278.1169 | 278.1141 | 278.1197 |
| gln-met | | 277.1096 | 278.1169 | 278.1141 | 278.1197 |
| S-(2-methylpropanoyl)-dihydrolipoamide | C12H23NO2S2 | 277.1170 | 278.1243 | 278.1215 | 278.1271 |
| cys-arg | | 277.1208 | 278.1281 | 278.1253 | 278.1309 |
| gly-thr-thr | | 277.1273 | 278.1346 | 278.1318 | 278.1374 |
| ala-ser-thr | | 277.1273 | 278.1346 | 278.1318 | 278.1374 |
| lys-met | | 277.1460 | 278.1533 | 278.1505 | 278.1560 |
| 2-C-methyl erythritol 2,4-cyclodiphosphate | C5H12O9P2 | 277.9945 | 279.0018 | 278.9990 | 279.0046 |
| glu-met | | 278.0936 | 279.1009 | 279.0981 | 279.1037 |
| α-ribazole | C14H18N2O4 | 278.1266 | 279.1339 | 279.1311 | 279.1367 |
| pro-tyr | | 278.1266 | 279.1339 | 279.1311 | 279.1367 |
| hyp-phe | | 278.1266 | 279.1339 | 279.1311 | 279.1367 |
| pantetheine | C11H22N2O4S | 278.1300 | 279.1373 | 279.1345 | 279.1401 |
| leu-phe | | 278.1630 | 279.1703 | 279.1675 | 279.1731 |
| ile-phe | | 278.1630 | 279.1703 | 279.1675 | 279.1731 |
| crepenynate | C18H30O2 | 278.2246 | 279.2318 | 279.2291 | 279.2346 |
| γ-linolenic acid | C18H30O2 | 278.2246 | 279.2318 | 279.2291 | 279.2346 |
| gly-thr-cys | | 279.0889 | 280.0961 | 280.0933 | 280.0989 |
| ala-ser-cys | | 279.0889 | 280.0961 | 280.0933 | 280.0989 |
| ser-ser-ser | | 279.1066 | 280.1139 | 280.1111 | 280.1167 |
| gly-gly-phe | | 279.1219 | 280.1292 | 280.1264 | 280.1320 |
| asn-phe | | 279.1219 | 280.1292 | 280.1264 | 280.1320 |
| met-met | | 280.0915 | 281.0988 | 281.0960 | 281.1016 |
| asp-phe | | 280.1059 | 281.1132 | 281.1104 | 281.1160 |
| 9-cis,11-trans-octadecadienoate | C18H32O2 | 280.2402 | 281.2475 | 281.2447 | 281.2503 |
| linoleic acid | C18H32O2 | 280.2402 | 281.2475 | 281.2447 | 281.2503 |
| gly-cys-cys | | 281.0504 | 282.0576 | 282.0548 | 282.0605 |
| 4-hydroxyphenylacetylglutamine | C13H15NO6 | 281.0899 | 282.0972 | 282.0944 | 282.1000 |
| indican | C13H16NO6 | 282.0977 | 283.1050 | 283.1022 | 283.1078 |
| thr-tyr | | 282.1215 | 283.1288 | 283.1260 | 283.1316 |
| cis-vaccenate | C18H34O2 | 282.2559 | 283.2631 | 283.2603 | 283.2660 |
| N2-acetylaminoadipyl-γ-phosphate | C8H14NO8P | 283.0451 | 284.0524 | 284.0495 | 284.0552 |
| guanosine | C10H13N5O5 | 283.0916 | 284.0989 | 284.0961 | 284.1017 |
| gly-ala-his | | 283.1280 | 284.1353 | 284.1325 | 284.1381 |
| gln-his | | 283.1280 | 284.1353 | 284.1325 | 284.1381 |

TABLE 1-continued

Endogenous Metabolism Database

| Metabolite | Elemental formula | Precise Mass | M + 1H | 10 ppm− | 10 ppm+ |
|---|---|---|---|---|---|
| ala-pro-pro | | 283.1532 | 284.1605 | 284.1576 | 284.1633 |
| lys-his | | 283.1644 | 284.1717 | 284.1688 | 284.1745 |
| 5-P ribosylglycinamide (GAR) | C7H13N2O8P | 284.0404 | 285.0476 | 285.0448 | 285.0505 |
| cys-tyr | | 284.0831 | 285.0903 | 285.0875 | 285.0932 |
| glu-his | | 284.1120 | 285.1193 | 285.1165 | 285.1222 |
| 11-cis-retinal | C20H28O | 284.2140 | 285.2213 | 285.2184 | 285.2241 |
| all-trans-retinal | C20H28O | 284.2140 | 285.2213 | 285.2184 | 285.2241 |
| gly-pro-leu | | 285.1688 | 286.1761 | 286.1732 | 286.1790 |
| gly-pro-ile | | 285.1688 | 286.1761 | 286.1732 | 286.1790 |
| 7P-2-dehydro-3-dexoyarabionheptonate | C7H11O10P | 286.0084 | 287.0157 | 287.0128 | 287.0185 |
| (3-indolyl)-glycerol-P | C11H13NO6P | 286.0475 | 287.0547 | 287.0519 | 287.0576 |
| salicin | C13H18O7 | 286.1052 | 287.1125 | 287.1096 | 287.1154 |
| met-his | | 286.1099 | 287.1172 | 287.1143 | 287.1201 |
| gly-pro-asn | | 286.1277 | 287.1350 | 287.1321 | 287.1378 |
| 16α-hydroxyestrone | C18H22O3 | 286.1569 | 287.1642 | 287.1613 | 287.1670 |
| 2-hydroxyestrone | C18H22O3 | 286.1569 | 287.1642 | 287.1613 | 287.1670 |
| androst-4-ene-3,17-dione | C19H26O2 | 286.1933 | 287.2005 | 287.1977 | 287.2034 |
| all-trans-retinol | C20H30O | 286.2297 | 287.2369 | 287.2341 | 287.2398 |
| indoleglycerol | C11H14NO6P | 287.0553 | 288.0626 | 288.0597 | 288.0654 |
| gly-pro-asp | | 287.1117 | 288.1190 | 288.1161 | 288.1219 |
| gly-ala-val | | 287.1467 | 288.1540 | 288.1511 | 288.1569 |
| gln-val | | 287.1467 | 288.1540 | 288.1511 | 288.1569 |
| ala-pro-thr | | 287.1481 | 288.1554 | 288.1525 | 288.1582 |
| hyp-arg | | 287.1593 | 288.1666 | 288.1637 | 288.1695 |
| lys-val | | 287.1831 | 288.1904 | 288.1875 | 288.1933 |
| leu-arg | | 287.1957 | 288.2030 | 288.2001 | 288.2059 |
| ile-arg | | 287.1957 | 288.2030 | 288.2001 | 288.2059 |
| dehydroepiandrosterone | C19H27O2 | 287.2011 | 288.2084 | 288.2055 | 288.2113 |
| 2-dehydro-3-deoxy-arabino-heptonate 7-phosphate | C7H13O10P | 288.0240 | 289.0313 | 289.0284 | 289.0342 |
| glu-val | | 288.1308 | 289.1380 | 289.1351 | 289.1409 |
| ala-ala-gln | | 288.1433 | 289.1506 | 289.1477 | 289.1535 |
| gly-gly-arg | | 288.1546 | 289.1618 | 289.1589 | 289.1647 |
| asn-arg | | 288.1546 | 289.1618 | 289.1589 | 289.1647 |
| 2-hydroxyestradiol-17β | C18H24O3 | 288.1725 | 289.1798 | 289.1769 | 289.1827 |
| 6β-hydroxyestradiol-17β | C18H24O3 | 288.1725 | 289.1798 | 289.1769 | 289.1827 |
| estriol | C18H24O3 | 288.1725 | 289.1798 | 289.1769 | 289.1827 |
| ala-ala-lys | | 288.1797 | 289.1870 | 289.1841 | 289.1899 |
| 3β,17β-dihydroxyandrost-5-ene | C19H28O2 | 288.2089 | 289.2162 | 289.2133 | 289.2191 |
| 5β-androstane-3,17-dione | C19H28O2 | 288.2089 | 289.2162 | 289.2133 | 289.2191 |
| androstanedione | C19H28O2 | 288.2089 | 289.2162 | 289.2133 | 289.2191 |
| testosterone | C19H28O2 | 288.2089 | 289.2162 | 289.2133 | 289.2191 |
| N-succinyl-2-amino-6-oxopimelate | C11H15NO8 | 289.0797 | 290.0870 | 290.0841 | 290.0899 |
| cys-ala-pro | | 289.1096 | 290.1169 | 290.1140 | 290.1198 |
| ala-ala-glu | | 289.1273 | 290.1346 | 290.1317 | 290.1375 |
| ser-ser-pro | | 289.1273 | 290.1346 | 290.1317 | 290.1375 |
| asp-arg | | 289.1386 | 290.1459 | 290.1430 | 290.1488 |
| gly-thr-leu | | 289.1637 | 290.1710 | 290.1681 | 290.1739 |
| gly-thr-ile | | 289.1637 | 290.1710 | 290.1681 | 290.1739 |
| ala-ser-leu | | 289.1637 | 290.1710 | 290.1681 | 290.1739 |
| ala-ser-ile | | 289.1637 | 290.1710 | 290.1681 | 290.1739 |
| sedoheptulose 7-P | C7H15O10P | 290.0397 | 291.0470 | 291.0441 | 291.0499 |
| N-succinyl-2,6-diaminopimelate | C11H18N2O7 | 290.1114 | 291.1186 | 291.1157 | 291.1215 |
| arginosuccinic acid | C10H18N4O6 | 290.1226 | 291.1299 | 291.1270 | 291.1328 |
| N-(arginino) succinate | C10H18N4O6 | 290.1226 | 291.1299 | 291.1270 | 291.1328 |
| gly-ser-gln | | 290.1226 | 291.1299 | 291.1270 | 291.1328 |
| gly-thr-asn | | 290.1226 | 291.1299 | 291.1270 | 291.1328 |
| ala-ser-asn | | 290.1226 | 291.1299 | 291.1270 | 291.1328 |
| met-val | | 290.1287 | 291.1359 | 291.1330 | 291.1388 |
| gly-ser-lys | | 290.1590 | 291.1663 | 291.1633 | 291.1692 |
| 2-methoxyestradiol-17β | C18H26O3 | 290.1882 | 291.1955 | 291.1925 | 291.1984 |
| 3α-hydroxy-5β-androstan-17-one | C19H30O2 | 290.2246 | 291.2318 | 291.2289 | 291.2348 |
| 5β-dihydrotestosterone | C19H30O2 | 290.2246 | 291.2318 | 291.2289 | 291.2348 |
| androstanolone | C19H30O2 | 290.2246 | 291.2318 | 291.2289 | 291.2348 |
| Androstenediol | C19H30O2 | 290.2246 | 291.2318 | 291.2289 | 291.2348 |
| gly-ser-glu | | 291.1066 | 292.1139 | 292.1110 | 292.1168 |
| gly-thr-asp | | 291.1066 | 292.1139 | 292.1110 | 292.1168 |
| ala-ser-asp | | 291.1066 | 292.1139 | 292.1110 | 292.1168 |
| gly-cys-leu | | 291.1252 | 292.1325 | 292.1296 | 292.1354 |
| gly-cys-ile | | 291.1252 | 292.1325 | 292.1296 | 292.1354 |
| ala-ala-met | | 291.1252 | 292.1325 | 292.1296 | 292.1354 |
| ser-try | | 291.1292 | 292.1364 | 292.1335 | 292.1394 |
| S-(2-methylbutanoyl)-dihydrolipoamide | C13H25NO2S2 | 291.1327 | 292.1399 | 292.1370 | 292.1429 |

TABLE 1-continued

Endogenous Metabolism Database

| Metabolite | Elemental formula | Precise Mass | M + 1H | 10 ppm− | 10 ppm+ |
|---|---|---|---|---|---|
| S-(3-methylbutanoyl)-dihydrolipoamide | C13H25NO2S2 | 291.1327 | 292.1399 | 292.1370 | 292.1429 |
| ala-thr-thr | | 291.1430 | 292.1503 | 292.1474 | 292.1532 |
| gly-cys-asn | | 292.0841 | 293.0914 | 293.0884 | 293.0943 |
| his-his | | 292.1284 | 293.1356 | 293.1327 | 293.1386 |
| 5-phosphoribosyl-5-aminoimidazole | C8H12N3O7P | 293.0407 | 294.0480 | 294.0450 | 294.0509 |
| 2-amino-4-hydroxy-6-hydroxymethyl-dihydropteridine-PP | C7H11N5O8 | 293.0607 | 294.0680 | 294.0650 | 294.0709 |
| gly-cys-asp | | 293.0681 | 294.0754 | 294.0725 | 294.0783 |
| ala-thr-cys | | 293.1045 | 294.1118 | 294.1088 | 294.1147 |
| gly-ser-met | | 293.1045 | 294.1118 | 294.1088 | 294.1147 |
| ser-ser-thr | | 293.1223 | 294.1295 | 294.1266 | 294.1325 |
| gly-ala-phe | | 293.1375 | 294.1448 | 294.1419 | 294.1477 |
| gln-phe | | 293.1375 | 294.1448 | 294.1419 | 294.1477 |
| lys-phe | | 293.1739 | 294.1812 | 294.1783 | 294.1841 |
| hyp-tyr | | 294.1215 | 295.1288 | 295.1259 | 295.1318 |
| glu-phe | | 294.1215 | 295.1288 | 295.1259 | 295.1318 |
| leu-tyr | | 294.1579 | 295.1652 | 295.1623 | 295.1682 |
| ile-tyr | | 294.1579 | 295.1652 | 295.1623 | 295.1682 |
| 13-oxoODE | C18H30O3 | 294.2195 | 295.2268 | 295.2238 | 295.2297 |
| 9-oxoODE | C18H30O3 | 294.2195 | 295.2268 | 295.2238 | 295.2297 |
| aminoimidazole ribotide | C8H14N3O7P | 295.0563 | 296.0636 | 296.0607 | 296.0666 |
| ala-cys-cys | | 295.0660 | 296.0733 | 296.0703 | 296.0763 |
| ser-ser-cys | | 295.0838 | 296.0910 | 296.0881 | 296.0940 |
| gly-gly-tyr | | 295.1168 | 296.1241 | 296.1211 | 296.1270 |
| asn-tyr | | 295.1168 | 296.1241 | 296.1211 | 296.1270 |
| asp-tyr | | 296.1008 | 297.1081 | 297.1051 | 297.1110 |
| met-phe | | 296.1194 | 297.1267 | 297.1237 | 297.1297 |
| his-val | | 296.1471 | 297.1543 | 297.1514 | 297.1573 |
| 10-EpOME | C18H32O3 | 296.2351 | 297.2424 | 297.2394 | 297.2454 |
| 12-EpOME | C18H32O3 | 296.2351 | 297.2424 | 297.2394 | 297.2454 |
| 13-HODE | C18H32O3 | 296.2351 | 297.2424 | 297.2394 | 297.2454 |
| 9-HODE | C18H32O3 | 296.2351 | 297.2424 | 297.2394 | 297.2454 |
| thromboxane | C20H40O | 296.3079 | 297.3152 | 297.3122 | 297.3182 |
| methylthioadenosine | C11H15N5O3S | 297.0895 | 298.0968 | 298.0938 | 298.0998 |
| ala-ala-his | | 297.1437 | 298.1509 | 298.1480 | 298.1539 |
| tuberculosterate | C19H38O2 | 298.2872 | 299.2944 | 299.2915 | 299.2974 |
| N-acetyl glucosamine 1-P | C8H14NO9P | 299.0400 | 300.0473 | 300.0443 | 300.0503 |
| N-acetyl glucosamine 6-P | C8H14NO9P | 299.0400 | 300.0473 | 300.0443 | 300.0503 |
| 4-P-pantothenate | C9H18NO8 | 299.0764 | 300.0837 | 300.0807 | 300.0867 |
| gly-ser-his | | 299.1229 | 300.1302 | 300.1272 | 300.1332 |
| ser-pro-pro | | 299.1481 | 300.1554 | 300.1524 | 300.1584 |
| leu-ala-pro | | 299.1845 | 300.1918 | 300.1888 | 300.1948 |
| ile-ala-pro | | 299.1845 | 300.1918 | 300.1888 | 300.1948 |
| 3-dehydrosphinganine | C18H37NO2 | 299.2824 | 300.2897 | 300.2867 | 300.2927 |
| spingosine | C18H37NO2 | 299.2824 | 300.2897 | 300.2867 | 300.2927 |
| cinnavalininate | C14H8N2O6 | 300.0382 | 301.0455 | 301.0425 | 301.0485 |
| salidroside | C14H20O7 | 300.1209 | 301.1281 | 301.1251 | 301.1312 |
| gly-pro-gln | | 300.1433 | 301.1506 | 301.1476 | 301.1536 |
| ala-pro-asn | | 300.1433 | 301.1506 | 301.1476 | 301.1536 |
| val-val | | 300.1658 | 301.1731 | 301.1701 | 301.1761 |
| 16α-hydroxyandrost-4-ene-3,17-dione | C19H24O3 | 300.1725 | 301.1798 | 301.1768 | 301.1828 |
| 19-oxo-androst-4-ene-3,17-dione | C19H24O3 | 300.1725 | 301.1798 | 301.1768 | 301.1828 |
| 2-methoxyestrone | C19H24O3 | 300.1725 | 301.1798 | 301.1768 | 301.1828 |
| adrenosterone | C19H24O3 | 300.1725 | 301.1798 | 301.1768 | 301.1828 |
| andrensterone | C19H24O3 | 300.1725 | 301.1798 | 301.1768 | 301.1828 |
| gly-pro-lys | | 300.1797 | 301.1870 | 301.1840 | 301.1900 |
| retinoate | C20H28O2 | 300.2089 | 301.2162 | 301.2132 | 301.2192 |
| gly-pro-glu | | 301.1273 | 302.1346 | 302.1316 | 302.1376 |
| ala-pro-asp | | 301.1273 | 302.1346 | 302.1316 | 302.1376 |
| pro-try | | 301.1499 | 302.1572 | 302.1541 | 302.1602 |
| ala-ala-val | | 301.1624 | 302.1697 | 302.1666 | 302.1727 |
| gly-leu-leu | | 301.2001 | 302.2074 | 302.2044 | 302.2104 |
| gly-leu-ile | | 301.2001 | 302.2074 | 302.2044 | 302.2104 |
| gly-ile-ile | | 301.2001 | 302.2074 | 302.2044 | 302.2104 |
| sphinganine | C18H39NO2 | 301.2981 | 302.3053 | 302.3023 | 302.3084 |
| his-phe | | 302.1379 | 303.1451 | 303.1421 | 303.1482 |
| leu-gly-asn | | 302.1590 | 303.1663 | 303.1632 | 303.1693 |
| ile-gly-asn | | 302.1590 | 303.1663 | 303.1632 | 303.1693 |
| gly-ala-arg | | 302.1702 | 303.1775 | 303.1745 | 303.1805 |
| gln-arg | | 302.1702 | 303.1775 | 303.1745 | 303.1805 |

TABLE 1-continued

Endogenous Metabolism Database

| Metabolite | Elemental formula | Precise Mass | M + 1H | 10 ppm− | 10 ppm+ |
|---|---|---|---|---|---|
| 11β-hydroxyandrost-4-ene-3,17-dione | C19H26O3 | 302.1882 | 303.1955 | 303.1924 | 303.1985 |
| 16α-hydroxydehydroepiandrosterone | C19H26O3 | 302.1882 | 303.1955 | 303.1924 | 303.1985 |
| 19-hydroxyandrost-4-ene-3,17-dione | C19H26O3 | 302.1882 | 303.1955 | 303.1924 | 303.1985 |
| 19-oxo-testosterone | C19H26O3 | 302.1882 | 303.1955 | 303.1924 | 303.1985 |
| 7α-hydroxyandrostenedione | C19H26O3 | 302.1882 | 303.1955 | 303.1924 | 303.1985 |
| testololactone | C19H26O3 | 302.1882 | 303.1955 | 303.1924 | 303.1985 |
| lys-arg | | 302.2066 | 303.2139 | 303.2108 | 303.2169 |
| eicosapentaenoic acid | C20H30O2 | 302.2246 | 303.2318 | 303.2288 | 303.2349 |
| retinyl ester | C20H30O2 | 302.2246 | 303.2318 | 303.2288 | 303.2349 |
| cyclic GMP | C10H12N2O7P | 303.0376 | 304.0449 | 304.0419 | 304.0479 |
| gly-asn-asn | | 303.1178 | 304.1251 | 304.1221 | 304.1282 |
| gly-pro-met | | 303.1252 | 304.1325 | 304.1295 | 304.1356 |
| ser-gly-val | | 303.1416 | 304.1489 | 304.1459 | 304.1520 |
| ser-pro-thr | | 303.1430 | 304.1503 | 304.1472 | 304.1533 |
| leu-gly-asp | | 303.1430 | 304.1503 | 304.1472 | 304.1533 |
| ile-gly-asp | | 303.1430 | 304.1503 | 304.1472 | 304.1533 |
| glu-arg | | 303.1542 | 304.1615 | 304.1585 | 304.1645 |
| ala-thr-leu | | 303.1794 | 304.1867 | 304.1836 | 304.1897 |
| ala-thr-ile | | 303.1794 | 304.1867 | 304.1836 | 304.1897 |
| gly-asn-asp | | 304.1019 | 305.1091 | 305.1061 | 305.1122 |
| Nopaline | C11H20N4O6 | 304.1382 | 305.1455 | 305.1425 | 305.1486 |
| gly-thr-gln | | 304.1382 | 305.1455 | 305.1425 | 305.1486 |
| ala-ser-gln | | 304.1382 | 305.1455 | 305.1425 | 305.1486 |
| ala-thr-asn | | 304.1382 | 305.1455 | 305.1425 | 305.1486 |
| gly-thr-lys | | 304.1746 | 305.1819 | 305.1789 | 305.1850 |
| ala-ser-lys | | 304.1746 | 305.1819 | 305.1789 | 305.1850 |
| 19-hydroxytestosterone | C19H28O3 | 304.2038 | 305.2111 | 305.2081 | 305.2142 |
| 7α-hydroxytestosterone | C19H28O3 | 304.2038 | 305.2111 | 305.2081 | 305.2142 |
| arachidonic acid | C20H32O2 | 304.2402 | 305.2475 | 305.2444 | 305.2505 |
| cyclic CMP | C9H12N3O7P | 305.0407 | 306.0480 | 306.0449 | 306.0510 |
| gly-asp-asp | | 305.0859 | 306.0931 | 306.0901 | 306.0962 |
| cys-ser-pro | | 305.1045 | 306.1118 | 306.1087 | 306.1148 |
| gly-thr-glu | | 305.1223 | 306.1295 | 306.1265 | 306.1326 |
| ala-ser-glu | | 305.1223 | 306.1295 | 306.1265 | 306.1326 |
| ala-thr-asp | | 305.1223 | 306.1295 | 306.1265 | 306.1326 |
| ala-cys-leu | | 305.1409 | 306.1482 | 306.1451 | 306.1512 |
| ala-cys-ile | | 305.1409 | 306.1482 | 306.1451 | 306.1512 |
| thr-try | | 305.1448 | 306.1521 | 306.1490 | 306.1551 |
| met-arg | | 305.1521 | 306.1594 | 306.1563 | 306.1625 |
| ser-ser-leu | | 305.1586 | 306.1659 | 306.1629 | 306.1690 |
| ser-ser-ile | | 305.1586 | 306.1659 | 306.1629 | 306.1690 |
| cyclic UMP | C9H11N2O8P | 306.0247 | 307.0320 | 307.0289 | 307.0351 |
| gly-cys-gln | | 306.0998 | 307.1070 | 307.1040 | 307.1101 |
| ala-cys-asn | | 306.0998 | 307.1070 | 307.1040 | 307.1101 |
| ser-ser-asn | | 306.1175 | 307.1248 | 307.1217 | 307.1278 |
| gly-cys-lys | | 306.1361 | 307.1434 | 307.1403 | 307.1465 |
| val-phe | | 306.1566 | 307.1639 | 307.1608 | 307.1669 |
| corrinoid | C19H22N4 | 306.1844 | 307.1917 | 307.1886 | 307.1948 |
| 8,11,14-icosatrienoate | C20H34O2 | 306.2559 | 307.2631 | 307.2601 | 307.2662 |
| 3-iodotyrosine | C9H10NO3I | 306.9700 | 307.9772 | 307.9742 | 307.9803 |
| dCMP | C9H14N3O7P | 307.0563 | 308.0636 | 308.0605 | 308.0667 |
| glutathione | C10H17N3O6S | 307.0838 | 308.0910 | 308.0880 | 308.0941 |
| gly-cys-glu | | 307.0838 | 308.0910 | 308.0880 | 308.0941 |
| ala-cys-asp | | 307.0838 | 308.0910 | 308.0880 | 308.0941 |
| S-succinyldihydrolipoamide | C12H21NO4S2 | 307.0912 | 308.0985 | 308.0954 | 308.1015 |
| ser-ser-asp | | 307.1015 | 308.1088 | 308.1057 | 308.1119 |
| cys-try | | 307.1063 | 308.1136 | 308.1105 | 308.1167 |
| gly-thr-met | | 307.1202 | 308.1274 | 308.1244 | 308.1305 |
| ala-ser-met | | 307.1202 | 308.1274 | 308.1244 | 308.1305 |
| ser-thr-thr | | 307.1379 | 308.1452 | 308.1421 | 308.1483 |
| ala-ala-phe | | 307.1532 | 308.1605 | 308.1574 | 308.1635 |
| dUMP | C9H14N2O8P | 309.0482 | 310.0555 | 310.0524 | 310.0586 |
| cys-gly-met | | 309.0817 | 310.0889 | 310.0858 | 310.0920 |
| ser-thr-cys | | 309.0994 | 310.1067 | 310.1036 | 310.1098 |
| sialate | C11H19NO9 | 309.1059 | 310.1132 | 310.1101 | 310.1163 |
| gly-ala-tyr | | 309.1324 | 310.1397 | 310.1366 | 310.1428 |
| gly-ser-phe | | 309.1324 | 310.1397 | 310.1366 | 310.1428 |
| gln-tyr | | 309.1324 | 310.1397 | 310.1366 | 310.1428 |
| gly-pro-his | | 309.1437 | 310.1509 | 310.1478 | 310.1540 |
| pro-pro-pro | | 309.1688 | 310.1761 | 310.1730 | 310.1792 |
| lys-tyr | | 309.1688 | 310.1761 | 310.1730 | 310.1792 |
| ribose-1,5-bisphosphate | C5H12O11P2 | 309.9843 | 310.9916 | 310.9885 | 310.9947 |

TABLE 1-continued

Endogenous Metabolism Database

| Metabolite | Elemental formula | Precise Mass | M + 1H | 10 ppm− | 10 ppm+ |
|---|---|---|---|---|---|
| ribulose 1,5-bisphosphate | C5H12O11P2 | 309.9843 | 310.9916 | 310.9885 | 310.9947 |
| glu-tyr | | 310.1165 | 311.1237 | 311.1206 | 311.1268 |
| ser-cys-cys | | 311.0609 | 312.0682 | 312.0651 | 312.0713 |
| dhurrin | C14H17NO7 | 311.1005 | 312.1077 | 312.1046 | 312.1109 |
| taxiphyllin | C14H17NO7 | 311.1005 | 312.1077 | 312.1046 | 312.1109 |
| his-arg | | 311.1705 | 312.1778 | 312.1747 | 312.1809 |
| met-tyr | | 312.1144 | 313.1216 | 313.1185 | 313.1248 |
| phe-phe | | 312.1474 | 313.1546 | 313.1515 | 313.1578 |
| 11-hydroperoxyoctadeca-9,12-dienoic acid | C18H32O4 | 312.2300 | 313.2373 | 313.2342 | 313.2404 |
| 12,13-epoxy-9-hydroxy-10-octadecenoate | C18H32O4 | 312.2300 | 313.2373 | 313.2342 | 313.2404 |
| 13-hydroperoxyoctadeca-9,11-dienoic acid | C18H32O4 | 312.2300 | 313.2373 | 313.2342 | 313.2404 |
| 7,8-DiHODE | C18H32O4 | 312.2300 | 313.2373 | 313.2342 | 313.2404 |
| 8-HPODE | C18H32O4 | 312.2300 | 313.2373 | 313.2342 | 313.2404 |
| 9,10-12,13-diepoxyoctadecanoate | C18H32O4 | 312.2300 | 313.2373 | 313.2342 | 313.2404 |
| 9,10-epoxy-13-hydroxy-11-octadecenoate | C18H32O4 | 312.2300 | 313.2373 | 313.2342 | 313.2404 |
| 9-HPODE | C18H32O4 | 312.2300 | 313.2373 | 313.2342 | 313.2404 |
| phytanic acid | C20H40O2 | 312.3028 | 313.3101 | 313.3070 | 313.3132 |
| 5-phosphoribosyl-N-formylglycinamidine | C8H16N3O8P | 313.0669 | 314.0742 | 314.0710 | 314.0773 |
| gly-thr-his | | 313.1386 | 314.1459 | 314.1427 | 314.1490 |
| ala-ser-his | | 313.1386 | 314.1459 | 314.1427 | 314.1490 |
| gly-pro-val | | 313.1624 | 314.1697 | 314.1665 | 314.1728 |
| pro-pro-thr | | 313.1637 | 314.1710 | 314.1679 | 314.1742 |
| 5′-phosphoribosyl-N-formylglycinamide | C8H15N2O9P | 314.0509 | 315.0582 | 315.0550 | 315.0613 |
| geranyl-PP | C10H20O7P2 | 314.0673 | 315.0746 | 315.0714 | 315.0777 |
| 7,8-dihydropteroate | C14H14N6O3 | 314.1127 | 315.1200 | 315.1168 | 315.1231 |
| ala-pro-gln | | 314.1590 | 315.1663 | 315.1631 | 315.1694 |
| lys-ala-pro | | 314.1954 | 315.2026 | 315.1995 | 315.2058 |
| progesterone | C21H30O2 | 314.2246 | 315.2318 | 315.2287 | 315.2350 |
| 12,13-DHOME | C18H34O4 | 314.2457 | 315.2530 | 315.2498 | 315.2561 |
| 9,10-DHOME | C18H34O4 | 314.2457 | 315.2530 | 315.2498 | 315.2561 |
| adenosine | C10H13N5O4 | 315.0814 | 316.0887 | 316.0856 | 316.0919 |
| cys-gly-his | | 315.1001 | 316.1074 | 316.1042 | 316.1105 |
| pro-pro-cys | | 315.1252 | 316.1325 | 316.1294 | 316.1357 |
| ala-pro-glu | | 315.1430 | 316.1503 | 316.1471 | 316.1534 |
| leu-ser-pro | | 315.1794 | 316.1867 | 316.1835 | 316.1898 |
| ile-ser-pro | | 315.1794 | 316.1867 | 316.1835 | 316.1898 |
| val-arg | | 315.1893 | 316.1965 | 316.1934 | 316.1997 |
| ala-leu-leu | | 315.2158 | 316.2231 | 316.2199 | 316.2262 |
| ala-leu-ile | | 315.2158 | 316.2231 | 316.2199 | 316.2262 |
| ala-ile-ile | | 315.2158 | 316.2231 | 316.2199 | 316.2262 |
| 5β-pregnane-3,20-dione | C21H31O2 | 315.2324 | 316.2397 | 316.2365 | 316.2428 |
| ser-pro-asn | | 316.1382 | 317.1455 | 317.1423 | 317.1487 |
| gly-leu-gln | | 316.1746 | 317.1819 | 317.1787 | 317.1851 |
| gly-ile-gln | | 316.1746 | 317.1819 | 317.1787 | 317.1851 |
| ala-leu-asn | | 316.1746 | 317.1819 | 317.1787 | 317.1851 |
| ala-ile-asn | | 316.1746 | 317.1819 | 317.1787 | 317.1851 |
| ala-ala-arg | | 316.1859 | 317.1931 | 317.1900 | 317.1963 |
| 15-deoxy-δ-12,14-prostoglandin J2 | C20H28O3 | 316.2038 | 317.2111 | 317.2079 | 317.2143 |
| gly-leu-lys | | 316.2110 | 317.2183 | 317.2151 | 317.2215 |
| gly-ile-lys | | 316.2110 | 317.2183 | 317.2151 | 317.2215 |
| 20α-hydroxy-4-pregnen-3-one | C21H32O2 | 316.2402 | 317.2475 | 317.2443 | 317.2507 |
| pregnenolone | C21H32O2 | 316.2402 | 317.2475 | 317.2443 | 317.2507 |
| ser-pro-asp | | 317.1223 | 318.1295 | 318.1264 | 318.1327 |
| gly-asn-gln | | 317.1335 | 318.1408 | 318.1376 | 318.1439 |
| ala-asn-asn | | 317.1335 | 318.1408 | 318.1376 | 318.1439 |
| ala-pro-met | | 317.1409 | 318.1482 | 318.1450 | 318.1514 |
| hyp-try | | 317.1448 | 318.1521 | 318.1489 | 318.1553 |
| gly-thr-val | | 317.1573 | 318.1646 | 318.1614 | 318.1678 |
| ala-ser-val | | 317.1573 | 318.1646 | 318.1614 | 318.1678 |
| gly-leu-glu | | 317.1586 | 318.1659 | 318.1627 | 318.1691 |
| gly-ile-glu | | 317.1586 | 318.1659 | 318.1627 | 318.1691 |
| pro-thr-thr | | 317.1586 | 318.1659 | 318.1627 | 318.1691 |
| ala-leu-asp | | 317.1586 | 318.1659 | 318.1627 | 318.1691 |
| ala-ile-asp | | 317.1586 | 318.1659 | 318.1627 | 318.1691 |
| asn-gly-lys | | 317.1699 | 318.1772 | 318.1740 | 318.1803 |
| leu-try | | 317.1812 | 318.1885 | 318.1853 | 318.1917 |
| ile-try | | 317.1812 | 318.1885 | 318.1853 | 318.1917 |
| 3α-hydroxy-5β-pregnan-20-one | C21H33O2 | 317.2480 | 318.2553 | 318.2521 | 318.2585 |
| phytosphingosine | C18H39NO3 | 317.2930 | 318.3003 | 318.2971 | 318.3034 |

TABLE 1-continued

Endogenous Metabolism Database

| Metabolite | Elemental formula | Precise Mass | M + 1H | 10 ppm− | 10 ppm+ |
|---|---|---|---|---|---|
| gly-asn-glu | | 318.1175 | 319.1248 | 319.1216 | 319.1280 |
| gly-asp-gln | | 318.1175 | 319.1248 | 319.1216 | 319.1280 |
| ala-asn-asp | | 318.1175 | 319.1248 | 319.1216 | 319.1280 |
| his-tyr | | 318.1328 | 319.1400 | 319.1369 | 319.1432 |
| gly-gly-try | | 318.1400 | 319.1473 | 319.1441 | 319.1505 |
| asn-try | | 318.1400 | 319.1473 | 319.1441 | 319.1505 |
| ala-thr-gln | | 318.1539 | 319.1612 | 319.1580 | 319.1644 |
| asp-gly-lys | | 318.1539 | 319.1612 | 319.1580 | 319.1644 |
| gly-ser-arg | | 318.1651 | 319.1724 | 319.1692 | 319.1756 |
| ala-thr-lys | | 318.1903 | 319.1976 | 319.1944 | 319.2007 |
| 12-oxoETE | C20H30O3 | 318.2195 | 319.2268 | 319.2236 | 319.2299 |
| 15-oxoicosa-5,8,11,13-tetraeonic acid | C20H30O3 | 318.2195 | 319.2268 | 319.2236 | 319.2299 |
| 5-oxoETE | C20H30O3 | 318.2195 | 319.2268 | 319.2236 | 319.2299 |
| leukotriene A4 | C20H30O3 | 318.2195 | 319.2268 | 319.2236 | 319.2299 |
| gly-asp-glu | | 319.1015 | 320.1088 | 320.1056 | 320.1120 |
| ala-asp-asp | | 319.1015 | 320.1088 | 320.1056 | 320.1120 |
| gly-cys-val | | 319.1188 | 320.1261 | 320.1229 | 320.1293 |
| pro-thr-cys | | 319.1202 | 320.1274 | 320.1242 | 320.1306 |
| asp-try | | 319.1241 | 320.1313 | 320.1281 | 320.1345 |
| ala-thr-glu | | 319.1379 | 320.1452 | 320.1420 | 320.1484 |
| phe-gly-pro | | 319.1532 | 320.1605 | 320.1573 | 320.1637 |
| leu-gly-met | | 319.1565 | 320.1638 | 320.1606 | 320.1670 |
| ile-gly-met | | 319.1565 | 320.1638 | 320.1606 | 320.1670 |
| ser-thr-leu | | 319.1743 | 320.1816 | 320.1784 | 320.1848 |
| ser-thr-ile | | 319.1743 | 320.1816 | 320.1784 | 320.1848 |
| ala-cys-gln | | 320.1154 | 321.1227 | 321.1195 | 321.1259 |
| gly-asn-met | | 320.1154 | 321.1227 | 321.1195 | 321.1259 |
| ser-ser-gln | | 320.1332 | 321.1404 | 321.1372 | 321.1436 |
| ser-thr-asn | | 320.1332 | 321.1404 | 321.1372 | 321.1436 |
| ala-cys-lys | | 320.1518 | 321.1591 | 321.1559 | 321.1623 |
| ser-ser-lys | | 320.1695 | 321.1768 | 321.1736 | 321.1800 |
| 11,12-EET | C20H32O3 | 320.2351 | 321.2424 | 321.2392 | 321.2456 |
| 11-HETE | C20H32O3 | 320.2351 | 321.2424 | 321.2392 | 321.2456 |
| 12-HETE | C20H32O3 | 320.2351 | 321.2424 | 321.2392 | 321.2456 |
| 14,15-EET | C20H32O3 | 320.2351 | 321.2424 | 321.2392 | 321.2456 |
| 15-hydoxy-5,8,11-cis-13-trans-eicosatetraenoate | C20H32O3 | 320.2351 | 321.2424 | 321.2392 | 321.2456 |
| 16-HETE | C20H32O3 | 320.2351 | 321.2424 | 321.2392 | 321.2456 |
| 19-HETE | C20H32O3 | 320.2351 | 321.2424 | 321.2392 | 321.2456 |
| 20-HETE | C20H32O3 | 320.2351 | 321.2424 | 321.2392 | 321.2456 |
| 5,6-EET | C20H32O3 | 320.2351 | 321.2424 | 321.2392 | 321.2456 |
| 5-hydroxyeicosatetraenoate | C20H32O3 | 320.2351 | 321.2424 | 321.2392 | 321.2456 |
| 8,9-EET | C20H32O3 | 320.2351 | 321.2424 | 321.2392 | 321.2456 |
| 8-HETE | C20H32O3 | 320.2351 | 321.2424 | 321.2392 | 321.2456 |
| 9-HETE | C20H32O3 | 320.2351 | 321.2424 | 321.2392 | 321.2456 |
| pro-cys-cys | | 321.0817 | 322.0889 | 322.0857 | 322.0922 |
| ala-cys-glu | | 321.0994 | 322.1067 | 322.1035 | 322.1099 |
| gly-asp-met | | 321.0994 | 322.1067 | 322.1035 | 322.1099 |
| S-glutaryldihydrolipoamide | C13H23NO4S2 | 321.1068 | 322.1141 | 322.1109 | 322.1173 |
| ser-ser-glu | | 321.1172 | 322.1244 | 322.1212 | 322.1277 |
| ser-thr-asp | | 321.1172 | 322.1244 | 322.1212 | 322.1277 |
| ala-thr-met | | 321.1358 | 322.1431 | 322.1399 | 322.1463 |
| ser-cys-leu | | 321.1358 | 322.1431 | 322.1399 | 322.1463 |
| ser-cys-ile | | 321.1358 | 322.1431 | 322.1399 | 322.1463 |
| thr-thr-thr | | 321.1536 | 322.1608 | 322.1576 | 322.1641 |
| phe-arg | | 321.1801 | 322.1873 | 322.1841 | 322.1906 |
| pregnanediol | C21H37O2 | 321.2793 | 322.2866 | 322.2834 | 322.2898 |
| 1-carboxyvinal-3-P-shikimate | C10H11O10P | 322.0084 | 323.0157 | 323.0124 | 323.0189 |
| thymidine monophosphate (TMP) | C10H15N2O8P | 322.0560 | 323.0633 | 323.0601 | 323.0665 |
| ser-cys-asn | | 322.0947 | 323.1019 | 323.0987 | 323.1052 |
| N-pantothenoyl-cysteine | C12H22N2O6S | 322.1198 | 323.1271 | 323.1239 | 323.1303 |
| val-tyr | | 322.1515 | 323.1588 | 323.1555 | 323.1620 |
| cytidine monophosphate (CMP) | C9H14N3O8P | 323.0513 | 324.0585 | 324.0553 | 324.0618 |
| ser-cys-asp | | 323.0787 | 324.0860 | 324.0827 | 324.0892 |
| ala-cys-met | | 323.0973 | 324.1046 | 324.1014 | 324.1078 |
| ser-ser-met | | 323.1151 | 324.1223 | 324.1191 | 324.1256 |
| thr-thr-cys | | 323.1151 | 324.1223 | 324.1191 | 324.1256 |
| ala-ala-tyr | | 323.1481 | 324.1554 | 324.1521 | 324.1586 |
| ala-ser-phe | | 323.1481 | 324.1554 | 324.1521 | 324.1586 |
| thr-gly-phe | | 323.1481 | 324.1554 | 324.1521 | 324.1586 |
| ala-pro-his | | 323.1593 | 324.1666 | 324.1634 | 324.1698 |
| mevalonate-5-PP | C6H14O11P2 | 324.0000 | 325.0073 | 325.0040 | 325.0105 |
| O5-(1-carboxyvinyl)-3-phoshoshikimate | C10H13O10P | 324.0240 | 325.0313 | 325.0281 | 325.0346 |

TABLE 1-continued

Endogenous Metabolism Database

| Metabolite | Elemental formula | Precise Mass | M + 1H | 10 ppm− | 10 ppm+ |
|---|---|---|---|---|---|
| pseudouridine 5'-phosphate | C9H13N2O9P | 324.0353 | 325.0425 | 325.0393 | 325.0458 |
| uridine monophosphate (UMP) | C9H13N2O9P | 324.0353 | 325.0425 | 325.0393 | 325.0458 |
| urothione | C11H11N5O3S2 | 325.0303 | 326.0376 | 326.0343 | 326.0408 |
| thr-cys-cys | | 325.0766 | 326.0839 | 326.0806 | 326.0871 |
| N-glycoloyl-neuraminate | C11H19NO10 | 325.1008 | 326.1081 | 326.1049 | 326.1114 |
| gly-cys-phe | | 325.1096 | 326.1169 | 326.1136 | 326.1201 |
| gly-ser-tyr | | 325.1273 | 326.1346 | 326.1314 | 326.1379 |
| leu-gly-his | | 325.1750 | 326.1822 | 326.1790 | 326.1855 |
| ile-gly-his | | 325.1750 | 326.1822 | 326.1790 | 326.1855 |
| pro-pro-leu | | 325.2001 | 326.2074 | 326.2041 | 326.2107 |
| pro-pro-ile | | 325.2001 | 326.2074 | 326.2041 | 326.2107 |
| gly-asn-his | | 326.1338 | 327.1411 | 327.1378 | 327.1444 |
| pro-pro-asn | | 326.1590 | 327.1663 | 327.1630 | 327.1695 |
| 2,3-dinor-8-iso prostaglandin F2α | C18H30O5 | 326.2093 | 327.2166 | 327.2133 | 327.2198 |
| homophytanic acid | C21H42O2 | 326.3185 | 327.3257 | 327.3225 | 327.3290 |
| cys-cys-cys | | 327.0381 | 328.0454 | 328.0421 | 328.0486 |
| gly-asp-his | | 327.1178 | 328.1251 | 328.1218 | 328.1284 |
| pro-pro-asp | | 327.1430 | 328.1503 | 328.1470 | 328.1536 |
| ala-thr-his | | 327.1542 | 328.1615 | 328.1582 | 328.1648 |
| val-ala-pro | | 327.1780 | 328.1853 | 328.1820 | 328.1886 |
| cyclic AMP | C10H11N5O6P | 328.0441 | 329.0514 | 329.0481 | 329.0547 |
| phe-tyr | | 328.1423 | 329.1496 | 329.1463 | 329.1528 |
| gly-pro-arg | | 328.1859 | 329.1931 | 329.1898 | 329.1964 |
| 2,3-dinor-8-iso prostaglandin F1α | C18H32O5 | 328.2250 | 329.2322 | 329.2289 | 329.2355 |
| ala-cys-his | | 329.1157 | 330.1230 | 330.1197 | 330.1263 |
| ser-ser-his | | 329.1335 | 330.1408 | 330.1375 | 330.1441 |
| gly-leu-val | | 329.1937 | 330.2010 | 330.1977 | 330.2043 |
| gly-ile-val | | 329.1937 | 330.2010 | 330.1977 | 330.2043 |
| pro-thr-leu | | 329.1950 | 330.2023 | 330.1990 | 330.2056 |
| pro-thr-ile | | 329.1950 | 330.2023 | 330.1990 | 330.2056 |
| asn-gly-val | | 330.1525 | 331.1598 | 331.1565 | 331.1631 |
| ser-pro-gln | | 330.1539 | 331.1612 | 331.1579 | 331.1645 |
| pro-thr-asn | | 330.1539 | 331.1612 | 331.1579 | 331.1645 |
| ala-leu-gln | | 330.1903 | 331.1976 | 331.1942 | 331.2009 |
| ala-ile-gln | | 330.1903 | 331.1976 | 331.1942 | 331.2009 |
| lys-ser-pro | | 330.1903 | 331.1976 | 331.1942 | 331.2009 |
| arg-arg | | 330.2127 | 331.2200 | 331.2167 | 331.2233 |
| 11-dexsycorticosterone | C21H30O3 | 330.2195 | 331.2268 | 331.2234 | 331.2301 |
| 11β-hydroxyprogesterone | C21H30O3 | 330.2195 | 331.2268 | 331.2234 | 331.2301 |
| 17α-hydroxyprogesterone | C21H30O3 | 330.2195 | 331.2268 | 331.2234 | 331.2301 |
| ala-leu-lys | | 330.2267 | 331.2339 | 331.2306 | 331.2373 |
| ala-ile-lys | | 330.2267 | 331.2339 | 331.2306 | 331.2373 |
| 9,10,13-TriHOME | C18H34O5 | 330.2406 | 331.2479 | 331.2446 | 331.2512 |
| 9,10-dihydroxy-12,13-epoxyoctadecanoate | C18H34O5 | 330.2406 | 331.2479 | 331.2446 | 331.2512 |
| 9,12,13-TriHOME | C18H34O5 | 330.2406 | 331.2479 | 331.2446 | 331.2512 |
| inosine-5-phosphate | C10H13N4O7P | 331.0438 | 332.0510 | 332.0477 | 332.0544 |
| dAMP | C10H14N5O6P | 331.0676 | 332.0748 | 332.0715 | 332.0782 |
| asp-gly-val | | 331.1366 | 332.1438 | 332.1405 | 332.1472 |
| ser-pro-glu | | 331.1379 | 332.1452 | 332.1419 | 332.1485 |
| pro-thr-asp | | 331.1379 | 332.1452 | 332.1419 | 332.1485 |
| gly-gln-gln | | 331.1491 | 332.1564 | 332.1531 | 332.1597 |
| ala-asn-gln | | 331.1491 | 332.1564 | 332.1531 | 332.1597 |
| pro-cys-leu | | 331.1565 | 332.1638 | 332.1605 | 332.1671 |
| pro-cys-ile | | 331.1565 | 332.1638 | 332.1605 | 332.1671 |
| ala-thr-val | | 331.1729 | 332.1802 | 332.1769 | 332.1835 |
| ala-leu-glu | | 331.1743 | 332.1816 | 332.1783 | 332.1849 |
| ala-ile-glu | | 331.1743 | 332.1816 | 332.1783 | 332.1849 |
| gly-gln-lys | | 331.1855 | 332.1928 | 332.1895 | 332.1961 |
| ala-asn-lys | | 331.1855 | 332.1928 | 332.1895 | 332.1961 |
| ser-leu-leu | | 331.2107 | 332.2180 | 332.2146 | 332.2213 |
| ser-leu-ile | | 331.2107 | 332.2180 | 332.2146 | 332.2213 |
| ser-ile-ile | | 331.2107 | 332.2180 | 332.2146 | 332.2213 |
| gly-lys-lys | | 331.2219 | 332.2292 | 332.2259 | 332.2325 |
| dIMP | C10H13N4O7P | 332.0516 | 333.0589 | 333.0555 | 333.0622 |
| cys-pro-asn | | 332.1154 | 333.1227 | 333.1193 | 333.1260 |
| gly-gln-glu | | 332.1332 | 333.1404 | 333.1371 | 333.1438 |
| ala-asn-glu | | 332.1332 | 333.1404 | 333.1371 | 333.1438 |
| ala-asp-gln | | 332.1332 | 333.1404 | 333.1371 | 333.1438 |
| ala-gly-try | | 332.1557 | 333.1630 | 333.1596 | 333.1663 |
| gln-try | | 332.1557 | 333.1630 | 333.1596 | 333.1663 |
| gly-lys-glu | | 332.1695 | 333.1768 | 333.1735 | 333.1801 |
| ala-asp-lys | | 332.1695 | 333.1768 | 333.1735 | 333.1801 |
| ser-leu-asn | | 332.1695 | 333.1768 | 333.1735 | 333.1801 |
| ser-ile-asn | | 332.1695 | 333.1768 | 333.1735 | 333.1801 |

TABLE 1-continued

Endogenous Metabolism Database

| Metabolite | Elemental formula | Precise Mass | M + 1H | 10 ppm− | 10 ppm+ |
|---|---|---|---|---|---|
| gly-thr-arg | | 332.1808 | 333.1880 | 333.1847 | 333.1914 |
| ala-ser-arg | | 332.1808 | 333.1880 | 333.1847 | 333.1914 |
| lys-try | | 332.1921 | 333.1994 | 333.1960 | 333.2027 |
| 17α-hydroxypregnenolone | C21H32O3 | 332.2351 | 333.2424 | 333.2391 | 333.2457 |
| 17α,20α-dihydroxypregn-4-en-3-one | C21H32O3 | 332.2351 | 333.2424 | 333.2391 | 333.2457 |
| 21-hydroxypregnenolone | C21H32O3 | 332.2351 | 333.2424 | 333.2391 | 333.2457 |
| cys-pro-asp | | 333.0994 | 334.1067 | 334.1034 | 334.1100 |
| gly-glu-glu | | 333.1172 | 334.1244 | 334.1211 | 334.1278 |
| ala-asp-glu | | 333.1172 | 334.1244 | 334.1211 | 334.1278 |
| ser-asn-asn | | 333.1284 | 334.1357 | 334.1323 | 334.1390 |
| ala-cys-val | | 333.1345 | 334.1417 | 334.1384 | 334.1451 |
| ser-pro-met | | 333.1358 | 334.1431 | 334.1397 | 334.1464 |
| glu-try | | 333.1397 | 334.1470 | 334.1436 | 334.1503 |
| ser-ser-val | | 333.1522 | 334.1595 | 334.1561 | 334.1628 |
| ser-leu-asp | | 333.1536 | 334.1608 | 334.1575 | 334.1642 |
| ser-ile-asp | | 333.1536 | 334.1608 | 334.1575 | 334.1642 |
| ala-pro-phe | | 333.1688 | 334.1761 | 334.1728 | 334.1794 |
| ala-leu-met | | 333.1722 | 334.1795 | 334.1761 | 334.1828 |
| ala-ile-met | | 333.1722 | 334.1795 | 334.1761 | 334.1828 |
| thr-thr-leu | | 333.1899 | 334.1972 | 334.1939 | 334.2006 |
| thr-thr-ile | | 333.1899 | 334.1972 | 334.1939 | 334.2006 |
| ser-asn-asp | | 334.1124 | 335.1197 | 335.1163 | 335.1230 |
| gly-gln-met | | 334.1311 | 335.1383 | 335.1350 | 335.1417 |
| ala-asn-met | | 334.1311 | 335.1383 | 335.1350 | 335.1417 |
| cys-gly-arg | | 334.1423 | 335.1496 | 335.1462 | 335.1529 |
| ser-thr-gln | | 334.1488 | 335.1561 | 335.1527 | 335.1594 |
| thr-thr-asn | | 334.1488 | 335.1561 | 335.1527 | 335.1594 |
| lys-gly-met | | 334.1674 | 335.1747 | 335.1714 | 335.1781 |
| ser-thr-lys | | 334.1852 | 335.1925 | 335.1891 | 335.1958 |
| 12-keto-leukotriene B4 | C20H30O4 | 334.2144 | 335.2217 | 335.2183 | 335.2250 |
| 5,6-epoxytetraene | C20H30O4 | 334.2144 | 335.2217 | 335.2183 | 335.2250 |
| prostaglandin A2 | C20H30O4 | 334.2144 | 335.2217 | 335.2183 | 335.2250 |
| prostaglandin B2 | C20H30O4 | 334.2144 | 335.2217 | 335.2183 | 335.2250 |
| prostaglandin C2 | C20H30O4 | 334.2144 | 335.2217 | 335.2183 | 335.2250 |
| prostaglandin J2 | C20H30O4 | 334.2144 | 335.2217 | 335.2183 | 335.2250 |
| δ-12-prostaglandin J2 | C20H30O4 | 334.2144 | 335.2217 | 335.2183 | 335.2250 |
| nicotinate nucleotide | C11H14NO9P | 335.0400 | 336.0473 | 336.0439 | 336.0507 |
| S-formylglutathione | C11H17N3O7S | 335.0787 | 336.0860 | 336.0826 | 336.0893 |
| ser-asp-asp | | 335.0964 | 336.1037 | 336.1003 | 336.1071 |
| gly-glu-met | | 335.1151 | 336.1223 | 336.1190 | 336.1257 |
| ala-asp-met | | 335.1151 | 336.1223 | 336.1190 | 336.1257 |
| ser-thr-glu | | 335.1328 | 336.1401 | 336.1367 | 336.1435 |
| thr-thr-asp | | 335.1328 | 336.1401 | 336.1367 | 336.1435 |
| met-try | | 335.1376 | 336.1449 | 336.1415 | 336.1483 |
| gly-pro-tyr | | 335.1481 | 336.1554 | 336.1520 | 336.1587 |
| thr-cys-leu | | 335.1515 | 336.1587 | 336.1554 | 336.1621 |
| thr-cys-ile | | 335.1515 | 336.1587 | 336.1554 | 336.1621 |
| gly-leu-phe | | 335.1845 | 336.1918 | 336.1884 | 336.1951 |
| gly-ile-phe | | 335.1845 | 336.1918 | 336.1884 | 336.1951 |
| fructose 2,6-bisphosphate | C6H10O12P2 | 335.9636 | 336.9709 | 336.9675 | 336.9742 |
| fructose-1,6-bisphosphate | C6H10O12P2 | 335.9636 | 336.9709 | 336.9675 | 336.9742 |
| glucose 1,6-bisphosphate | C6H10O12P2 | 335.9636 | 336.9709 | 336.9675 | 336.9742 |
| ser-cys-gln | | 336.1103 | 337.1176 | 337.1142 | 337.1210 |
| thr-cys-asn | | 336.1103 | 337.1176 | 337.1142 | 337.1210 |
| gly-asn-phe | | 336.1433 | 337.1506 | 337.1472 | 337.1540 |
| ser-cys-lys | | 336.1467 | 337.1540 | 337.1506 | 337.1573 |
| 9-HPETE | C20H32O4 | 336.2300 | 337.2373 | 337.2339 | 337.2407 |
| 11-HPETE | C20H32O4 | 336.2300 | 337.2373 | 337.2339 | 337.2407 |
| 11-hydroxy-14,15-EETA | C20H32O4 | 336.2300 | 337.2373 | 337.2339 | 337.2407 |
| 12-HPETE | C20H32O4 | 336.2300 | 337.2373 | 337.2339 | 337.2407 |
| 15-H-11,12-EETA | C20H32O4 | 336.2300 | 337.2373 | 337.2339 | 337.2407 |
| 15-HPETE | C20H32O4 | 336.2300 | 337.2373 | 337.2339 | 337.2407 |
| 5-HPETE | C20H32O4 | 336.2300 | 337.2373 | 337.2339 | 337.2407 |
| 8-HPETE | C20H32O4 | 336.2300 | 337.2373 | 337.2339 | 337.2407 |
| 8-hydroxyperoxyeicosa-5,9,11,14-tetraenoate | C20H32O4 | 336.2300 | 337.2373 | 337.2339 | 337.2407 |
| hepoxilin A3 | C20H32O4 | 336.2300 | 337.2373 | 337.2339 | 337.2407 |
| hepoxilin B3 | C20H32O4 | 336.2300 | 337.2373 | 337.2339 | 337.2407 |
| leukotriene B4 | C20H32O4 | 336.2300 | 337.2373 | 337.2339 | 337.2407 |
| prostaglandin A1 | C20H32O4 | 336.2300 | 337.2373 | 337.2339 | 337.2407 |
| prostaglandin B1 | C20H32O4 | 336.2300 | 337.2373 | 337.2339 | 337.2407 |
| phosphoinositolphosphate | C6H11O12P2 | 336.9714 | 337.9787 | 337.9753 | 337.9821 |
| 5-hydroxymethyldeoxycytidylate | C10H16N3O8P | 337.0669 | 338.0742 | 338.0708 | 338.0776 |
| S-(hydroxymethyl) glutathione | C11H19N3O7S | 337.0943 | 338.1016 | 338.0982 | 338.1050 |

TABLE 1-continued

Endogenous Metabolism Database

| Metabolite | Elemental formula | Precise Mass | M + 1H | 10 ppm− | 10 ppm+ |
|---|---|---|---|---|---|
| ser-cys-glu | | 337.0943 | 338.1016 | 338.0982 | 338.1050 |
| thr-cys-asp | | 337.0943 | 338.1016 | 338.0982 | 338.1050 |
| cys-cys-leu | | 337.1130 | 338.1202 | 338.1169 | 338.1236 |
| cys-cys-ile | | 337.1130 | 338.1202 | 338.1169 | 338.1236 |
| gly-met-met | | 337.1130 | 338.1202 | 338.1169 | 338.1236 |
| gly-asp-phe | | 337.1273 | 338.1346 | 338.1312 | 338.1380 |
| ser-thr-met | | 337.1307 | 338.1346 | 338.1346 | 338.1414 |
| ala-thr-phe | | 337.1637 | 338.1710 | 338.1676 | 338.1744 |
| arg-tyr | | 337.1750 | 338.1822 | 338.1789 | 338.1856 |
| 1-(5-phosphoribosyl) imidazole-4-acetate | C10H15N2O9P | 338.0509 | 339.0582 | 339.0548 | 339.0616 |
| 5′-phosphoribosyl-4-carbamoyl-5-aminoimidazole (AICAR) | C9H15N4O8P | 338.0621 | 339.0694 | 339.0660 | 339.0728 |
| cys-cys-asn | | 338.0718 | 339.0791 | 339.0757 | 339.0825 |
| 11,12-DHET | C20H34O4 | 338.2457 | 339.2530 | 339.2496 | 339.2564 |
| 14,15-DHET | C20H34O4 | 338.2457 | 339.2530 | 339.2496 | 339.2564 |
| 5,6-DHET | C20H34O4 | 338.2457 | 339.2530 | 339.2496 | 339.2564 |
| 8,9-DHET | C20H34O4 | 338.2457 | 339.2530 | 339.2496 | 339.2564 |
| thromboxane B2 | C20H34O4 | 338.2457 | 339.2530 | 339.2496 | 339.2564 |
| 5P-ribosyl-4-carboxy-5-aminoimidazole | C9H14N3O9P | 339.0462 | 340.0534 | 340.0500 | 340.0568 |
| cys-cys-asp | | 339.0558 | 340.0631 | 340.0597 | 340.0665 |
| ser-cys-met | | 339.0922 | 340.0995 | 340.0961 | 340.1029 |
| ala-cys-phe | | 339.1252 | 340.1325 | 340.1291 | 340.1359 |
| gly-thr-tyr | | 339.1430 | 340.1503 | 340.1469 | 340.1537 |
| ala-ser-tyr | | 339.1430 | 340.1503 | 340.1469 | 340.1537 |
| ser-ser-phe | | 339.1430 | 340.1503 | 340.1469 | 340.1537 |
| ser-pro-his | | 339.1542 | 340.1615 | 340.1581 | 340.1649 |
| ala-leu-his | | 339.1906 | 340.1979 | 340.1945 | 340.2013 |
| ala-ile-his | | 339.1906 | 340.1979 | 340.1945 | 340.2013 |
| inositol 1,4-bisphosphate | C6H14O12P2 | 339.9949 | 341.0022 | 340.9988 | 341.0056 |
| inositol 3,4-bisphosphate | C6H14O12P2 | 339.9949 | 341.0022 | 340.9988 | 341.0056 |
| tagatose 1,6-bisphosphate | C6H14O12P2 | 339.9949 | 341.0022 | 340.9988 | 341.0056 |
| 3-ketolactose | C12H20O11 | 340.1005 | 341.1078 | 341.1044 | 341.1112 |
| 3-ketosucrose | C12H20O11 | 340.1005 | 341.1078 | 341.1044 | 341.1112 |
| (5-galactosyloxy)-lysine | C12H24N2O9 | 340.1481 | 341.1554 | 341.1520 | 341.1588 |
| gly-gln-his | | 340.1495 | 341.1567 | 341.1533 | 341.1602 |
| ala-asn-his | | 340.1495 | 341.1567 | 341.1533 | 341.1602 |
| pro-pro-gln | | 340.1746 | 341.1819 | 341.1785 | 341.1853 |
| lys-gly-his | | 340.1859 | 341.1931 | 341.1897 | 341.1965 |
| pro-pro-lys | | 340.2110 | 341.2183 | 341.2149 | 341.2217 |
| cys-gly-tyr | | 341.1045 | 342.1118 | 342.1084 | 342.1152 |
| gly-glu-his | | 341.1335 | 342.1408 | 342.1373 | 342.1442 |
| ala-asp-his | | 341.1335 | 342.1408 | 342.1373 | 342.1442 |
| his-try | | 341.1560 | 342.1633 | 342.1599 | 342.1667 |
| pro-pro-glu | | 341.1586 | 342.1659 | 342.1625 | 342.1693 |
| pro-leu-leu | | 341.2314 | 342.2387 | 342.2353 | 342.2421 |
| pro-leu-ile | | 341.2314 | 342.2387 | 342.2353 | 342.2421 |
| pro-ile-ile | | 341.2314 | 342.2387 | 342.2353 | 342.2421 |
| cellobiose | C12H22O11 | 342.1162 | 343.1234 | 343.1200 | 343.1269 |
| cellulose | C12H22O11 | 342.1162 | 343.1234 | 343.1200 | 343.1269 |
| epimelibiose | C12H22O11 | 342.1162 | 343.1234 | 343.1200 | 343.1269 |
| galactinol | C12H22O11 | 342.1162 | 343.1234 | 343.1200 | 343.1269 |
| isomaltose | C12H22O11 | 342.1162 | 343.1234 | 343.1200 | 343.1269 |
| lactose | C12H22O11 | 342.1162 | 343.1234 | 343.1200 | 343.1269 |
| maltose | C12H22O11 | 342.1162 | 343.1234 | 343.1200 | 343.1269 |
| melibiose | C12H22O11 | 342.1162 | 343.1234 | 343.1200 | 343.1269 |
| sucrose | C12H22O11 | 342.1162 | 343.1234 | 343.1200 | 343.1269 |
| trehalose | C12H22O11 | 342.1162 | 343.1234 | 343.1200 | 343.1269 |
| leu-pro-asn | | 342.1903 | 343.1976 | 343.1941 | 343.2010 |
| ile-pro-asn | | 342.1903 | 343.1976 | 343.1941 | 343.2010 |
| ala-pro-arg | | 342.2015 | 343.2088 | 343.2054 | 343.2122 |
| gly-met-his | | 343.1314 | 344.1387 | 344.1352 | 344.1421 |
| ser-thr-his | | 343.1491 | 344.1564 | 344.1530 | 344.1599 |
| pro-asn-asn | | 343.1491 | 344.1564 | 344.1530 | 344.1599 |
| pro-pro-met | | 343.1565 | 344.1638 | 344.1604 | 344.1673 |
| val-ser-pro | | 343.1729 | 344.1802 | 344.1768 | 344.1837 |
| leu-pro-asp | | 343.1743 | 344.1816 | 344.1781 | 344.1850 |
| ile-pro-asp | | 343.1743 | 344.1816 | 344.1781 | 344.1850 |
| ala-leu-val | | 343.2093 | 344.2166 | 344.2132 | 344.2201 |
| ala-ile-val | | 343.2093 | 344.2166 | 344.2132 | 344.2201 |
| melibiitol | C12H24O11 | 344.1318 | 345.1391 | 345.1356 | 345.1425 |
| pro-asn-asp | | 344.1332 | 345.1404 | 345.1370 | 345.1439 |
| tyr-tyr | | 344.1372 | 345.1445 | 345.1410 | 345.1479 |
| gly-gln-val | | 344.1682 | 345.1755 | 345.1720 | 345.1789 |

TABLE 1-continued

Endogenous Metabolism Database

| Metabolite | Elemental formula | Precise Mass | M + 1H | 10 ppm− | 10 ppm+ |
|---|---|---|---|---|---|
| ala-asn-val | | 344.1682 | 345.1755 | 345.1720 | 345.1789 |
| pro-thr-gln | | 344.1695 | 345.1768 | 345.1734 | 345.1803 |
| 11-dehydro-corticosterone | C21H28O4 | 344.1987 | 345.2060 | 345.2026 | 345.2095 |
| gly-lys-val | | 344.2046 | 345.2119 | 345.2084 | 345.2153 |
| pro-thr-lys | | 344.2059 | 345.2132 | 345.2098 | 345.2167 |
| leu-gly-arg | | 344.2172 | 345.2244 | 345.2210 | 345.2279 |
| ile-gly-arg | | 344.2172 | 345.2244 | 345.2210 | 345.2279 |
| cGMP | C10H12N5O7P | 345.0468 | 346.0541 | 346.0506 | 346.0576 |
| ser-cys-his | | 345.1106 | 346.1179 | 346.1145 | 346.1214 |
| pro-asp-asp | | 345.1172 | 346.1244 | 346.1210 | 346.1279 |
| gly-glu-val | | 345.1522 | 346.1595 | 346.1560 | 346.1629 |
| ala-asp-val | | 345.1522 | 346.1595 | 346.1560 | 346.1629 |
| pro-thr-glu | | 345.1536 | 346.1608 | 346.1574 | 346.1643 |
| ala-gln-gln | | 345.1648 | 346.1721 | 346.1686 | 346.1755 |
| val-try | | 345.1748 | 346.1820 | 346.1786 | 346.1855 |
| gly-asn-arg | | 345.1760 | 346.1833 | 346.1798 | 346.1868 |
| ala-gln-lys | | 345.2012 | 346.2085 | 346.2050 | 346.2119 |
| thr-leu-leu | | 345.2263 | 346.2336 | 346.2301 | 346.2371 |
| thr-leu-ile | | 345.2263 | 346.2336 | 346.2301 | 346.2371 |
| thr-ile-ile | | 345.2263 | 346.2336 | 346.2301 | 346.2371 |
| ala-lys-lys | | 345.2376 | 346.2448 | 346.2414 | 346.2483 |
| pro-cys-gln | | 346.1311 | 347.1383 | 347.1349 | 347.1418 |
| ala-gln-glu | | 346.1488 | 347.1561 | 347.1526 | 347.1595 |
| gly-asp-arg | | 346.1600 | 347.1673 | 347.1638 | 347.1708 |
| pro-cys-lys | | 346.1674 | 347.1747 | 347.1712 | 347.1782 |
| ala-ala-try | | 346.1713 | 347.1786 | 347.1752 | 347.1821 |
| ala-lys-glu | | 346.1852 | 347.1925 | 347.1890 | 347.1959 |
| ser-leu-gln | | 346.1852 | 347.1925 | 347.1890 | 347.1959 |
| ser-ile-gln | | 346.1852 | 347.1925 | 347.1890 | 347.1959 |
| leu-thr-asn | | 346.1852 | 347.1925 | 347.1890 | 347.1959 |
| ile-thr-asn | | 346.1852 | 347.1925 | 347.1890 | 347.1959 |
| ala-thr-arg | | 346.1964 | 347.2037 | 347.2002 | 347.2072 |
| 11-deoxycortisol(17α-hydroxycortexone) | C21H30O4 | 346.2144 | 347.2217 | 347.2182 | 347.2251 |
| 21-deoxycortisol | C21H30O4 | 346.2144 | 347.2217 | 347.2182 | 347.2251 |
| 21-hydroxy-5β-pregnane-3,11,20-trione | C21H30O4 | 346.2144 | 347.2217 | 347.2182 | 347.2251 |
| corticosterone | C21H30O4 | 346.2144 | 347.2217 | 347.2182 | 347.2251 |
| ser-leu-lys | | 346.2216 | 347.2289 | 347.2254 | 347.2323 |
| ser-ile-lys | | 346.2216 | 347.2289 | 347.2254 | 347.2323 |
| N-acetylmannosamine-6-P | C8H14NO9P | 347.0248 | 348.0320 | 348.0285 | 348.0355 |
| dGMP | C10H14N5O7P | 347.0625 | 348.0698 | 348.0663 | 348.0732 |
| propionyl adenylate | C13H18N5O8P | 347.0764 | 348.0837 | 348.0802 | 348.0872 |
| pro-cys-glu | | 347.1151 | 348.1223 | 348.1189 | 348.1258 |
| ala-glu-glu | | 347.1328 | 348.1401 | 348.1366 | 348.1436 |
| ser-asn-gln | | 347.1440 | 348.1513 | 348.1478 | 348.1548 |
| thr-asn-asn | | 347.1440 | 348.1513 | 348.1478 | 348.1548 |
| met-gly-val | | 347.1501 | 348.1574 | 348.1539 | 348.1609 |
| pro-thr-met | | 347.1515 | 348.1587 | 348.1553 | 348.1622 |
| ser-thr-val | | 347.1679 | 348.1751 | 348.1717 | 348.1786 |
| ser-leu-glu | | 347.1692 | 348.1765 | 348.1730 | 348.1800 |
| ser-ile-glu | | 347.1692 | 348.1765 | 348.1730 | 348.1800 |
| leu-thr-asp | | 347.1692 | 348.1765 | 348.1730 | 348.1800 |
| ile-thr-asp | | 347.1692 | 348.1765 | 348.1730 | 348.1800 |
| ser-asn-lys | | 347.1804 | 348.1877 | 348.1842 | 348.1912 |
| cys-leu-leu | | 347.1878 | 348.1951 | 348.1916 | 348.1986 |
| cys-leu-ile | | 347.1878 | 348.1951 | 348.1916 | 348.1986 |
| cys-ile-ile | | 347.1878 | 348.1951 | 348.1916 | 348.1986 |
| 1-(2-carbosyphenylamino)-1'deoxyribulose-5'-P | C12H15NO9P | 348.0478 | 349.0551 | 349.0516 | 349.0586 |
| ser-asn-glu | | 348.1281 | 349.1353 | 349.1318 | 349.1388 |
| ser-asp-gln | | 348.1281 | 349.1353 | 349.1318 | 349.1388 |
| thr-asn-asp | | 348.1281 | 349.1353 | 349.1318 | 349.1388 |
| ala-gln-met | | 348.1467 | 349.1540 | 349.1505 | 349.1575 |
| leu-cys-asn | | 348.1467 | 349.1540 | 349.1505 | 349.1575 |
| ile-cys-asn | | 348.1467 | 349.1540 | 349.1505 | 349.1575 |
| ser-gly-try | | 348.1506 | 349.1579 | 349.1544 | 349.1614 |
| ala-cys-arg | | 348.1579 | 349.1652 | 349.1617 | 349.1687 |
| thr-thr-gln | | 348.1645 | 349.1717 | 349.1682 | 349.1752 |
| ser-asp-lys | | 348.1645 | 349.1717 | 349.1682 | 349.1752 |
| ser-ser-arg | | 348.1757 | 349.1830 | 349.1795 | 349.1864 |
| ala-lys-met | | 348.1831 | 349.1904 | 349.1869 | 349.1939 |
| thr-thr-lys | | 348.2008 | 349.2081 | 349.2046 | 349.2116 |
| 11β,21-dihydroxy-5β-pregnane-3,20-dione | C21H32O4 | 348.2300 | 349.2373 | 349.2338 | 349.2408 |

TABLE 1-continued

Endogenous Metabolism Database

| Metabolite | Elemental formula | Precise Mass | M + 1H | 10 ppm− | 10 ppm+ |
|---|---|---|---|---|---|
| 17α,21-dihydroxypregnenolone | C21H32O4 | 348.2300 | 349.2373 | 349.2338 | 349.2408 |
| 3α,21-dihydroxy-5β-pregnane-11,20-dione | C21H32O4 | 348.2300 | 349.2373 | 349.2338 | 349.2408 |
| N-(5-phosphoribosyl) anthranilate | C12H16NO9P | 349.0557 | 350.0629 | 350.0594 | 350.0664 |
| cys-asn-asn | | 349.1056 | 350.1128 | 350.1093 | 350.1163 |
| ser-asp-glu | | 349.1121 | 350.1194 | 350.1159 | 350.1229 |
| thr-asp-asp | | 349.1121 | 350.1194 | 350.1159 | 350.1229 |
| cys-pro-met | | 349.1130 | 350.1202 | 350.1167 | 350.1237 |
| ser-cys-val | | 349.1294 | 350.1366 | 350.1331 | 350.1401 |
| ala-glu-met | | 349.1307 | 350.1380 | 350.1345 | 350.1415 |
| leu-cys-asp | | 349.1307 | 350.1380 | 350.1345 | 350.1415 |
| ile-cys-asp | | 349.1307 | 350.1380 | 350.1345 | 350.1415 |
| thr-thr-glu | | 349.1485 | 350.1557 | 350.1522 | 350.1592 |
| gly-his-his | | 349.1498 | 350.1571 | 350.1536 | 350.1606 |
| ala-pro-tyr | | 349.1637 | 350.1710 | 350.1675 | 350.1745 |
| pro-ser-phe | | 349.1637 | 350.1710 | 350.1675 | 350.1745 |
| ser-leu-met | | 349.1671 | 350.1744 | 350.1709 | 350.1779 |
| ser-ile-met | | 349.1671 | 350.1744 | 350.1709 | 350.1779 |
| pro-pro-his | | 349.1750 | 350.1822 | 350.1787 | 350.1857 |
| ala-leu-phe | | 349.2001 | 350.2074 | 350.2039 | 350.2109 |
| ala-ile-phe | | 349.2001 | 350.2074 | 350.2039 | 350.2109 |
| N-phospho lombricine | C6H16N4O9P2 | 350.0381 | 351.0454 | 351.0419 | 351.0489 |
| cys-asn-asp | | 350.0896 | 351.0968 | 351.0933 | 351.1004 |
| estrone sulfate | C18H22O5S | 350.1188 | 351.1260 | 351.1225 | 351.1296 |
| thr-cys-gln | | 350.1260 | 351.1332 | 351.1297 | 351.1367 |
| ser-asn-met | | 350.1260 | 351.1332 | 351.1297 | 351.1367 |
| ala-asn-phe | | 350.1590 | 351.1663 | 351.1627 | 351.1698 |
| gln-gly-phe | | 350.1590 | 351.1663 | 351.1627 | 351.1698 |
| thr-cys-lys | | 350.1624 | 351.1696 | 351.1661 | 351.1731 |
| gly-lys-phe | | 350.1954 | 351.2026 | 351.1991 | 351.2062 |
| 15-keto-prostaglandin E2 | C20H30O5 | 350.2093 | 351.2166 | 351.2131 | 351.2201 |
| prostaglandin E3 | C20H30O5 | 350.2093 | 351.2166 | 351.2131 | 351.2201 |
| 3α,11β,21-trihydroxy-5β-pregnan-11-al | C21H34O4 | 350.2457 | 351.2530 | 351.2495 | 351.2565 |
| 3α,20α,21-trihydroxy-5β-pregnane-11-one | C21H34O4 | 350.2457 | 351.2530 | 351.2495 | 351.2565 |
| tetrahydrocorticosterone | C21H34O4 | 350.2457 | 351.2530 | 351.2495 | 351.2565 |
| cys-asp-asp | | 351.0736 | 352.0809 | 352.0773 | 352.0844 |
| thr-cys-glu | | 351.1100 | 352.1173 | 352.1137 | 352.1208 |
| ser-asp-met | | 351.1100 | 352.1173 | 352.1137 | 352.1208 |
| ala-met-met | | 351.1286 | 352.1359 | 352.1324 | 352.1394 |
| ala-asp-phe | | 351.1430 | 352.1503 | 352.1468 | 352.1538 |
| glu-gly-phe | | 351.1430 | 352.1503 | 352.1468 | 352.1538 |
| thr-thr-met | | 351.1464 | 352.1536 | 352.1501 | 352.1572 |
| phe-try | | 351.1655 | 352.1728 | 352.1693 | 352.1763 |
| leu-gly-tyr | | 351.1794 | 352.1867 | 352.1831 | 352.1902 |
| ile-gly-tyr | | 351.1794 | 352.1867 | 352.1831 | 352.1902 |
| arbutin-6P | C12H17O10P | 352.0553 | 353.0626 | 353.0591 | 353.0661 |
| 4-(4-deoxy-α-gluc-4-enuronosyl)-galacturonate | C12H16O12 | 352.0641 | 353.0714 | 353.0679 | 353.0749 |
| 4-(4-deoxy-β-gluc-4-enuronosyl)-galacturonate | C12H16O12 | 352.0641 | 353.0714 | 353.0679 | 353.0749 |
| cys-cys-gln | | 352.0875 | 353.0947 | 353.0912 | 353.0983 |
| cys-cys-lys | | 352.1239 | 353.1311 | 353.1276 | 353.1347 |
| estradiol-17β 3-sulfate | C18H24O5S | 352.1344 | 353.1417 | 353.1382 | 353.1452 |
| gly-asn-tyr | | 352.1382 | 353.1455 | 353.1420 | 353.1490 |
| 13,14-dihydro-15-keto-prostaglandin E2 | C20H32O5 | 352.2250 | 353.2322 | 353.2287 | 353.2358 |
| 15-keto-prostaglandin F2α | C20H32O5 | 352.2250 | 353.2322 | 353.2287 | 353.2358 |
| 20-hydroxy-leukotriene B4 | C20H32O5 | 352.2250 | 353.2322 | 353.2287 | 353.2358 |
| 9α,15-dihydroxy-11-oxoprosta-5,13-dienoic acid | C20H32O5 | 352.2250 | 353.2322 | 353.2287 | 353.2358 |
| dinoprostone | C20H32O5 | 352.2250 | 353.2322 | 353.2287 | 353.2358 |
| lipoxin A4 | C20H32O5 | 352.2250 | 353.2322 | 353.2287 | 353.2358 |
| lipoxin B4 | C20H32O5 | 352.2250 | 353.2322 | 353.2287 | 353.2358 |
| prostaglandin E2 | C20H32O5 | 352.2250 | 353.2322 | 353.2287 | 353.2358 |
| prostaglandin H2 | C20H32O5 | 352.2250 | 353.2322 | 353.2287 | 353.2358 |
| prostaglandin I2 | C20H32O5 | 352.2250 | 353.2322 | 353.2287 | 353.2358 |
| thromboxane A2 | C20H32O5 | 352.2250 | 353.2322 | 353.2287 | 353.2358 |
| 2'deoxy-5-hydroxymethyl-cytidine monophosphate | C10H16N3O9P | 353.0618 | 354.0691 | 354.0655 | 354.0726 |
| cys-cys-glu | | 353.0715 | 354.0788 | 354.0752 | 354.0823 |
| cys-thr-met | | 353.1079 | 354.1152 | 354.1116 | 354.1187 |
| gly-asp-tyr | | 353.1223 | 354.1295 | 354.1260 | 354.1331 |
| gly-met-phe | | 353.1409 | 354.1482 | 354.1446 | 354.1517 |

TABLE 1-continued

Endogenous Metabolism Database

| Metabolite | Elemental formula | Precise Mass | M + 1H | 10 ppm− | 10 ppm+ |
|---|---|---|---|---|---|
| ala-thr-tyr | | 353.1586 | 354.1659 | 354.1624 | 354.1695 |
| thr-ser-phe | | 353.1586 | 354.1659 | 354.1624 | 354.1695 |
| his-gly-val | | 353.1685 | 354.1758 | 354.1723 | 354.1793 |
| pro-thr-his | | 353.1699 | 354.1772 | 354.1736 | 354.1807 |
| pro-pro-val | | 353.1937 | 354.2010 | 354.1974 | 354.2045 |
| ala-gln-his | | 354.1651 | 355.1724 | 355.1688 | 355.1759 |
| ala-lys-his | | 354.2015 | 355.2088 | 355.2052 | 355.2123 |
| 11,12,15-THETA | C20H34O5 | 354.2406 | 355.2479 | 355.2443 | 355.2514 |
| 11,14,15-THETA | C20H34O5 | 354.2406 | 355.2479 | 355.2443 | 355.2514 |
| 11-epi-prostaglandin F2α | C20H34O5 | 354.2406 | 355.2479 | 355.2443 | 355.2514 |
| 8-isoprostane | C20H34O5 | 354.2406 | 355.2479 | 355.2443 | 355.2514 |
| 9,11,15-trihydroxy-prosta-5,13-dien-1-oic acid | C20H34O5 | 354.2406 | 355.2479 | 355.2443 | 355.2514 |
| dinoprost | C20H34O5 | 354.2406 | 355.2479 | 355.2443 | 355.2514 |
| panacelan | C20H34O5 | 354.2406 | 355.2479 | 355.2443 | 355.2514 |
| prostaglandin E1 | C20H34O5 | 354.2406 | 355.2479 | 355.2443 | 355.2514 |
| trioxilin A3 | C20H34O5 | 354.2406 | 355.2479 | 355.2443 | 355.2514 |
| trioxilin B3 | C20H34O5 | 354.2406 | 355.2479 | 355.2443 | 355.2514 |
| met-cys-cys | | 355.0694 | 356.0767 | 356.0731 | 356.0802 |
| ala-cys-tyr | | 355.1202 | 356.1274 | 356.1239 | 356.1310 |
| ser-cys-phe | | 355.1202 | 356.1274 | 356.1239 | 356.1310 |
| cys-pro-his | | 355.1314 | 356.1387 | 356.1351 | 356.1422 |
| ser-ser-tyr | | 355.1379 | 356.1452 | 356.1416 | 356.1487 |
| ala-glu-his | | 355.1491 | 356.1564 | 356.1529 | 356.1600 |
| S-adenosylmethioninamine | C14H23N6O3S | 355.1552 | 356.1625 | 356.1589 | 356.1660 |
| ser-leu-his | | 355.1855 | 356.1928 | 356.1892 | 356.1964 |
| ser-ile-his | | 355.1855 | 356.1928 | 356.1892 | 356.1964 |
| ser-asn-his | | 356.1444 | 357.1517 | 357.1481 | 357.1552 |
| pro-leu-gln | | 356.2059 | 357.2132 | 357.2096 | 357.2168 |
| pro-ile-gln | | 356.2059 | 357.2132 | 357.2096 | 357.2168 |
| pro-leu-lys | | 356.2423 | 357.2496 | 357.2460 | 357.2532 |
| pro-ile-lys | | 356.2423 | 357.2496 | 357.2460 | 357.2532 |
| prostaglandin F1α | C20H36O5 | 356.2563 | 357.2635 | 357.2600 | 357.2671 |
| ser-asp-his | | 357.1284 | 358.1357 | 358.1321 | 358.1393 |
| ala-met-his | | 357.1470 | 358.1543 | 358.1507 | 358.1579 |
| pro-asn-gln | | 357.1648 | 358.1721 | 358.1685 | 358.1756 |
| thr-thr-his | | 357.1648 | 358.1721 | 358.1685 | 358.1756 |
| gly-val-val | | 357.1872 | 358.1945 | 358.1909 | 358.1981 |
| pro-thr-val | | 357.1886 | 358.1959 | 358.1923 | 358.1995 |
| pro-leu-glu | | 357.1899 | 358.1972 | 358.1936 | 358.2008 |
| pro-ile-glu | | 357.1899 | 358.1972 | 358.1936 | 358.2008 |
| lys-pro-asn | | 357.2012 | 358.2085 | 358.2049 | 358.2120 |
| leu-leu-leu | | 357.2627 | 358.2700 | 358.2664 | 358.2736 |
| leu-leu-ile | | 357.2627 | 358.2700 | 358.2664 | 358.2736 |
| leu-ile-ile | | 357.2627 | 358.2700 | 358.2664 | 358.2736 |
| ile-ile-ile | | 357.2627 | 358.2700 | 358.2664 | 358.2736 |
| 4'P-pantetheine | C11H23N2O7SP | 358.0958 | 359.1030 | 359.0995 | 359.1066 |
| pro-asn-glu | | 358.1488 | 359.1561 | 359.1525 | 359.1597 |
| pro-asp-gln | | 358.1488 | 359.1561 | 359.1525 | 359.1597 |
| pro-gly-try | | 358.1713 | 359.1786 | 359.1750 | 359.1822 |
| ala-gln-val | | 358.1838 | 359.1911 | 359.1875 | 359.1947 |
| lys-pro-asp | | 358.1852 | 359.1925 | 359.1889 | 359.1961 |
| ser-pro-arg | | 358.1964 | 359.2037 | 359.2001 | 359.2073 |
| ala-lys-val | | 358.2202 | 359.2275 | 359.2239 | 359.2311 |
| asn-leu-leu | | 358.2216 | 359.2289 | 359.2253 | 359.2324 |
| asn-leu-ile | | 358.2216 | 359.2289 | 359.2253 | 359.2324 |
| asn-ile-ile | | 358.2216 | 359.2289 | 359.2253 | 359.2324 |
| ala-leu-arg | | 358.2328 | 359.2401 | 359.2365 | 359.2437 |
| ala-ile-arg | | 358.2328 | 359.2401 | 359.2365 | 359.2437 |
| cys-thr-his | | 359.1263 | 360.1336 | 360.1300 | 360.1372 |
| pro-asp-glu | | 359.1328 | 360.1401 | 360.1365 | 360.1437 |
| pro-cys-val | | 359.1501 | 360.1574 | 360.1538 | 360.1610 |
| gly-his-phe | | 359.1593 | 360.1666 | 360.1630 | 360.1702 |
| ala-glu-val | | 359.1679 | 360.1751 | 360.1715 | 360.1787 |
| leu-asn-asn | | 359.1804 | 360.1877 | 360.1841 | 360.1913 |
| ile-asn-asn | | 359.1804 | 360.1877 | 360.1841 | 360.1913 |
| pro-pro-phe | | 359.1845 | 360.1918 | 360.1882 | 360.1954 |
| leu-pro-met | | 359.1878 | 360.1951 | 360.1915 | 360.1987 |
| ile-pro-met | | 359.1878 | 360.1951 | 360.1915 | 360.1987 |
| gly-gln-arg | | 359.1917 | 360.1989 | 360.1953 | 360.2025 |
| ala-asn-arg | | 359.1917 | 360.1989 | 360.1953 | 360.2025 |
| ser-leu-val | | 359.2042 | 360.2115 | 360.2079 | 360.2151 |
| ser-ile-val | | 359.2042 | 360.2115 | 360.2079 | 360.2151 |
| asp-leu-leu | | 359.2056 | 360.2129 | 360.2093 | 360.2165 |
| asp-leu-ile | | 359.2056 | 360.2129 | 360.2093 | 360.2165 |

TABLE 1-continued

Endogenous Metabolism Database

| Metabolite | Elemental formula | Precise Mass | M + 1H | 10 ppm− | 10 ppm+ |
|---|---|---|---|---|---|
| asp-ile-ile | | 359.2056 | 360.2129 | 360.2093 | 360.2165 |
| lys-gly-arg | | 359.2281 | 360.2353 | 360.2317 | 360.2389 |
| rosmarinate | C18H16O8 | 360.0845 | 361.0918 | 361.0881 | 361.0954 |
| asn-asn-asn | | 360.1393 | 361.1466 | 361.1430 | 361.1502 |
| pro-asn-met | | 360.1467 | 361.1540 | 361.1504 | 361.1576 |
| ser-asn-val | | 360.1631 | 361.1704 | 361.1668 | 361.1740 |
| leu-asn-asp | | 360.1645 | 361.1717 | 361.1681 | 361.1753 |
| ile-asn-asp | | 360.1645 | 361.1717 | 361.1681 | 361.1753 |
| gly-glu-arg | | 360.1757 | 361.1830 | 361.1793 | 361.1866 |
| ala-asp-arg | | 360.1757 | 361.1830 | 361.1793 | 361.1866 |
| cortisone | C21H28O5 | 360.1937 | 361.2009 | 361.1973 | 361.2045 |
| arg-try | | 360.1982 | 361.2055 | 361.2019 | 361.2091 |
| thr-leu-gln | | 360.2008 | 361.2081 | 361.2045 | 361.2117 |
| thr-ile-gln | | 360.2008 | 361.2081 | 361.2045 | 361.2117 |
| thr-leu-lys | | 360.2372 | 361.2445 | 361.2409 | 361.2481 |
| thr-ile-lys | | 360.2372 | 361.2445 | 361.2409 | 361.2481 |
| his-cys-cys | | 361.0878 | 362.0951 | 362.0915 | 362.0987 |
| asn-asn-asp | | 361.1233 | 362.1306 | 362.1270 | 362.1342 |
| pro-asp-met | | 361.1307 | 362.1380 | 362.1344 | 362.1416 |
| ser-asp-val | | 361.1471 | 362.1544 | 362.1508 | 362.1580 |
| leu-asp-asp | | 361.1485 | 362.1557 | 362.1521 | 362.1594 |
| ile-asp-asp | | 361.1485 | 362.1557 | 362.1521 | 362.1594 |
| ser-gln-gln | | 361.1597 | 362.1670 | 362.1634 | 362.1706 |
| thr-asn-gln | | 361.1597 | 362.1670 | 362.1634 | 362.1706 |
| ala-met-val | | 361.1658 | 362.1730 | 362.1694 | 362.1767 |
| thr-thr-val | | 361.1835 | 362.1908 | 362.1872 | 362.1944 |
| thr-leu-glu | | 361.1849 | 362.1921 | 362.1885 | 362.1958 |
| thr-ile-glu | | 361.1849 | 362.1921 | 362.1885 | 362.1958 |
| ser-gln-lys | | 361.1961 | 362.2034 | 362.1997 | 362.2070 |
| asn-thr-lys | | 361.1961 | 362.2034 | 362.1997 | 362.2070 |
| Aldosterone | C21H29O5 | 361.2015 | 362.2088 | 362.2051 | 362.2124 |
| ser-lys-lys | | 361.2325 | 362.2398 | 362.2361 | 362.2434 |
| asn-asp-asp | | 362.1073 | 363.1146 | 363.1110 | 363.1182 |
| ser-gln-glu | | 362.1437 | 363.1510 | 363.1474 | 363.1546 |
| thr-asn-glu | | 362.1437 | 363.1510 | 363.1474 | 363.1546 |
| thr-asp-gln | | 362.1437 | 363.1510 | 363.1474 | 363.1546 |
| cys-leu-gln | | 362.1624 | 363.1696 | 363.1660 | 363.1733 |
| cys-ile-gln | | 362.1624 | 363.1696 | 363.1660 | 363.1733 |
| gly-thr-try | | 362.1663 | 363.1735 | 363.1699 | 363.1772 |
| ala-ser-try | | 362.1663 | 363.1735 | 363.1699 | 363.1772 |
| gly-met-arg | | 362.1736 | 363.1809 | 363.1772 | 363.1845 |
| ser-lys-glu | | 362.1801 | 363.1874 | 363.1837 | 363.1910 |
| asp-thr-lys | | 362.1801 | 363.1874 | 363.1837 | 363.1910 |
| ser-thr-arg | | 362.1913 | 363.1986 | 363.1950 | 363.2022 |
| cys-leu-lys | | 362.1987 | 363.2060 | 363.2024 | 363.2096 |
| cys-ile-lys | | 362.1987 | 363.2060 | 363.2024 | 363.2096 |
| 11β,21-dihydroxy-3,20-oxo-5β-pregnan-18-al | C21H30O5 | 362.2093 | 363.2166 | 363.2129 | 363.2202 |
| 17α,21-dihydroxy-5β-pregnane-3,11,20-trione | C21H30O5 | 362.2093 | 363.2166 | 363.2129 | 363.2202 |
| 18-hydroxycorticosterone | C21H30O5 | 362.2093 | 363.2166 | 363.2129 | 363.2202 |
| aldosterone heiacetal | C21H30O5 | 362.2093 | 363.2166 | 363.2129 | 363.2202 |
| Cortisol | C21H30O5 | 362.2093 | 363.2166 | 363.2129 | 363.2202 |
| guanosine monophosphate (GMP) | C10H14N5O8P | 363.0574 | 364.0647 | 364.0610 | 364.0683 |
| asp-asp-asp | | 363.0913 | 364.0986 | 364.0950 | 364.1023 |
| cys-asn-gln | | 363.1212 | 364.1285 | 364.1248 | 364.1321 |
| ser-glu-glu | | 363.1277 | 364.1350 | 364.1314 | 364.1386 |
| thr-asp-glu | | 363.1277 | 364.1350 | 364.1314 | 364.1386 |
| thr-cys-val | | 363.1450 | 364.1523 | 364.1487 | 364.1559 |
| cys-leu-glu | | 363.1464 | 364.1536 | 364.1500 | 364.1573 |
| cys-ile-glu | | 363.1464 | 364.1536 | 364.1500 | 364.1573 |
| asn-cys-lys | | 363.1576 | 364.1649 | 364.1612 | 364.1685 |
| ala-his-his | | 363.1655 | 364.1727 | 364.1691 | 364.1764 |
| gly-val-phe | | 363.1780 | 364.1853 | 364.1817 | 364.1890 |
| phe-pro-thr | | 363.1794 | 364.1867 | 364.1830 | 364.1903 |
| leu-thr-met | | 363.1828 | 364.1900 | 364.1864 | 364.1937 |
| ile-thr-met | | 363.1828 | 364.1900 | 364.1864 | 364.1937 |
| 5P-ribosyl-5-formamido-4-imidazole carboxamide | C10H13N4O9P | 364.0414 | 365.0487 | 365.0450 | 365.0523 |
| xanthosine-5-phosphate | C10H13N4O9P | 364.0414 | 365.0487 | 365.0450 | 365.0523 |
| cys-asn-glu | | 364.1052 | 365.1125 | 365.1088 | 365.1161 |
| cys-asp-gln | | 364.1052 | 365.1125 | 365.1088 | 365.1161 |
| gly-cys-try | | 364.1278 | 365.1350 | 365.1314 | 365.1387 |
| ser-gln-met | | 364.1416 | 365.1489 | 365.1452 | 365.1525 |
| thr-asn-met | | 364.1416 | 365.1489 | 365.1452 | 365.1525 |

TABLE 1-continued

Endogenous Metabolism Database

| Metabolite | Elemental formula | Precise Mass | M + 1H | 10 ppm− | 10 ppm+ |
|---|---|---|---|---|---|
| asp-cys-lys | | 364.1416 | 365.1489 | 365.1452 | 365.1525 |
| ser-cys-arg | | 364.1528 | 365.1601 | 365.1565 | 365.1638 |
| ala-gln-phe | | 364.1746 | 365.1819 | 365.1783 | 365.1856 |
| ser-lys-met | | 364.1780 | 365.1853 | 365.1816 | 365.1889 |
| ala-lys-phe | | 364.2110 | 365.2183 | 365.2146 | 365.2219 |
| 11β,17α,21-trihydroxy-5β-pregnane-3,20-dione | C21H32O5 | 364.2250 | 365.2322 | 365.2286 | 365.2359 |
| 11β,17α,21-trihydroxypregnenolone | C21H32O5 | 364.2250 | 365.2322 | 365.2286 | 365.2359 |
| 3α,11β,21-trihydroxy20-oxo-5β-pregnan-18-al | C21H32O5 | 364.2250 | 365.2322 | 365.2286 | 365.2359 |
| urocortisone | C21H32O5 | 364.2250 | 365.2322 | 365.2286 | 365.2359 |
| glutathione-carboxymethyl | C12H19N3O8S | 365.0892 | 366.0965 | 366.0929 | 366.1002 |
| cys-asp-glu | | 365.0892 | 366.0965 | 366.0929 | 366.1002 |
| cys-cys-val | | 365.1065 | 366.1138 | 366.1101 | 366.1175 |
| ser-glu-met | | 365.1256 | 366.1329 | 366.1292 | 366.1366 |
| thr-asp-met | | 365.1256 | 366.1329 | 366.1292 | 366.1366 |
| pro-cys-phe | | 365.1409 | 366.1482 | 366.1445 | 366.1518 |
| met-cys-leu | | 365.1443 | 366.1515 | 366.1479 | 366.1552 |
| met-cys-ile | | 365.1443 | 366.1515 | 366.1479 | 366.1552 |
| ser-pro-tyr | | 365.1586 | 366.1659 | 366.1623 | 366.1696 |
| ala-glu-phe | | 365.1586 | 366.1659 | 366.1623 | 366.1696 |
| ala-leu-tyr | | 365.1950 | 366.2023 | 366.1986 | 366.2060 |
| ala-ile-tyr | | 365.1950 | 366.2023 | 366.1986 | 366.2060 |
| ser-leu-phe | | 365.1950 | 366.2023 | 366.1986 | 366.2060 |
| ser-ile-phe | | 365.1950 | 366.2023 | 366.1986 | 366.2060 |
| leu-pro-his | | 365.2063 | 366.2135 | 366.2099 | 366.2172 |
| ile-pro-his | | 365.2063 | 366.2135 | 366.2099 | 366.2172 |
| sedoheptulose 1,7 bisphosphate | C7H12O13P2 | 365.9742 | 366.9814 | 366.9778 | 366.9851 |
| salicin-6P | C13H19O10P | 366.0710 | 367.0783 | 367.0746 | 367.0819 |
| cys-asn-met | | 366.1031 | 367.1104 | 367.1067 | 367.1141 |
| gly-gln-tyr | | 366.1539 | 367.1612 | 367.1575 | 367.1648 |
| ala-asn-tyr | | 366.1539 | 367.1612 | 367.1575 | 367.1648 |
| ser-asn-phe | | 366.1539 | 367.1612 | 367.1575 | 367.1648 |
| pro-asn-his | | 366.1651 | 367.1724 | 367.1687 | 367.1761 |
| lys-gly-tyr | | 366.1903 | 367.1976 | 367.1939 | 367.2012 |
| 20-COOH-leukotriene B4 | C20H30O6 | 366.2042 | 367.2115 | 367.2078 | 367.2152 |
| cortolone | C21H34O5 | 366.2406 | 367.2479 | 367.2442 | 367.2515 |
| urocortisol | C21H34O5 | 366.2406 | 367.2479 | 367.2442 | 367.2515 |
| orotidine-5′-phosphate | C10H13N2O11P | 367.0173 | 368.0245 | 368.0209 | 368.0282 |
| cys-asp-met | | 367.0871 | 368.0944 | 368.0907 | 368.0981 |
| ser-met-met | | 367.1235 | 368.1308 | 368.1271 | 368.1345 |
| gly-glu-tyr | | 367.1379 | 368.1452 | 368.1415 | 368.1489 |
| ala-asp-tyr | | 367.1379 | 368.1452 | 368.1415 | 368.1489 |
| ser-asp-phe | | 367.1379 | 368.1452 | 368.1415 | 368.1489 |
| pro-asp-his | | 367.1491 | 368.1564 | 368.1527 | 368.1601 |
| ala-met-phe | | 367.1565 | 368.1638 | 368.1601 | 368.1675 |
| tyr-try | | 367.1605 | 368.1677 | 368.1640 | 368.1714 |
| phe-thr-thr | | 367.1743 | 368.1816 | 368.1779 | 368.1853 |
| ala-his-val | | 367.1842 | 368.1915 | 368.1878 | 368.1951 |
| dehydroepiandrosterone sulfate | C19H28O5S | 368.1657 | 369.1730 | 369.1693 | 369.1767 |
| gly-his-arg | | 368.1920 | 369.1993 | 369.1956 | 369.2030 |
| pro-pro-arg | | 368.2172 | 369.2244 | 369.2207 | 369.2281 |
| 11-dehydro-thromboxane B2 | C20H32O6 | 368.2199 | 369.2271 | 369.2234 | 369.2308 |
| 20-hydroxy-prostaglandin E2 | C20H32O6 | 368.2199 | 369.2271 | 369.2234 | 369.2308 |
| 6-keto-prostaglandin E1 | C20H32O6 | 368.2199 | 369.2271 | 369.2234 | 369.2308 |
| prostaglandin G2 | C20H32O6 | 368.2199 | 369.2271 | 369.2234 | 369.2308 |
| cortol | C21H36O5 | 368.2563 | 369.2635 | 369.2598 | 369.2672 |
| zymosterol | C26H40O | 368.3079 | 369.3152 | 369.3115 | 369.3189 |
| gly-met-tyr | | 369.1358 | 370.1431 | 370.1394 | 370.1468 |
| thr-cys-phe | | 369.1358 | 370.1431 | 370.1394 | 370.1468 |
| S-adenosyl homocysteine | C14H21N6O6 | 369.1522 | 370.1595 | 370.1558 | 370.1632 |
| ser-thr-tyr | | 369.1536 | 370.1608 | 370.1571 | 370.1645 |
| gly-phe-phe | | 369.1688 | 370.1761 | 370.1724 | 370.1798 |
| leu-thr-his | | 369.2012 | 370.2085 | 370.2047 | 370.2122 |
| ile-thr-his | | 369.2012 | 370.2085 | 370.2047 | 370.2122 |
| pro-leu-val | | 369.2250 | 370.2323 | 370.2286 | 370.2360 |
| pro-ile-val | | 369.2250 | 370.2323 | 370.2286 | 370.2360 |
| ser-gln-his | | 370.1600 | 371.1673 | 371.1636 | 371.1710 |
| thr-asn-his | | 370.1600 | 371.1673 | 371.1636 | 371.1710 |
| androsterone sulfate | C19H30O5S | 370.1814 | 371.1886 | 371.1849 | 371.1924 |
| val-pro-asn | | 370.1838 | 371.1911 | 371.1874 | 371.1948 |
| ser-lys-his | | 370.1964 | 371.2037 | 371.2000 | 371.2074 |
| 6-keto-prostaglandin F1α | C20H34O6 | 370.2355 | 371.2428 | 371.2391 | 371.2465 |
| cys-cys-phe | | 371.0973 | 372.1046 | 372.1009 | 372.1083 |

TABLE 1-continued

Endogenous Metabolism Database

| Metabolite | Elemental formula | Precise Mass | M + 1H | 10 ppm− | 10 ppm+ |
|---|---|---|---|---|---|
| ser-cys-tyr | | 371.1151 | 372.1223 | 372.1186 | 372.1261 |
| ser-glu-his | | 371.1440 | 372.1513 | 372.1476 | 372.1550 |
| thr-asp-his | | 371.1440 | 372.1513 | 372.1476 | 372.1550 |
| his-cys-leu | | 371.1627 | 372.1700 | 372.1662 | 372.1737 |
| his-cys-ile | | 371.1627 | 372.1700 | 372.1662 | 372.1737 |
| val-pro-asp | | 371.1679 | 372.1751 | 372.1714 | 372.1789 |
| pro-gln-gln | | 371.1804 | 372.1877 | 372.1840 | 372.1914 |
| ala-val-val | | 371.2029 | 372.2102 | 372.2064 | 372.2139 |
| pro-gln-lys | | 371.2168 | 372.2241 | 372.2204 | 372.2278 |
| pro-lys-lys | | 371.2532 | 372.2605 | 372.2568 | 372.2642 |
| cys-asn-his | | 372.1215 | 373.1288 | 373.1251 | 373.1325 |
| pro-gln-glu | | 372.1645 | 373.1717 | 373.1680 | 373.1755 |
| try-ala-pro | | 372.1870 | 373.1943 | 373.1905 | 373.1980 |
| pro-lys-glu | | 372.2008 | 373.2081 | 373.2044 | 373.2118 |
| val-gly-arg | | 372.2107 | 373.2180 | 373.2143 | 373.2217 |
| pro-thr-arg | | 372.2121 | 373.2193 | 373.2156 | 373.2231 |
| leu-leu-gln | | 372.2372 | 373.2445 | 373.2408 | 373.2482 |
| leu-ile-gln | | 372.2372 | 373.2445 | 373.2408 | 373.2482 |
| leu-leu-lys | | 372.2736 | 373.2809 | 373.2772 | 373.2846 |
| leu-ile-lys | | 372.2736 | 373.2809 | 373.2772 | 373.2846 |
| ile-ile-lys | | 372.2736 | 373.2809 | 373.2772 | 373.2846 |
| cys-asp-his | | 373.1056 | 374.1128 | 374.1091 | 374.1166 |
| ser-met-his | | 373.1419 | 374.1492 | 374.1455 | 374.1530 |
| pro-glu-glu | | 373.1485 | 374.1557 | 374.1520 | 374.1595 |
| ala-his-phe | | 373.1750 | 374.1822 | 374.1785 | 374.1860 |
| leu-asn-gln | | 373.1961 | 374.2034 | 374.1996 | 374.2071 |
| ile-asn-gln | | 373.1961 | 374.2034 | 374.1996 | 374.2071 |
| ala-gln-arg | | 373.2073 | 374.2146 | 374.2108 | 374.2183 |
| thr-leu-val | | 373.2199 | 374.2272 | 374.2234 | 374.2309 |
| thr-ile-val | | 373.2199 | 374.2272 | 374.2234 | 374.2309 |
| leu-leu-glu | | 373.2212 | 374.2285 | 374.2248 | 374.2323 |
| leu-ile-glu | | 373.2212 | 374.2285 | 374.2248 | 374.2323 |
| ile-ile-glu | | 373.2212 | 374.2285 | 374.2248 | 374.2323 |
| asn-leu-lys | | 373.2325 | 374.2398 | 374.2360 | 374.2435 |
| asn-ile-lys | | 373.2325 | 374.2398 | 374.2360 | 374.2435 |
| ala-lys-arg | | 373.2437 | 374.2510 | 374.2472 | 374.2547 |
| asn-asn-gln | | 374.1549 | 375.1622 | 375.1585 | 375.1660 |
| pro-gln-met | | 374.1624 | 375.1696 | 375.1659 | 375.1734 |
| cys-pro-arg | | 374.1736 | 375.1809 | 375.1771 | 375.1846 |
| ser-gln-val | | 374.1788 | 375.1860 | 375.1823 | 375.1898 |
| thr-asn-val | | 374.1788 | 375.1860 | 375.1823 | 375.1898 |
| leu-asn-glu | | 374.1801 | 375.1874 | 375.1836 | 375.1911 |
| leu-asp-gln | | 374.1801 | 375.1874 | 375.1836 | 375.1911 |
| ile-asn-glu | | 374.1801 | 375.1874 | 375.1836 | 375.1911 |
| ile-asp-gln | | 374.1801 | 375.1874 | 375.1836 | 375.1911 |
| ala-glu-arg | | 374.1913 | 375.1986 | 375.1949 | 375.2024 |
| asn-asn-lys | | 374.1913 | 375.1986 | 375.1949 | 375.2024 |
| lys-pro-met | | 374.1987 | 375.2060 | 375.2023 | 375.2098 |
| gly-leu-try | | 374.2026 | 375.2099 | 375.2062 | 375.2137 |
| gly-ile-try | | 374.2026 | 375.2099 | 375.2062 | 375.2137 |
| ser-lys-val | | 374.2151 | 375.2224 | 375.2187 | 375.2262 |
| asp-leu-lys | | 374.2165 | 375.2238 | 375.2200 | 375.2275 |
| asp-ile-lys | | 374.2165 | 375.2238 | 375.2200 | 375.2275 |
| ser-leu-arg | | 374.2277 | 375.2350 | 375.2312 | 375.2387 |
| ser-ile-arg | | 374.2277 | 375.2350 | 375.2312 | 375.2387 |
| asn-asn-glu | | 375.1390 | 376.1462 | 376.1425 | 376.1500 |
| asn-asp-gln | | 375.1390 | 376.1462 | 376.1425 | 376.1500 |
| pro-glu-met | | 375.1464 | 376.1536 | 376.1499 | 376.1574 |
| gly-his-tyr | | 375.1542 | 376.1615 | 376.1577 | 376.1653 |
| asn-gly-try | | 375.1615 | 376.1688 | 376.1650 | 376.1725 |
| ser-glu-val | | 375.1628 | 376.1700 | 376.1663 | 376.1738 |
| asp-thr-val | | 375.1628 | 376.1700 | 376.1663 | 376.1738 |
| leu-asp-glu | | 375.1641 | 376.1714 | 376.1676 | 376.1752 |
| ile-asp-glu | | 375.1641 | 376.1714 | 376.1676 | 376.1752 |
| thr-gln-gln | | 375.1753 | 376.1826 | 376.1789 | 376.1864 |
| asn-asp-lys | | 375.1753 | 376.1826 | 376.1789 | 376.1864 |
| pro-pro-tyr | | 375.1794 | 376.1867 | 376.1829 | 376.1904 |
| cys-leu-val | | 375.1814 | 376.1887 | 376.1849 | 376.1924 |
| cys-ile-val | | 375.1814 | 376.1887 | 376.1849 | 376.1924 |
| ser-asn-arg | | 375.1866 | 376.1939 | 376.1901 | 376.1976 |
| thr-gln-lys | | 375.2117 | 376.2190 | 376.2152 | 376.2228 |
| pro-leu-phe | | 375.2158 | 376.2231 | 376.2193 | 376.2268 |
| pro-ile-phe | | 375.2158 | 376.2231 | 376.2193 | 376.2268 |
| met-leu-leu | | 375.2191 | 376.2264 | 376.2227 | 376.2302 |
| met-leu-ile | | 375.2191 | 376.2264 | 376.2227 | 376.2302 |

TABLE 1-continued

Endogenous Metabolism Database

| Metabolite | Elemental formula | Precise Mass | M + 1H | 10 ppm− | 10 ppm+ |
|---|---|---|---|---|---|
| met-ile-ile | | 375.2191 | 376.2264 | 376.2227 | 376.2302 |
| thr-lys-lys | | 375.2481 | 376.2554 | 376.2516 | 376.2592 |
| asn-asp-glu | | 376.1230 | 377.1302 | 377.1265 | 377.1340 |
| asp-asp-gln | | 376.1230 | 377.1302 | 377.1265 | 377.1340 |
| riboflavin | C17H20N4O6 | 376.1382 | 377.1455 | 377.1417 | 377.1493 |
| asn-cys-val | | 376.1403 | 377.1475 | 377.1438 | 377.1513 |
| asp-gly-try | | 376.1455 | 377.1528 | 377.1490 | 377.1566 |
| thr-gln-glu | | 376.1594 | 377.1666 | 377.1629 | 377.1704 |
| asp-asp-lys | | 376.1594 | 377.1666 | 377.1629 | 377.1704 |
| ser-asp-arg | | 376.1706 | 377.1779 | 377.1741 | 377.1816 |
| pro-asn-phe | | 376.1746 | 377.1819 | 377.1781 | 377.1857 |
| leu-asn-met | | 376.1780 | 377.1853 | 377.1815 | 377.1890 |
| ile-asn-met | | 376.1780 | 377.1853 | 377.1815 | 377.1890 |
| ala-thr-try | | 376.1819 | 377.1892 | 377.1854 | 377.1930 |
| ala-met-arg | | 376.1892 | 377.1965 | 377.1927 | 377.2003 |
| thr-lys-glu | | 376.1958 | 377.2030 | 377.1993 | 377.2068 |
| thr-thr-arg | | 376.2070 | 377.2143 | 377.2105 | 377.2180 |
| 3α,-hydroxy-5β-cholanate | C24H40O3 | 376.2977 | 377.3050 | 377.3012 | 377.3088 |
| asp-asp-glu | | 377.1070 | 378.1143 | 378.1105 | 378.1180 |
| asp-cys-val | | 377.1243 | 378.1316 | 378.1278 | 378.1353 |
| gln-cys-gln | | 377.1369 | 378.1441 | 378.1404 | 378.1479 |
| asn-asn-met | | 377.1369 | 378.1441 | 378.1404 | 378.1479 |
| thr-glu-glu | | 377.1434 | 378.1507 | 378.1469 | 378.1544 |
| pro-met-met | | 377.1443 | 378.1515 | 378.1478 | 378.1553 |
| pro-asp-phe | | 377.1586 | 378.1659 | 378.1621 | 378.1697 |
| ser-met-val | | 377.1607 | 378.1679 | 378.1642 | 378.1717 |
| leu-asp-met | | 377.1620 | 378.1693 | 378.1655 | 378.1731 |
| ile-asp-met | | 377.1620 | 378.1693 | 378.1655 | 378.1731 |
| cys-gln-lys | | 377.1732 | 378.1805 | 378.1767 | 378.1843 |
| ala-val-phe | | 377.1937 | 378.2010 | 378.1972 | 378.2047 |
| cys-lys-lys | | 377.2096 | 378.2169 | 378.2131 | 378.2207 |
| gln-cys-glu | | 378.1209 | 379.1281 | 379.1244 | 379.1319 |
| asn-asp-met | | 378.1209 | 379.1281 | 379.1244 | 379.1319 |
| ala-cys-try | | 378.1434 | 379.1507 | 379.1469 | 379.1545 |
| thr-gln-met | | 378.1573 | 379.1645 | 379.1607 | 379.1683 |
| cys-lys-glu | | 378.1573 | 379.1645 | 379.1607 | 379.1683 |
| ser-ser-try | | 378.1612 | 379.1684 | 379.1647 | 379.1722 |
| cys-thr-arg | | 378.1685 | 379.1758 | 379.1720 | 379.1796 |
| lys-thr-met | | 378.1937 | 379.2009 | 379.1971 | 379.2047 |
| gly-phe-arg | | 378.2015 | 379.2088 | 379.2050 | 379.2126 |
| S-lactoylglutathione | C13H21N3O8S | 379.1049 | 380.1122 | 380.1084 | 380.1160 |
| glu-cys-glu | | 379.1049 | 380.1122 | 380.1084 | 380.1160 |
| asp-asp-met | | 379.1049 | 380.1122 | 380.1084 | 380.1160 |
| thr-glu-met | | 379.1413 | 380.1486 | 380.1448 | 380.1524 |
| ser-his-his | | 379.1604 | 380.1676 | 380.1638 | 380.1714 |
| val-gly-tyr | | 379.1729 | 380.1802 | 380.1764 | 380.1840 |
| pro-thr-tyr | | 379.1743 | 380.1816 | 380.1778 | 380.1854 |
| thr-leu-phe | | 379.2107 | 380.2180 | 380.2142 | 380.2218 |
| thr-ile-phe | | 379.2107 | 380.2180 | 380.2142 | 380.2218 |
| sphingosine 1-phosphate | C18H38NO5P | 379.2482 | 380.2555 | 380.2517 | 380.2593 |
| cys-gln-met | | 380.1188 | 381.1260 | 381.1222 | 381.1299 |
| 2-methoxyestrone 3-sulfate | C19H24O6S | 380.1293 | 381.1366 | 381.1328 | 381.1404 |
| cys-cys-arg | | 380.1300 | 381.1373 | 381.1335 | 381.1411 |
| met-cys-lys | | 380.1552 | 381.1624 | 381.1586 | 381.1662 |
| ala-gln-tyr | | 380.1695 | 381.1768 | 381.1730 | 381.1806 |
| thr-asn-phe | | 380.1695 | 381.1768 | 381.1730 | 381.1806 |
| gln-ser-phe | | 380.1695 | 381.1768 | 381.1730 | 381.1806 |
| pro-gln-his | | 380.1808 | 381.1880 | 381.1842 | 381.1919 |
| ala-lys-tyr | | 380.2059 | 381.2132 | 381.2094 | 381.2170 |
| ser-lys-phe | | 380.2059 | 381.2132 | 381.2094 | 381.2170 |
| lys-pro-his | | 380.2172 | 381.2244 | 381.2206 | 381.2282 |
| cys-glu-met | | 381.1028 | 382.1101 | 382.1062 | 382.1139 |
| cys-pro-tyr | | 381.1358 | 382.1431 | 382.1393 | 382.1469 |
| thr-met-met | | 381.1392 | 382.1465 | 382.1426 | 382.1503 |
| ala-glu-tyr | | 381.1536 | 382.1608 | 382.1570 | 382.1647 |
| thr-asp-phe | | 381.1536 | 382.1608 | 382.1570 | 382.1647 |
| glu-ser-phe | | 381.1536 | 382.1608 | 382.1570 | 382.1647 |
| pro-glu-his | | 381.1648 | 382.1721 | 382.1682 | 382.1759 |
| cys-leu-phe | | 381.1722 | 382.1795 | 382.1757 | 382.1833 |
| cys-ile-phe | | 381.1722 | 382.1795 | 382.1757 | 382.1833 |
| ser-leu-tyr | | 381.1899 | 382.1972 | 382.1934 | 382.2010 |
| ser-ile-tyr | | 381.1899 | 382.1972 | 382.1934 | 382.2010 |
| his-leu-leu | | 381.2376 | 382.2448 | 382.2410 | 382.2487 |
| his-leu-ile | | 381.2376 | 382.2448 | 382.2410 | 382.2487 |
| his-ile-ile | | 381.2376 | 382.2448 | 382.2410 | 382.2487 |

TABLE 1-continued

Endogenous Metabolism Database

| Metabolite | Elemental formula | Precise Mass | M + 1H | 10 ppm− | 10 ppm+ |
|---|---|---|---|---|---|
| sphinganine 1-phosphate | C18H40NO5P | 381.2638 | 382.2711 | 382.2673 | 382.2749 |
| farnesyl-PP | C15H28O7P2 | 382.1299 | 383.1372 | 383.1333 | 383.1410 |
| cys-asn-phe | | 382.1311 | 383.1383 | 383.1345 | 383.1422 |
| 2-methoxyestradiole-17β 3-sulfate | C19H26O6S | 382.1450 | 383.1523 | 383.1484 | 383.1561 |
| ser-asn-tyr | | 382.1488 | 383.1561 | 383.1522 | 383.1599 |
| leu-asn-his | | 382.1964 | 383.2037 | 383.1999 | 383.2075 |
| ile-asn-his | | 382.1964 | 383.2037 | 383.1999 | 383.2075 |
| ala-his-arg | | 382.2077 | 383.2149 | 383.2111 | 383.2188 |
| 7-dehydrodesmosterol | C27H42O | 382.3236 | 383.3308 | 383.3270 | 383.3347 |
| cys-met-met | | 383.1007 | 384.1080 | 384.1041 | 384.1118 |
| cys-asp-phe | | 383.1151 | 384.1223 | 384.1185 | 384.1262 |
| ser-asp-tyr | | 383.1328 | 384.1401 | 384.1363 | 384.1439 |
| ala-met-tyr | | 383.1515 | 384.1587 | 384.1549 | 384.1626 |
| ser-met-phe | | 383.1515 | 384.1587 | 384.1549 | 384.1626 |
| asn-asn-his | | 383.1553 | 384.1626 | 384.1587 | 384.1664 |
| pro-met-his | | 383.1627 | 384.1700 | 384.1661 | 384.1738 |
| thr-thr-tyr | | 383.1692 | 384.1765 | 384.1726 | 384.1803 |
| ser-his-val | | 383.1791 | 384.1864 | 384.1825 | 384.1902 |
| leu-asp-his | | 383.1804 | 384.1877 | 384.1839 | 384.1916 |
| ile-asp-his | | 383.1804 | 384.1877 | 384.1839 | 384.1916 |
| ala-phe-phe | | 383.1845 | 384.1918 | 384.1879 | 384.1956 |
| Cholestadien-3β-ol | C27H43O | 383.3314 | 384.3387 | 384.3348 | 384.3425 |
| desmosterol | C27H43O | 383.3314 | 384.3387 | 384.3348 | 384.3425 |
| asn-asp-his | | 384.1393 | 385.1466 | 385.1427 | 385.1504 |
| thr-gln-his | | 384.1757 | 385.1830 | 385.1791 | 385.1868 |
| S-adenosyl methionine (SAM) | C15H24N6O6 | 384.1757 | 385.1830 | 385.1791 | 385.1868 |
| pro-gln-val | | 384.1995 | 385.2068 | 385.2029 | 385.2106 |
| lys-thr-his | | 384.2121 | 385.2193 | 385.2155 | 385.2232 |
| pro-lys-val | | 384.2359 | 385.2432 | 385.2393 | 385.2470 |
| leu-pro-arg | | 384.2485 | 385.2557 | 385.2519 | 385.2596 |
| ile-pro-arg | | 384.2485 | 385.2557 | 385.2519 | 385.2596 |
| 5α-cholesta-7,24-dien-3β-ol | C27H44O | 384.3392 | 385.3465 | 385.3426 | 385.3503 |
| 7-dehydrocholesterol | C27H44O | 384.3392 | 385.3465 | 385.3426 | 385.3503 |
| cholecalciferol | C27H44O | 384.3392 | 385.3465 | 385.3426 | 385.3503 |
| cholesten-3β-ol | C27H44O | 384.3392 | 385.3465 | 385.3426 | 385.3503 |
| cholestenone | C27H44O | 384.3392 | 385.3465 | 385.3426 | 385.3503 |
| phosphoribosyl pyrophosphate | C5H8O14P3 | 384.9110 | 385.9182 | 385.9144 | 385.9221 |
| asp-asp-his | | 385.1233 | 386.1306 | 386.1267 | 386.1344 |
| cys-thr-tyr | | 385.1307 | 386.1380 | 386.1341 | 386.1419 |
| thr-glu-his | | 385.1597 | 386.1670 | 386.1631 | 386.1708 |
| gly-phe-tyr | | 385.1637 | 386.1710 | 386.1672 | 386.1749 |
| pro-glu-val | | 385.1835 | 386.1908 | 386.1869 | 386.1946 |
| pro-asn-arg | | 385.2073 | 386.2146 | 386.2107 | 386.2185 |
| leu-leu-val | | 385.2563 | 386.2636 | 386.2597 | 386.2674 |
| leu-ile-val | | 385.2563 | 386.2636 | 386.2597 | 386.2674 |
| ile-ile-val | | 385.2563 | 386.2636 | 386.2597 | 386.2674 |
| cys-gln-his | | 386.1372 | 387.1445 | 387.1406 | 387.1483 |
| his-cys-lys | | 386.1736 | 387.1809 | 387.1770 | 387.1847 |
| pro-asp-arg | | 386.1913 | 387.1986 | 387.1947 | 387.2025 |
| asn-leu-val | | 386.2151 | 387.2224 | 387.2185 | 387.2263 |
| asn-ile-val | | 386.2151 | 387.2224 | 387.2185 | 387.2263 |
| ala-val-arg | | 386.2264 | 387.2336 | 387.2298 | 387.2375 |
| cholesterol | C27H46O | 386.3549 | 387.3621 | 387.3583 | 387.3660 |
| Lathosterol | C27H46O | 386.3549 | 387.3621 | 387.3583 | 387.3660 |
| dUDP | C9H13N2O11P2 | 386.9983 | 388.0056 | 388.0017 | 388.0095 |
| dCDP | C9H15N3O10P2 | 387.0221 | 388.0294 | 388.0255 | 388.0333 |
| N-acetylneuraminate-9-P | C11H18NO12P | 387.0561 | 388.0633 | 388.0594 | 388.0672 |
| tyr-cys-cys | | 387.0922 | 388.0995 | 388.0956 | 388.1034 |
| cys-glu-his | | 387.1212 | 388.1285 | 388.1246 | 388.1324 |
| thr-met-his | | 387.1576 | 388.1649 | 388.1610 | 388.1688 |
| asn-asn-val | | 387.1740 | 388.1813 | 388.1774 | 388.1852 |
| val-pro-met | | 387.1814 | 388.1887 | 388.1848 | 388.1926 |
| ser-val-val | | 387.1978 | 388.2051 | 388.2012 | 388.2090 |
| asp-leu-val | | 387.1992 | 388.2064 | 388.2025 | 388.2103 |
| asp-ile-val | | 387.1992 | 388.2064 | 388.2025 | 388.2103 |
| gln-leu-gln | | 387.2117 | 388.2190 | 388.2151 | 388.2229 |
| gln-ile-gln | | 387.2117 | 388.2190 | 388.2151 | 388.2229 |
| gly-arg-arg | | 387.2342 | 388.2415 | 388.2376 | 388.2454 |
| leu-gln-lys | | 387.2481 | 388.2554 | 388.2515 | 388.2593 |
| ile-gln-lys | | 387.2481 | 388.2554 | 388.2515 | 388.2593 |
| leu-lys-lys | | 387.2845 | 388.2918 | 388.2879 | 388.2957 |
| ile-lys-lys | | 387.2845 | 388.2918 | 388.2879 | 388.2957 |
| asn-asp-val | | 388.1580 | 389.1653 | 389.1614 | 389.1692 |
| asn-gln-gln | | 388.1706 | 389.1779 | 389.1740 | 389.1818 |
| try-ser-pro | | 388.1819 | 389.1892 | 389.1853 | 389.1931 |

TABLE 1-continued

Endogenous Metabolism Database

| Metabolite | Elemental formula | Precise Mass | M + 1H | 10 ppm− | 10 ppm+ |
|---|---|---|---|---|---|
| thr-gln-val | | 388.1944 | 389.2017 | 389.1978 | 389.2056 |
| gln-leu-glu | | 388.1958 | 389.2030 | 389.1991 | 389.2069 |
| gln-ile-glu | | 388.1958 | 389.2030 | 389.1991 | 389.2069 |
| asn-gln-lys | | 388.2070 | 389.2143 | 389.2104 | 389.2181 |
| ala-leu-try | | 388.2183 | 389.2256 | 389.2217 | 389.2295 |
| ala-ile-try | | 388.2183 | 389.2256 | 389.2217 | 389.2295 |
| thr-lys-val | | 388.2308 | 389.2381 | 389.2342 | 389.2420 |
| leu-lys-glu | | 388.2321 | 389.2394 | 389.2355 | 389.2433 |
| ile-lys-glu | | 388.2321 | 389.2394 | 389.2355 | 389.2433 |
| leu-thr-arg | | 388.2434 | 389.2506 | 389.2468 | 389.2545 |
| ile-thr-arg | | 388.2434 | 389.2506 | 389.2468 | 389.2545 |
| asn-lys-lys | | 388.2434 | 389.2506 | 389.2468 | 389.2545 |
| 5'-acetylphosphoadenosine | C12H16N5O8P | 389.0730 | 390.0803 | 390.0764 | 390.0842 |
| cys-met-his | | 389.1191 | 390.1264 | 390.1225 | 390.1303 |
| asp-asp-val | | 389.1420 | 390.1493 | 390.1454 | 390.1532 |
| asn-gln-glu | | 389.1546 | 390.1619 | 390.1580 | 390.1658 |
| asp-gln-gln | | 389.1546 | 390.1619 | 390.1580 | 390.1658 |
| ala-his-tyr | | 389.1699 | 390.1772 | 390.1733 | 390.1811 |
| ser-his-phe | | 389.1699 | 390.1772 | 390.1733 | 390.1811 |
| gly-gln-try | | 389.1772 | 390.1844 | 390.1805 | 390.1883 |
| ala-asn-try | | 389.1772 | 390.1844 | 390.1805 | 390.1883 |
| thr-glu-val | | 389.1784 | 390.1857 | 390.1818 | 390.1896 |
| glu-leu-glu | | 389.1798 | 390.1870 | 390.1831 | 390.1909 |
| glu-ile-glu | | 389.1798 | 390.1870 | 390.1831 | 390.1909 |
| pro-his-his | | 389.1811 | 390.1884 | 390.1845 | 390.1923 |
| asn-lys-glu | | 389.1910 | 390.1983 | 390.1944 | 390.2022 |
| asp-gln-lys | | 389.1910 | 390.1983 | 390.1944 | 390.2022 |
| ser-gln-arg | | 389.2022 | 390.2095 | 390.2056 | 390.2134 |
| thr-asn-arg | | 389.2022 | 390.2095 | 390.2056 | 390.2134 |
| gly-lys-try | | 389.2135 | 390.2208 | 390.2169 | 390.2247 |
| asp-lys-lys | | 389.2274 | 390.2347 | 390.2308 | 390.2386 |
| ser-lys-arg | | 389.2386 | 390.2459 | 390.2420 | 390.2498 |
| calcidiol | C27H44O2 | 389.2480 | 390.2553 | 390.2514 | 390.2592 |
| acetyl adenylate | C12H17N5O8P | 390.0809 | 391.0881 | 391.0842 | 391.0921 |
| asn-glu-glu | | 390.1386 | 391.1459 | 391.1420 | 391.1498 |
| asp-gln-glu | | 390.1386 | 391.1459 | 391.1420 | 391.1498 |
| cys-gln-val | | 390.1559 | 391.1632 | 391.1593 | 391.1671 |
| gly-glu-try | | 390.1612 | 391.1684 | 391.1645 | 391.1724 |
| ala-asp-try | | 390.1612 | 391.1684 | 391.1645 | 391.1724 |
| asp-lys-glu | | 390.1750 | 391.1823 | 391.1784 | 391.1862 |
| try-try | | 390.1837 | 391.1910 | 391.1871 | 391.1949 |
| ser-glu-arg | | 390.1862 | 391.1935 | 391.1896 | 391.1974 |
| thr-asp-arg | | 390.1862 | 391.1935 | 391.1896 | 391.1974 |
| phe-pro-gln | | 390.1903 | 391.1976 | 391.1936 | 391.2015 |
| cys-lys-val | | 390.1923 | 391.1996 | 391.1957 | 391.2035 |
| leu-gln-met | | 390.1937 | 391.2009 | 391.1970 | 391.2048 |
| ile-gln-met | | 390.1937 | 391.2009 | 391.1970 | 391.2048 |
| arg-cys-leu | | 390.2049 | 391.2122 | 391.2082 | 391.2161 |
| arg-cys-ile | | 390.2049 | 391.2122 | 391.2082 | 391.2161 |
| pro-lys-phe | | 390.2267 | 391.2339 | 391.2300 | 391.2379 |
| met-leu-lys | | 390.2300 | 391.2373 | 391.2334 | 391.2412 |
| met-ile-lys | | 390.2300 | 391.2373 | 391.2334 | 391.2412 |
| 3α,12α-dihydroxy-5β-chol-5-enoate | C24H38O4 | 390.2770 | 391.2843 | 391.2804 | 391.2882 |
| 3α-hydroxy-12-oxo-5β-cholanate | C24H38O4 | 390.2770 | 391.2843 | 391.2804 | 391.2882 |
| asp-glu-glu | | 391.1226 | 392.1299 | 392.1260 | 392.1338 |
| cys-glu-val | | 391.1399 | 392.1472 | 392.1433 | 392.1511 |
| asn-gln-met | | 391.1525 | 392.1598 | 392.1559 | 392.1637 |
| cys-asn-arg | | 391.1637 | 392.1710 | 392.1671 | 392.1749 |
| phe-pro-glu | | 391.1743 | 392.1816 | 392.1777 | 392.1855 |
| met-thr-val | | 391.1763 | 392.1836 | 392.1797 | 392.1875 |
| leu-glu-met | | 391.1777 | 392.1849 | 392.1810 | 392.1889 |
| ile-glu-met | | 391.1777 | 392.1849 | 392.1810 | 392.1889 |
| asn-lys-met | | 391.1889 | 392.1962 | 392.1923 | 392.2001 |
| leu-pro-tyr | | 391.2107 | 392.2180 | 392.2140 | 392.2219 |
| ile-pro-tyr | | 391.2107 | 392.2180 | 392.2140 | 392.2219 |
| leu-leu-phe | | 391.2471 | 392.2544 | 392.2504 | 392.2583 |
| leu-ile-phe | | 391.2471 | 392.2544 | 392.2504 | 392.2583 |
| ile-ile-phe | | 391.2471 | 392.2544 | 392.2504 | 392.2583 |
| asn-glu-met | | 392.1365 | 393.1438 | 393.1399 | 393.1477 |
| asp-gln-met | | 392.1365 | 393.1438 | 393.1399 | 393.1477 |
| cys-asp-arg | | 392.1478 | 393.1550 | 393.1511 | 393.1590 |
| met-gly-try | | 392.1591 | 393.1663 | 393.1624 | 393.1703 |
| pro-asn-tyr | | 392.1695 | 393.1768 | 393.1729 | 393.1807 |
| asp-lys-met | | 392.1729 | 393.1802 | 393.1763 | 393.1841 |

TABLE 1-continued

Endogenous Metabolism Database

| Metabolite | Elemental formula | Precise Mass | M + 1H | 10 ppm− | 10 ppm+ |
|---|---|---|---|---|---|
| ser-thr-try | | 392.1768 | 393.1841 | 393.1802 | 393.1880 |
| ser-met-arg | | 392.1841 | 393.1914 | 393.1875 | 393.1953 |
| leu-asn-phe | | 392.2059 | 393.2132 | 393.2093 | 393.2171 |
| ile-asn-phe | | 392.2059 | 393.2132 | 393.2093 | 393.2171 |
| ala-phe-arg | | 392.2172 | 393.2244 | 393.2205 | 393.2284 |
| chenodeoxycholate | C24H40O4 | 392.2926 | 393.2999 | 393.2960 | 393.3038 |
| deoxycholate | C24H40O4 | 392.2926 | 393.2999 | 393.2960 | 393.3038 |
| ergosta-5,7,22,24,(28)-tetraen-3β-ol | C28H40O | 392.3079 | 393.3152 | 393.3113 | 393.3191 |
| asp-glu-met | | 393.1205 | 394.1278 | 394.1239 | 394.1318 |
| met-cys-val | | 393.1378 | 394.1451 | 394.1412 | 394.1490 |
| pro-asp-tyr | | 393.1536 | 394.1608 | 394.1569 | 394.1648 |
| asn-asn-phe | | 393.1648 | 394.1721 | 394.1681 | 394.1760 |
| pro-met-phe | | 393.1722 | 394.1795 | 394.1755 | 394.1834 |
| leu-met-met | | 393.1756 | 394.1828 | 394.1789 | 394.1868 |
| ile-met-met | | 393.1756 | 394.1828 | 394.1789 | 394.1868 |
| thr-his-his | | 393.1760 | 394.1833 | 394.1794 | 394.1872 |
| ala-val-tyr | | 393.1886 | 394.1959 | 394.1919 | 394.1998 |
| ser-val-phe | | 393.1886 | 394.1959 | 394.1919 | 394.1998 |
| leu-asp-phe | | 393.1899 | 394.1972 | 394.1933 | 394.2012 |
| ile-asp-phe | | 393.1899 | 394.1972 | 394.1933 | 394.2012 |
| val-pro-his | | 393.1998 | 394.2071 | 394.2032 | 394.2110 |
| asn-met-met | | 394.1344 | 395.1417 | 395.1377 | 395.1456 |
| ser-cys-try | | 394.1383 | 395.1456 | 395.1417 | 395.1496 |
| asn-asp-phe | | 394.1488 | 395.1561 | 395.1521 | 395.1600 |
| phe-thr-gln | | 394.1852 | 395.1925 | 395.1885 | 395.1964 |
| gly-arg-tyr | | 394.1964 | 395.2037 | 395.1997 | 395.2076 |
| phe-thr-lys | | 394.2216 | 395.2289 | 395.2249 | 395.2328 |
| ergosterol | C28H42O | 394.3236 | 395.3308 | 395.3269 | 395.3348 |
| adenosine monophosphate | C10H14N5O7P | 395.0472 | 396.0545 | 396.0505 | 396.0584 |
| asp-met-met | | 395.1184 | 396.1257 | 396.1218 | 396.1297 |
| asp-asp-phe | | 395.1328 | 396.1401 | 396.1361 | 396.1441 |
| cys-his-his | | 395.1375 | 396.1448 | 396.1408 | 396.1488 |
| phe-thr-glu | | 395.1692 | 396.1765 | 396.1725 | 396.1804 |
| leu-thr-tyr | | 395.2056 | 396.2129 | 396.2089 | 396.2168 |
| ile-thr-tyr | | 395.2056 | 396.2129 | 396.2089 | 396.2168 |
| phe-cys-gln | | 396.1467 | 397.1540 | 397.1500 | 397.1579 |
| ser-gln-tyr | | 396.1645 | 397.1717 | 397.1678 | 397.1757 |
| thr-asn-tyr | | 396.1645 | 397.1717 | 397.1678 | 397.1757 |
| cys-lys-phe | | 396.1831 | 397.1904 | 397.1864 | 397.1943 |
| ser-lys-tyr | | 396.2008 | 397.2081 | 397.2041 | 397.2121 |
| leu-gln-his | | 396.2121 | 397.2193 | 397.2154 | 397.2233 |
| ile-gln-his | | 396.2121 | 397.2193 | 397.2154 | 397.2233 |
| his-leu-lys | | 396.2485 | 397.2557 | 397.2518 | 397.2597 |
| his-ile-lys | | 396.2485 | 397.2557 | 397.2518 | 397.2597 |
| ergocalciferol | C28H44O | 396.3392 | 397.3465 | 397.3425 | 397.3505 |
| phe-cys-glu | | 397.1307 | 398.1380 | 398.1340 | 398.1420 |
| ser-glu-tyr | | 397.1485 | 398.1557 | 398.1518 | 398.1597 |
| thr-asp-tyr | | 397.1485 | 398.1557 | 398.1518 | 398.1597 |
| thr-met-phe | | 397.1671 | 398.1744 | 398.1704 | 398.1784 |
| tyr-cys-leu | | 397.1671 | 398.1744 | 398.1704 | 398.1784 |
| tyr-cys-ile | | 397.1671 | 398.1744 | 398.1704 | 398.1784 |
| asn-gln-his | | 397.1709 | 398.1742 | 398.1782 | 398.1822 |
| his-thr-val | | 397.1947 | 398.2020 | 398.1980 | 398.2060 |
| leu-glu-his | | 397.1961 | 398.2034 | 398.1994 | 398.2073 |
| ile-glu-his | | 397.1961 | 398.2034 | 398.1994 | 398.2073 |
| asn-lys-his | | 397.2073 | 398.2146 | 398.2106 | 398.2186 |
| pro-val-val | | 397.2185 | 398.2258 | 398.2218 | 398.2298 |
| cys-asn-tyr | | 398.1260 | 399.1332 | 399.1292 | 399.1372 |
| asn-glu-his | | 398.1549 | 399.1622 | 399.1582 | 399.1662 |
| asp-gln-his | | 398.1549 | 399.1622 | 399.1582 | 399.1662 |
| his-gly-try | | 398.1775 | 399.1848 | 399.1808 | 399.1888 |
| asp-lys-his | | 398.1913 | 399.1986 | 399.1946 | 399.2026 |
| ser-his-arg | | 398.2026 | 399.2098 | 399.2058 | 399.2138 |
| pro-pro-try | | 398.2026 | 399.2099 | 399.2059 | 399.2139 |
| cys-asp-tyr | | 399.1100 | 400.1173 | 400.1133 | 400.1213 |
| cys-met-phe | | 399.1286 | 400.1359 | 400.1319 | 400.1399 |
| asp-glu-his | | 399.1390 | 400.1462 | 400.1422 | 400.1502 |
| ser-met-tyr | | 399.1464 | 400.1536 | 400.1496 | 400.1576 |
| his-cys-val | | 399.1562 | 400.1635 | 400.1595 | 400.1675 |
| ala-phe-tyr | | 399.1794 | 400.1867 | 400.1827 | 400.1907 |
| phe-ser-phe | | 399.1794 | 400.1867 | 400.1827 | 400.1907 |
| pro-his-phe | | 399.1906 | 400.1979 | 400.1939 | 400.2019 |
| leu-met-his | | 399.1940 | 400.2013 | 400.1973 | 400.2053 |
| ile-met-his | | 399.1940 | 400.2013 | 400.1973 | 400.2053 |

TABLE 1-continued

Endogenous Metabolism Database

| Metabolite | Elemental formula | Precise Mass | M + 1H | 10 ppm− | 10 ppm+ |
|---|---|---|---|---|---|
| pro-gln-arg | | 399.2230 | 400.2302 | 400.2262 | 400.2342 |
| lys-pro-arg | | 399.2594 | 400.2666 | 400.2626 | 400.2706 |
| palmitylcarnitine | C23H45NO4 | 399.3348 | 400.3421 | 400.3381 | 400.3461 |
| asn-met-his | | 400.1528 | 401.1601 | 401.1561 | 401.1641 |
| pro-glu-arg | | 400.2070 | 401.2143 | 401.2102 | 401.2183 |
| leu-gln-val | | 400.2308 | 401.2381 | 401.2341 | 401.2421 |
| ile-gln-val | | 400.2308 | 401.2381 | 401.2341 | 401.2421 |
| leu-lys-val | | 400.2672 | 401.2745 | 401.2704 | 401.2785 |
| ile-lys-val | | 400.2672 | 401.2745 | 401.2704 | 401.2785 |
| arg-leu-leu | | 400.2798 | 401.2870 | 401.2830 | 401.2910 |
| arg-leu-ile | | 400.2798 | 401.2870 | 401.2830 | 401.2910 |
| arg-ile-ile | | 400.2798 | 401.2870 | 401.2830 | 401.2910 |
| 4α-methylcholesta-8-ene-3β-ol | C28H48O | 400.3705 | 401.3778 | 401.3738 | 401.3818 |
| methostenol | C28H48O | 400.3705 | 401.3778 | 401.3738 | 401.3818 |
| phytoene | C28H48O | 400.3705 | 401.3778 | 401.3738 | 401.3818 |
| asp-met-his | | 401.1369 | 402.1441 | 402.1401 | 402.1482 |
| gly-tyr-tyr | | 401.1586 | 402.1659 | 402.1619 | 402.1699 |
| asn-gln-val | | 401.1896 | 402.1969 | 402.1929 | 402.2009 |
| thr-val-val | | 401.2135 | 402.2207 | 402.2167 | 402.2248 |
| leu-glu-val | | 401.2148 | 402.2221 | 402.2181 | 402.2261 |
| ile-glu-val | | 401.2148 | 402.2221 | 402.2181 | 402.2261 |
| asn-lys-val | | 401.2260 | 402.2333 | 402.2293 | 402.2373 |
| leu-asn-arg | | 401.2386 | 402.2459 | 402.2419 | 402.2499 |
| ile-asn-arg | | 401.2386 | 402.2459 | 402.2419 | 402.2499 |
| ala-arg-arg | | 401.2498 | 402.2571 | 402.2531 | 402.2611 |
| 4P-N-pantothenoylcysteine | C12H23N2O9SP | 402.0856 | 403.0929 | 403.0888 | 403.0969 |
| asn-glu-val | | 402.1737 | 403.1809 | 403.1769 | 403.1850 |
| asp-gln-val | | 402.1737 | 403.1809 | 403.1769 | 403.1850 |
| gln-gln-gln | | 402.1862 | 403.1935 | 403.1895 | 403.1975 |
| gly-val-try | | 402.1962 | 403.2035 | 403.1995 | 403.2075 |
| asn-asn-arg | | 402.1975 | 403.2047 | 403.2007 | 403.2088 |
| pro-thr-try | | 402.1976 | 403.2048 | 403.2008 | 403.2089 |
| pro-met-arg | | 402.2049 | 403.2122 | 403.2081 | 403.2162 |
| asp-lys-val | | 402.2101 | 403.2173 | 403.2133 | 403.2214 |
| ser-val-arg | | 402.2213 | 403.2286 | 403.2245 | 403.2326 |
| gln-gln-lys | | 402.2226 | 403.2299 | 403.2259 | 403.2339 |
| leu-asp-arg | | 402.2226 | 403.2299 | 403.2259 | 403.2339 |
| gln-lys-lys | | 402.2590 | 403.2663 | 403.2623 | 403.2703 |
| 20α-hydroxycholesterol | C27H46O2 | 402.3498 | 403.3570 | 403.3530 | 403.3611 |
| 22β-hydroxycholesterol | C27H46O2 | 402.3498 | 403.3570 | 403.3530 | 403.3611 |
| 7α-hydroxycholest-4-en-3-one | C27H46O2 | 402.3498 | 403.3570 | 403.3530 | 403.3611 |
| 7α-hydroxycholesterol | C27H46O2 | 402.3498 | 403.3570 | 403.3530 | 403.3611 |
| cholesterol-5α,6α-epoxide | C27H46O2 | 402.3498 | 403.3570 | 403.3530 | 403.3611 |
| cholesterol-5β,6β-epoxide | C27H46O2 | 402.3498 | 403.3570 | 403.3530 | 403.3611 |
| cytidine diphosphate (CDP) | C9H15N3O11P2 | 403.0170 | 404.0243 | 404.0203 | 404.0283 |
| asp-glu-val | | 403.1577 | 404.1650 | 404.1609 | 404.1690 |
| gln-gln-glu | | 403.1703 | 404.1775 | 404.1735 | 404.1816 |
| cys-val-val | | 403.1750 | 404.1822 | 404.1782 | 404.1863 |
| asn-asp-arg | | 403.1815 | 404.1888 | 404.1847 | 404.1928 |
| thr-his-phe | | 403.1855 | 404.1928 | 404.1888 | 404.1968 |
| ala-gln-try | | 403.1928 | 404.2001 | 404.1960 | 404.2041 |
| gln-lys-glu | | 403.2066 | 404.2139 | 404.2099 | 404.2180 |
| pro-val-phe | | 403.2093 | 404.2166 | 404.2126 | 404.2207 |
| met-leu-val | | 403.2127 | 404.2200 | 404.2159 | 404.2240 |
| met-ile-val | | 403.2127 | 404.2200 | 404.2159 | 404.2240 |
| thr-gln-arg | | 403.2179 | 404.2252 | 404.2211 | 404.2292 |
| ala-lys-try | | 403.2292 | 404.2365 | 404.2324 | 404.2405 |
| lys-lys-glu | | 403.2430 | 404.2503 | 404.2463 | 404.2544 |
| lys-thr-arg | | 403.2543 | 404.2615 | 404.2575 | 404.2656 |
| uridine diphosphate (UDP) | C9H14N2O12P2 | 404.0010 | 405.0083 | 405.0043 | 405.0124 |
| gln-glu-glu | | 404.1543 | 405.1615 | 405.1575 | 405.1656 |
| pro-cys-try | | 404.1591 | 405.1663 | 405.1623 | 405.1704 |
| asp-asp-arg | | 404.1655 | 405.1728 | 405.1687 | 405.1768 |
| asn-met-val | | 404.1716 | 405.1788 | 405.1748 | 405.1829 |
| ala-glu-try | | 404.1768 | 405.1841 | 405.1800 | 405.1881 |
| glu-lys-glu | | 404.1907 | 405.1979 | 405.1939 | 405.2020 |
| thr-glu-arg | | 404.2019 | 405.2092 | 405.2051 | 405.2132 |
| ser-leu-try | | 404.2132 | 405.2205 | 405.2164 | 405.2245 |
| ser-ile-try | | 404.2132 | 405.2205 | 405.2164 | 405.2245 |
| | | 404.2560 | 405.2633 | 405.2592 | 405.2673 |
| 7α-hydroxy-5β-cholestan-3-one | C27H48O2 | 404.3654 | 405.3727 | 405.3686 | 405.3768 |
| glu-glu-glu | | 405.1383 | 406.1456 | 406.1415 | 406.1496 |
| cys-his-phe | | 405.1470 | 406.1543 | 406.1503 | 406.1584 |
| asp-met-val | | 405.1556 | 406.1629 | 406.1588 | 406.1669 |
| ser-his-tyr | | 405.1648 | 406.1721 | 406.1680 | 406.1761 |

TABLE 1-continued

Endogenous Metabolism Database

| Metabolite | Elemental formula | Precise Mass | M + 1H | 10 ppm− | 10 ppm+ |
|---|---|---|---|---|---|
| gln-gln-met | | 405.1682 | 406.1754 | 406.1714 | 406.1795 |
| ser-asn-try | | 405.1721 | 406.1793 | 406.1753 | 406.1834 |
| cys-gln-arg | | 405.1794 | 406.1867 | 406.1826 | 406.1907 |
| lys-gln-met | | 405.2045 | 406.2118 | 406.2078 | 406.2159 |
| leu-his-his | | 405.2124 | 406.2197 | 406.2156 | 406.2237 |
| ile-his-his | | 405.2124 | 406.2197 | 406.2156 | 406.2237 |
| arg-cys-lys | | 405.2158 | 406.2231 | 406.2190 | 406.2271 |
| met-lys-lys | | 405.2409 | 406.2482 | 406.2441 | 406.2523 |
| gln-glu-met | | 406.1522 | 407.1594 | 407.1554 | 407.1635 |
| ser-asp-try | | 406.1561 | 407.1634 | 407.1593 | 407.1674 |
| cys-glu-arg | | 406.1634 | 407.1707 | 407.1666 | 407.1747 |
| asn-his-his | | 406.1713 | 407.1785 | 407.1745 | 407.1826 |
| ala-met-try | | 406.1747 | 407.1820 | 407.1779 | 407.1861 |
| pro-gln-tyr | | 406.1852 | 407.1925 | 407.1884 | 407.1965 |
| lys-glu-met | | 406.1886 | 407.1958 | 407.1918 | 407.1999 |
| thr-thr-try | | 406.1925 | 407.1997 | 407.1957 | 407.2038 |
| thr-met-arg | | 406.1998 | 407.2071 | 407.2030 | 407.2111 |
| lys-pro-tyr | | 406.2216 | 407.2289 | 407.2248 | 407.2329 |
| phe-leu-gln | | 406.2216 | 407.2289 | 407.2248 | 407.2329 |
| phe-ile-gln | | 406.2216 | 407.2289 | 407.2248 | 407.2329 |
| leu-lys-phe | | 406.2580 | 407.2652 | 407.2612 | 407.2693 |
| ile-lys-phe | | 406.2580 | 407.2652 | 407.2612 | 407.2693 |
| 3α,7α-dihydroxy-5β-cholestane | $C_{27}H_{50}O_2$ | 406.3811 | 407.3883 | 407.3843 | 407.3924 |
| glu-glu-met | | 407.1362 | 408.1435 | 408.1394 | 408.1475 |
| asp-his-his | | 407.1553 | 408.1626 | 408.1585 | 408.1666 |
| pro-glu-tyr | | 407.1692 | 408.1765 | 408.1724 | 408.1806 |
| gln-asn-phe | | 407.1804 | 408.1877 | 408.1836 | 408.1918 |
| phe-thr-val | | 407.2042 | 408.2115 | 408.2074 | 408.2156 |
| phe-leu-glu | | 407.2056 | 408.2129 | 408.2088 | 408.2170 |
| phe-ile-glu | | 407.2056 | 408.2129 | 408.2088 | 408.2170 |
| asn-lys-phe | | 407.2168 | 408.2241 | 408.2200 | 408.2282 |
| tyr-leu-leu | | 407.2420 | 408.2493 | 408.2452 | 408.2533 |
| tyr-leu-ile | | 407.2420 | 408.2493 | 408.2452 | 408.2533 |
| tyr-ile-ile | | 407.2420 | 408.2493 | 408.2452 | 408.2533 |
| gln-met-met | | 408.1501 | 409.1573 | 409.1533 | 409.1614 |
| thr-cys-try | | 408.1540 | 409.1613 | 409.1572 | 409.1653 |
| cys-met-arg | | 408.1613 | 409.1686 | 409.1645 | 409.1727 |
| gln-asp-phe | | 408.1645 | 409.1717 | 409.1676 | 409.1758 |
| glu-asn-phe | | 408.1645 | 409.1717 | 409.1676 | 409.1758 |
| lys-met-met | | 408.1865 | 409.1937 | 409.1896 | 409.1978 |
| phe-gly-try | | 408.1870 | 409.1943 | 409.1902 | 409.1984 |
| leu-asn-tyr | | 408.2008 | 409.2081 | 409.2040 | 409.2122 |
| ile-asn-tyr | | 408.2008 | 409.2081 | 409.2040 | 409.2122 |
| asp-lys-phe | | 408.2008 | 409.2081 | 409.2040 | 409.2122 |
| ala-arg-tyr | | 408.2121 | 409.2193 | 409.2153 | 409.2234 |
| ser-phe-arg | | 408.2121 | 409.2193 | 409.2153 | 409.2234 |
| pro-his-arg | | 408.2233 | 409.2306 | 409.2265 | 409.2347 |
| cholate | $C_{24}H_{40}O_5$ | 408.2876 | 409.2948 | 409.2907 | 409.2989 |
| glu-met-met | | 409.1341 | 410.1414 | 410.1373 | 410.1455 |
| glu-asp-phe | | 409.1485 | 410.1557 | 410.1516 | 410.1598 |
| asn-asn-tyr | | 409.1597 | 410.1670 | 410.1629 | 410.1711 |
| cys-val-phe | | 409.1658 | 410.1730 | 410.1689 | 410.1771 |
| pro-met-tyr | | 409.1671 | 410.1744 | 410.1703 | 410.1785 |
| ser-val-tyr | | 409.1835 | 410.1908 | 410.1867 | 410.1949 |
| leu-asp-tyr | | 409.1849 | 410.1921 | 410.1880 | 410.1962 |
| ile-asp-tyr | | 409.1849 | 410.1921 | 410.1880 | 410.1962 |
| pro-phe-phe | | 409.2001 | 410.2074 | 410.2033 | 410.2115 |
| leu-met-phe | | 409.2035 | 410.2108 | 410.2067 | 410.2149 |
| ile-met-phe | | 409.2035 | 410.2108 | 410.2067 | 410.2149 |
| his-leu-val | | 409.2311 | 410.2384 | 410.2343 | 410.2425 |
| his-ile-val | | 409.2311 | 410.2384 | 410.2343 | 410.2425 |
| cys-cys-try | | 410.1155 | 411.1228 | 411.1187 | 411.1269 |
| asn-asp-tyr | | 410.1437 | 411.1510 | 411.1469 | 411.1551 |
| asn-met-phe | | 410.1624 | 411.1696 | 411.1655 | 411.1737 |
| thr-gln-tyr | | 410.1801 | 411.1874 | 411.1833 | 411.1915 |
| asn-his-val | | 410.1900 | 411.1973 | 411.1931 | 411.2014 |
| lys-thr-tyr | | 410.2165 | 411.2238 | 411.2197 | 411.2279 |
| squalene | $C_{30}H_{50}$ | 410.3913 | 411.3985 | 411.3944 | 411.4026 |
| dADP | $C_{10}H_{15}N_5O_9P_2$ | 411.0333 | 412.0406 | 412.0365 | 412.0447 |
| asp-asp-tyr | | 411.1277 | 412.1350 | 412.1309 | 412.1391 |
| met-met-met | | 411.1320 | 412.1393 | 412.1351 | 412.1434 |
| asp-met-phe | | 411.1464 | 412.1536 | 412.1495 | 412.1578 |
| thr-glu-tyr | | 411.1641 | 412.1714 | 412.1673 | 412.1755 |
| asp-his-val | | 411.1740 | 412.1813 | 412.1772 | 412.1854 |
| gln-gln-his | | 411.1866 | 412.1939 | 412.1897 | 412.1980 |

TABLE 1-continued

Endogenous Metabolism Database

| Metabolite | Elemental formula | Precise Mass | M + 1H | 10 ppm− | 10 ppm+ |
|---|---|---|---|---|---|
| lys-gln-his | | 411.2230 | 412.2302 | 412.2261 | 412.2344 |
| his-lys-lys | | 411.2594 | 412.2666 | 412.2625 | 412.2708 |
| stigmasterol | C29H47O | 411.3627 | 412.3700 | 412.3658 | 412.3741 |
| dIDP | C10H14N4O10P2 | 412.0174 | 413.0246 | 413.0205 | 413.0288 |
| cys-gln-tyr | | 412.1416 | 413.1489 | 413.1448 | 413.1530 |
| gln-glu-his | | 412.1706 | 413.1779 | 413.1737 | 413.1820 |
| tyr-cys-lys | | 412.1780 | 413.1853 | 413.1811 | 413.1894 |
| ala-his-try | | 412.1931 | 413.2004 | 413.1963 | 413.2045 |
| lys-glu-his | | 412.2070 | 413.2143 | 413.2101 | 413.2184 |
| thr-his-arg | | 412.2182 | 413.2255 | 413.2214 | 413.2296 |
| val-pro-arg | | 412.2420 | 413.2493 | 413.2452 | 413.2534 |
| cys-glu-tyr | | 413.1256 | 414.1329 | 414.1288 | 414.1370 |
| glu-glu-his | | 413.1546 | 414.1619 | 414.1577 | 414.1660 |
| thr-met-tyr | | 413.1620 | 414.1693 | 414.1652 | 414.1734 |
| thr-phe-phe | | 413.1950 | 414.2023 | 414.1982 | 414.2065 |
| leu-val-val | | 413.2498 | 414.2571 | 414.2530 | 414.2613 |
| ile-val-val | | 413.2498 | 414.2571 | 414.2530 | 414.2613 |
| gln-met-his | | 414.1685 | 415.1758 | 415.1716 | 415.1799 |
| cys-his-arg | | 414.1797 | 415.1870 | 415.1828 | 415.1911 |
| lys-met-his | | 414.2049 | 415.2122 | 415.2080 | 415.2163 |
| asn-val-val | | 414.2087 | 415.2160 | 415.2118 | 415.2201 |
| pro-leu-try | | 414.2339 | 415.2412 | 415.2371 | 415.2454 |
| pro-ile-try | | 414.2339 | 415.2412 | 415.2371 | 415.2454 |
| cys-met-tyr | | 415.1235 | 416.1308 | 416.1266 | 416.1350 |
| glu-met-his | | 415.1525 | 416.1598 | 416.1556 | 416.1639 |
| cys-phe-phe | | 415.1565 | 416.1638 | 416.1597 | 416.1680 |
| ala-tyr-tyr | | 415.1743 | 416.1816 | 416.1774 | 416.1857 |
| ser-phe-tyr | | 415.1743 | 416.1816 | 416.1774 | 416.1857 |
| pro-his-tyr | | 415.1855 | 416.1928 | 416.1886 | 416.1970 |
| asp-val-val | | 415.1927 | 416.2000 | 416.1958 | 416.2042 |
| try-pro-asn | | 415.1928 | 416.2001 | 416.1959 | 416.2042 |
| gln-gln-val | | 415.2053 | 416.2126 | 416.2084 | 416.2167 |
| leu-his-phe | | 415.2219 | 416.2292 | 416.2250 | 416.2334 |
| ile-his-phe | | 415.2219 | 416.2292 | 416.2250 | 416.2334 |
| gln-lys-val | | 415.2417 | 416.2490 | 416.2448 | 416.2531 |
| leu-gln-arg | | 415.2543 | 416.2615 | 416.2574 | 416.2657 |
| ile-gln-arg | | 415.2543 | 416.2615 | 416.2574 | 416.2657 |
| lys-lys-val | | 415.2781 | 416.2854 | 416.2812 | 416.2895 |
| arg-leu-lys | | 415.2907 | 416.2979 | 416.2938 | 416.3021 |
| arg-ile-lys | | 415.2907 | 416.2979 | 416.2938 | 416.3021 |
| inositol triphosphate | C6H11O15P3 | 415.9294 | 416.9366 | 416.9325 | 416.9408 |
| try-pro-asp | | 416.1768 | 417.1841 | 417.1799 | 417.1883 |
| asn-his-phe | | 416.1808 | 417.1880 | 417.1839 | 417.1922 |
| gln-glu-val | | 416.1893 | 417.1966 | 417.1924 | 417.2008 |
| ala-val-try | | 416.2119 | 417.2191 | 417.2150 | 417.2233 |
| asn-gln-arg | | 416.2131 | 417.2204 | 417.2162 | 417.2246 |
| lys-glu-val | | 416.2257 | 417.2330 | 417.2288 | 417.2371 |
| val-thr-arg | | 416.2369 | 417.2442 | 417.2400 | 417.2484 |
| leu-glu-arg | | 416.2383 | 417.2456 | 417.2414 | 417.2497 |
| ile-glu-arg | | 416.2383 | 417.2456 | 417.2414 | 417.2497 |
| asn-lys-arg | | 416.2495 | 417.2568 | 417.2526 | 417.2610 |
| 1,25-dihydroxycalciferol | C27H44O3 | 416.3290 | 417.3363 | 417.3321 | 417.3405 |
| calcitriol | C27H44O3 | 416.3290 | 417.3363 | 417.3321 | 417.3405 |
| dihydroxycholecalciferol | C27H44O3 | 416.3290 | 417.3363 | 417.3321 | 417.3405 |
| met-met-his | | 417.1504 | 418.1577 | 418.1535 | 418.1619 |
| asp-his-phe | | 417.1648 | 418.1721 | 418.1679 | 418.1762 |
| glu-glu-val | | 417.1733 | 418.1806 | 418.1764 | 418.1848 |
| asn-glu-arg | | 417.1971 | 418.2044 | 418.2002 | 418.2086 |
| asp-gln-arg | | 417.1971 | 418.2044 | 418.2002 | 418.2086 |
| arg-gly-try | | 417.2197 | 418.2270 | 418.2228 | 418.2311 |
| asp-lys-arg | | 417.2335 | 418.2408 | 418.2366 | 418.2450 |
| ser-arg-arg | | 417.2448 | 418.2520 | 418.2478 | 418.2562 |
| 5'-butyrylphosphoinosine | C14H19N4O9P | 418.0884 | 419.0956 | 419.0914 | 419.0998 |
| asp-glu-arg | | 418.1812 | 419.1884 | 419.1842 | 419.1926 |
| met-gln-val | | 418.1872 | 419.1945 | 419.1903 | 419.1987 |
| arg-cys-val | | 418.1984 | 419.2057 | 419.2015 | 419.2099 |
| met-lys-val | | 418.2236 | 419.2309 | 419.2267 | 419.2351 |
| thr-leu-try | | 418.2289 | 419.2361 | 419.2319 | 419.2403 |
| thr-ile-try | | 418.2289 | 419.2361 | 419.2319 | 419.2403 |
| pro-phe-arg | | 418.2328 | 419.2401 | 419.2359 | 419.2443 |
| leu-met-arg | | 418.2362 | 419.2435 | 419.2393 | 419.2476 |
| ile-met-arg | | 418.2362 | 419.2435 | 419.2393 | 419.2476 |
| 17α,20α-dihydroxycholesterol | C27H46O3 | 418.3447 | 419.3520 | 419.3478 | 419.3562 |
| 20α,22β-dihydroxycholesterol | C27H46O3 | 418.3447 | 419.3520 | 419.3478 | 419.3562 |

TABLE 1-continued

Endogenous Metabolism Database

| Metabolite | Elemental formula | Precise Mass | M + 1H | 10 ppm− | 10 ppm+ |
|---|---|---|---|---|---|
| 3α,7α-dihydroxy-5β-cholestan-26-al | C27H46O3 | 418.3447 | 419.3520 | 419.3478 | 419.3562 |
| 7α,12α-dihydroxy-5α-cholestan-3-one | C27H46O3 | 418.3447 | 419.3520 | 419.3478 | 419.3562 |
| 7α,12α-dihydroxy-cholest-4-en-3-one | C27H46O3 | 418.3447 | 419.3520 | 419.3478 | 419.3562 |
| met-glu-val | | 419.1712 | 420.1785 | 420.1743 | 420.1827 |
| thr-his-tyr | | 419.1804 | 420.1877 | 420.1835 | 420.1919 |
| ser-gln-try | | 419.1877 | 420.1950 | 420.1908 | 420.1992 |
| asn-thr-try | | 419.1877 | 420.1950 | 420.1908 | 420.1992 |
| asn-met-arg | | 419.1950 | 420.2023 | 420.1981 | 420.2065 |
| val-pro-tyr | | 419.2042 | 420.2115 | 420.2073 | 420.2157 |
| ser-lys-try | | 419.2241 | 420.2314 | 420.2272 | 420.2356 |
| leu-val-phe | | 419.2406 | 420.2479 | 420.2437 | 420.2521 |
| ile-val-phe | | 419.2406 | 420.2479 | 420.2437 | 420.2521 |
| ser-glu-try | | 420.1717 | 421.1790 | 421.1748 | 421.1832 |
| asp-thr-try | | 420.1717 | 421.1790 | 421.1748 | 421.1832 |
| asp-met-arg | | 420.1791 | 421.1863 | 421.1821 | 421.1905 |
| gln-his-his | | 420.1869 | 421.1942 | 421.1900 | 421.1984 |
| cys-leu-try | | 420.1904 | 421.1976 | 421.1934 | 421.2019 |
| cys-ile-try | | 420.1904 | 421.1976 | 421.1934 | 421.2019 |
| asn-val-phe | | 420.1995 | 421.2068 | 421.2026 | 421.2110 |
| lys-his-his | | 420.2233 | 421.2306 | 421.2264 | 421.2348 |
| 3,7,11 phytanic acid | C29H40O2 | 420.3028 | 421.3101 | 421.3059 | 421.3143 |
| 3β,5α,6β-cholestanetriole | C27H48O3 | 420.3603 | 421.3676 | 421.3634 | 421.3718 |
| 7α,12α-dihydroxy-5β-cholestan-3-one | C27H48O3 | 420.3603 | 421.3676 | 421.3634 | 421.3718 |
| cys-his-tyr | | 421.1419 | 422.1492 | 422.1450 | 422.1534 |
| asn-cys-try | | 421.1492 | 422.1565 | 422.1523 | 422.1607 |
| met-met-val | | 421.1691 | 422.1764 | 422.1722 | 422.1806 |
| glu-his-his | | 421.1709 | 422.1782 | 422.1740 | 422.1824 |
| asp-val-phe | | 421.1835 | 422.1908 | 422.1866 | 422.1950 |
| phe-gln-gln | | 421.1961 | 422.2034 | 422.1991 | 422.2076 |
| phe-gln-lys | | 421.2325 | 422.2398 | 422.2355 | 422.2440 |
| lys-lys-phe | | 421.2689 | 422.2761 | 422.2719 | 422.2804 |
| lactose 6-phosphate | C12H23O14P | 422.0819 | 423.0892 | 423.0850 | 423.0934 |
| Maltose 6-phosphate | C12H23O14P | 422.0819 | 423.0892 | 423.0850 | 423.0934 |
| sucrose 6-phosphate | C12H23O14P | 422.0819 | 423.0892 | 423.0850 | 423.0934 |
| trehalose 6-phosphate | C12H23O14P | 422.0819 | 423.0892 | 423.0850 | 423.0934 |
| asp-cys-try | | 422.1332 | 423.1405 | 423.1363 | 423.1447 |
| ser-met-try | | 422.1696 | 423.1769 | 423.1727 | 423.1811 |
| phe-gln-glu | | 422.1801 | 423.1874 | 423.1831 | 423.1916 |
| ala-phe-try | | 422.2026 | 423.2099 | 423.2057 | 423.2142 |
| leu-gln-tyr | | 422.2165 | 423.2238 | 423.2195 | 423.2280 |
| ile-gln-tyr | | 422.2165 | 423.2238 | 423.2195 | 423.2280 |
| phe-lys-glu | | 422.2165 | 423.2238 | 423.2195 | 423.2280 |
| thr-phe-arg | | 422.2277 | 423.2350 | 423.2308 | 423.2392 |
| tyr-leu-lys | | 422.2529 | 423.2602 | 423.2559 | 423.2644 |
| tyr-ile-lys | | 422.2529 | 423.2602 | 423.2559 | 423.2644 |
| 3α,7α,12α-trihydroxy-5β-cholestane | C27H50O3 | 422.3760 | 423.3833 | 423.3790 | 423.3875 |
| phe-glu-glu | | 423.1641 | 424.1714 | 424.1672 | 424.1756 |
| met-his-his | | 423.1688 | 424.1761 | 424.1719 | 424.1803 |
| asn-gln-tyr | | 423.1753 | 424.1826 | 424.1784 | 424.1869 |
| val-thr-tyr | | 423.1992 | 424.2064 | 424.2022 | 424.2107 |
| leu-glu-tyr | | 423.2005 | 424.2078 | 424.2035 | 424.2120 |
| ile-glu-tyr | | 423.2005 | 424.2078 | 424.2035 | 424.2120 |
| asn-lys-tyr | | 423.2117 | 424.2190 | 424.2148 | 424.2233 |
| asn-glu-tyr | | 424.1594 | 425.1666 | 425.1624 | 425.1709 |
| asp-gln-tyr | | 424.1594 | 425.1666 | 425.1624 | 425.1709 |
| chitobiose | C16H28N2O11 | 424.1693 | 425.1765 | 425.1723 | 425.1808 |
| gln-met-phe | | 424.1780 | 425.1853 | 425.1810 | 425.1895 |
| tyr-gly-try | | 424.1819 | 425.1892 | 425.1849 | 425.1934 |
| cys-phe-arg | | 424.1892 | 425.1965 | 425.1923 | 425.2008 |
| asp-lys-tyr | | 424.1958 | 425.2030 | 425.1988 | 425.2073 |
| his-gln-val | | 424.2056 | 425.2129 | 425.2087 | 425.2172 |
| ser-arg-tyr | | 424.2070 | 425.2143 | 425.2100 | 425.2185 |
| lys-met-phe | | 424.2144 | 425.2217 | 425.2174 | 425.2259 |
| his-lys-val | | 424.2420 | 425.2493 | 425.2450 | 425.2535 |
| leu-his-arg | | 424.2546 | 425.2619 | 425.2576 | 425.2661 |
| ile-his-arg | | 424.2546 | 425.2619 | 425.2576 | 425.2661 |
| thiamine pyrophosphate (TPP) | C12H19N4O7SP2 | 425.0438 | 426.0511 | 426.0468 | 426.0554 |
| asp-glu-tyr | | 425.1434 | 426.1507 | 426.1464 | 426.1549 |
| tyr-cys-val | | 425.1607 | 426.1679 | 426.1637 | 426.1722 |
| glu-met-phe | | 425.1620 | 426.1693 | 426.1650 | 426.1736 |

TABLE 1-continued

Endogenous Metabolism Database

| Metabolite | Elemental formula | Precise Mass | M + 1H | 10 ppm− | 10 ppm+ |
|---|---|---|---|---|---|
| his-glu-val | | 425.1896 | 426.1969 | 426.1927 | 426.2012 |
| pro-phe-tyr | | 425.1950 | 426.2023 | 426.1980 | 426.2066 |
| leu-met-tyr | | 425.1984 | 426.2057 | 426.2014 | 426.2099 |
| ile-met-tyr | | 425.1984 | 426.2057 | 426.2014 | 426.2099 |
| asn-his-arg | | 425.2135 | 426.2207 | 426.2165 | 426.2250 |
| leu-phe-phe | | 425.2314 | 426.2387 | 426.2344 | 426.2430 |
| ile-phe-phe | | 425.2314 | 426.2387 | 426.2344 | 426.2430 |
| phytyl diphosphate | C20H42O7P | 425.2662 | 426.2735 | 426.2692 | 426.2778 |
| asn-met-tyr | | 426.1573 | 427.1645 | 427.1603 | 427.1688 |
| asn-phe-phe | | 426.1903 | 427.1976 | 427.1933 | 427.2018 |
| asp-his-arg | | 426.1975 | 427.2047 | 427.2005 | 427.2090 |
| 14-desmethyl-lanosterol | C30H50O | 426.3862 | 427.3934 | 427.3892 | 427.3977 |
| cycloartenol | C30H50O | 426.3862 | 427.3934 | 427.3892 | 427.3977 |
| lanosterol | C30H50O | 426.3862 | 427.3934 | 427.3892 | 427.3977 |
| squalene-2,3-epoxide | C30H50O | 426.3862 | 427.3934 | 427.3892 | 427.3977 |
| adenosine diphosphate | C10H15N5O10P2 | 427.0282 | 428.0355 | 428.0312 | 428.0398 |
| adenosine-3',5'-diphosphate (PAP) | C10H15N5O10P2 | 427.0282 | 428.0355 | 428.0312 | 428.0398 |
| dGDP | C10H15N5O10P2 | 427.0282 | 428.0355 | 428.0312 | 428.0398 |
| asp-met-tyr | | 427.1413 | 428.1486 | 428.1443 | 428.1528 |
| met-met-phe | | 427.1599 | 428.1672 | 428.1629 | 428.1715 |
| phe-asp-phe | | 427.1743 | 428.1816 | 428.1773 | 428.1859 |
| met-his-val | | 427.1875 | 428.1948 | 428.1905 | 428.1991 |
| pro-arg-arg | | 427.2655 | 428.2728 | 428.2685 | 428.2771 |
| inosine diphosphate | C10H14N4O11P2 | 428.0123 | 429.0195 | 429.0152 | 429.0238 |
| ser-his-try | | 428.1880 | 429.1953 | 429.1910 | 429.1996 |
| gln-val-val | | 428.2244 | 429.2316 | 429.2273 | 429.2359 |
| lys-val-val | | 428.2607 | 429.2680 | 429.2637 | 429.2723 |
| arg-leu-val | | 428.2733 | 429.2806 | 429.2763 | 429.2849 |
| arg-ile-val | | 428.2733 | 429.2806 | 429.2763 | 429.2849 |
| 24,25-dihydrolanosterol | C30H52O | 428.4018 | 429.4091 | 429.4048 | 429.4134 |
| leukotriene E4 | C23H37NO5S | 429.1610 | 430.1682 | 430.1639 | 430.1725 |
| his-his-his | | 429.1872 | 430.1945 | 430.1902 | 430.1988 |
| thr-phe-tyr | | 429.1899 | 430.1972 | 430.1929 | 430.2015 |
| glu-val-val | | 429.2084 | 430.2156 | 430.2113 | 430.2199 |
| pro-gln-try | | 429.2085 | 430.2157 | 430.2114 | 430.2200 |
| asn-val-arg | | 429.2322 | 430.2395 | 430.2351 | 430.2438 |
| pro-lys-try | | 429.2448 | 430.2521 | 430.2478 | 430.2564 |
| pro-glu-try | | 430.1925 | 431.1997 | 431.1954 | 431.2041 |
| gln-his-phe | | 430.1964 | 431.2037 | 431.1994 | 431.2080 |
| asp-val-arg | | 430.2162 | 431.2235 | 431.2192 | 431.2278 |
| gln-gln-arg | | 430.2288 | 431.2360 | 431.2317 | 431.2404 |
| lys-his-phe | | 430.2328 | 431.2401 | 431.2358 | 431.2444 |
| lys-gln-arg | | 430.2652 | 431.2724 | 431.2681 | 431.2767 |
| leu-leu-try | | 430.2652 | 431.2725 | 431.2682 | 431.2768 |
| leu-ile-try | | 430.2652 | 431.2725 | 431.2682 | 431.2768 |
| ile-ile-try | | 430.2652 | 431.2725 | 431.2682 | 431.2768 |
| arg-lys-lys | | 430.3016 | 431.3088 | 431.3045 | 431.3131 |
| α-tocopherol | C29H50O2 | 430.3811 | 431.3883 | 431.3840 | 431.3927 |
| cys-phe-tyr | | 431.1515 | 432.1587 | 432.1544 | 432.1631 |
| ser-tyr-tyr | | 431.1692 | 432.1765 | 432.1722 | 432.1808 |
| glu-his-phe | | 431.1804 | 432.1877 | 432.1834 | 432.1920 |
| met-val-val | | 431.2063 | 432.2135 | 432.2092 | 432.2179 |
| gln-glu-arg | | 431.2128 | 432.2201 | 432.2157 | 432.2244 |
| leu-his-tyr | | 431.2168 | 432.2241 | 432.2198 | 432.2284 |
| ile-his-tyr | | 431.2168 | 432.2241 | 432.2198 | 432.2284 |
| asn-leu-try | | 431.2241 | 432.2314 | 432.2271 | 432.2357 |
| asn-ile-try | | 431.2241 | 432.2314 | 432.2271 | 432.2357 |
| ala-arg-try | | 431.2353 | 432.2426 | 432.2383 | 432.2469 |
| lys-glu-arg | | 431.2492 | 432.2565 | 432.2521 | 432.2608 |
| thr-arg-arg | | 431.2604 | 432.2677 | 432.2634 | 432.2720 |
| asn-his-tyr | | 432.1757 | 433.1830 | 433.1786 | 433.1873 |
| asn-asn-try | | 432.1830 | 433.1902 | 433.1859 | 433.1946 |
| try-pro-met | | 432.1904 | 433.1976 | 433.1933 | 433.2020 |
| glu-glu-arg | | 432.1968 | 433.2041 | 433.1997 | 433.2084 |
| ser-val-try | | 432.2068 | 433.2140 | 433.2097 | 433.2184 |
| asp-leu-try | | 432.2081 | 433.2154 | 433.2111 | 433.2197 |
| asp-ile-try | | 432.2081 | 433.2154 | 433.2111 | 433.2197 |
| 3α,7α,12α-trihydroxy-5β-cholestanoate | C27H44O4 | 432.3239 | 433.3312 | 433.3269 | 433.3356 |
| 3,5-diiodotyrosine | C9H9NO3I2 | 432.8661 | 433.8733 | 433.8690 | 433.8777 |
| asp-his-tyr | | 433.1597 | 434.1670 | 434.1626 | 434.1713 |
| asn-asp-try | | 433.1670 | 434.1742 | 434.1699 | 434.1786 |
| met-his-phe | | 433.1783 | 434.1856 | 434.1813 | 434.1900 |
| thr-gln-try | | 433.2034 | 434.2106 | 434.2063 | 434.2150 |
| his-his-val | | 433.2060 | 434.2132 | 434.2089 | 434.2176 |

TABLE 1-continued

Endogenous Metabolism Database

| Metabolite | Elemental formula | Precise Mass | M + 1H | 10 ppm− | 10 ppm+ |
|---|---|---|---|---|---|
| gln-met-arg | | 433.2107 | 434.2180 | 434.2136 | 434.2223 |
| cys-arg-arg | | 433.2219 | 434.2292 | 434.2248 | 434.2335 |
| thr-lys-try | | 433.2398 | 434.2470 | 434.2427 | 434.2514 |
| lys-met-arg | | 433.2471 | 434.2544 | 434.2500 | 434.2587 |
| asp-asp-try | | 434.1510 | 435.1583 | 435.1539 | 435.1626 |
| thr-glu-try | | 434.1874 | 435.1947 | 435.1903 | 435.1990 |
| glu-met-arg | | 434.1947 | 435.2020 | 435.1976 | 435.2063 |
| phe-gln-val | | 434.2151 | 435.2224 | 435.2181 | 435.2268 |
| pro-arg-tyr | | 434.2277 | 435.2350 | 435.2306 | 435.2393 |
| lys-val-phe | | 434.2515 | 435.2588 | 435.2545 | 435.2632 |
| leu-phe-arg | | 434.2641 | 435.2714 | 435.2670 | 435.2757 |
| ile-phe-arg | | 434.2641 | 435.2714 | 435.2670 | 435.2757 |
| 3α,7α,12α,26-tetrahydroxy-5β-cholestane | C27H46O4 | 434.3396 | 435.3469 | 435.3425 | 435.3512 |
| 3α,7α,12α-trihydroxy-5β-cholestan-26-al | C27H46O4 | 434.3396 | 435.3469 | 435.3425 | 435.3512 |
| cys-gln-try | | 435.1649 | 436.1721 | 436.1678 | 436.1765 |
| phe-glu-val | | 435.1992 | 436.2064 | 436.2021 | 436.2108 |
| cys-lys-try | | 435.2013 | 436.2085 | 436.2042 | 436.2129 |
| asn-phe-arg | | 435.2230 | 436.2302 | 436.2259 | 436.2346 |
| tyr-leu-val | | 435.2355 | 436.2428 | 436.2385 | 436.2472 |
| tyr-ile-val | | 435.2355 | 436.2428 | 436.2385 | 436.2472 |
| cys-glu-try | | 436.1489 | 437.1562 | 437.1518 | 437.1605 |
| met-thr-try | | 436.1853 | 437.1926 | 437.1882 | 437.1969 |
| met-met-arg | | 436.1926 | 437.1999 | 437.1955 | 437.2042 |
| asn-val-tyr | | 436.1944 | 437.2017 | 437.1973 | 437.2060 |
| asp-phe-arg | | 436.2070 | 437.2143 | 437.2099 | 437.2186 |
| asp-val-tyr | | 437.1784 | 438.1857 | 438.1813 | 438.1901 |
| gln-gln-tyr | | 437.1910 | 438.1983 | 438.1939 | 438.2027 |
| met-val-phe | | 437.1971 | 438.2043 | 438.1999 | 438.2087 |
| his-val-val | | 437.2247 | 438.2320 | 438.2276 | 438.2363 |
| lys-gln-tyr | | 437.2274 | 438.2347 | 438.2303 | 438.2390 |
| tyr-lys-lys | | 437.2638 | 438.2711 | 438.2667 | 438.2754 |
| met-cys-try | | 438.1468 | 439.1541 | 439.1497 | 439.1585 |
| gln-glu-tyr | | 438.1750 | 439.1823 | 439.1779 | 439.1867 |
| ala-tyr-try | | 438.1976 | 439.2048 | 439.2004 | 439.2092 |
| ser-phe-try | | 438.1976 | 439.2048 | 439.2004 | 439.2092 |
| try-pro-his | | 438.2088 | 439.2161 | 439.2117 | 439.2205 |
| lys-glu-tyr | | 438.2114 | 439.2187 | 439.2143 | 439.2231 |
| thr-arg-tyr | | 438.2226 | 439.2299 | 439.2255 | 439.2343 |
| glu-glu-tyr | | 439.1590 | 440.1663 | 440.1619 | 440.1707 |
| his-his-phe | | 439.1968 | 440.2040 | 440.1996 | 440.2084 |
| gln-his-arg | | 439.2291 | 440.2364 | 440.2320 | 440.2408 |
| lys-his-arg | | 439.2655 | 440.2728 | 440.2684 | 440.2772 |
| gln-met-tyr | | 440.1729 | 441.1802 | 441.1758 | 441.1846 |
| cys-arg-tyr | | 440.1841 | 441.1914 | 441.1870 | 441.1958 |
| gln-phe-phe | | 440.2059 | 441.2132 | 441.2088 | 441.2176 |
| lys-met-tyr | | 440.2093 | 441.2166 | 441.2122 | 441.2210 |
| glu-his-arg | | 440.2131 | 441.2204 | 441.2160 | 441.2248 |
| lys-phe-phe | | 440.2423 | 441.2496 | 441.2452 | 441.2540 |
| folic acid | C19H19N7O6 | 441.1396 | 442.1469 | 442.1425 | 442.1513 |
| glu-met-tyr | | 441.1569 | 442.1642 | 442.1598 | 442.1686 |
| pro-tyr-tyr | | 441.1899 | 442.1972 | 442.1928 | 442.2016 |
| glu-phe-phe | | 441.1899 | 442.1972 | 442.1928 | 442.2016 |
| leu-phe-tyr | | 441.2263 | 442.2336 | 442.2292 | 442.2380 |
| ile-phe-tyr | | 441.2263 | 442.2336 | 442.2292 | 442.2380 |
| val-val-val | | 441.2434 | 442.2507 | 442.2463 | 442.2551 |
| asn-phe-tyr | | 442.1852 | 443.1925 | 443.1880 | 443.1969 |
| his-thr-try | | 442.2037 | 443.2110 | 443.2065 | 443.2154 |
| met-his-arg | | 442.2110 | 443.2183 | 443.2139 | 443.2227 |
| pro-val-try | | 442.2275 | 443.2348 | 443.2304 | 443.2392 |
| guanosine diphosphate (GDP) | C10H15N5O11P2 | 443.0232 | 444.0304 | 444.0260 | 444.0349 |
| met-met-tyr | | 443.1548 | 444.1621 | 444.1577 | 444.1665 |
| 7,8-dihydrofolate | C19H21N7O6 | 443.1553 | 444.1626 | 444.1581 | 444.1670 |
| asp-phe-tyr | | 443.1692 | 444.1765 | 444.1720 | 444.1809 |
| phe-met-phe | | 443.1878 | 444.1951 | 444.1907 | 444.1996 |
| his-val-phe | | 443.2155 | 444.2228 | 444.2183 | 444.2272 |
| val-gln-arg | | 443.2478 | 444.2551 | 444.2507 | 444.2595 |
| arg-lys-val | | 443.2842 | 444.2915 | 444.2870 | 444.2959 |
| leu-arg-arg | | 443.2968 | 444.3041 | 444.2996 | 444.3085 |
| ile-arg-arg | | 443.2968 | 444.3041 | 444.2996 | 444.3085 |
| adenylylsulfate (APS) | C10H15N5O11SP | 444.0220 | 445.0293 | 445.0248 | 445.0337 |
| his-cys-try | | 444.1652 | 445.1725 | 445.1680 | 445.1769 |
| val-glu-arg | | 444.2318 | 445.2391 | 445.2347 | 445.2436 |
| asn-arg-arg | | 444.2557 | 445.2629 | 445.2585 | 445.2674 |

TABLE 1-continued

Endogenous Metabolism Database

| Metabolite | Elemental formula | Precise Mass | M + 1H | 10 ppm− | 10 ppm+ |
|---|---|---|---|---|---|
| menaquinone-4 | C31H40O2 | 444.3028 | 445.3101 | 445.3056 | 445.3146 |
| tetrahydrofolate (THF) | C19H23N7O6 | 445.1709 | 446.1782 | 446.1737 | 446.1827 |
| thr-tyr-tyr | | 445.1849 | 446.1921 | 446.1877 | 446.1966 |
| asp-arg-arg | | 445.2397 | 446.2469 | 446.2425 | 446.2514 |
| leu-gln-try | | 445.2398 | 446.2470 | 446.2426 | 446.2515 |
| ile-gln-try | | 445.2398 | 446.2470 | 446.2426 | 446.2515 |
| leu-lys-try | | 445.2761 | 446.2834 | 446.2790 | 446.2879 |
| ile-lys-try | | 445.2761 | 446.2834 | 446.2790 | 446.2879 |
| gln-his-tyr | | 446.1913 | 447.1986 | 447.1941 | 447.2031 |
| estrone glucuronide | C24H30O8 | 446.1940 | 447.2013 | 447.1968 | 447.2058 |
| asn-gln-try | | 446.1986 | 447.2059 | 447.2014 | 447.2104 |
| thr-val-try | | 446.2224 | 447.2297 | 447.2252 | 447.2342 |
| leu-glu-try | | 446.2238 | 447.2310 | 447.2266 | 447.2355 |
| ile-glu-try | | 446.2238 | 447.2310 | 447.2266 | 447.2355 |
| lys-his-tyr | | 446.2277 | 447.2350 | 447.2305 | 447.2395 |
| met-val-arg | | 446.2297 | 447.2370 | 447.2325 | 447.2415 |
| asn-lys-try | | 446.2350 | 447.2423 | 447.2378 | 447.2467 |
| CDP-ethanolamine | C11H21N4O11P2 | 447.0670 | 448.0743 | 448.0698 | 448.0788 |
| cys-tyr-tyr | | 447.1464 | 448.1536 | 448.1492 | 448.1581 |
| glu-his-tyr | | 447.1753 | 448.1826 | 448.1781 | 448.1871 |
| asn-glu-try | | 447.1826 | 448.1899 | 448.1854 | 448.1944 |
| asp-gln-try | | 447.1826 | 448.1899 | 448.1854 | 448.1944 |
| gly-try-try | | 447.2052 | 448.2124 | 448.2080 | 448.2169 |
| asp-lys-try | | 447.2190 | 448.2263 | 448.2218 | 448.2308 |
| ser-arg-try | | 447.2302 | 448.2375 | 448.2330 | 448.2420 |
| val-val-phe | | 447.2342 | 448.2415 | 448.2370 | 448.2460 |
| glucobrassicin | C16H20N2O9S2 | 448.0610 | 449.0682 | 449.0638 | 449.0727 |
| asp-glu-try | | 448.1666 | 449.1739 | 449.1694 | 449.1784 |
| cys-val-try | | 448.1839 | 449.1912 | 449.1867 | 449.1957 |
| pro-phe-try | | 448.2183 | 449.2256 | 449.2211 | 449.2301 |
| met-leu-try | | 448.2217 | 449.2289 | 449.2245 | 449.2334 |
| met-ile-try | | 448.2217 | 449.2289 | 449.2245 | 449.2334 |
| his-his-arg | | 448.2294 | 449.2367 | 449.2322 | 449.2412 |
| met-his-tyr | | 449.1732 | 450.1805 | 450.1760 | 450.1850 |
| asn-met-try | | 449.1805 | 450.1878 | 450.1833 | 450.1923 |
| phe-his-phe | | 449.2063 | 450.2135 | 450.2090 | 450.2180 |
| gln-phe-arg | | 449.2386 | 450.2459 | 450.2414 | 450.2504 |
| lys-phe-arg | | 449.2750 | 450.2823 | 450.2778 | 450.2868 |
| glycochenodeoxycholate | C26H43NO5 | 449.3141 | 450.3214 | 450.3169 | 450.3259 |
| glycodeoxycholate | C26H43NO5 | 449.3141 | 450.3214 | 450.3169 | 450.3259 |
| asp-met-try | | 450.1645 | 451.1718 | 451.1673 | 451.1763 |
| geranylgeranyl diphosphate | C20H36O7P2 | 450.1925 | 451.1998 | 451.1953 | 451.2043 |
| val-gln-tyr | | 450.2101 | 451.2173 | 451.2128 | 451.2218 |
| glu-phe-arg | | 450.2226 | 451.2299 | 451.2254 | 451.2344 |
| tyr-lys-val | | 450.2464 | 451.2537 | 451.2492 | 451.2582 |
| leu-arg-tyr | | 450.2590 | 451.2663 | 451.2618 | 451.2708 |
| ile-arg-tyr | | 450.2590 | 451.2663 | 451.2618 | 451.2708 |
| phylloquinone | C31H46O2 | 450.3498 | 451.3570 | 451.3525 | 451.3616 |
| 5'-benzoylphosphoadenosine | C17H18N5O8P | 451.0887 | 452.0960 | 452.0914 | 452.1005 |
| val-glu-tyr | | 451.1941 | 452.2013 | 452.1968 | 452.2059 |
| asn-arg-tyr | | 451.2179 | 452.2252 | 452.2206 | 452.2297 |
| asp-arg-tyr | | 452.2019 | 453.2092 | 453.2046 | 453.2137 |
| all-trans-geranylgeranyl-PP | C20H38O7P2 | 452.2081 | 453.2154 | 453.2109 | 453.2199 |
| phe-thr-try | | 452.2132 | 453.2205 | 453.2160 | 453.2250 |
| met-phe-arg | | 452.2205 | 453.2278 | 453.2233 | 453.2323 |
| his-val-arg | | 452.2482 | 453.2554 | 453.2509 | 453.2600 |
| phylloquinol | C31H48O2 | 452.3654 | 453.3727 | 453.3682 | 453.3772 |
| met-val-tyr | | 453.1920 | 454.1992 | 454.1947 | 454.2038 |
| val-phe-phe | | 453.2250 | 454.2323 | 454.2277 | 454.2368 |
| 5P-ribosyl-4-(N-succinocarboxamide)-5-aminoimidazole | C13H19N4O12P | 454.0731 | 455.0804 | 455.0758 | 455.0849 |
| 5,10-methyenyl THF | C20H20N7O6 | 454.1475 | 455.1547 | 455.1502 | 455.1593 |
| cys-phe-try | | 454.1747 | 455.1820 | 455.1774 | 455.1865 |
| ser-tyr-try | | 454.1925 | 455.1997 | 455.1952 | 455.2043 |
| CMP-N-acetylneuraminate | C20H31N4O6P | 454.1975 | 455.2048 | 455.2002 | 455.2094 |
| his-leu-try | | 454.2401 | 455.2474 | 455.2428 | 455.2519 |
| his-ile-try | | 454.2401 | 455.2474 | 455.2428 | 455.2519 |
| 5,10-methylene-THF | C20H21N7O6 | 455.1553 | 456.1626 | 456.1580 | 456.1671 |
| his-his-tyr | | 455.1917 | 456.1989 | 456.1944 | 456.2035 |
| asn-his-try | | 455.1989 | 456.2062 | 456.2017 | 456.2108 |
| 20-hydroxyleukotriene E4 | C23H37NO6S | 455.2341 | 456.2414 | 456.2368 | 456.2460 |
| asp-his-try | | 456.1830 | 457.1902 | 457.1857 | 457.1948 |
| gln-phe-tyr | | 456.2008 | 457.2081 | 457.2035 | 457.2127 |
| lys-phe-tyr | | 456.2372 | 457.2445 | 457.2399 | 457.2491 |

TABLE 1-continued

Endogenous Metabolism Database

| Metabolite | Elemental formula | Precise Mass | M + 1H | 10 ppm− | 10 ppm+ |
|---|---|---|---|---|---|
| arg-val-val | | 456.2669 | 457.2742 | 457.2696 | 457.2787 |
| 5-methyl-THF | C20H23N7O6 | 457.1709 | 458.1782 | 458.1736 | 458.1828 |
| glu-phe-tyr | | 457.1849 | 458.1921 | 458.1876 | 458.1967 |
| leu-tyr-tyr | | 457.2212 | 458.2285 | 458.2239 | 458.2331 |
| ile-tyr-tyr | | 457.2212 | 458.2285 | 458.2239 | 458.2331 |
| try-pro-arg | | 457.2510 | 458.2583 | 458.2537 | 458.2628 |
| asn-tyr-tyr | | 458.1801 | 459.1874 | 459.1828 | 459.1920 |
| his-phe-arg | | 458.2390 | 459.2462 | 459.2416 | 459.2508 |
| leu-val-try | | 458.2588 | 459.2661 | 459.2615 | 459.2707 |
| ile-val-try | | 458.2588 | 459.2661 | 459.2615 | 459.2707 |
| gln-arg-arg | | 458.2713 | 459.2786 | 459.2740 | 459.2832 |
| lys-arg-arg | | 458.3077 | 459.3150 | 459.3104 | 459.3196 |
| asp-tyr-tyr | | 459.1641 | 460.1714 | 460.1668 | 460.1760 |
| met-phe-tyr | | 459.1828 | 460.1900 | 460.1854 | 460.1946 |
| his-val-tyr | | 459.2104 | 460.2177 | 460.2131 | 460.2223 |
| phe-phe-phe | | 459.2158 | 460.2231 | 460.2184 | 460.2277 |
| asn-val-try | | 459.2177 | 460.2249 | 460.2203 | 460.2295 |
| glu-arg-arg | | 459.2553 | 460.2626 | 460.2580 | 460.2672 |
| asp-val-try | | 460.2017 | 461.2090 | 461.2043 | 461.2136 |
| gln-gln-try | | 460.2143 | 461.2215 | 461.2169 | 461.2261 |
| gln-lys-try | | 460.2506 | 461.2579 | 461.2533 | 461.2625 |
| lys-lys-try | | 460.2870 | 461.2943 | 461.2897 | 461.2989 |
| gln-glu-try | | 461.1983 | 462.2055 | 462.2009 | 462.2102 |
| ala-try-try | | 461.2208 | 462.2281 | 462.2235 | 462.2327 |
| lys-glu-try | | 461.2347 | 462.2419 | 462.2373 | 462.2466 |
| arg-thr-try | | 461.2459 | 462.2532 | 462.2485 | 462.2578 |
| met-arg-arg | | 461.2532 | 462.2605 | 462.2559 | 462.2651 |
| glucosylsphingosine | C24H47NO7 | 461.3352 | 462.3425 | 462.3379 | 462.3471 |
| adenylosuccinate | C14H17N5O11P | 462.0656 | 463.0729 | 463.0682 | 463.0775 |
| glu-glu-try | | 462.1823 | 463.1896 | 463.1849 | 463.1942 |
| val-phe-arg | | 462.2577 | 463.2649 | 463.2603 | 463.2696 |
| met-gln-try | | 463.1962 | 464.2034 | 464.1988 | 464.2081 |
| arg-cys-try | | 463.2074 | 464.2147 | 464.2100 | 464.2193 |
| tyr-val-val | | 463.2291 | 464.2364 | 464.2317 | 464.2410 |
| met-lys-try | | 463.2326 | 464.2398 | 464.2352 | 464.2445 |
| met-glu-try | | 464.1802 | 465.1875 | 465.1828 | 465.1921 |
| 16-glucuronide-estriol | C24H32O9 | 464.2046 | 465.2119 | 465.2072 | 465.2165 |
| try-pro-tyr | | 464.2132 | 465.2205 | 465.2158 | 465.2251 |
| testosterone glucuronide | C25H36O8 | 464.2410 | 465.2483 | 465.2436 | 465.2529 |
| leu-phe-try | | 464.2496 | 465.2569 | 465.2522 | 465.2615 |
| ile-phe-try | | 464.2496 | 465.2569 | 465.2522 | 465.2615 |
| his-phe-tyr | | 465.2012 | 466.2085 | 466.2038 | 466.2131 |
| asn-phe-try | | 465.2085 | 466.2157 | 466.2111 | 466.2204 |
| gln-arg-tyr | | 465.2335 | 466.2408 | 466.2361 | 466.2455 |
| lys-arg-tyr | | 465.2699 | 466.2772 | 466.2725 | 466.2819 |
| glycocholate | C26H43NO6 | 465.3090 | 466.3163 | 466.3116 | 466.3209 |
| sphingosyl-phosphocholine | C23H50N2O5P | 465.3452 | 466.3524 | 466.3478 | 466.3571 |
| met-met-try | | 466.1781 | 467.1854 | 467.1807 | 467.1900 |
| asp-phe-try | | 466.1925 | 467.1997 | 467.1951 | 467.2044 |
| glu-arg-tyr | | 466.2175 | 467.2248 | 467.2201 | 467.2295 |
| androsterone glucuronide | C25H38O8 | 466.2566 | 467.2639 | 467.2592 | 467.2686 |
| etiocholan-3α-ol-17-one 3-glucuronide | C25H38O8 | 466.2566 | 467.2639 | 467.2592 | 467.2686 |
| (2,3-epoxyphytyl) menaquinone | C31H46O3 | 466.3447 | 467.3520 | 467.3473 | 467.3566 |
| dUTP | C9H14N2O14P3 | 466.9641 | 467.9713 | 467.9667 | 467.9760 |
| dCTP | C9H16N3O13P3 | 466.9879 | 467.9951 | 467.9905 | 467.9998 |
| his-arg-arg | | 467.2716 | 468.2789 | 468.2742 | 468.2836 |
| tyr-thr-try | | 468.2081 | 469.2154 | 469.2107 | 469.2201 |
| met-arg-tyr | | 468.2154 | 469.2227 | 469.2180 | 469.2274 |
| phe-phe-arg | | 468.2485 | 469.2557 | 469.2510 | 469.2604 |
| 2-hydroxyethyl-ThPP | C14H23N4O8SP2 | 469.0700 | 470.0773 | 470.0726 | 470.0820 |
| his-gln-try | | 469.2146 | 470.2219 | 470.2172 | 470.2266 |
| val-phe-tyr | | 469.2199 | 470.2272 | 470.2225 | 470.2319 |
| his-lys-try | | 469.2510 | 470.2583 | 470.2536 | 470.2630 |
| 5-formimino-THF | C20H22N8O6 | 470.1662 | 471.1734 | 471.1687 | 471.1782 |
| tyr-cys-try | | 470.1696 | 471.1769 | 471.1722 | 471.1816 |
| his-glu-try | | 470.1986 | 471.2059 | 471.2012 | 471.2106 |
| reduced vitamin K | C31H50O3 | 470.3760 | 471.3833 | 471.3785 | 471.3880 |
| 2-(α-hydroxyethyl-)TPP | C14H25N4O8SP2 | 471.0857 | 472.0930 | 472.0882 | 472.0977 |
| 5-formyl-THF | C20H21N7O7 | 471.1502 | 472.1575 | 472.1527 | 472.1622 |
| val-arg-arg | | 471.2904 | 472.2976 | 472.2929 | 472.3024 |
| gln-tyr-tyr | | 472.1958 | 473.2030 | 473.1983 | 473.2078 |
| met-his-try | | 472.1965 | 473.2038 | 473.1991 | 473.2085 |
| lys-tyr-tyr | | 472.2321 | 473.2394 | 473.2347 | 473.2441 |
| 10-formyl-THF | C20H23N7O7 | 473.1658 | 474.1731 | 474.1684 | 474.1779 |

TABLE 1-continued

Endogenous Metabolism Database

| Metabolite | Elemental formula | Precise Mass | M + 1H | 10 ppm− | 10 ppm+ |
|---|---|---|---|---|---|
| glu-tyr-tyr | | 473.1798 | 474.1870 | 474.1823 | 474.1918 |
| gln-val-try | | 473.2333 | 474.2406 | 474.2358 | 474.2453 |
| lys-val-try | | 473.2697 | 474.2770 | 474.2722 | 474.2817 |
| arg-leu-try | | 473.2823 | 474.2896 | 474.2848 | 474.2943 |
| arg-ile-try | | 473.2823 | 474.2896 | 474.2848 | 474.2943 |
| glu-val-try | | 474.2173 | 475.2246 | 475.2199 | 475.2294 |
| his-arg-tyr | | 474.2339 | 475.2411 | 475.2364 | 475.2459 |
| asn-arg-try | | 474.2411 | 475.2484 | 475.2437 | 475.2532 |
| citicoline | C14H27N4O11P2 | 475.1109 | 476.1182 | 476.1134 | 476.1230 |
| met-tyr-tyr | | 475.1777 | 476.1849 | 476.1802 | 476.1897 |
| phe-phe-tyr | | 475.2107 | 476.2180 | 476.2132 | 476.2227 |
| asp-arg-try | | 475.2252 | 476.2324 | 476.2277 | 476.2372 |
| 2-methoxyestrone 3-glucuronide | C25H32O9 | 476.2046 | 477.2119 | 477.2071 | 477.2166 |
| met-val-try | | 476.2152 | 477.2225 | 477.2177 | 477.2273 |
| CDP-glycerol | C12H21N3O13P2 | 477.0538 | 478.0611 | 478.0563 | 478.0658 |
| ser-try-try | | 477.2157 | 478.2230 | 478.2182 | 478.2278 |
| phe-arg-arg | | 477.2811 | 478.2884 | 478.2836 | 478.2932 |
| his-his-try | | 478.2149 | 479.2222 | 479.2174 | 479.2270 |
| 2-methoxy-estradiol-17β 3-glucuronide | C25H34O9 | 478.2202 | 479.2275 | 479.2227 | 479.2323 |
| val-arg-tyr | | 478.2526 | 479.2599 | 479.2551 | 479.2646 |
| phe-gln-try | | 479.2241 | 480.2314 | 480.2266 | 480.2362 |
| lys-phe-try | | 479.2605 | 480.2678 | 480.2630 | 480.2726 |
| phe-glu-try | | 480.2081 | 481.2154 | 481.2106 | 481.2202 |
| tyr-leu-try | | 480.2445 | 481.2518 | 481.2470 | 481.2566 |
| tyr-ile-try | | 480.2445 | 481.2518 | 481.2470 | 481.2566 |
| his-tyr-tyr | | 481.1961 | 482.2034 | 482.1985 | 482.2082 |
| asn-tyr-try | | 481.2034 | 482.2106 | 482.2058 | 482.2155 |
| thymidine triphosphate (TTP) | C10H17N2O14P3 | 481.9875 | 482.9948 | 482.9900 | 482.9996 |
| asp-tyr-try | | 482.1874 | 483.1947 | 483.1898 | 483.1995 |
| met-phe-try | | 482.2060 | 483.2133 | 483.2085 | 483.2181 |
| his-val-try | | 482.2336 | 483.2409 | 483.2361 | 483.2458 |
| molybdopterin (MPT) | C10H12(10)N5O6S2P(Mo) | 482.8867 | 483.8939 | 483.8891 | 483.8988 |
| cytidine triphosphate (CTP) | C9H16N3O14P3 | 482.9828 | 483.9901 | 483.9852 | 483.9949 |
| uridine triphosphate (UTP) | C9H15N2O15P3 | 483.9668 | 484.9741 | 484.9692 | 484.9789 |
| phe-arg-tyr | | 484.2434 | 485.2506 | 485.2458 | 485.2555 |
| val-tyr-tyr | | 485.2148 | 486.2221 | 486.2172 | 486.2269 |
| val-val-try | | 486.2524 | 487.2596 | 487.2548 | 487.2645 |
| arg-arg-arg | | 486.3138 | 487.3211 | 487.3162 | 487.3260 |
| pro-try-try | | 487.2365 | 488.2437 | 488.2389 | 488.2486 |
| his-phe-try | | 488.2244 | 489.2317 | 489.2268 | 489.2366 |
| arg-gln-try | | 488.2568 | 489.2641 | 489.2592 | 489.2690 |
| arg-lys-try | | 488.2932 | 489.3005 | 489.2956 | 489.3053 |
| CDP-choline | C14H27N4O11P2 | 489.1140 | 490.1213 | 490.1164 | 490.1262 |
| arg-glu-try | | 489.2408 | 490.2481 | 490.2432 | 490.2530 |
| 2-aminoadipate adenylate | C16H23N6O10P | 490.1207 | 491.1280 | 491.1231 | 491.1329 |
| dATP | C10H16N5O12P3 | 490.9991 | 492.0064 | 492.0015 | 492.0113 |
| phe-tyr-tyr | | 491.2056 | 492.2129 | 492.2079 | 492.2178 |
| thr-try-try | | 491.2314 | 492.2387 | 492.2337 | 492.2436 |
| met-arg-try | | 491.2387 | 492.2460 | 492.2411 | 492.2509 |
| dITP | C10H15N4O13P3 | 491.9831 | 492.9904 | 492.9855 | 492.9953 |
| val-phe-try | | 492.2432 | 493.2504 | 493.2455 | 493.2554 |
| cys-try-try | | 493.1929 | 494.2002 | 494.1952 | 494.2051 |
| arg-arg-tyr | | 493.2761 | 494.2833 | 494.2784 | 494.2883 |
| 2-amino-4-hydroxy-(erythro-1-2-3-trihydroxypropyl-)di-hydropteridine-P3 | C9H16N5O13P3 | 494.9940 | 496.0013 | 495.9963 | 496.0062 |
| gln-tyr-try | | 495.2190 | 496.2263 | 496.2213 | 496.2313 |
| tyr-lys-try | | 495.2554 | 496.2627 | 496.2577 | 496.2676 |
| glu-tyr-try | | 496.2030 | 497.2103 | 497.2053 | 497.2153 |
| leukotriene D4 | C25H40N2O6S | 496.2607 | 497.2679 | 497.2630 | 497.2729 |
| 2′-deoxy-5-hydroxymethylcytidine-5′-triphosphate | C10H18N3O14P3 | 496.9984 | 498.0057 | 498.0007 | 498.0107 |
| his-arg-try | | 497.2571 | 498.2644 | 498.2594 | 498.2694 |
| met-tyr-try | | 498.2009 | 499.2082 | 499.2032 | 499.2132 |
| phe-phe-try | | 498.2339 | 499.2412 | 499.2362 | 499.2462 |
| taurochenodeoxycholate | C26H45NO6S | 499.2967 | 500.3040 | 500.2990 | 500.3090 |
| taurodeoxycholate | C26H45NO6S | 499.2967 | 500.3040 | 500.2990 | 500.3090 |
| inositol 1,3,4,5-tetrakisphosphate | C6H16O18P4 | 499.9264 | 500.9337 | 500.9287 | 500.9387 |
| inositol 1,3,4,6-tetrakisphosphate | C6H16O18P4 | 499.9264 | 500.9337 | 500.9287 | 500.9387 |
| inositol 1,4,5,6-tetrakisphosphate | C6H16O18P4 | 499.9264 | 500.9337 | 500.9287 | 500.9387 |
| inositol 3,4,5,6-tetrakisphosphate | C6H16O18P4 | 499.9264 | 500.9337 | 500.9287 | 500.9387 |
| arg-tyr-tyr | | 500.2383 | 501.2456 | 501.2405 | 501.2506 |
| arg-val-try | | 501.2758 | 502.2831 | 502.2781 | 502.2881 |

TABLE 1-continued

Endogenous Metabolism Database

| Metabolite | Elemental formula | Precise Mass | M + 1H | 10 ppm− | 10 ppm+ |
|---|---|---|---|---|---|
| leu-try-try | | 503.2678 | 504.2750 | 504.2700 | 504.2801 |
| ile-try-try | | 503.2678 | 504.2750 | 504.2700 | 504.2801 |
| cellotriose | C18H32O16 | 504.1690 | 505.1762 | 505.1712 | 505.1813 |
| Gal α 1->6-gal α 1->6-glucose | C18H32O16 | 504.1690 | 505.1762 | 505.1712 | 505.1813 |
| his-tyr-try | | 504.2193 | 505.2266 | 505.2216 | 505.2317 |
| asn-try-try | | 504.2266 | 505.2339 | 505.2288 | 505.2390 |
| asp-try-try | | 505.2106 | 506.2179 | 506.2129 | 506.2230 |
| adenosine triphosphate | C10H16N5O13P3 | 506.9940 | 508.0013 | 507.9962 | 508.0064 |
| dGTP | C10H16N5O13P3 | 506.9940 | 508.0013 | 507.9962 | 508.0064 |
| tyr-tyr-tyr | | 507.2005 | 508.2078 | 508.2027 | 508.2129 |
| phe-arg-try | | 507.2666 | 508.2739 | 508.2688 | 508.2790 |
| Inosine triphosphate | C10H15N4O14P3 | 507.9780 | 508.9853 | 508.9802 | 508.9904 |
| tyr-val-try | | 508.2381 | 509.2453 | 509.2403 | 509.2504 |
| taurocholate | C26H43NO7S | 513.2760 | 514.2833 | 514.2781 | 514.2884 |
| phe-tyr-try | | 514.2289 | 515.2361 | 515.2310 | 515.2413 |
| arg-arg-try | | 516.2993 | 517.3066 | 517.3014 | 517.3118 |
| gln-try-try | | 518.2423 | 519.2496 | 519.2444 | 519.2547 |
| all-trans-pentaprenyl diphosphate | C25H44O7P2 | 518.2551 | 519.2624 | 519.2572 | 519.2676 |
| lys-try-try | | 518.2787 | 519.2859 | 519.2807 | 519.2911 |
| glu-try-try | | 519.2263 | 520.2336 | 520.2284 | 520.2388 |
| 4-(cytidine 5'-diphospho)-2-C-methyl erythritol | C14H25N3O14P2 | 521.0800 | 522.0873 | 522.0821 | 522.0925 |
| met-try-try | | 521.2242 | 522.2315 | 522.2262 | 522.2367 |
| oleoyl lysophosphatidylcholine | C26H53NO7P | 522.3554 | 523.3627 | 523.3574 | 523.3679 |
| guanosine triphosphate (GTP) | C10H16N5O14P3 | 522.9889 | 523.9962 | 523.9910 | 524.0014 |
| arg-tyr-try | | 523.2615 | 524.2688 | 524.2636 | 524.2741 |
| XTP | C10H15N4O15P3 | 523.9729 | 524.9802 | 524.9750 | 524.9855 |
| 3'-phosphoadenylylsulfate (PAPS) | C10H16N5O14SP2 | 523.9878 | 524.9951 | 524.9898 | 525.0003 |
| 3-carboxy-1-hydroxypropyl-ThPP | C16H25N4O10SP2 | 527.0755 | 528.0828 | 528.0775 | 528.0881 |
| his-try-try | | 527.2426 | 528.2499 | 528.2446 | 528.2552 |
| tyr-tyr-try | | 530.2238 | 531.2310 | 531.2257 | 531.2364 |
| CDP-4-dehydro-1,6-dideoxy glucose | C15H23N3O14P2 | 531.0643 | 532.0716 | 532.0663 | 532.0769 |
| CDP-4-dehydro-6-deoxy glucose | C15H23N3O15P2 | 531.0643 | 532.0716 | 532.0663 | 532.0769 |
| val-try-try | | 531.2613 | 532.2686 | 532.2633 | 532.2739 |
| 5β-cyprinolsulfate | C27H48O8S | 532.3070 | 533.3142 | 533.3089 | 533.3196 |
| CDP-3,6-dideoxy glucose | C15H25N3O14P2 | 533.0800 | 534.0873 | 534.0819 | 534.0926 |
| CDP-3,6-dideoxy mannose | C15H25N3O14P2 | 533.0800 | 534.0873 | 534.0819 | 534.0926 |
| UDP-apiose | C14H22N2O16P2 | 536.0433 | 537.0505 | 537.0452 | 537.0559 |
| lycopene | C40H56 | 536.4382 | 537.4455 | 537.4401 | 537.4509 |
| α-carotene | C40H56 | 536.4382 | 537.4455 | 537.4401 | 537.4509 |
| β-carotene | C40H56 | 536.4382 | 537.4455 | 537.4401 | 537.4509 |
| γ-carotene | C40H56 | 536.4382 | 537.4455 | 537.4401 | 537.4509 |
| δ-carotene | C40H56 | 536.4382 | 537.4455 | 537.4401 | 537.4509 |
| UDP-arabinose | C14H23N2O16P2 | 537.0511 | 538.0584 | 538.0530 | 538.0638 |
| UDP-xylose | C14H23N2O16P2 | 537.0511 | 538.0584 | 538.0530 | 538.0638 |
| CDP-ribitol | C14H25N3O15P2 | 537.0749 | 538.0822 | 538.0768 | 538.0876 |
| phe-try-try | | 537.2521 | 538.2594 | 538.2540 | 538.2648 |
| neurosporene | C40H58 | 538.4539 | 539.4611 | 539.4557 | 539.4665 |
| trans-neurosporene | C40H58 | 538.4539 | 539.4611 | 539.4557 | 539.4665 |
| α-zeacarotene | C40H58 | 538.4539 | 539.4611 | 539.4557 | 539.4665 |
| β-zeacarotene | C40H58 | 538.4539 | 539.4611 | 539.4557 | 539.4665 |
| ζ-carotene | C40H60 | 540.4695 | 541.4768 | 541.4714 | 541.4822 |
| phytofluene | C40H62 | 542.4852 | 543.4924 | 543.4870 | 543.4979 |
| phosphoribosyl-AMP | C14H20N5O14P2 | 544.0470 | 545.0543 | 545.0488 | 545.0597 |
| dTDP-4-dehydro-6-deoxy mannose | C16H24N2O15P2 | 546.0640 | 547.0713 | 547.0658 | 547.0768 |
| dTDP-4-oxo-6-deoxy-glucose | C16H24N2O15P2 | 546.0640 | 547.0713 | 547.0658 | 547.0768 |
| dTDP-4-oxo-rhamnose | C16H24N2O15P2 | 546.0640 | 547.0713 | 547.0658 | 547.0768 |
| arg-try-try | | 546.2848 | 547.2921 | 547.2866 | 547.2976 |
| cis-phytoene | C40H66 | 546.5165 | 547.5237 | 547.5183 | 547.5292 |
| UDP-4-dehydro-6-deoxy glucose | C15H22N2O16P2 | 548.0433 | 549.0505 | 549.0451 | 549.0560 |
| dTDP-6-deoxy mannose | C16H26N2O15P2 | 548.0797 | 549.0869 | 549.0814 | 549.0924 |
| dTDP-6-deoxy talose | C16H26N2O15P2 | 548.0797 | 549.0869 | 549.0814 | 549.0924 |
| dTDP-rhamnose | C16H27N2O15P2 | 549.0875 | 550.0948 | 550.0893 | 550.1003 |
| UDP-rhamnose | C15H24N2O16P2 | 550.0589 | 551.0662 | 551.0607 | 551.0717 |
| echinenone | C40H54O | 550.4175 | 551.4247 | 551.4192 | 551.4303 |
| tyr-try-try | | 553.2470 | 554.2543 | 554.2488 | 554.2598 |
| ADP-ribose | C15H24N5O14P2 | 560.0783 | 561.0856 | 561.0800 | 561.0912 |
| protoporphyrin | C34H34N4O4 | 562.2580 | 563.2652 | 563.2596 | 563.2709 |
| CDP-glucose | C15H25N3O16P2 | 563.0542 | 564.0614 | 564.0558 | 564.0671 |
| aerobactin | C22H36N4O13 | 564.2278 | 565.2351 | 565.2294 | 565.2407 |
| dTDP-galactose | C16H27N2O16P2 | 565.0824 | 566.0897 | 566.0840 | 566.0953 |
| dTDP-glucose | C16H27N2O16P2 | 565.0824 | 566.0897 | 566.0840 | 566.0953 |
| UDP-galactose | C15H25N2O17P2 | 567.0617 | 568.0689 | 568.0633 | 568.0746 |

TABLE 1-continued

Endogenous Metabolism Database

| Metabolite | Elemental formula | Precise Mass | M + 1H | 10 ppm− | 10 ppm+ |
|---|---|---|---|---|---|
| UDP-glucose | C15H25N2O17P2 | 567.0617 | 568.0689 | 568.0633 | 568.0746 |
| leukotriene F4 | C28H44N2O8S | 568.2818 | 569.2891 | 569.2834 | 569.2948 |
| protoporphyrinogen | C34H40N4O4 | 568.3049 | 569.3122 | 569.3065 | 569.3179 |
| lutein | C40H56O2 | 568.4280 | 569.4353 | 569.4296 | 569.4410 |
| zeaxanthin | C40H56O2 | 568.4280 | 569.4353 | 569.4296 | 569.4410 |
| phosphoribulosylformimino-aicar-P | C15H21N5O15P2 | 573.0497 | 574.0570 | 574.0513 | 574.0628 |
| try-try-try | | 576.2703 | 577.2776 | 577.2718 | 577.2833 |
| dTDP-galacturonate | C16H24N2O17P2 | 578.0538 | 579.0611 | 579.0553 | 579.0669 |
| dTDP-glucoronate | C16H24N2O17P2 | 578.0538 | 579.0611 | 579.0553 | 579.0669 |
| inositol 1,2,3,4,5-pentakisphosphate | C6H17O21P5 | 579.8922 | 580.8995 | 580.8937 | 580.9053 |
| inositol 1,3,4,5,6-pentakisphosphate | C6H17O21P5 | 579.8922 | 580.8995 | 580.8937 | 580.9053 |
| UDP-iduronate | C15H22N2O18P2 | 580.0331 | 581.0404 | 581.0346 | 581.0462 |
| menaquinone-6 | C41H56O2 | 580.4280 | 581.4353 | 581.4295 | 581.4411 |
| UDP-galacturonate | C15H23N2O18P2 | 581.0409 | 582.0482 | 582.0424 | 582.0540 |
| UDP-glucuronate | C15H23N2O18P2 | 581.0409 | 582.0482 | 582.0424 | 582.0540 |
| bilirubin | C33H36N4O6 | 584.2634 | 585.2707 | 585.2649 | 585.2766 |
| antheraxanthin | C40H56O3 | 584.4229 | 585.4302 | 585.4244 | 585.4361 |
| phycocyanobilin | C33H38N4O6 | 586.2791 | 587.2864 | 587.2805 | 587.2922 |
| all-trans-hexaprenyl diphosphate | C30H52O7P2 | 586.3177 | 587.3250 | 587.3191 | 587.3308 |
| presqualene diphosphate | C30H52O7P2 | 586.3177 | 587.3250 | 587.3191 | 587.3308 |
| adensoine tetraphosphate | C10H17N5O16P4 | 586.9598 | 587.9671 | 587.9612 | 587.9729 |
| GDP-4-dehydro-6-dexoy mannose | C16H23N5O15P2 | 587.0654 | 588.0727 | 588.0668 | 588.0786 |
| GDP-4-oxo-rhamnose | C16H23N5O15P2 | 587.0654 | 588.0727 | 588.0668 | 588.0786 |
| inosine tetraphosphate | C10H16N4O17P4 | 587.9438 | 588.9511 | 588.9452 | 588.9570 |
| urobilin | C33H40N4O6 | 588.2947 | 589.3020 | 589.2961 | 589.3079 |
| ADPmannose | C16H25N5O15P2 | 589.0810 | 590.0883 | 590.0824 | 590.0942 |
| GDP-mannose | C16H25N5O15P2 | 589.0810 | 590.0883 | 590.0824 | 590.0942 |
| GDP-rhamnose | C16H25N5O15P2 | 589.0810 | 590.0883 | 590.0824 | 590.0942 |
| dTDP-4-acetamido-4,6-dideoxy glucose | C18H29N3O15P2 | 589.1062 | 590.1135 | 590.1076 | 590.1194 |
| ADP-glucose | C16H26N5O15P2 | 590.0889 | 591.0961 | 591.0902 | 591.1021 |
| i-urobilin (IX α) | C33H42N4O6 | 590.3104 | 591.3177 | 591.3118 | 591.3236 |
| urobilinogen | C33H42N4O6 | 590.3104 | 591.3177 | 591.3118 | 591.3236 |
| mesobilirubinogen | C33H44N4O6 | 592.3260 | 593.3333 | 593.3274 | 593.3393 |
| l-stercobilin | C33H46N4O6 | 594.3417 | 595.3490 | 595.3430 | 595.3549 |
| l-stercobilinogen | C33H48N4O6 | 596.3573 | 597.3646 | 597.3586 | 597.3706 |
| 9'-cis-neoxanthin | C40H56O4 | 600.4178 | 601.4251 | 601.4191 | 601.4311 |
| 9-cis-violaxanthin | C40H56O4 | 600.4178 | 601.4251 | 601.4191 | 601.4311 |
| neoxanthin | C40H56O4 | 600.4178 | 601.4251 | 601.4191 | 601.4311 |
| 2-phospho-4-(cytidine 5'-diphospho)-2-C-methyl erythritol | C14H26N3O17P3 | 601.0458 | 602.0530 | 602.0470 | 602.0591 |
| guanosine 3',5'-bis(diphosphate) | C10H17N5O17P4 | 602.9547 | 603.9620 | 603.9559 | 603.9680 |
| UDP-N-acetyl mannosamine | C17H27N3O17P2 | 607.0804 | 608.0877 | 608.0816 | 608.0937 |
| GDP-glucose | C16H27N5O16P2 | 607.0916 | 608.0989 | 608.0928 | 608.1050 |
| UDP-N-acetyl galactosamine | C17H28N3O17P2 | 608.0882 | 609.0955 | 609.0894 | 609.1016 |
| UDP-N-acetyl glucosamine | C17H28N3O17P2 | 608.0882 | 609.0955 | 609.0894 | 609.1016 |
| rutin | C27H30O16 | 610.1533 | 611.1606 | 611.1545 | 611.1667 |
| glutathione disulfide | C20H32N6O12S2 | 612.1519 | 613.1592 | 613.1530 | 613.1653 |
| biliverdin | C33H34N4O8 | 614.2376 | 615.2449 | 615.2387 | 615.2510 |
| CMP-sialate | C20H32N4O16P | 615.1545 | 616.1617 | 616.1556 | 616.1679 |
| heme | C34H32N4O4Fe(II) | 616.1750 | 617.1822 | 617.1761 | 617.1884 |
| UDP-N-acetyl-2-amino-2-deoxy glucuronate | C17H23N3O18P2 | 619.0440 | 620.0513 | 620.0451 | 620.0575 |
| UDP-N-acetyl galactosaminuronic acid | C17H25N3O18P2 | 621.0596 | 622.0669 | 622.0607 | 622.0731 |
| UDP-N-acetyl mannosaminouronate | C17H25N3O18P2 | 621.0596 | 622.0669 | 622.0607 | 622.0731 |
| Leukotriene C4 | C30H47N3O9S | 625.3032 | 626.3105 | 626.3043 | 626.3168 |
| UDP-6-sulfoquinovose | C15H23N2O19SP2 | 629.0079 | 630.0152 | 630.0089 | 630.0215 |
| CMP-N-glycoloylneuraminate | C20H31N4O17P | 630.1415 | 631.1488 | 631.1425 | 631.1551 |
| triiodothyronine | C15H11NO4I3 | 649.7805 | 650.7878 | 650.7813 | 650.7943 |
| coproporphyrin | C36H38N4O8 | 654.2689 | 655.2762 | 655.2696 | 655.2827 |
| all-trans-heptaprenyl diphosphate | C35H60O7P2 | 654.3803 | 655.3876 | 655.3810 | 655.3941 |
| inositol-1,2,3,4,5,6-hexakisphosphate | C6H18O24P6 | 659.8580 | 660.8652 | 660.8586 | 660.8718 |
| coproporphyrinogen | C36H44N4O8 | 660.3159 | 661.3231 | 661.3165 | 661.3298 |
| nicotinamide adenine dinucleotide (NAD) | C21H28N7O14P2 | 664.1158 | 665.1230 | 665.1164 | 665.1297 |
| deamido-NAD | C21H27N6O15P2 | 665.0998 | 666.1070 | 666.1004 | 666.1137 |
| NADH + H+ | C21H30N7O14P2 | 666.1314 | 667.1387 | 667.1320 | 667.1453 |
| cellotetraose | C24H42O21 | 666.2218 | 667.2290 | 667.2224 | 667.2357 |
| stachyose | C24H42O21 | 666.2218 | 667.2290 | 667.2224 | 667.2357 |
| UDP-N-acetyl muramate | C19H32N3O19P2 | 668.1093 | 669.1166 | 669.1099 | 669.1233 |

TABLE 1-continued

Endogenous Metabolism Database

| Metabolite | Elemental formula | Precise Mass | M + 1H | 10 ppm− | 10 ppm+ |
|---|---|---|---|---|---|
| UDP-N-acetyl-3-(1-carboxyvinyl) glucosamine | C20H29N3O19P2 | 677.0858 | 678.0931 | 678.0863 | 678.0999 |
| guanosine 3'-diphosphate 5'-triphosphate | C10H18N5O20P5 | 682.9205 | 683.9277 | 683.9209 | 683.9346 |
| dephospho-CoA | C21H35N7O13SP2 | 687.1477 | 688.1550 | 688.1481 | 688.1618 |
| phosphoribosyl-ATP | C14H20N5O20P4 | 701.9629 | 702.9702 | 702.9631 | 702.9772 |
| all-trans-octaprenyl diphosphate | C40H68O7P2 | 722.4429 | 723.4502 | 723.4429 | 723.4574 |
| prephytoene diphosphate | C40H68O7P2 | 722.4429 | 723.4502 | 723.4429 | 723.4574 |
| dipalmitoylphosphatidylcholine | C40H80NO8P | 733.5616 | 734.5688 | 734.5615 | 734.5762 |
| NADP | C21H29N7O17P3 | 744.0815 | 745.0888 | 745.0813 | 745.0962 |
| NADPH + H+ | C21H31N7O17P3 | 746.0972 | 747.1044 | 747.0970 | 747.1119 |
| methanofuran | C34H44N4O15 | 748.2802 | 749.2875 | 749.2800 | 749.2950 |
| P1,P3-bis (5'adenosyl) triphosphate | C20H27N10O16P3 | 756.0802 | 757.0874 | 757.0799 | 757.0950 |
| 1-stearoyl-2-palmitoylphosphatidylcholine | C42H84NO8P | 761.5929 | 762.6001 | 762.5925 | 762.6078 |
| tetrahydromethanopterin (THMPT) | C30H45N6O17P | 775.2545 | 776.2618 | 776.2540 | 776.2695 |
| formyl-MFR | C35H44N4O16 | 776.2751 | 777.2824 | 777.2746 | 777.2902 |
| thyroxine | C15H11NO4I4 | 776.6845 | 777.6917 | 777.6840 | 777.6995 |
| 5,10-methenyl-THMPT | C31H45N6O16P | 788.2623 | 789.2696 | 789.2617 | 789.2775 |
| 5,10-methylene-THMPT | C31H46N6O16P | 789.2701 | 790.2774 | 790.2695 | 790.2853 |
| 5-methyl-THMPT | C31H46N6O16P | 789.2701 | 790.2774 | 790.2695 | 790.2853 |
| P1,P4-bis (5'-uridyl) tetraphosphate | C18H26N4O23P4 | 789.9915 | 790.9988 | 790.9909 | 791.0067 |
| 7,8 dihydroxmethanopterin | C30H43N6O17P | 790.2416 | 791.2489 | 791.2409 | 791.2568 |
| all-trans-nonaprenyl diphosphate | C45H76O7P2 | 790.5055 | 791.5128 | 791.5049 | 791.5207 |
| coenzyme F | C40H51N6O11 | 791.3615 | 792.3688 | 792.3609 | 792.3767 |
| formyl-CoA | C22H36N7O17SP3 | 795.1084 | 796.1156 | 796.1077 | 796.1236 |
| 5-formyl-THMPT | C31H46N6O17P | 805.2651 | 806.2723 | 806.2643 | 806.2804 |
| acetyl-CoA | C23H38N7O17SP3 | 809.1240 | 810.1313 | 810.1232 | 810.1394 |
| acryloyl-CoA | C24H38N7O17SP3 | 821.1240 | 822.1313 | 822.1231 | 822.1395 |
| propionyl-CoA | C24H40N7O17SP3 | 823.1397 | 824.1469 | 824.1387 | 824.1552 |
| cellopentaose | C30H52O26 | 828.2746 | 829.2818 | 829.2735 | 829.2901 |
| uroporphyrin | C40H38N4O16 | 830.2282 | 831.2355 | 831.2272 | 831.2438 |
| crotonyl-CoA | C25H40N7O17SP3 | 835.1397 | 836.1469 | 836.1386 | 836.1553 |
| methacrylyl-CoA | C25H40N7O17SP3 | 835.1397 | 836.1469 | 836.1386 | 836.1553 |
| uroporphyrinogen | C40H44N4O16 | 836.2751 | 837.2824 | 837.2740 | 837.2908 |
| 3-oxopropionyl-CoA | C24H38N7O18SP3 | 837.1189 | 838.1262 | 838.1178 | 838.1346 |
| butyryl-CoA | C25H42N7O17SP3 | 837.1553 | 838.1626 | 838.1542 | 838.1710 |
| 2-methylpropanoyl-CoA | C25H42N7O17SP3 | 837.1553 | 838.1626 | 838.1542 | 838.1710 |
| β-alanyl-CoA | C24H41N8O17SP3 | 838.1506 | 839.1578 | 839.1494 | 839.1662 |
| oxalyl-CoA | C23H36N7O19SP3 | 839.0982 | 840.1055 | 840.0971 | 840.1139 |
| 3-hydroxypropionyl-CoA | C24H40N7O18SP3 | 839.1346 | 840.1418 | 840.1334 | 840.1502 |
| lactoyl-CoA | C24H40N7O18SP3 | 839.1346 | 840.1418 | 840.1334 | 840.1502 |
| tiglyl-CoA | C26H42N7O17SP3 | 849.1553 | 850.1626 | 850.1541 | 850.1711 |
| 3-methyl-crotonyl-CoA | C26H42N7O17SP3 | 849.1553 | 850.1626 | 850.1541 | 850.1711 |
| acetoacetyl-CoA | C25H40N7O18SP3 | 851.1346 | 852.1418 | 852.1333 | 852.1504 |
| 2-methyl-butyryl-CoA | C26H44N7O17SP3 | 851.1710 | 852.1782 | 852.1697 | 852.1868 |
| isovaleryl-CoA | C26H44N7O17SP3 | 851.1710 | 852.1782 | 852.1697 | 852.1868 |
| pentanoyl-CoA | C26H44N7O17SP3 | 851.1710 | 852.1782 | 852.1697 | 852.1868 |
| malonyl-CoA | C24H38N7O19SP3 | 853.1138 | 854.1211 | 854.1126 | 854.1296 |
| 3-hydroxybutyryl-CoA | C25H42N7O18SP3 | 853.1502 | 854.1575 | 854.1490 | 854.1660 |
| preuroporphyriogen | C40H46N4O17 | 854.2857 | 855.2930 | 855.2844 | 855.3015 |
| ubiquinone 10 | C59H90O4 | 862.6839 | 863.6912 | 863.6825 | 863.6998 |
| trans-hex-2-enoyl-CoA | C27H44N7O17SP3 | 863.1710 | 864.1782 | 864.1696 | 864.1869 |
| 2-methyl-acetoacetyl-CoA | C26H42N7O18SP3 | 865.1502 | 866.1575 | 866.1488 | 866.1662 |
| hexanoyl-CoA | C27H46N7O17SP3 | 865.1866 | 866.1939 | 866.1852 | 866.2025 |
| methylmalonyl-CoA | C25H40N7O19SP3 | 867.1295 | 868.1368 | 868.1281 | 868.1454 |
| succinyl-CoA | C25H40N7O19SP3 | 867.1295 | 868.1368 | 868.1281 | 868.1454 |
| 2-methyl-3-hydroxybutyryl-CoA | C26H44N7O18SP3 | 867.1659 | 868.1731 | 868.1645 | 868.1818 |
| P1,P4 bis (5'-guanosyl) tetraphosphate | C20H28N10O21P4 | 868.0358 | 869.0430 | 869.0343 | 869.0517 |
| precorrin 2 | C42H52N4O16 | 868.3377 | 869.3450 | 869.3363 | 869.3537 |
| 3-hydroxyisovaleryl-CoA | C26H46N7O18SP3 | 869.1815 | 870.1888 | 870.1801 | 870.1975 |
| P1,P4-bis (5'-xanthosyl) tetraphosphate | C20H26N8O23P4 | 870.0038 | 871.0111 | 871.0023 | 871.0198 |
| benzoyl-CoA | C28H40N7O17SP3 | 871.1397 | 872.1469 | 872.1382 | 872.1557 |
| precorrin 3 | C43H50N4O16 | 878.3221 | 879.3294 | 879.3206 | 879.3382 |
| glutaconyl-CoA | C26H40N7O19SP3 | 879.1295 | 880.1368 | 880.1280 | 880.1456 |
| itaconyl-CoA | C26H40N7O19SP3 | 879.1295 | 880.1368 | 880.1280 | 880.1456 |
| mesaconyl-CoA | C26H40N7O19SP3 | 879.1295 | 880.1368 | 880.1280 | 880.1456 |
| 3-oxo-hexanoyl-CoA | C27H44N7O18SP3 | 879.1659 | 880.1731 | 880.1643 | 880.1819 |
| glutaryl-CoA | C26H42N7O19SP3 | 881.1451 | 882.1524 | 882.1436 | 882.1612 |
| 3-hydroxyhexanoyl-CoA | C27H46N7O18SP3 | 881.1815 | 882.1888 | 882.1800 | 882.1976 |
| 3-carboxy-3-hydroxypropanoyl-CoA | C25H40N7O20SP3 | 883.1244 | 884.1317 | 884.1228 | 884.1405 |

TABLE 1-continued

Endogenous Metabolism Database

| Metabolite | Elemental formula | Precise Mass | M + 1H | 10 ppm− | 10 ppm+ |
|---|---|---|---|---|---|
| phenylacetyl-CoA | C29H42N7O17SP3 | 885.1553 | 886.1626 | 886.1537 | 886.1714 |
| trans-oct-2-enoyl-CoA | C29H48N7O17SP3 | 891.2023 | 892.2095 | 892.2006 | 892.2185 |
| 3-methylglutaconyl-CoA | C27H42N7O19SP3 | 893.1451 | 894.1524 | 894.1435 | 894.1613 |
| octanoyl-CoA | C29H50N7O17SP3 | 893.2179 | 894.2252 | 894.2162 | 894.2341 |
| 2-hydroxyglutaryl-CoA | C26H42N7O20SP3 | 897.1400 | 898.1473 | 898.1383 | 898.1563 |
| citramalyl-CoA | C26H42N7O20SP3 | 897.1400 | 898.1473 | 898.1383 | 898.1563 |
| erythro-3-methylmalyl-CoA | C26H44N7O20SP3 | 899.1557 | 900.1630 | 900.1540 | 900.1720 |
| 4-hydroxyphenylacethyl-CoA | C29H42N7O18SP3 | 901.1502 | 902.1575 | 902.1485 | 902.1665 |
| 3-oxo-octanoyl-CoA | C29H48N7O18SP3 | 907.1972 | 908.2044 | 908.1954 | 908.2135 |
| 3-oxo-adipyl-CoA | C27H42N7O20SP3 | 909.1400 | 910.1473 | 910.1382 | 910.1564 |
| 3-hydroxyoctanoyl-CoA | C29H50N7O18SP3 | 909.2128 | 910.2201 | 910.2110 | 910.2292 |
| 3-hydroxy-3-methylglutaryl-CoA (HMG-CoA) | C27H44N7O20SP3 | 911.1557 | 912.1630 | 912.1538 | 912.1721 |
| trans-dec-2-enoyl-CoA | C31H52N7O17SP3 | 919.2336 | 920.2408 | 920.2316 | 920.2500 |
| siroheme | C42H48N4O16Fe(II) | 920.2391 | 921.2464 | 921.2372 | 921.2556 |
| decanoyl-CoA | C31H54N7O17SP3 | 921.2492 | 922.2565 | 922.2473 | 922.2657 |
| cobinamide | C45H65N10O8Co | 932.4313 | 933.4385 | 933.4292 | 933.4479 |
| 3-oxo-decanoyl-CoA | C31H52N7O18SP3 | 935.2285 | 936.2357 | 936.2264 | 936.2451 |
| 3-hydroxydecanoyl-CoA | C31H54N7O18SP3 | 937.2441 | 938.2514 | 938.2420 | 938.2608 |
| cobyrinate | C45H59N4O14Co | 938.3353 | 939.3426 | 939.3332 | 939.3520 |
| citryl-CoA | C27H42N7O22SP3 | 941.1299 | 942.1371 | 942.1277 | 942.1466 |
| trans-dodec-2-enoyl-CoA | C33H56N7O17SP3 | 947.2649 | 948.2721 | 948.2627 | 948.2816 |
| dodecanoyl-CoA | C33H58N7O17SP3 | 949.2805 | 950.2878 | 950.2783 | 950.2973 |
| 3-oxo-dodecanoyl-CoA | C33H56N7O18SP3 | 963.2598 | 964.2670 | 964.2574 | 964.2767 |
| 3-hydroxydodecanoyl-CoA | C33H58N7O18SP3 | 965.2754 | 966.2827 | 966.2730 | 966.2924 |
| trans-tetradec-2-enoyl-CoA | C35H60N7O17SP3 | 975.2962 | 976.3034 | 976.2937 | 976.3132 |
| myristoyl-CoA | C35H62N7O17SP3 | 977.3118 | 978.3191 | 978.3093 | 978.3289 |
| palmitoyl-CoA | C37H66N7O17SP3 | 990.2257 | 991.2330 | 991.2231 | 991.2429 |
| cellohexose | C36H62O31 | 990.3274 | 991.3346 | 991.3247 | 991.3446 |
| 3-oxo-tetradecanoyl-CoA | C35H60N7O18SP3 | 991.2911 | 992.2983 | 992.2884 | 992.3083 |
| 3-hydroxytetradecanoyl-CoA | C35H62N7O18SP3 | 993.3067 | 994.3140 | 994.3041 | 994.3239 |
| P1,P4 bis (5'-adensoyl) tetraphosphate | C20H28N10O19P4 | 995.9950 | 997.0023 | 996.9923 | 997.0123 |
| bilirubin β-diglucuronide | C45H52N4O22 | 1000.3072 | 1001.3145 | 1001.3045 | 1001.32449 |
| trans-hexadec-2-enoyl-CoA | C37H64N7O17SP3 | 1003.3275 | 1004.3347 | 1004.3247 | 1004.34478 |
| 3-oxo-hexadecanoyl-CoA | C37H64N7O18SP3 | 1019.3224 | 1020.3296 | 1020.3194 | 1020.33985 |
| 3-hydroxyhexadecanoyl-CoA | C37H66N7O18SP3 | 1021.3380 | 1022.3453 | 1022.3351 | 1022.35552 |
| UDP-N-acetylmuramoylalanyl-γ-glutamyl-meso-2,6-diaminopimelate | C35H55N7O26P2 | 1051.2659 | 1052.2732 | 1052.2627 | 1052.28374 |
| vasopressin | C46H65N13O12S2 | 1055.4316 | 1056.4389 | 1056.4283 | 1056.44944 |
| bradykinin | C50H73N15O11 | 1059.5613 | 1060.5686 | 1060.5580 | 1060.57917 |
| phytanoyl-CoA | C41H74N7O17SP3 | 1061.4057 | 1062.4130 | 1062.4024 | 1062.42361 |
| chenodeoxycholoyl-CoA | C45H74N7O19SP3 | 1141.3955 | 1142.4028 | 1142.3914 | 1142.41423 |
| chenodeoxyglycocholoyl-CoA | C45H74N7O19SP3 | 1141.3955 | 1142.4028 | 1142.3914 | 1142.41423 |
| celloheptaose | C42H72O36 | 1152.3802 | 1153.3874 | 1153.3759 | 1153.39897 |
| choloyl-CoA | C45H74N7O20SP3 | 1157.3904 | 1158.3977 | 1158.3861 | 1158.4093 |
| 3α,7α-dihydroxy-5β-cholest-24-enoyl-CoA | C48H78N7O19SP3 | 1181.4268 | 1182.4341 | 1182.4223 | 1182.44593 |
| 3α,7α-dihydroxy-5β-cholestanoyl-CoA | C48H80N7O19SP3 | 1183.4425 | 1184.4498 | 1184.4379 | 1184.4616 |
| UDP-N-acetylmuramoylalanylglutamyl-meso-2,6-diaminopimeloylalanyl alanine | C41H65N9O28P2 | 1193.3402 | 1194.3474 | 1194.3355 | 1194.35938 |
| 3α,7α,12α-trihydroxy-5β-cholest-24-enoyl-CoA | C48H78N7O20SP3 | 1197.4217 | 1198.4290 | 1198.4170 | 1198.441 |
| 3α,7α-dihydroxy-5β-24-oxocholestanoyl-CoA | C48H78N7O20SP3 | 1197.4217 | 1198.4290 | 1198.4170 | 1198.441 |
| 3α,7α,12α,24ξ-tetrahydroxy-5β-cholestanoyl-CoA | C48H64N7O21SP3 | 1199.3071 | 1200.3144 | 1200.3024 | 1200.32638 |
| 3α,7α,12α-trihydroxy-5β-cholestanoyl-CoA | C48H80N7O20SP3 | 1199.4374 | 1200.4447 | 1200.4327 | 1200.45667 |
| 3α,7α,12α-trihydroxy-5β-24-oxocholelestanoyl-CoA | C48H78N7O21SP3 | 1213.4167 | 1214.4239 | 1214.4118 | 1214.43607 |
| methylcobalamin | C63H91N13O14PCo | 1343.5866 | 1344.5939 | 1344.5804 | 1344.60731 |
| Hydroxycobalamin | C62H90N13O15PCo | 1346.5737 | 1347.5809 | 1347.5675 | 1347.59442 |
| cyanocobalamin | C63H88CoN14O14P | 1354.5662 | 1355.5735 | 1355.5599 | 1355.58701 |
| 5'-deoxyadenosyl cobalamin | C72H100N18O17PCo | 1578.6571 | 1579.6644 | 1579.6486 | 1579.68016 |
| glutathionylcobalamin | C72H104N16O20SPCo | 1634.6391 | 1635.6463 | 1635.6300 | 1635.66268 |
| adenosylcobalamin | C72H101N18O20P2Co | 1658.6229 | 1659.6301 | 1659.6135 | 1659.64673 |

Example 3: Failure of Standardization Against Identical Complex Mixture of Standards To evaluate standardization of a complex biological mixture relative to a complex authentic standard, a complex mixture of stable isotopic standards, designated "I" was created by growing yeast on $^{13}$C-glucose and $^{15}$N-ammonium chloride as sole carbon and nitrogen sources, respectively. Mass spectrum patterns of high accuracy m/z features, co-elution and fragmentation analyses established the identical nature of the standard compared to extracts of yeast grown under identical conditions with normal isotopic versions of the carbon and nitrogen sources, designated "N", in terms of chemical compositions. Aliquots of the complex standard mixture I was then added to control extracts N and analyzed by LC-FTMS to determine whether the observed ratio of N:I (normal isotopic chemical:stable isotopic form of that chemical) was equal to the actual ratio of N:I which was added.

Figure 16:
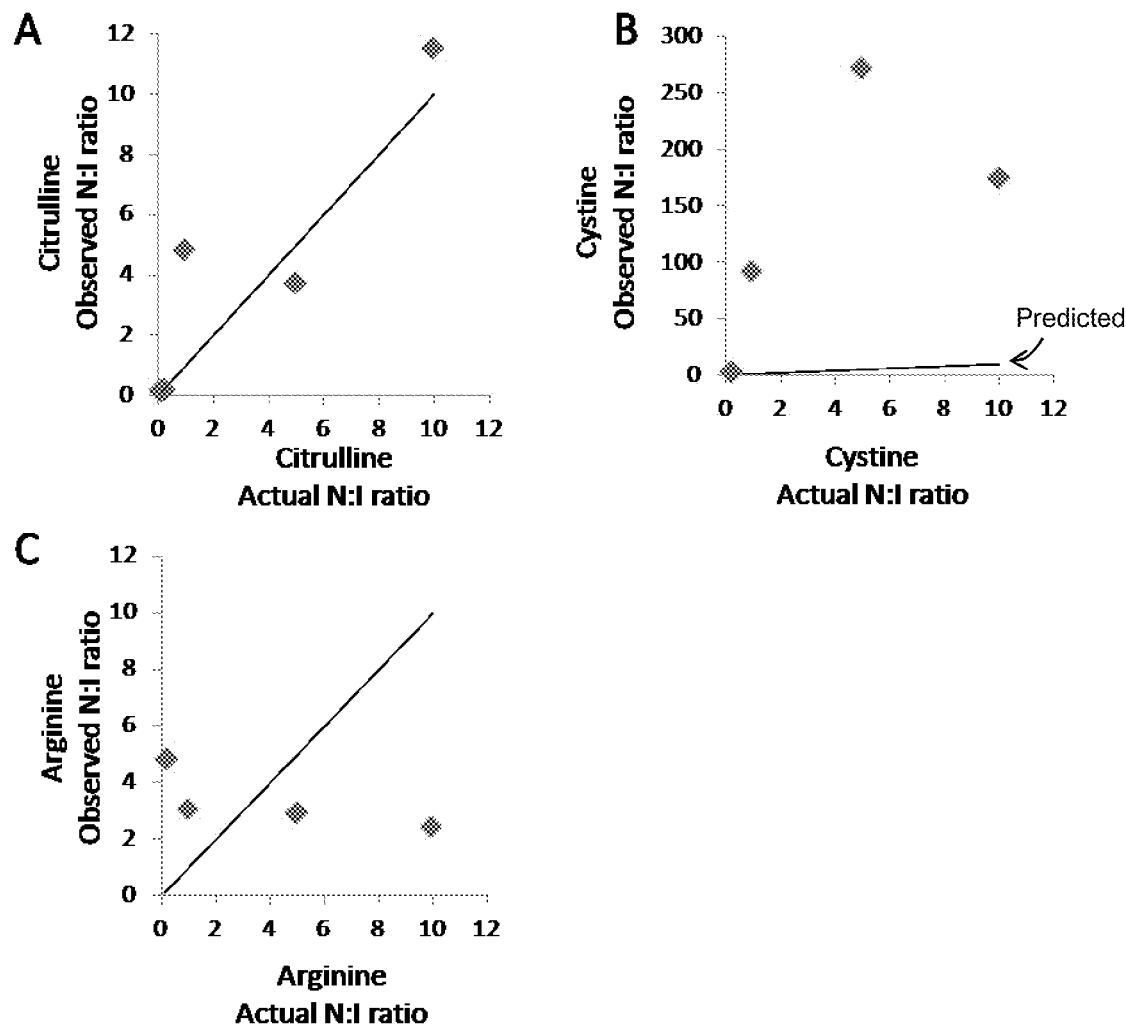
FIGS. 16A, 16B and 16C provide data showing the failure of standardization against an identical complex mixture of standards.

The results for 3 chemicals are shown in FIG. 16, which illustrate 3 types of responses observed. FIG. 16A shows the observed N:I signal for citrulline corresponded to the actual ratio added. FIG. 16B shows the observed N:I for cystine showed considerable variability but was very large relative to the actual N:I added. The effect could be due to dynamic range limitations for standardization, variable ion suppression, or a complex interaction which affected ion detection. FIG. 16C shows the observed N:I for arginine showed a lack of responsiveness relative to the actual amount of N:I added. This effect could be due to ion suppression or a threshold effect which seriously limited sensitivity over the dynamic range used. Together these results show that a complex standard mixture causes ion suppression or other effects which limit the dynamic range of operation and renders a complex mixture of authentic standards to be unacceptable to standardize analysis of complex mixtures. The diagonal lines in FIGS. 16A, 16B and 16C represent the expected responses for amounts added.

Example 4: Failure of Standardization of m/z 147.07581 Against Surrogate Internal Standards A common approach to standardize multiple chemicals within a mixture is to reference each to another chemical, termed a "Surrogate Standard", which is added in a known amount. To test the reliability of surrogate standardization for features in human plasma, an unknown chemical in plasma with m/z 147.07581 was quantified against added stable isotopic chemicals ($^{15}$N-tyrosine, trimethyl-$^{13}$C$_3$-caffeine, $^{13}$C$_5$-L-glutamic acid) which were added in a fixed and known amount. Samples were analyzed in duplicate on 2 LC columns on 3 days which were at least 2 weeks apart.

Figure 17:
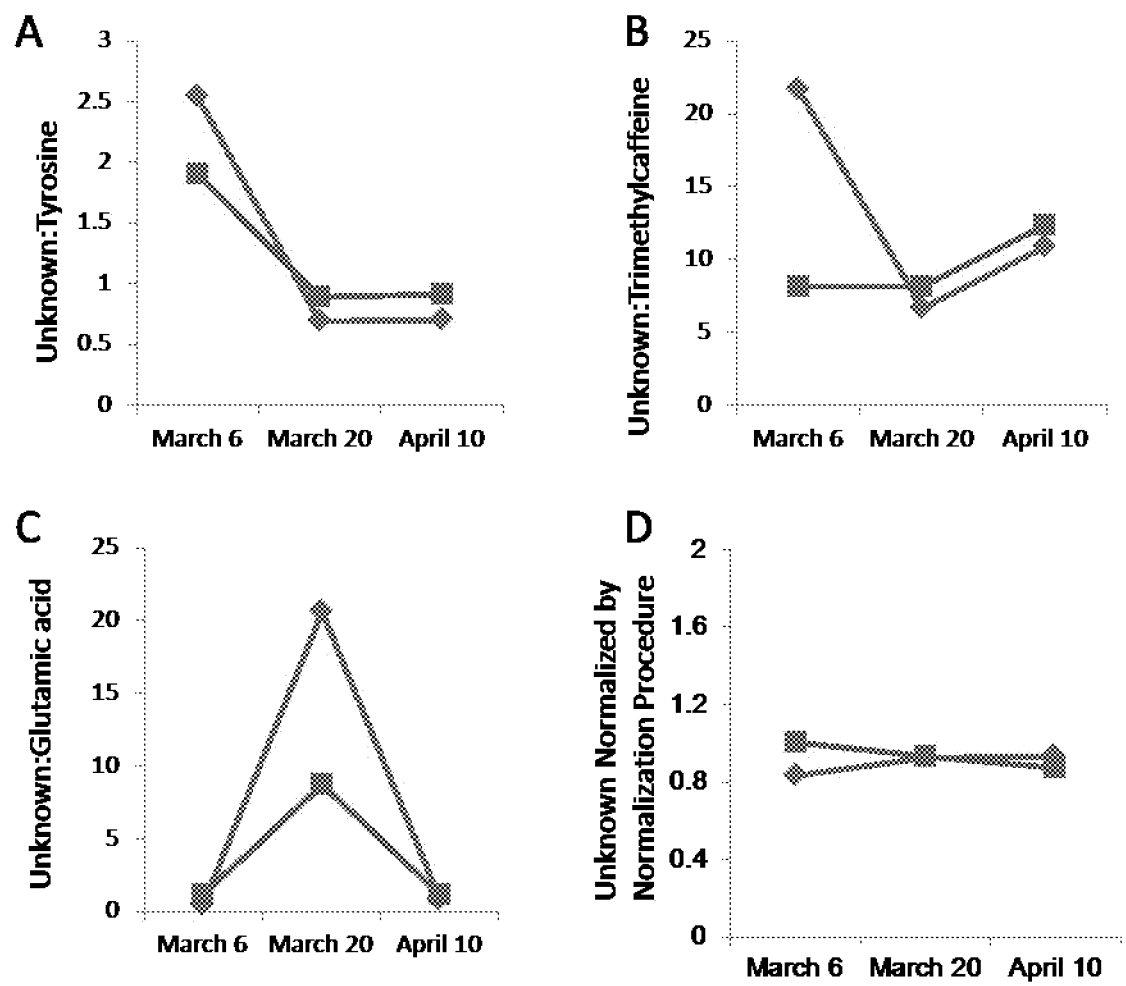
FIGS. 17A, 17B and 17C provide data showing the failure of standardization against different Surrogate Internal Standards.
FIG. 17D provides data showing successful normalization using methods described herein.

FIG. 17A shows the actual ratio of amounts of unknown:tyrosine was constant for all analyses but the observed ratios of signal intensities for unknown:tyrosine (shown for LC Columns A and B) differed by more than 3-fold among samples run on different days. FIG. 17B shows the actual ratio of amounts of the unknown:caffeine was constant for all analyses but the observed ratios of signal intensities for unknown:caffeine (shown for LC Columns A and B) differed by more than 3-fold among samples run on different days. FIG. 17C show the actual ratio of amounts of unknown:glutamate was constant for all analyses but the observed ratios of measured unknown:glutamate (shown for LC Columns A and B) differed by more than 20-fold among samples run on different days.

The results show that use of a Surrogate Standardization approach which depends upon the signals derived from individual chemicals being constant relative to the signal derived from added chemicals (Surrogate Standard, not chemically identical to chemical of interest) does not provide a reliable approach for standardization of chemicals in a biologic extract. FIG. 17D shows, for comparison, the unknown m/z 147.07581 feature normalized using the normalization procedure for chemical profiles described above where the week-to-week and column-to-column comparisons had coefficients of variation of less than 10%.

Example 5: Multiple m/z Features Resulting from a Single Chemical Species

For certain embodiments, multiple m/z features in a mass spectrum correspond to a single chemical species. For example, isotopic variations can result in observation of distinct mass to charge ratios for a single substance.

Figure 18:
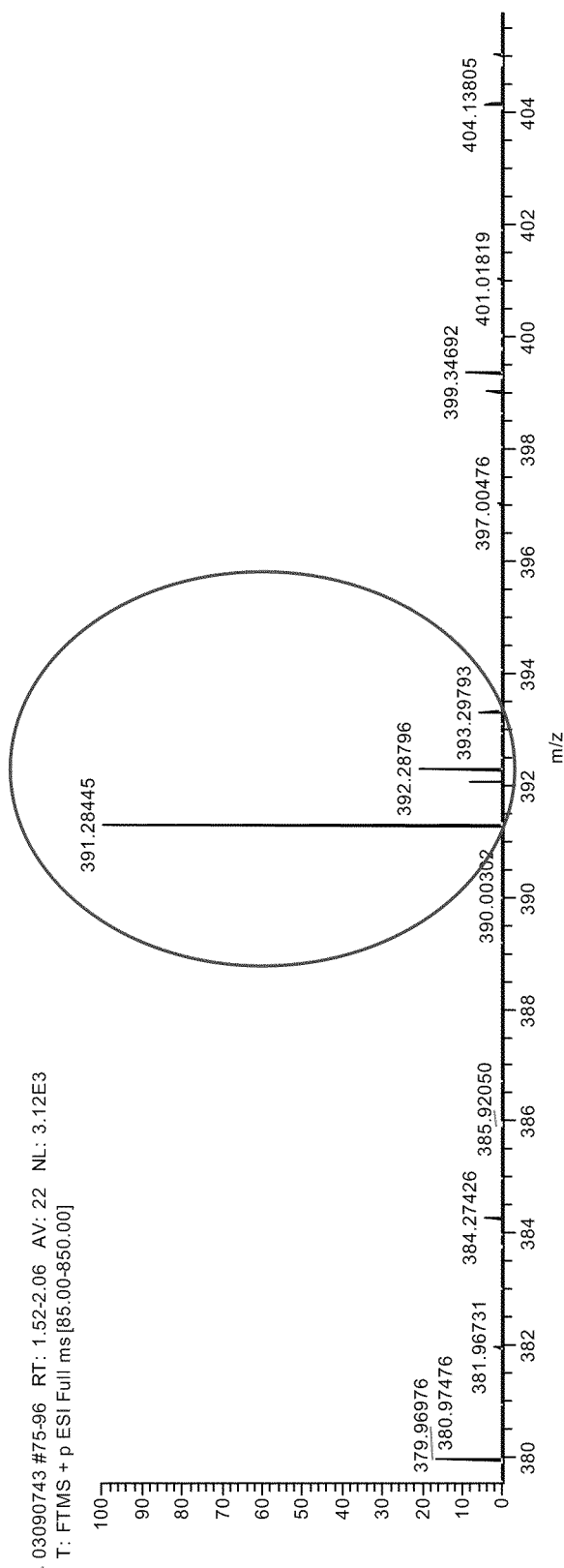
FIG. 18 illustrates a portion of a mass spectrum, showing multiple m/z peaks arising from a single chemical formula.

FIG. 18 illustrates this phenomenon. In FIG. 18, the mass spectrum is zoomed into to an m/z range of 380-406 to highlight that more than one distinct m/z can represent one elemental formula. These peaks represent a single distinct chemical with a chemical formula of $C_{24}H_{38}O_4$, the same as a number of bile acids, with m/z of 391.28445. The peak at 392.28796 represents the elemental formula $^{13}C_1C_{23}H_{38}O_4$ (approximately 25% of the monoisotopic peak) with the peak at 393.29793 representing the same chemical with $^{13}C_2$.

REFERENCES

W. Weckwerth, Annu Rev Plant Biol 54, 669 (2003).
M. J. Gibney, M. Walsh, L. Brennan et al., Am J Clin Nutr 82 (3), 497 (2005).
T. Kuhara, Mass Spectrom Rev 24 (6), 814 (2005).
H. G. Gika, G. A. Theodoridis, and I. D. Wilson, J Chromatogr A 1189 (1-2), 314 (2008).
M. G. Miller, J Proteome Res 6 (2), 540 (2007).
T. Yu, Y. Park, J. M. Johnson et al., Bioinformatics 25 (15), 1930 (2009).
E. J. Want, G. O'Maille, C. A. Smith et al., Anal Chem 78 (3), 743 (2006).
J. M. Johnson, F. H. Strobel, M. Reed et al., Clin Chim Acta 396 (1-2), 43 (2008).
Q. Cui, I. A. Lewis, A. D. Hegeman et al., Nat Biotechnol 26 (2), 162 (2008).
O. Fiehn, Plant Mol Biol 48 (1-2), 155 (2002).
J. C. Lindon, H. C. Keun, T. M. Ebbels et al., Pharmacogenomics 6 (7), 691 (2005).
E. Bohus, M. Coen, H. C. Keun et al., J Proteome Res 7 (10), 4435 (2008).
M. Coen, Y. S. Hong, T. A. Clayton et al., J Proteome Res 6 (7), 2711 (2007).
H. Li, Y. Ni, M. Su et al., J Proteome Res 6 (4), 1364 (2007).
E. K. Kemsley, G. Le Gall, J. R. Dainty et al., Br J Nutr 98 (1), 1 (2007).
T. Kuhara, J Chromatogr B Analyt Technol Biomed Life Sci 855 (1), 42 (2007).
N. Raikos, G. Theodoridis, E. Alexiadou et al., J Sep Sci (2009).
S. Rezzi, Z. Ramadan, F. P. Martin et al., J Proteome Res 6 (11), 4469 (2007).
M. C. Walsh, L. Brennan, J. P. Malthouse et al., Am J Clin Nutr 84 (3), 531 (2006).
M. C. Walsh, L. Brennan, E. Pujos-Guillot et al., Am J Clin Nutr 86 (6), 1687 (2007).

U.S. Patent Application Publication No. US 2006/0200316.
International Patent Application Publication No. WO 2009/134439.
U.S. Pat. Nos. 7,632,686, 7,451,052, 6,974,702 and 6,680,203.
Deport et al., Comprehensive combinatory standard correction: A calibration method for handling instrumental drifts of gas chromatography-mass spectrometry systems, J. Chrom A, 2006, 1116, 248-258.
Kanani et al., Data correction strategy for metabolomics analysis using gas chromatography-mass spectrometry, Metab. Engr., 2007, 9, 39-51.
Nordström et al., Nonlinear Data Alignment for HPLC-MS and HPLC-MS Based Metabolomics: Quantitative Analysis of Endogenous and Exogenous Metabolites in Human Serum, Anal. Chem., 2006, 78, 3289-3295.
Pavón et al., Calibration Transfer for Solving the Signal Instability in Quantitative Headspace-Mass spectrometry, Anal. Chem. 2003, 75, 6361-6367.
Pavon et al., Strategies for qualitative and quantitative analyses with mass spectrometry-based electronic noses, Trends Anal. Chem., 2006, 25, 257-266.
Sysi-Aho et al., Normalization method for metabolomics data using optimal selection of multiple internal standards, BMC Bioinformatics, 2007, 8:93.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the disclosure pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the disclosure, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the disclosure without resort to undue experimentation. All art-known functional equivalents, of any such methods, device elements, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The disclosure illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

We claim:

1. A method of analyzing a test sample of a material type via a mass spectrometry instrument, the method comprising the steps of:

providing normalization data for a material type, the normalization data including one or more mass to charge (m/z) intensity ratios for one or more m/z features, the normalization data being based on at least one reference set of mass spectrometry data obtained from a first external standard sample including a first reference sample of the material type and one or more isotopic standards;

receiving a first set of mass spectrometry data obtained from a test sample of a material type and the one or more isotopic standards analyzed by a mass spectrometry instrument, wherein the first set of mass spectrometry data comprises one or more m/z intensity ratios for each m/z feature;

receiving at least a second set of mass spectrometry data obtained from a second external standard sample including a second reference sample of the material type and the one or more isotopic standards analyzed by the mass spectrometry instrument, wherein the second set of mass spectrometry data comprises one or more m/z intensity ratios;

generating one or more m/z intensity ratio normalization factors using the second set of mass spectrometry data and the normalization data, each m/z intensity ratio normalization factor representing a response for the mass spectrometry instrument for each m/z feature; and generating normalized mass spectrometry data for the test sample using the one or more m/z intensity ratio normalization factors and the first set of mass spectrometry data, the normalized mass spectrometry data including a normalized intensity ratio for each m/z feature included in the test sample.

2. The method of claim 1, wherein the first reference sample and the second reference sample are same, substantially the same or from a same biologically derived material.

3. The method of claim 1, wherein each m/z feature refers to a portion of the at least one reference set of mass spectrometry data.

4. The method of claim 1, further comprising:
generating a normalization data table including the normalization data for the material type.

5. The method of claim 1, further comprising:
generating the normalization data, wherein the generating the normalization data includes:
processing the at least one reference set of mass spectrometry data obtained from the first external standard sample to determine the m/z intensity ratios of each m/z feature for each isotropic standard;
comparing the m/z intensity ratios for each m/z features with the m/z intensity ratios for the one or more isotopic standards to determine an intensity ratio coefficient of variation for the one or more m/z features;
selecting a reference isotopic standard or a combination of reference isotopic standards for each m/z feature from the at least one reference set of mass spectrometry data based on the intensity ratio coefficient of variation; and
generating the normalization data, wherein the normalization data includes the one or more m/z features from the at least one reference set of mass spectrometry data associated with at least each selected corresponding intensity ratio.

6. The method of claim 5, wherein the step of receiving includes receiving a plurality of reference sets of mass spectrometry data.

7. The method of claim 5, wherein the criteria for selecting the reference isotopic standard or the combination of reference isotopic standards for each m/z feature from the at least one reference set of mass spectrometry data includes a lowest intensity ratio coefficient of variation for that m/z feature.

8. The method of claim 1, wherein the first, second and reference sets of mass spectrometry data comprise liquid chromatography-mass spectrometry data, gas chromatography-mass spectrometry data or Fourier transform mass spectrometry data, direct infusion mass spectrometry data, capillary electrophoresis mass spectrometry data, ion mobility shift mass spectrometry data, desorption electrospray ionization mass spectrometry data, nanostructure initiator mass spectrometry or matrix assisted mass spectrometry data.

9. The method of claim 1, wherein concentrations of the one or more isotopic standards in the test sample, the first external standard sample and the second standard sample are the same.

10. The method of claim 1, wherein the first reference sample, the test sample and the second reference sample is a biological fluid.

11. The method of claim 10, wherein the first set of mass spectrometry data, the second set of mass spectrometry data and the normalization data comprise metabolomic data or metabonomic data.

12. The method of claim 1,
wherein the normalization data is received before or after the second set of mass spectrometry data, and
wherein the second set of mass spectrometry data is received before or after the first set of mass spectrometry data.

13. The method of claim 1, wherein the providing the normalization data includes providing a generated normalization data table and the providing the normalization data includes:
receiving a mass spectrometry data set on a standard sample including one or more isotopic standards and a sample of the material type, the mass spectrometry data set comprising intensities for one or more m/z features and corresponding one or more isotopic standards;
comparing intensities for the one or more m/z features with intensities for the one or more isotopic standards to determine a coefficient of variation for the one or more m/z features;
determining a reference isotopic standard or a combination of reference isotopic standards for each of the one or more m/z features based on the coefficient of variation; and
generating the normalization data table for the material type, the data table including one or more m/z entries corresponding to the one or more m/z features, wherein each m/z entry of the data table comprises an intensity ratio of the one or more m/z features divided by an intensity of the reference isotopic standard or the combination of reference isotopic standards for the one or more m/z features.

14. The method of claim 13, wherein the step of receiving the mass spectrometry data is repeated one or more times.

15. The method of claim 14,
wherein the determining the reference isotopic standard or the combination of reference isotopic standards for each of the one or more m/z features is based on criteria for the coefficient of variation, and the criteria includes a lowest intensity ratio coefficient of variation for that m/z feature.

16. The method of claim 1, wherein the mass spectrometry instrument is a liquid chromatography-mass spectrometry instrument.

17. A non-transitory computer readable storage medium for storing instructions for analyzing a test sample of a material type via mass spectrometry instrument, the instructions comprising:
providing normalization data for a material type, the normalization data including one or more mass to charge (m/z) intensity ratios for one or more m/z features, the normalization data being based on at least one reference set of mass spectrometry data obtained from a first external standard sample including a first reference sample and one or more isotopic standards;
receiving a first set of mass spectrometry data obtained from a test sample of the material type and the one or more isotopic standards analyzed by a mass spectrometry instrument, wherein the first set of mass spectrometry data comprises one or more m/z intensity ratios;

receiving at least a second set of mass spectrometry data obtained from a second external standard sample including a second reference sample of the material type and the one or more isotopic standards analyzed by the mass spectrometry instrument, wherein the second set of mass spectrometry data comprises one or more m/z intensity ratios;

generating one or more m/z intensity ratio normalization factors using the second mass spectrometry data set and the normalization data, each m/z intensity ratio normalization factor representing a response for the mass spectrometry instrument for each m/z feature; and generating normalized mass spectrometry data for the test sample using the one or more m/z intensity normalization factors and the first mass spectrometry data set, the normalized mass spectrometry data including a normalized intensity ratio for each m/z feature included in the test sample.

18. The medium of claim 17, wherein each m/z feature refers to a portion of the at least one set of reference mass spectrometry data.

19. The medium of claim 17, further comprising:
generating a normalization data table including the normalization data for the material type.

20. The medium of claim 17, further comprising:
generating the normalization data, wherein the generating the normalization data includes:

processing the at least one reference set of mass spectrometry data obtained from the first external standard sample to determine the m/z intensity ratios of each m/z feature for each isotropic standard;

comparing the m/z intensity ratios for each m/z features with the m/z intensity ratios for the one or more isotopic standards to determine an intensity ratio coefficient of variation for the one or more m/z features;

selecting a reference isotopic standard or a reference combination of isotopic standards for each m/z feature from the reference set of mass spectrometry data based on the intensity ratio coefficient of variation; and generating the normalization data, the normalization data including the one or more m/z features from the reference set of mass spectrometry data associated with at least each selected corresponding intensity ratio.

* * * * *